US012788782B2

(12) United States Patent
Gojo et al.

(10) Patent No.: US 12,788,782 B2
(45) **Date of Patent: *Nov. 10, 2026**

(54) METHODS OF PREPARING MITOCHONDRIA REPLACED CELLS WITH IMPROVED MITOCHONDRIAL FUNCTION

(71) Applicant: Imel Biotherapeutics, Inc., Waltham, MA (US)

(72) Inventors: Satoshi Gojo, Kyoto-Fu (JP); Daisuke Kami, Kyoto-Fu (JP); Hideki Maeda, Kyoto-Fu (JP)

(73) Assignee: Imel Biotherapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/924,887

(22) Filed: Oct. 23, 2024

(65) Prior Publication Data

US 2026/0109999 A1 Apr. 23, 2026

Related U.S. Application Data

(63) Continuation of application No. 16/539,993, filed on Aug. 13, 2019, now abandoned.

(60) Provisional application No. 62/817,987, filed on Mar. 13, 2019, provisional application No. 62/731,731, filed on Sep. 14, 2018, provisional application No. 62/718,891, filed on Aug. 14, 2018.

(51) Int. Cl.

| | |
|---|---|
| ***A61K 35/28*** | (2015.01) |
| ***A61K 40/10*** | (2025.01) |
| ***A61K 40/11*** | (2025.01) |
| ***A61K 40/22*** | (2025.01) |
| ***A61K 40/41*** | (2025.01) |
| ***A61K 40/42*** | (2025.01) |
| ***C12N 5/077*** | (2010.01) |
| ***C12N 5/0783*** | (2010.01) |
| ***C12N 5/0789*** | (2010.01) |
| ***C12N 9/22*** | (2006.01) |
| ***C12N 15/87*** | (2006.01) |
| *A61K 31/436* | (2006.01) |
| *A61K 45/06* | (2006.01) |

(52) U.S. Cl.

CPC .............. *A61K 35/28* (2013.01); *A61K 40/10* (2025.01); *A61K 40/11* (2025.01); *A61K 40/22* (2025.01); *A61K 40/416* (2025.01); *A61K 40/42* (2025.01); *C12N 5/0636* (2013.01); *C12N 5/0647* (2013.01); *C12N 5/0656* (2013.01); *C12N 5/0669* (2013.01); *C12N 9/22* (2013.01); *C12N 15/87* (2013.01); *A61K 31/436* (2013.01); *A61K 45/06* (2013.01); *A61K 2239/31* (2023.05); *A61K 2239/38* (2023.05); *A61K 2239/46* (2023.05); *C07K 2319/07* (2013.01); *C12N 2510/00* (2013.01)

(58) Field of Classification Search

None

See application file for complete search history.

(56) References Cited

U.S. PATENT DOCUMENTS

| | | | | |
|---|---|---|---|---|
| 8,039,587 | B2 | 10/2011 | Khan | |
| 8,058,065 | B2 | 11/2011 | Yamanaka et al. | |
| 8,278,104 | B2 | 10/2012 | Yamanaka et al. | |
| 2011/0008310 | A1 | 1/2011 | Cataldo et al. | |
| 2011/0008778 | A1 | 1/2011 | Seibel | |
| 2011/0281269 | A1 | 11/2011 | Deckman et al. | |
| 2013/0034527 | A1 | 2/2013 | Hyde et al. | |
| 2013/0136726 | A1 | 5/2013 | Sobenin et al. | |
| 2014/0193511 | A1 | 7/2014 | Yivgi-Ohana et al. | |
| 2015/0361450 | A1 | 12/2015 | Tarassov et al. | |
| 2018/0030413 | A1 | 2/2018 | Yivgi-Ohana et al. | |
| 2018/0057610 | A1 | 3/2018 | McCully et al. | |
| 2019/0024073 | A1 | 1/2019 | Ekker et al. | |
| 2020/0054682 | A1 * | 2/2020 | Gojo | C12N 5/0636 |
| 2020/0087685 | A1 * | 3/2020 | Wu | B01L 3/502715 |
| 2020/0181578 | A1 | 6/2020 | Kheradvar et al. | |
| 2021/0228642 | A1 | 7/2021 | Yivgi Ohana et al. | |
| 2021/0275597 | A1 | 9/2021 | Yivgi Ohana et al. | |
| 2024/0228960 | A1 | 7/2024 | Gojo | |

FOREIGN PATENT DOCUMENTS

| | | | | |
|---|---|---|---|---|
| CA | 2590552 | A1 | 11/2007 | |
| JP | 2016168763 | A | 9/2016 | |
| JP | 2016535598 | A | 11/2016 | |
| JP | 2017124037 | A | 7/2017 | |
| WO | WO-2009074337 | A1 | 6/2009 | |
| WO | WO-2016008937 | A1 * | 1/2016 | A61K 38/193 |
| WO | WO-2016135723 | A1 | 9/2016 | |
| WO | WO-2017015567 | A1 | 1/2017 | |
| WO | WO-2017124037 | A1 | 7/2017 | |
| WO | WO-2018093954 | A1 | 5/2018 | |

(Continued)

OTHER PUBLICATIONS

Xu et al. Drug Delivery Trends in Clinical Trails and Translational Medicine: challenges and opportunities in the delivery of nucleic acid-based therapeutics. J Pharm Sci. Jan. 2011;100(1):38-52. (Year: 2011).*

(Continued)

*Primary Examiner* — Valerie E Bertoglio
*Assistant Examiner* — Briana N Ebbinghaus

(57) ABSTRACT

The present invention provides methods and compositions for generation of mitochondria replaced cells (MirC), and therapeutic methods for using such compositions for treating a subject having an age-related disease or syndrome, mitochondrial disease or disorder, or otherwise in need of mitochondrial replacement. Also provided are methods and compositions for producing a recipient cell having a mitochondrial disease or disorder, as well as methods and compositions for producing or enhancing production of an inducible pluripotent stem cell (iPSC). In addition, methods and compositions to enhance mitochondrial transfer are also included.

7 Claims, 77 Drawing Sheets

Specification includes a Sequence Listing.

(56) References Cited

FOREIGN PATENT DOCUMENTS

| | | | |
|---|---|---|---|
| WO | WO-2020036973 A1 | 2/2020 | |
| WO | WO-2020149026 A1 | 7/2020 | |
| WO | WO-2022243905 A1 * | 11/2022 | ......... A61K 39/4611 |

OTHER PUBLICATIONS

Verma et al. Gene therapy—promises, problems and prospects. Nature. Sep. 18, 1997;389(6648):239-42. (Year: 1997).*

Clemente-Suárez et al. Mitochondrial Transfer as a Novel Therapeutic Approach in Disease Diagnosis and Treatment. Int J Mol Sci. May 16, 2023;24(10):8848. (Year: 2023).*

Gollihue et al. Effects of Mitochondrial Transplantation on Bioenergetics, Cellular Incorporation, and Functional Recovery after Spinal Cord Injury. J Neurotrauma. Aug. 1, 2018;35(15):1800-1818. Epub Apr. 30, 2018. (Year: 2018).*

Aird et al., "Analyzing and minimizing PCR amplification bias in Illumina sequencing libraries," Genome biology. Feb. 2011; 12: 1-4.

Albaryak et al., "The ability of human nuclear DNA to cause false positive low-abundance heteroplasmy calls varies across the mitochondrial genome," BMC genomics. Dec. 2016;17: pp. 1-10.

Alexeyev, "Is there more to aging than mitochondrial DNA and reactive oxygen species?," The FEBS journal. Oct. 2009; 276(20): 5768-87.

Amyere et al., "Origin, originality, functions, subversions and molecular singalling of micropinocytosis," International journal of medical microbiology. Jan. 1, 2001; 291(6-7): 487-94.

Angulo et al., "A new generation of companion diagnostics: cobas BRAF, KRAS and EGFR mutation detection tests," Expert review of molecular diagnostics. Jun. 1, 2014; 14(5): 517-24.

Aryaman et al., Mitochondrial Heterogeneity Frontiers in genetics. Jan. 25, 2019;9: 16 pages.

Aryaman et al., "Mitochondrial network fragmentation modulates mutant mtDNA accumulation independently of absolute fission-fusion rates," bioRxiv: 409128., 38 pages. Sep. 2018.

Attardi et al., "Complementation and segregation behavior of disease-causing mitochondrial DNA mutations in cellular model systems," Biochimica et Biophysica Acta (BBA)—Molecular Basis of Disease. May 24, 1995; 1271(1): 241-8.

Bacman et al., "Modulating mtDNA heteroplasmy by mitochondria-targeted restriction endonucleases in a 'differential multiple cleavage-site' model," Gene therapy. Sep. 2007; 14(18): 1309-18.

Bacman et al., "Organ-specific shifts in mtDNA heteroplasmy following systemic delivery of a mitochondria-targeted restriction endonuclease," Gene Ther., 17(6):713-720 (2010).

Bacman et al., "Specific elimination of mutant mitochondrial genomes in patient-derived cells by mitoTALENs," Nat. Med., 19(9): 1111-1113 (2013).

Bacman et al., "The use of mitochondria-targeted endonucleases to manipulate mtDNA," Methods in enzymology. vol. 547. Academic Press, 2014. 373-397 (2014).

Bacman et al., "Transmitochondrial technology in animal cells," Methods Cell Biol., 80:503-524 (2007).

Bai et al., "Detection and quantification of heteroplasmic mutant mitochondrial DNA by real-time amplification refractory mutation system quantitative PCR analysis: a single-step approach,". Clin. Chem. 50: 996-1001. https ://doi.org/10.1373/ dinehem.2004.03115 3 (2004).

Barritt et al., "Cytoplasmic transfer in assisted reproduction," Human Reproduction Update, 7(4): 428-435 (2001).

Barritt et al., "Mitochondria in human offspring derived from ooplasmic transplantation," Hum. Reprod., 16(3): 513-516 (2001).

Bates et al., "Cardiac involvement in mitochondrial DNA disease: clinical spectrum, diagnosis, and management," Eur. Heart J., 33(24): 3023-3033 (2012).

Bayona-Bafaluy et al., "A chemical enucleation method for the transfer of mitochondrial DNA to p0 cells," Nucl. Acids Res., 31(16): 4 pages, (2003).

Bedwell et al., "Sequence and structural requirements of a mitochondrial protein import signal defined by saturation cassette mutagenesis," Mol. Cell. Biol., 9(3):1014-1025 (1989).

Bender et al., "High levels of mitochondrial DNA deletions in substantia nigra neurons in aging and Parkinson disease," Nat Genet 38, 515-517, doi: 10.1038/ngl769 (2006).

Berridge et al., "Horizontal transfer of mitochondria between mammalian cells: beyond co-culture approaches," Curr. Opin. Genet. Dev., 38: 75-82 (2016).

Berry et al., "Herpes Simplex Vims Type 1 Infection Disturbs the Mitochondrial Network, Leading to Type I Interferon Production through the RNA Polymerase III/RIG-I Pathway," Mbio 12.6 (2021): 19 pages.

Bertero et al., "Calcium Signaling and Reactive Oxygen Species in Mitochondria," Circ. Res., 122: 1460-1478 (2018).

Birky et al., "An Approach To Population And Evolutionary Genetic Theory For Genes In Mitochondria And Chloroplasts, And Some Results", Genetics. Mar. 1, 1983; 103(3): 513-27.

Birky Jr, "Relaxed and stringent genomes: why cytoplasmic genes don't obey Mendel's laws," Journal of Heredity 85, 355-365 (1994).

Blazej et al., "Polymorphism ratio sequencing: a new approach for single nucleotide polymorphism discovery and genotyping," Genome Res. 13: 287-293. https://doi.org/10.1101/gr.39620 3 (2003).

Bodnar et al., "Extension of life-span by introduction of telomerase into normal human cells," Science, 279: 349-352 (1998).

Brandon et al., "MITOMAP: a human mitochondrial genome database—2004 update," Nucleic Acids Res. 33: D611-613. https://doi.org/10.1093/nar/gki07 9 (2005).

Bredenoord et al., "Mitochondrial Replacement Techniques: Remaining Ethical Challenges," Cell Stem Cell, 21(3): 301-304 (2017).

Brehme et al., "A chaperome subnetwork safeguards proteostasis in aging and neurodegenerative disease," Cell Reports, 9: 1135-1150 (2014).

Brown et al., "Rapid evolution of animal mitochondrial DNA," Proceedings of the National Academy of Sciences 76.4 (1979): 1967-1971.

Burke et al., "Mitochondria, Bioenergetics and Apoptosis in Cancer," Trends Cancer, 3(12):857-870 (2017).

Burrows et al., "Rapid and transient inhibition of mitochondrial function following methamphetamine or 3,4-methylenedioxymethamphetamine administration," Eur. J. Pharmacol., 398: 11-18 (2000).

Caicedo et al., "Artificial Mitochondria Transfer: Current Challenges, Advances, and Future Applications," Stem cells international. 2017; 2017(1): 23 pages.

Calabrese et al., "Primates and mouse NumtS in the UCSC genome browser," BMC bioinformatics. Dec. 2012; 13:1-9.

Cantuti-Castlevestri et al., "Somatic mitochondrial DNA mutations in single neurons and glia," Neurobiol. Aging 26:1343-1355 (2005).

CAS Registry No. 159351-69-6, date entered STN: Dec. 6, 1994; Rapamycin, 42-O-(2-hydroxyethyl)-, 2 pages.

CAS Registry No. 162635-04-3, date entered STN: May 3, 1995; 42-[3-hydroxy-2-(hydroxymethyl)-2-methylpropanoate]-, 2 pages.

Chang et al., "Functional recovery of human cells harbouring the mitochondrial DNA mutation MERRF A8344G via peptide-mediated mitochondrial delivery". Neurosignals. Sep. 21, 2013; 21(3-4): 160-73.

Chang et al., "Treatment of human cells derived from MERRF syndrome by peptide-mediated mitochondrial delivery," Cytotherapy 15(12):1580-1596 (2013).

Chen et al., "BEAMing and droplet digital PCR analysis of mutant IDHI mRNA in glioma patient serum and cerebrospinal fluid extracellular vesicles," Molecular Therapy—Nucleic Acids. Jan. 1, 2013; 10 pages.

Cherry et al., "Induced pluripotent stem cells with a mitochondrial DNA deletion," Stem Cells, 31:1287-1297 (2013).

Chinnery et al., "Mitochondrial disease in adults: what's old and what's new?," EMBO Mol. Med., 7(12):1503-1512 (2015).

Chinnery et al., "Molecular pathology of MELAS and MERRF. The relationship between mutation load and clinical phenotypes," Brain, 120(Pt 10): 1713-1721 (1997).

(56) References Cited

OTHER PUBLICATIONS

Chinnery et al., "Relaxed replication of mtDNA: a model with implications for the expression of disease,". The American Journal of Human Genetics 64: 1158-1165 (1999).
Chondrogianni et al., "Proteasome activation: an innovative promising approach for delaying aging and retarding age-related diseases," Ageing Res. Rev., 23:37-55 (2015).
Chou et al., "Impaired ROS Scavenging System in Human Induced Pluripotent Stem Cells Generated from Patients with MERRF Syndrome," Scientific reports. Mar. 30, 2016; 6(1): 14 pages.
Clark et al., "Selfish little circles: transmission bias and evolution of large deletion-bearing mitochondrial DNA in Caenorhabditis briggsae nematodes," PLoS One. 2012;7(7): 8 pages. doi: 10.1371/journal.pone.0041433. Epub Jul. 31, 2012.
Coppe et al., "Senescence-associated secretory phenotypes reveal cell-nonautonomous functions of oncogenic RAS and the p53 tumor suppressor," PLoS Biol., 6(12): 2853-2868 (2008).
Correia-Melo et al., "Mitochondria are required for pro-ageing features of the senescent phenotype," EMBO J., 35(7): 724-742 (2016).
Cree et al., "A reduction of mitochondrial DNA molecules during embryogenesis explains the rapid segregation of genotypes," Nat Genet 40, 249-254, doi: 10.1038/ng.2007.63 (2008).
Dong et al., "Horizontal transfer of whole mitochondria restores tumorigenic potential in mitochondrial DNA-deficient cancer cells," Elife, 6: 22 pages, (2017).
Dotti, et al., "Design and development of therapies using chimeric antigen receptor-expressing T cells." Immunol Rev. (2014); 257 (1): 107-126, 35 pages. First published: Dec. 13, 2013.
Duan et al., "Evaluating heteroplasmic variations of the mitochondrial genome from whole genome sequencing data". Gene 699, 145-154. https://doi.org/10.1016/j.gene.2019 .03.016 (2019).
Duguay et al., "Elimination of mitochondrial DNA is not required for herpes simplex vims 1 replication," Journal of Virology 88.5 (2014): 2967-2976.
Duguay et al., "Mitochondrial nucleases ENDOG and EXOG participate in mitochondrial DNA depletion initiated by herpes simplex vims 1UL12. 5," Journal of virology 87.21 (2013): 11787-11797.
Dunham-Snary et al., "Mitochondrial-nuclear DNA mismatch matters," Science, 349: 1449-1450 (2015).
Durham et al., "Progressive depletion of mtDNA in mitochondrial myopathy ," Neurology 67, 502-504 (2006).
El-Hattab et al., "Mitochondrial DNA maintenance defects". Biochim Biophys Acta Mol Basis Dis 1863, 1539-1555, doi:l0.1016/j.bbadis.2017.02.017 (2017).
Extended European Search Report dated Apr. 5, 2022 for EP 19849540.0, 9 pages.
Facucho-Oliveira et al., "Mitochondrial DNA replication during differentiation of murine embryonic stem cells," J. Cell Sci., 120(Pt 22):4025-4034 (2007).
Fiorese et al., "The Transcription Factor ATF5 Mediates a Mammalian Mitochondrial UPR," Curr. Biol., 26:2037-2043 (2016).
Fisicaro et al., "Targeting mitochondrial dysfunction can restore antiviral activity of exhausted HBV-specific CD8 T cells in chronic hepatitis B," Nat Med., 23(3): 1-10 doi:l0.1038/nm.4275 (2017).
Fliedl et al., "Optimization of a quantitative PCR based method for plasmid copy number determination in human cell lines," New Biotechnol., 32(6):716-719 (2015).
Folmes et al., "Disease-causing mitochondrial heteroplasmy segregated within induced pluripotent stem cell clones derived from a patient with MELAS," Stem Cells, 31: 1298-1308 (2013).
Frezza et al., "Organelle isolation: functional mitochondria from mouse liver, muscle and cultured filroblasts," Nature Protocol, 2(2):287-295 (2007).
Fujikura et al., "Induced pluripotent stem cells generated from diabetic patients with mitochondrial DNA A3243G mutation," Diabetologia, 55:1689-1698 (2012).
Galera et al., "Generation of a human iPSC line from a patient with Leigh syndrome," Stem Cell Res., 16:63-66 (2016).
Gasnier et al., "Use of Percoll Gradients for Isolation of Human Placenta Mitochondria Suitable for Investigating Outer Membrane Proteins," Analytical Biochemistry, 212:173-178 (1993).
Ghosh et al., "Use of cytoplasmic hybrid cell lines for elucidating the role of mitochondrial dysfunction in Alzheimer's disease and Parkinson's disease," Ann. N. Y. Acad. Sci., 893:176-191 (1999).
Gibson, N. J. "The use of real-time PCR methods in DNA sequence variation analysis," Clin Chim Acta 363, 32-47, doi:l0.1016/j.cccn.2005.06.022 (2006).
Gollihue et al., "Mitochondrial transplantation strategies as potential therapeutics for central nervous system trauma," Neural Re2en. Res., 13(2):194-197 (2018).
Gollihue et al., "Prospects for therapeutic mitochondrial transplantation," Mitochondrian 35:70-79 (2017).
Gomes et al., "Declining NAD+ induces a pseudohypoxic state disrupting nuclear-mitochondrial communication during aging," Cell, 155:1624-1638 (2013).
Gonzalez et al., "Nutrient sensing and TOR signaling in yeast and mammals," EMBO J., 36:397-408 (2017).
Gorman et al., "Mitochondrial diseases," Nat Rev Dis Primers 2, 16080, doi: l0.1038/mdp.2016.80 (2016).
Greenfield et al., "Assisted reproductive technologies to prevent human mitochondrial disease transmission," Nat. Biotechnol., 35:1059-1068 (2017).
Guedan et al., "Engineering and Design of Chimeric Antigen Receptors," Mol. Ther. Methods Clin. Dev., 12:145-156 (2018).
Hamalainen et al., "Tissue- and cell-type-specific manifestations of heteroplasmic mtDNA 3243AG mutation in human induced pluripotent stem cell-derived disease model," Proc. Natl. Acad. Sci. USA, I 10:E3622-E3630 (2013).
Harley et al., "Telomeres shorten during ageing of human fibroblasts," Nature, 345:458- 460 (1990).
Hartwig et al., "A critical comparison between two classical and a kit-based method for mitochondria isolation," Proteomics, 9(11):3209-3214 (2009).
Harvey et al., "Characterization and applications of CataCleave probe in real-time detection assays," Anal Biochem 333, 246-255, doi: 10.1016/j.ab.2004.05.037 (2004).
Hashimoto et al., "MitoTALEN: A General Approach to Reduce Mutant mtDNA Loads and Restore Oxidative Phosphorylation Function in Mitochondrial Diseases," Mol. Ther., 23: 1592-1599 (2015).
Hatakeyama et al., "Concise Review: Heteroplasmic Mitochondrial DNA Mutations and Mitochondrial Diseases: Toward iPSC-Based Disease Modeling, Drug Discovery, and Regenerative Therapeutics," Stem Cells, 34(4):801-808 (2016).
Hayakawa et al., "Transfer of mitochondria from astrocytes to neurons after stroke," Nature, 535:551-555 (2016).
Hayflick, "The limited in vitro lifetime of human diploid cell strains," Experimental Cell Res., 37:614-636 (1965).
He et al., "Heteroplasmic mitochondrial DNA mutations in normal and tumour cells," Nature 464, 610-614; https://doi.org/10.1038/nature 08 802 (2010).
Heller et al., "Efficient repopulation of genetically derived rho zero cells with exogenous mitochondria," PLoS One, 8(9): 8 pages (2013).
Holland et al., "Detection of specific polymerase chain reaction product by utilizing the 5'-3' exonuclease activity of Thermus aquaticus DNA polymerase," Proceedings of the National Academy of Sciences 88, 7276, doi:10.1073/onas.88.16.7276 (1991).
Holt et al., "Deletions of muscle mitochondrial DNA in patients with mitochondrial myopathies," Nature 331, 717-719, doi:l0.1038/331717a0 (1988).
Hsu et al., "Mitochondrial resetting and metabolic reprogramming in induced pluripotent stem cells and mitochondrial disease modeling," Biochim. Biophys. Acta, 1860:686-693 (2016).
Huang et al., "Extension of base mispairs by Taq DNA polymerase: implications for single nucleotide discrimination in PCR," Nucleic Acids Research 20, 4567-4573, doi: l0.1093/nar/20.17.4567 (1992).
Huang et al., "Kissing and nanotunneling mediate intermitochondrial communication in the heart," Proc. Natl. Acad. Sci. U.S.A., 110(8):2846-2851 (2013).

(56) References Cited

OTHER PUBLICATIONS

Huang et al., "Multiplex fluorescence melting curve analysis for mutation detection with dual-labeled, self-quenched probes," PLoS One 6, el9206, doi: 10.1371/iournal.oone.0019206 (2011).
Huggett et al., "The digital MIQE guidelines update: minimum information for publication of quantitative digital PCR experiments for 2020." Clinical Chemistry 66.8 (2020): 1012-1029.
Igarashi et al., "Single cell-based vector tracing in patients with ADA-SCID treated with stem cell gene therapy," Mol. Ther. Methods Clin. Dev. 6, 8-16 (2017).
International Search Report and Written Opinion for PCT Application No. PCT/US2019/046370, mailed Jan. 6, 2020, 25 pages.
Islam et al., "Mitochondrial transfer from bone-marrow-derived stromal cells to pulmonary alveoli protects against acute lung injury," Nat. Med., 18(5):759-765 (2012).
Jackaman et al., "CD8+ cytotoxic T cell responses to dominant tumor-associated antigens are profoundly weakened by aging yet subdominant responses retain functionality and expand in response to chemotheranv," Oncoimmunology, 8(4):el564452 (2019).
Jayaprakash et al., "Stable heteroplasmy at the single-cell level is facilitated by intercellular exchange of mtDNA," Nucleic Acids Res. 43, 2177-2187. https://doi.org/10.1093/nar/Q:kv05 2 (2015).
Ji et al., "Enucleation of cultured mouse fetal erythroblasts requires Rae GTPases and mDia2," Nat. Cell Biol., 10(3):314-321 (2008).
Jo et al., "Efficient Mitochondrial Genome Editing by CRISPR/Cas9," BioMed Res. Int., 2015:1-10 (2015).
Johne et al., "Rolling-circle amplification of viral DNA genomes using phi29 polymerase," Trends Microbiol. 17, 205-211. https://doi.org/10.1016/i.tim.2009.02.004 (2009).
Jorgensen et al., "Companion and complementary diagnostics: clinical and regulatory perspectives," Trends in cancer 2, 706-712 (2016).
Kagawa et al., "Gene therapy of mitochondrial diseases using human cytoplasts," Gene Ther., 4:6-10 (1997).
Kang et al., "Age-Related Accumulation of Somatic Mitochondrial DNA Mutations in Adult-Derived Human iPSC," Cell Stem Cell, 18(5):625-636 (2016).
Kang et al., "The DNA damage response induces inflammation and senescence by inhibiting autophagy of GATA4," Science, 349(6255):aaa5612-I-aaa5612-II (2015).
Kauppila et al., "Mammalian Mitochondria and Aging: An Update," Cell Metabolism, 25:57-71 (2017).
Kauppila et al., "Mitochondrial DNA: Radically free of free-radical driven mutations," Biochim Biophys Acta 1847, 1354-1361, doi:l0.1016/j.bbabio.2015.06.001 (2015).
Kesner et al., "Characteristics of Mitochondrial Transformation into Human Cells," Sci. Rep., 6:26057; 15 pages, (2016).
Kim et al., "Delivery of exogenous mitochondria via centrifugation enhances cellular metabolic function," Sci. Rep., 8(1):3330; 13 pages, (2018).
King et al., "Human cells lacking mtDNA: repopulation with exogenous mitochondria by complementation," Science, 246:500-503 (1989).
King et al., "Injection of Mitochondria into Human Cells Leads to a Rapid Replacement of the Endogenous Mitochondrial DNA," Cell 52:811-819 (1988).
Kitani et al., "Direct human mitochondrial transfer: a novel concept based on the endosymbiotic theory," Transplant Proc., 46(4): 1233-1236 (2014).
Kitani et al., "Internalization of isolated functional mitochondria: involvement of micropinocytosis," J. Cell Mol. Med., 18(8):1694-1703 (2014).
Kodaira et al., "Impaired respiratory function in MELAS-induced pluripotent stem cells with high heteroplasmy levels," FEBS Open Bio., 5:219-225 (2015).
Kraytsberg et al., "Recombination of human mitochondrial DNA," Science, 304:981; 1 page, (2004).
Kuilman et al., "Senescence-messaging secretome: SMS-ing cellular stress," Nature Rev. Cancer, 9:81-94 (2009).
Kukat et al., "Generation of rhoO cells utilizing a mitochondrially targeted restriction endonuclease and comparative analyses," Nucleic Acids Res., 36(7):10 pages, (2008).
Kunkel et al., "Mitochondrial pathways to cardiac recovery: TFAM," Heart Fail Rev., 21(5):499-517 (2016).
Kyriakouli et al., "Progress and prospects: gene therapy for mitochondrial DNA disease," Gene Ther., 15(14):1017-1023 (2008).
Labbadia et al., "The biology of proteostasis in aging and disease," Ann. Rev. Biochem., 84:435-464 (2015).
Lane et al., "The energetics of genome complexity," Nature 467, 929-934, doi: 10.1038/nature09486 (2010).
Lang et al., "Purification of mitochondrial and plastid DNA". Nat Protoc. 2, 652-660; https://doi.org/10.1038/nprot2007.58 (2007).
Lapasset et al., "Rejuvenating senescent and centenarian human cells by reprogramming through the pluripotent state," Genes Dev., 25:2248-2253 (2011).
Le Saux et al., "Mechanisms of immunosenescence: lessons from models of accelerated immune aging," Ann N Y Acad Sci., 1247:69-82 (2012).
Leng et al., "Agarose Droplet Microfluidics for Highly Parallel and Efficient Single Molecule Emulsion PCR," Lab Chip 10, 2841-2843. https://doi.org/10.1039/COLCO0145G (2010). emulsion PCR. Lab Chip 10, 2841-2843. httos://doi.org/10.1039/COLCO 0145G (2010).
Li et al., "Droplet digital PCR shows the D-loop to be an error prone locus for mitochondrial DNA copy number determination," Sci. Rep. 8, 11392; 13 pages. https://doi.org/10.1038/s41598-018-29621-I (2018).
Liang et al., "Generation of MERRF patient-derived induced pluripotent stem cell line iMERRF-C7," Stem Cell Res., 17:616-618 (2016).
Lightowlers et al., "Mutations causing mitochondrial disease: What is new and what challenges remain?," Science, 349(6255):1494-1499 (2015).
Lin et al., "Maintenance and propagation of a deleterious mitochondrial genome by the mitochondrial unfolded protein response," Nature, 533(7603):416-419 (2016).
Linnane et al., "Mitochondrial DNA mutations as an important contributor to ageing and degenerative diseases," Lancet 333:642-645 (1989).
Lis et al., "Conversion of adult endothelium to immunocompetent haematopoietic stem cells," Nature, 545:439-445 (2017).
Liu et al., "DNA repair in mammalian mitochondria: Much more than we thought?," Environ. Mol. Mutagen., 51:417-426 (2010).
Liu et al., "Mitochondrial 'kiss-and-run': interplay between mitochondrial motility and fusion-fission dynamics," EMBO J., 28(20):3074-3089 (2009).
Lopez-Otin et al., "The hallmarks of aging," Cell, 153:1194-1217 (2013).
Ma et al., "Metabolic rescue in pluripotent cells from patients with mtDNA disease," Nature, 524(7564):234-238 (2015).
Machado et al., "Real-time PCR quantification of heteroplasmy in a mouse model with mitochondrial DNA of C57BL/6 and NZB/BINJ strains," PLoS ONE 10, e0133650. https://doi.org/10.1371/iournal.oone.0133650 (2015).
Madeo et al., "Essential role for autophagy in life span extension," J. Clin. Invest., 125(1):85-93 (2015).
Maeda et al., "Generation of somatic mitochondrial DNA-replaced cells for mitochondrial dysfunction treatment," Scientific Reports 11(1):1-16 (2021).
Maricic et al., "Multiplexed DNA sequence capture of mitochondrial genomes using PCR products," PLoS ONE 5, 5 pages. https ://doi.org/10.1371/joum al.oone.00140 04 (2010).
Marquis et al., "MitoRS, a method for high throughput, sensitive, and accurate detection of mitochondrial DNA Heteroplasmy," BMC Genom. 18, 19 pages. https://doi.org/10. I 186/sl286 4-017-3695-5 (2017).
Mazaika et al., "Digital Droplet PCR: CNV Analysis and Other Applications," Curr Protoc Hum Genet 82, 7.24.1-7.24.13 (2014).
Mckernan et al., "Expanded genetic codes in next generation sequencing enable decontamination and mitochondrial enrichment," PLoS ONE 9, 9 pages. https://doi.org/10.1371/ioum al.oone.00964 92 (2014).

(56) References Cited

OTHER PUBLICATIONS

Melber et al., "UPR(mt) regulation and output: a stress response mediated by mitochondrial-nuclear communication," Cell Res., 28:281-295 (2018).
Mercer et al., "Virus entry by macropinocytosis," Nature Cell Biol., 11(5):510-520 (2009).
Mills et al., "Mitochondria are the powerhouses of immunity," Nat. Immunol., 18(5):488-498 (2017).
Morita et al., "mTOR controls mitochondrial dynamics and cell survival via MTFP1". Molecular Cell. Sep. 21, 2017; 67(6): 922-35.
Morris et al., "Pervasive within-Mitochondrion Single-Nucleotide Variant Heteroplasmy as Revealed by Single-Mitochondrion Sequencing," Cell Rep 21, 2706-2713, doi: 10.1016/j.celrep.2017.11.031 (2017).
Moschoi et al., "Protective mitochondrial transfer from bone marrow stromal cells to acute myeloid leukemic cells during chemotherapy," Blood, 128(2):253-264 (2016).
Nacarelli et al., "Inhibition of mTOR prevents ROS production initiated by ethidium bromide-induced mitochondrial DNA depletion," Frontiers in endocrinology 5 (2014): 122.
Nargund, A. M. et al., "Mitochondrial and Nuclear Accumulation of the Transcription Factor ATFS-1 Promotes OXPHOS Recovery during the UPRmt," Molecular Cell, 58:123-133 (2015).
Newton et al., "Analysis of any point mutation in DNA. The amplification refractory mutation system (ARMS)," Nucleic Acids Research 17, 2503-2516, doi: l0.1093/nar/17.7.2503 (1989).
Niazi et al., "Targeting nucleic acids into mitochondria: progress and prospects," Mitochondrion., 13:548-558 (2013).
Nunnari et al., "A. Mitochondria: in sickness and in health," Cell, 148:1145-1159 (2012).
Nurmi et al., "A new label technology for the detection of specific polymerase chain reaction products in a closed tube," Nucleic acids research 2S, e2S-OO (2000).
Office Action for Japanese Application No. JP20210532266 dated Oct. 3, 2023, 5 pages.
O'Hara et al., "Quantitative mitochondrial DNA copy number determination using droplet digital PCR with single-cell resolution." Genome research 29 .11 (2019): 1878-1888.
Osborne et al., "Single-molecule LATE-PCR analysis of human mitochondrial genomic sequence variations," PLoS ONE 4(5): 8 pages, (2009).
Pace et al., "Repeated horizontal transfer of a DNA transposon in mammals and other tetrapods," Proc. Natl.Acad. Sci. USA, 105(44): 17023-17028 (2008).
Palm et al., "The Utilization of Extracellular Proteins as Nutrients Is Suppressed by mTORCI," Cell, 162(2): 259-270 (2015).
Patel et al., "Macropinocytic entry of isolated mitochondria in epidermal growth factor- activated human osteosarcoma cells," Sci. Rep., 7(1): 13 pages, (2017).
Payungporn et al., "Simultaneous quantitation and genotyping of hepatitis B vims by real-time PCR and melting cmve analysis," J Virol Methods 120, 131-140, doi: 10.1016/i.iviromet.2004.04.012 (2004).
Perry et al., "Mitochondrial membrane potential probes and the proton gradient: a practical usage guide," Biotechniques, 50(2):98-115 (2011).
Preble et al., "Rapid Isolation And Purification Of Mitochondria For Transplantation By Tissue Dissociation And Differential Filtration," J. Vis. Exp., (91): 6 pages, doi:10.3791/51682 (2014).
Pye et al., "Production of transmitochondrial cybrids containing naturally occurring pathogenic mtDNA variants," Nucleic Acids Res., 34(13): 8 pages, (2006).
Quinn et al., "Age-Related Decline in Primary CD8+ T Cell Responses Is Associated with the Development of Senescence in Virtual Memory CD8+ T Cells," Cell Reports, 23 :3512-3524 (2018).
Quiros et al., "Mitonuclear communication in homeostasis and stress," Nat. Rev. Mal. Cell. Biol., 17:213-226 (2016).
Rajasimha et al., "Selection against pathogenic mtDNA mutations in a stem cell population leads to the loss of the 3243A—G mutation in blood," Am J Hum Genet 82, 333-343, doi: 10.1016/i.aihg.2007.10.007 (2008).
Rampelt et al., "Coordination of Two Genomes by Mitochondrial Translational Plasticity," Cell, 167:308-310 (2016).
Raval et al., "Cardiomyopathy, mitochondria and Barth syndrome: iPSCs reveal a connection," Nat. Med., 20:585-586 (2014).
Rocca et al., "Transplantation of wild-type mouse hematopoietic stem and progenitor cells ameliorates deficits in a mouse model of Friedreich's ataxia," Sci. Transl. Med., 9(413): 26 pages, doi: l0.1126/scitranslmed.aai2347 (2017).
Rossignol et al., "Mitochondrial threshold effects," The Biochemical Journal 370, 751-762, doi: l0.1042/BJ20021594 (2003).
Rustom et al., "Nanotubular highways for intercellular organelle transport," Science, 303:1007-1010 (2004).
Ryser et al., 2008, "mRNA Transfection of CXCR4-GFP Fusion-Simply Generated by PCR-Results in Efficient Migration of Primary Human Mesenchymal Stem Cells," Tissue Engineering Part C: Methods, 14(3): 179-184.
Saeidi et al., "T-Cell Exhaustion in Chronic Infections: Reversing the State of Exhaustion and Reinvigorating Optimal Protective Immune Responses," Frontier Immunol., 9(2569): 1-12 doi: 10.3389/fmunu.2018.02569 (2018).
Saffran et al., "Herpes simplex vims eliminates host mitochondrial DNA," EMBO reports 8.2 (2007): 188-193.
Sahin et al., "Axis of ageing: telomeres, p53 and mitochondria," Nat. Rev. Mal. Cell Biol., 13(6):397-404 (2012).
Sahin et al., "Telomere dysfunction induces metabolic and mitochondrial compromise," Nature, 470(7334):359-365 (2011).
Santibanez-Koref et al., "Assessing mitochondrial heteroplasmy using next generation sequencing: a note of caution," Mitochondrion 46, 302-306. https://doi.org/10.1016/j.mito.2018.08.003 (2019).
Schmitt et al., "Detection of ultra-rare mutations by next-generation sequencing," Proc. Natl. Acad. Sci. U. S. A. 109, 14508-14513. https ://doi.org/10.1073/pnas.1208715109 (2012).
Sebastian et al., "Mitochondrial Dynamics: Coupling Mitochondrial Fitness with Healthy Aging," Trends Mol Med 23, 201-215, doi: 10.1016/i.molmed.2017.01.003 (2017).
Smeitink et al., "Mitochondrial medicine: a metabolic perspective on the pathology of oxidative phosphorylation disorders," Cell Metab., 3:9-13 (2006).
Smith et al., "Altering the balance between healthy and mutated mitochondrial DNA," J. Inherited Metabol. Dis., 34:309-313 (2011).
Spees et al., "Mitochondrial transfer between cells can rescue aerobic respiration," Proceedings of the National Academy of Sciences 103(5):1283-1288 (2006).
Stewart et al., "The dynamics of mitochondrial DNA heteroplasmy: implications for human health and disease," Nat Rev Genet 16, 530-542, doi:l0.1038/mg3966 (2015).
Sugimura, et al., Hematopoietic stem and progenitor cells from human pluripotent stem cells, Nature, May 2017, pp. 432-438.
Suhr et al. "Mitochondrial rejuvenation after induced pluripotency," PLoS One, 5(11): 9 pages, (2010).
Sun et al., "New strategy for in vitro activation of primordial follicles with mTOR and PBK stimulators," Cell Cycle, 14(5):721-731 (2015).
Sun et al., "The Mitochondrial Basis of Aging," Mal. Cell, 61(5):654-666 (2016).
Sung et al., "Catabolic pathways regulated by mTORCI are pivotal for survival and growth of cancer cells expressing mutant Ras," Oncotarget, 6:40405-40417 (2015).
Suomalainen et al., "FGF-21 as a biomarker for muscle-manifesting mitochondrial respiratory chain deficiencies: a diagnostic study," The Lancet Neurology 10, 806-818, doi:10.1016/sl474-4422(11)70155-7 (2011).
Suomalainen et al., "Mitochondrial diseases: the contribution of organelle stress responses to pathology," Nat. Rev. Mol. Cell Biol., 19:77-92 (2018).
Tachibana et al., "Human Embryonic Stem Cells Derived by Somatic Cell Nuclear Transfer," Cell, 153:1228-1238 (2013).
Tachibana et al., "Mitochondrial gene replacement in primate offspring and embryonic stem cells," Nature, 461:367-372 (2009).

(56) References Cited

OTHER PUBLICATIONS

Takahashi K. et al. Induction of pluripotent stem cells from adult human fibroblasts by defined factors. Cell. (2007); 131(5):861-72.
Takahashi, K., et al., Induction of pluripotent stem cells from mouse embryonic and adult fibroblast cultures by defined factors. Cell. Aug. 2006; 126(4): 663-76.
Tan et al., "Mitochondrial genome acquisition restores respiratory function and tumorigenic potential of cancer cells without mitochondrial DNA," Cell Metab., 21:81-94 (2015).
Tanaka et al., "Gene therapy for mitochondrial disease by delivering restriction endonuclease Smal into mitochondria," J. Biomed. Sci., 9:534-541 (2002).
Tatuch et al., "Heteroplasmic mtDNA mutation (T—G) at 8993 can cause Leigh disease when the percentage of abnormal mtDNA is high," American journal of human genetics 50, 852-858 (1992).
Tian et al., "Mitochondrial UPR: A Double-Edged Sword," Trends Cell Biol., 26:563-565 (2016).
Torralba et al., "Mitochondria know no boundaries: mechanisms and functions of intercellular mitochondrial transfer," Frontiers in cell and developmental biology 4 (2016): 11 pages.
Transient Transfection. Thermo Fisher Scientific. downloaded from web.archive.org/web/20150912051020/https://www.thermofisher.com/us/en/home/references/gibco-cell-culture-basics/transfection-basics/transfection- methods/transient-transfection.html. pp.1-2 (2015).
Tuppen et al., "Mitochondrial DNA mutations and human disease," Biochimica et Biophysica Acta, 1797(2):113-128 (2010).
Turro et al. "Whole-genome sequencing of patients with rare diseases in a national health system." Nature 583, 96-102 (2020).
Twig et al., "Fission and selective fusion govern mitochondrial segregation and elimination by autophagy," The EMBO Journal 27, 433-446, doi:l0.1038/si.emboi.7601963 (2008).
Urata et al., "High-sensitivity detection of the A3243G mutation of mitochondrial DNA by a combination of allele-specific PCR and peptide nucleic acid-directed PCR clamping," Clin Chem 50, 2045-2051, doi: 10.1373/clinchem.2004. 033761 (2004).
Vilchez et al., "The role of protein clearance mechanisms in organismal ageing and age-related diseases," Nat. Comm., 5:5659; 13 pages, (2014).
Wahlestedt et al., "Somatic Cells with a Heavy Mitochondrial DNA Mutational Load Render Induced Pluripotent Stem Cells with Distinct Differentiation Defects," Stem Cells, 32:1173-1182 (2014).
Wai et al., "The mitochondrial DNA genetic bottleneck results from replication of a subpopulation of genomes," Nature Genetics 40, 1484-1488, doi: 10.1038/ng.258 (2008).
Wang et al., "Modeling the mitochondrial cardiomyopathy of Barth syndrome with induced pluripotent stem cell and heart-on-chip technologies," Nat. Med., 20(6):616-623 (2014).
Watanabe et al., "Ultra-Sensitive Detection of the Pretreatment EGFR T790M Mutation in Non-Small Cell Lung Cancer Patients with an EGFR-Activating Mutation Using Droplet Digital PCR," Clinical Cancer Research 21, 3552, doi: 10.1158/1078-0432.CCR-14-215 1 (2015).
Wei et al., "Selective removal of mitochondria via mitophagy: distinct pathways for different mitochondrial stresses," Biochim Biophys Acta 1853, 2784-2790, doi: 10.1016/i.bbamcr.2015.03.013 (2015).
Weinberg et al., "Mitochondrial complex III is essential for regulatory T cell suppressive function," Nature, 565(7740):495-499, doi: l0.1038/s41586-018-0846-z (2019).
Wherry "T cell exhaustion," Nature immunology, 12(6):492-499 (2011).
Whitcombe et al., "Detection of PCR products using self-probing amplicons and fluorescence," Nature Biotechnology 17, 804-807, doi:l0.1038/11751 (1999).
Wilkinson et al., "Long-term ex vivo haematopoietic-stem-cell expansion allows nonconditioned transplantation," Nature, 571(7763): 117-121 (2019).
Wonnapinij et al., "The distribution of mitochondrial DNA heteroplasmy due to random genetic drift," Am J Hum Genet 83, 582-593, doi:l0.1016/i.aihg.2008.10.007 (2008).
Wu et al., "Generation of an induced pluripotent stem cell (iPSC) line from a 40-year-old patient with the A8344G mutation of mitochondrial DNA and MERRF (myoclonic epilepsy with ragged red fibers) syndrome," Stem Cell Res., 27: 10-14 (2018).
Wu et al., "Mitochondrial Transfer by Photothermal Nanoblade Restores Metabolite Profile in Mammalian Cells," Cell Metab., 23:921-929 (2016).
Xu et al., "Manipulating the metazoan mitochondrial genome with targeted restriction enzymes," Science, 321(5888):575-577 (2008).
Yatsuga et al., "Growth differentiation factor 15 as a useful biomarker for mitochondrial disorders," Ann Neurol 78, 814-823, doi: 10.1002/ana.24506 (2015).
Ye et al., "T-cell exhaustion in chronic hepatitis B infection: current knowledge and clinical significance," Cell Death and Disease, 6: 10 pages, doi:l0.1038/cddis.2015.42 (2015).
Yokota et al., "Mitochondrial respiratory dysfunction caused by a heteroplasmic mitochondrial DNA mutation blocks cellular reprogramming," Hum. Mol. Genet., 24(16):4698-4709 (2015).
Zeviani et al., "Mitochondrial disorders," Brain, 127(Pt 10):2153-2172 (2004).
Zhang et al., "Fmctose-1,6-bisphosphate and aldolase mediate glucose sensing by AMPK," Nature, 548(7665):112-116 (2017).
Zhang et al., "Pregnancy derived from human zygote pronuclear transfer in a patient who had arrested embryos after IVF," Reprod. Biomed. Online, 33(4):529-533 (2016).
Zhang et al., "Ultrasensitive and quantitative detection of EGFR mutations in plasma samples from patients with non-small-cell lung cancer using a dual PNA clamping-mediated LNA-PNA PCR clamp," Analyst 144, 1718-1724 (2019).
Office Action for European Application No. 19849540 mailed Dec. 19, 2024, 5 pages.
Stankov et al., "Mitochondrial DNA depletion and respiratory chain activity in primary human subcutaneous adipocytes treated with nucleoside analogue reverse transcriptase inhibitors". Antimicrobial agents and chemotherapy. Jan. 2010; 54(1): 280-7.

* cited by examiner

| | 7SP ctrl | | EPC100 ctrl | | 7SP p-Mt PDL 10 | | 7SP p-Mt PDL 50 | |
|---|---|---|---|---|---|---|---|---|
| TH01 | 6 | 7 | 7 | 9 | 6 | 7 | 6 | 7 |
| D21S11 | 28 | 30 | 29 | | 28 | 30 | 28 | 30 |
| D5S818 | 9 | 13 | 12 | 13 | 9 | 13 | 9 | 13 |
| D13S317 | 8 | 9 | 8 | | 8 | 9 | 8 | 9 |
| D7S820 | 8 | 12 | 11 | 12 | 8 | 12 | 8 | 12 |
| D16S539 | 9 | 13 | 11 | 12 | 9 | 13 | 9 | 13 |
| CSF1PO | 9 | 12 | 12 | | 9 | 12 | 9 | 12 |
| AMEL | X | | X | | X | | X | |
| vWA | 14 | 17 | 16 | 20 | 14 | 17 | 14 | 17 |
| TPOX | 8 | 11 | 8 | 11 | 8 | 11 | 8 | 11 |

7SP ctrl EPC100 ctrl 7SP p-Mt PDL 10 7SP p-Mt PDL 50

Body Weight

METHODS OF PREPARING MITOCHONDRIA REPLACED CELLS WITH IMPROVED MITOCHONDRIAL FUNCTION

CROSS-REFERENCE TO RELATED APPLICATIONS

This application is a continuation of U.S. Non-Provisional application Ser. No. 16/539,993, filed Aug. 13, 2019, which claims the benefit of U.S. Provisional Application No. 62/718,891, filed Aug. 14, 2018, U.S. Provisional Application No. 62/731,731, filed Sep. 14, 2018, and U.S. Provisional Application No. 62/817,987, filed Mar. 13, 2019, which are incorporated herein by reference in their entirety.

REFERENCE TO AN ELECTRONIC SEQUENCE LISTING

The contents of the electronic sequence listing (IMEL_001_04US_SeqList_ST26.xml; Size: 60,444 bytes; and Date of Creation: Oct. 17, 2024) are herein incorporated by reference in its entirety.

1. FIELD OF THE INVENTION

The present invention provides a composition of cells with reduced mitochondrial DNA and/or replacement of mitochondrial DNA, methods for their production, and methods for treating various diseases associated with genetic or age-related mitochondrial dysfunctions.

2. BACKGROUND OF THE INVENTION

Mitochondria play a major and critical role in cellular homeostasis, and are involved in a diverse range of disease processes. They participate in intracellular signaling, apoptosis and perform numerous biochemical tasks, such as pyruvate oxidation, the Krebs cycle, and metabolism of amino acids, fatty acids, nucleotides and steroids. One crucial task is their role in cellular energy metabolism. This includes β-oxidation of fatty acids and production of ATP by means of the electron-transport chain and the oxidative-phosphorylation system. The mitochondrial respiratory chain consists of five multi-subunit protein complexes embedded in the inner membrane, comprising: complex I (NADH-ubiquinone oxidoreductase), complex II (succinate-ubiquinone oxidoreductase), complex III (ubiquinol-ferricytochrome c oxidoreductase), complex IV (cytochrome c oxidoreductase), and complex V (FIFO ATPase).

The mammalian mitochondrial genome is a small, circular, double-stranded molecule containing 37 genes, including 13 protein-encoding genes, 22 transfer RNA (tRNA) genes and two ribosomal RNA (rRNA) genes. Of these, 24 (22 tRNAs and two rRNAs) are needed for mitochondrial DNA translation, and 13 encode subunits of the respiratory chain complexes. In addition, nuclear DNA (nDNA) encodes most of the approximately 900 gene products in the mitochondria.

Mitochondrial disease or disorders are a clinically heterogeneous group of disorders that are characterized by dysfunctional mitochondria. Disease onset can occur at any age and can manifest with a wide range of clinical symptoms. Mitochondrial disease or disorders can involve any organ or tissue, characteristically involve multiple systems, typically affecting organs that are highly dependent on aerobic metabolism, and are often relentlessly progressive with high morbidity and mortality. Mitochondrial disease or disorders are the most common group of inherited metabolic disorders and are among the most common forms of inherited neurological disorders.

Mitochondrial disease or disorders can be caused by mutations in genes in the nuclear DNA (nDNA) and/or mitochondrial DNA (mtDNA) that encode structural mitochondrial proteins or proteins involved in mitochondrial function. While some mitochondrial disorders only affect a single organ (e.g., the eye in Leber hereditary optic neuropathy [LHON]), many involve multiple organ systems and often present with prominent neurologic and myopathic features. Even though tissues with high energy demand, such as brain, muscle, and eye, are more frequently involved, patients' phenotype can be extremely varied and heterogeneous. This variation is due in part because of several factors, such as, the dual genetic control (nDNA and mtDNA), level of heteroplasmy (percentage of mutated DNA in single cells and tissues), tissue energy demand, maternal inheritance, and mitotic segregation.

Many patients with a mitochondrial disease or disorder have a mixture of mutated and wild-type mtDNA (known as heteroplasmy); the proportion of mutated and wild-type mtDNA is a key factor that determines whether a cell expresses a biochemical defect. The majority of pathogenetic mtDNA mutations are heteroplasmic, with a mixture of mutated and wild-type mtDNA inside an individual cell. High levels of heteroplasmy refer to cells with high levels of mutant mtDNA and low levels of wild-type mtDNA, whereas low levels of heteroplasmy refer to cells with low levels of mutant mtDNA and high levels of wild-type mtDNA. Studies in single cells from patients with mitochondrial disease or disorders have shown that the level of mutated and wild-type mtDNA is very important for determining the cellular phenotype. For example, cells become respiratory deficient if they contain high levels of mutated mtDNA and low levels of wild-type mtDNA (that is, high levels of heteroplasmy). The threshold at which this deficiency occurs depends on the precise mutation and the cell type. Typically, high percentage levels of mutated mtDNA (>50%) are required to result in cellular defects, but some mtDNA mutations only generate a deficiency if present at very high levels (typically mt (RNA mutations) and others (such as single, large-scale mtDNA deletions) produce a deficiency when there is ~60% deleted mtDNA. For example, in individuals harboring the m.8993T>G pathogenic variant, higher percentage levels of mutated mtDNA are seen in those presenting with Leigh syndrome than in those presenting with neurogenic weakness with ataxia and retinitis pigmentosa (NARP). In addition, clinical phenotypes in MELAS and MERRF correlate with heteroplasmy (see, e.g., Chionery, P F., et al., Brain 120 (Pt 10), 1713-1721 (1997)).

Advances in next-generation sequencing technology have revealed many mutations that cause mitochondrial disease or disorders. In addition, investigations into other organisms, such as *C. elegans*, have revealed some of the proteins involved in heteroplasmy. For example, a recent study using *C. elegans* demonstrated that mitochondrial unfolded protein response (UPRmt) functions to maintain the heteroplasmy and propagate mutated mtDNA following a disturbance of the original mtDNA (see, e.g., Lin, Y. F. et al. Nature 533, 416-419, doi:10.1038/nature 17989 (2016)). However, the mechanism related to heteroplasmy maintenance and propagation in mammalian cells remains unknown.

The management and treatment of patients with mitochondrial disease or disorders remains challenging. For the vast majority of patients, the condition is relentlessly progressive leading to considerable morbidity and, in those most severely affected, death. The classical method to remove endogenous mtDNA involves long term treatment of cells with low concentrations of ethidium bromide (EtBr), a known carcinogen and teratogen, limiting its application for therapeutic purposes. In addition to the potential for unwanted side effects, the EtBr protocol can take several months, which further limits its clinical use. Moreover, mitochondrial transfer protocols generally involve a complete depletion of endogenous mtDNA, termed rho (ρ) 0 cells, before transfer of exogenous mitochondria. This complete depletion of mtDNA severely hinders the ability of a cell to ingest exogenous mitochondria.

Other mitochondrial transfer protocols have attempted to add mitochondria without depletion of endogenous mtDNA, but this approach has been found to be inefficient or harmful to a cell. For example, mitochondrial transfer using simple coincubation has been reported to be ineffective and not equally efficient among different cell types. Additional techniques to transfer have involved injection using invasive instruments, which caused harm to the recipient cell, or other invasive instruments, such as nanoblades, but all were less efficient than coincubation (Caicedo et al, Stem Cells International, (2017), vol. 2017, Article ID 7610414, 23 pages).

Accordingly, current methods of mitochondrial transfer are not only impractical for the clinical setting, but they are also inefficient, harmful to recipient cells and/or time intensive. Thus, there is a significant unmet need to develop improved methods for mitochondrial transfer that can be optionally used in the treatment of a subject having or suspected having mitochondrial disease or disorders, and diseases or disorders associated with impaired or dysfunctional mitochondria, as well as improved models for studying mitochondrial disease or disorders.

3. SUMMARY OF THE INVENTION

In one aspect, provided herein is a method of generating a mitochondria replaced cell, comprising: (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell.

In another aspect, provided herein is a method of treating a subject in need of mitochondrial replacement, comprising (a) generating a mitochondria replaced cell ex vivo or in vitro, comprising the steps of (i) contacting a recipient cell with an agent that reduces mtDNA copy number (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell; and (b) administering a therapeutically effective amount of the mitochondria replaced recipient cell from step (a) to the subject in need of mitochondrial replacement.

In yet another aspect, provided herein is a method of treating a subject having or suspected of having an age-related disease, the method comprising: (a) generating a mitochondria replaced cell ex vivo or in vitro, comprising the steps of: (i) contacting a recipient cell with an agent that reduces mtDNA copy number; (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell; and (b) administering a therapeutically effective amount of the mitochondria replaced recipient cell from step (a) to the subject having or suspected of having an age-related disease.

In a further aspect, provided herein is a method of treating a subject having or suspected of having a mitochondrial disease or disorder, the method comprising: (a) generating a mitochondria replaced recipient cell ex vivo or in vitro, comprising the steps of: (i) contacting a recipient cell with an agent that reduces mtDNA copy number; (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell; and (b) administering a therapeutically effective amount of the mitochondria replaced recipient cell from step (a) to the subject having or suspected of having a mitochondrial disease or disorder.

In some embodiments of the methods provided herein, the exogenous mitochondria is a functional mitochondria. In certain embodiments, the exogenous mitochondria comprises wild-type mtDNA. In specific embodiments, the exogenous mitochondria is isolated mitochondria. In further embodiments, the isolated mitochondria is an intact mitochondria. In some embodiments, the exogenous mitochondria is allogeneic.

Also provided herein is a method of generating a mitochondria replaced cell, comprising (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mtDNA from a healthy donor, for a sufficient period of time to non-invasively transfer exogenous mtDNA into the recipient cell, thereby generating a mitochondria replaced cell.

The disclosure also provides a method of treating a subject in need of mitochondrial replacement, comprising (a) generating a mitochondria replaced cell ex vivo or in vitro, comprising the steps of: (i) contacting a recipient cell with an agent that reduces mtDNA copy number, (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mtDNA from a healthy donor, for a sufficient period of time to non-invasively transfer exogenous mtDNA into the recipient cell, thereby generating a mitochondria replaced cell; and (b) administering a therapeutically effective amount of the mitochondria replaced recipient cell from step (a) to the subject in need of mitochondrial replacement.

In another aspect, provided herein is a method of treating a subject having or suspected of having an age-related disease, the method comprising: (a) generating a mitochondria replaced cell ex vivo or in vitro, comprising the steps of: (i) contacting a recipient cell with an agent that reduces mtDNA copy number; (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mtDNA from a healthy donor, for a sufficient period of time to non-invasively transfer exogenous mtDNA into the recipient cell, thereby generating a mitochondria replaced cell; and (b) administering a therapeutically effective amount of the mitochondria replaced recipient cell from step (a) to the subject having or suspected of having an age-related disease.

In yet another aspect, provided herein is a method of treating a subject having or suspected of having a mitochondrial disease or disorder, the method comprising: (a) generating a mitochondria replaced recipient cell ex vivo or in vitro, comprising the steps of: (i) contacting a recipient cell with an agent that reduces mtDNA copy number; (ii) incubating the recipient cell for a sufficient period of time for the agent to partially reduce the mtDNA copy number in the recipient cell; and (iii) co-incubating (1) the recipient cell from step (ii) in which the endogenous mtDNA has been partially reduced, and (2) exogenous mtDNA from a healthy donor, for a sufficient period of time to non-invasively transfer exogenous mtDNA into the recipient cell, thereby generating a mitochondria replaced cell; and (b) administering a therapeutically effective amount of the mitochondria replaced recipient cell from step (a) to the subject having or suspected of having a mitochondrial disease or disorder.

In certain embodiments of the methods provided herein, the agent that reduces endogenous mtDNA copy number is selected from the group consisting of a polynucleotide encoding a fusion protein comprising a mitochondrial-targeted sequence (MTS) and an endonuclease, a polynucleotide encoding an endonuclease, and a small molecule. In some embodiments, the small molecule is a nucleoside reverse transcriptase inhibitor (NRTI). In other embodiments, the polynucleotide is comprised of messenger ribonucleic acid (mRNA) or deoxyribonucleic acid (DNA). In further embodiments, the recipient cell transiently expresses the fusion protein. In yet further embodiments, the endonuclease is selected from the group consisting of XbaI, EcoRI, BamHI, HindIII, PstI, Cas9, zinc finger nuclease (ZFN), and transcription activator-like effector nuclease (TALEN). In some embodiments, the MTS targets a mitochondrial matrix protein. In specific embodiments, the mitochondrial matrix protein is selected from the group consisting of cytochrome c oxidase subunit IV, cytochrome c oxidase subunit VIII, and cytochrome c oxidase subunit X.

In some embodiments of the methods provided herein, the agent that reduces endogenous mtDNA copy number reduces about 5% to about 99% of the endogenous mtDNA copy number. In certain embodiments, the agent that reduces endogenous mtDNA copy number reduces about 30% to about 70% of the endogenous mtDNA copy number. In further embodiments, the agent that reduces endogenous mtDNA copy number reduces about 50% to about 95% of the endogenous mtDNA copy number. In yet further embodiments, the agent that reduces endogenous mtDNA copy number reduces about 60% to about 90% of the endogenous mtDNA copy number. In some embodiments, the agent that reduces endogenous mtDNA copy number reduces mitochondrial mass.

Also provided herein is a method of generating a mitochondria replaced cell, comprising: (a) contacting a recipient cell with an agent that reduces mitochondrial function; (b) incubating the recipient cell for a sufficient period of time for the agent to partially reduce the endogenous mitochondrial function in the recipient cell; and (c) co-incubating (1) the recipient cell from step (b) in which the endogenous mitochondrial function has been partially reduced, and (2) exogenous mitochondria from a healthy donor, for a sufficient period of time to non-invasively transfer exogenous mitochondria into the recipient cell, thereby generating a mitochondria replaced cell.

The present disclosure also provides a method of generating a mitochondria replaced cell, comprising: (a) contacting a recipient cell with an agent that reduces mitochondrial function; (b) incubating the recipient cell for a sufficient period of time for the agent to partially reduce the endogenous mitochondrial function in the recipient cell; and (c) co-incubating (1) the recipient cell from step (b) in which the endogenous mitochondrial function has been partially reduced, and (2) exogenous mtDNA from a healthy donor, for a sufficient period of time to non-invasively transfer exogenous mtDNA into the recipient cell, thereby generating a mitochondria replaced cell.

In some embodiments of the methods provided herein, the agent that reduces mitochondrial function transiently reduces endogenous mitochondrial function. In other embodiments, the agent that reduces mitochondrial function permanently reduces endogenous mitochondrial function.

In certain embodiments of the methods provided herein, the subject in need of mitochondrial replacement has a dysfunctional mitochondria; a disease selected from the group consisting of an age-related disease, a mitochondrial disease or disorder, a neurodegenerative disease, a retinal disease, diabetes, a hearing disorder, a genetic disease; or a combination thereof. In some embodiments, the neurodegenerative disease is selected from the group consisting of amyotrophic lateral sclerosis (ALS), Huntington's disease, Alzheimer's disease, Parkinson's disease, Friedreich's ataxia, Charcot Marie Tooth disease and leukodystrophy. In specific embodiments, the retinal disease is selected from the group consisting of age-related macular degeneration, macular edema and glaucoma.

In some embodiments of the methods provided herein, the age-related disease is selected from the group consisting of an autoimmune disease, a metabolic disease, a genetic disease, cancer, a neurodegenerative disease, and immunosenescence. In certain embodiments of the methods provided herein, the metabolic disease is diabetes. In further embodiments, the neurodegenerative disease is Alzheimer's disease, or Parkinson's disease. In yet further embodiments, the genetic disease is selected from the group consisting of Hutchinson-Gilford Progeria Syndrome, Werner Syndrome, and Huntington's disease.

In certain embodiments of the methods provided herein, the mitochondrial disease or disorder is caused by mitochondrial DNA abnormalities, nuclear DNA abnormalities, or both. In specific embodiments, the mitochondrial disease or disorder caused by mitochondrial DNA abnormalities is selected from the group consisting of chronic progressive external ophthalmoplegia (CPEO), Pearson syndrome, Kearns-Sayre syndrome (KSS), diabetes and deafness (DAD), mitochondrial diabetes, Leber hereditary optic neuropathy (LHON), LHON-plus, neuropathy, ataxia, and retinitis pigmentosa syndrome (NARP), maternally-inherited Leigh syndrome (MILS), mitochondrial encephalomyopathy, lactic acidosis, and stroke-like episodes (MELAS), myoclonic epilepsy and ragged-red fiber disease (MERRF), familial bilateral striatal necrosis/striatonigral degeneration (FBSN), Luft disease, aminoglycoside-induced Deafness (AID), and multiple deletions of mitochondrial DNA syndrome. In yet other specific embodiments, the mitochondrial disease or disorder caused by nuclear DNA abnormalities is selected from the group consisting of Mitochondrial DNA depletion syndrome-4A, mitochondrial recessive ataxia syndrome (MIRAS), mitochondrial neurogastrointestinal encephalomyopathy (MNGIE), mitochondrial DNA depletion syndrome (MTDPS), DNA polymerase gamma (POLG)-related disorders, sensory ataxia neuropathy dysarthria ophthalmoplegia (SANDO), leukoencephalopathy with brainstem and spinal cord involvement and lactate elevation (LBSL), co-enzyme Q10 deficiency, Leigh syndrome, mitochondrial complex abnormalities, fumarase deficiency, α-ketoglutarate dehydrogenase complex (KGDHC) deficiency, succinyl-CoA ligase deficiency, pyruvate dehydrogenase complex deficiency (PDHC), pyruvate carboxylase deficiency (PCD), carnitine palmitoyltransferase I (CPT I) deficiency, carnitine palmitoyltransferase II (CPT II) deficiency, carnitine-acyl-carnitine (CACT) deficiency, autosomal dominant-/autosomal recessive-progressive external ophthalmoplegia (ad-far-PEO), infantile onset spinal cerebellar atrophy (IOSCA), mitochondrial myopathy (MM) spinal muscular atrophy (SMA), growth retardation, aminoaciduria, cholestasis, iron overload, early death (GRACILE), and Charcot-Marie-Tooth disease type 2A (CMT2A).

In some embodiments of the methods provided herein the endogenous mtDNA encodes for a dysfunctional mitochondria. In specific embodiments, the endogenous mtDNA comprises mutant mtDNA. In other embodiments, the endogenous mtDNA in the recipient cell comprises wild-type mtDNA. In yet further embodiments, the endogenous mtDNA comprises mtDNA associated with a mitochondrial disease or disorder. In some embodiments, the endogenous mtDNA is heteroplasmic. In specific embodiments, the recipient cell has endogenous mitochondria that is dysfunctional.

In certain embodiments of the methods provided herein, the mitochondria replaced cell has a total mtDNA copy number no greater than about 1.1 fold, about 1.2 fold, about 1.3 fold, about 1.4 fold, about 1.5 fold, or more, relative to the total mtDNA copy number of the recipient cell prior to contacting with the agent that reduces endogenous mtDNA copy number.

In some embodiments, the recipient cell is an animal cell or a plant cell. In certain embodiments, the animal cell is a mammalian cell. In specific embodiments, the recipient cell is a somatic cell. In other embodiments, the recipient cell is a bone marrow cell. In some embodiments, the bone marrow cell is a hematopoietic stem cell (HSC), or a mesenchymal stem cell (MSC). In other embodiments, the recipient cell is a cancer cell. In further embodiments, the recipient cell is a primary cell. In yet further embodiments, the recipient cell is an immune cell. In specific embodiments, the immune cells is selected from the group consisting of a T cell, a phagocyte, a microglial cell, and a macrophage. In further embodiments, the T cell is a CD4+ T cells. In other embodiments, the T cell is a CD8+ T cells. In certain embodiments, the T cell is a chimeric antigen receptor (CAR) T cell.

In another embodiment of the methods provided herein, the exogenous mitochondria and/or exogenous mtDNA is stable. In some embodiments, the exogenous mtDNA alters heteroplasmy in the recipient cell.

In some aspects of the methods provided herein, the method further comprises delivering a small molecule, a peptide, or a protein.

The disclosure also provides methods provided herein, further comprising contacting the recipient cell with a second active agent prior to co-incubating the recipient cell with exogenous mitochondria and/or exogenous mtDNA. In certain embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In some embodiments, the activator of endocytosis is a modulator of cellular metabolism. In specific embodiments, the modulator of cellular metabolism comprises nutrient starvation, a chemical inhibitor, or a small molecule. In yet further embodiments, the chemical inhibitor or the small molecule is an mTOR inhibitor. In even further embodiments, the mTOR inhibitor comprises rapamycin or a derivative thereof.

The disclosure also provides a composition comprising one or more mitochondria replaced cells obtained by the method of: (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell, wherein said mitochondria replaced cell comprises greater than 5% of exogenous mtDNA.

The disclosure further provides a composition of one or more mitochondria replaced cells obtained by the method of (a) contacting a recipient cell with an agent that reduces endogenous mtDNA copy number (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mtDNA from healthy donor, for a sufficient period of time to non-invasively transfer exogenous mtDNA into the recipient cell, thereby generating a mitochondria replaced cell, wherein said mitochondria replaced cell comprises greater than 5% of exogenous mtDNA. In some embodiments of the compositions provided herein, the one or more mitochondria replaced cells comprise a total mtDNA copy number no greater than about 1.1 fold, about 1.2 fold, about 1.3 fold, about 1.4 fold, about 1.5 fold, or more, relative to the total mtDNA copy number of the recipient cell prior to contacting with the agent that reduces endogenous mtDNA copy number.

In another aspect, provided herein is a composition for use in a method of generating one or more mitochondria replaced cells comprising an agent that reduces endogenous mtDNA copy number, and a second active agent. In some embodiments, the composition further comprising one or more recipient cells, or a combination thereof. In certain embodiments, the composition further comprising exogenous mtDNA exogenous mtDNA and/or exogenous mitochondria.

In certain embodiments of the compositions provided herein, the agent that reduces endogenous mtDNA copy number is a small molecule or a fusion protein. In some embodiments, the small molecule is a nucleoside reverse transcriptase inhibitor (NRTI). In other embodiments, the fusion protein comprises an endonuclease that cleaves mtDNA and a mitochondrial target sequence (MTS) In some embodiments, the endonuclease cleaves wild-type mtDNA. In specific embodiments, the endonuclease is selected from the group consisting of XbaI, EcoRI, BamHI, HindIII, PstI, Cas9, zinc finger nuclease (ZFN), and transcription activator-like effector nuclease (TALEN). In some embodiments, the MTS targets a mitochondrial matrix protein. In further embodiments, the mitochondrial matrix protein is cytochrome c oxidase subunit IV, cytochrome c oxidase subunit VIII, and cytochrome c oxidase subunit X. In specific embodiments, the fusion protein is transiently expressed.

In some embodiments of the compositions provided herein, the reduction of endogenous mtDNA copy number is a partial reduction. In certain embodiments, the partial reduction is a reduction of about 5% to about 99% of endogenous mtDNA. In specific embodiments, the partial reduction is a reduction of about 50% to about 95% of the endogenous mtDNA copy number. In further embodiments, the partial reduction is a reduction of about 60% to about 90% of the endogenous mtDNA copy number.

The disclosure also provides a composition comprising one or more mitochondria replaced cells obtained by the method of (a) contacting a recipient cell with an agent that reduces mitochondrial function; (b) incubating the recipient cell for a sufficient period of time for the agent to partially reduce endogenous mitochondrial function in the recipient cell; and (c) co-incubating (1) the recipient cell from step (b) in which the endogenous mitochondrial function has been partially reduced, and (2) exogenous mitochondria from a healthy donor, for a sufficient period of time to non-invasively transfer exogenous mitochondria into the recipient cell, thereby generating a mitochondria replaced cell, wherein said mitochondria replaced cell comprises greater than 5% of exogenous mtDNA.

In another aspect, provided herein is a composition of one or more mitochondria replaced cells obtained by the method of: (a) contacting a recipient cell with an agent that reduces mitochondrial function; (b) incubating the recipient cell for a sufficient period of time for the agent to partially reduce endogenous mitochondrial function in the recipient cell; and (c) co-incubating (1) the recipient cell from step (b) in which the endogenous mitochondrial function has been partially reduced, and (2) exogenous mtDNA from healthy donor, for a sufficient period of time to non-invasively transfer exogenous mtDNA into the recipient cell, thereby generating a mitochondria replaced cell, wherein said mitochondria replaced cell comprises greater than 5% of exogenous mtDNA. In some embodiments, the one or more mitochondria replaced cells comprise a total mtDNA copy number no greater than about 1.1 fold, about 1.2 fold, about 1.3 fold, about 1.4 fold, about 1.5 fold, or more, relative to the total mtDNA copy number of the recipient cell prior to contacting with the agent that reduces endogenous mtDNA copy number.

The disclosure also provides a composition for use in a method of generating one or more mitochondria replaced cells comprising an agent that reduces mitochondrial function, and a second active agent. In some embodiments, the composition further comprises an exogenous mitochondria, one or more recipient cells, or a combination thereof. In yet further embodiments, the composition further comprises exogenous mtDNA.

In some embodiments of the compositions provided herein, the one or more mitochondria replaced cells comprise wild-type exogenous mtDNA.

Also provided herein are compositions further comprising a second active agent. In some embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In specific embodiments, the activator of endocytosis is an activator of a clathrin-independent endocytosis pathway. In some embodiments, the activator of endocytosis is an activator of a clathrin-independent endocytosis pathway. In further embodiments, the clathrin-independent endocytosis pathway is selected from the group consisting of a CLIC/GEEC endocytic pathway, Arf6-dependent endocytosis, flotillin-dependent endocytosis, macropinocytosis, circular doral ruffles, phagocytosis, and trans-endocytosis. In yet further embodiments, the clathrin-independent endocytosis pathway is macropinocytosis. In specific embodiments, the activator of endocytosis comprises nutrient stress, and/or an mTOR inhibitor. In some embodiments, the mTOR inhibitor comprises rapamycin or a derivative thereof.

In certain embodiments, the disclosure further provides a composition where the total mtDNA copy number of the one or more mitochondria replaced cells comprises greater than 5% of exogenous mtDNA. In some embodiments, the total mtDNA copy number of the one or more mitochondria replaced cells comprises greater than 30% of exogenous mtDNA. In specific embodiments, the total mtDNA copy number of the one or more mitochondria replaced cells comprises greater than 50% of exogenous mtDNA. In further embodiments, the total mtDNA copy number of the one or more mitochondria replaced cells comprises greater than 75% of exogenous mtDNA.

In some embodiments of the compositions provided herein, the exogenous mitochondria is isolated mitochondria. In specific embodiments, the isolated mitochondria is intact. In some embodiments, the exogenous mitochondria and/or exogenous mtDNA is allogeneic. In specific embodiments, the exogenous mitochondria further comprises exogenous mtDNA.

In certain embodiments of the compositions provided herein, the one or more cells are animal cells or plant cells. In some embodiments, the animal cells are mammalian cells In specific embodiments, the cells are somatic cells. In further embodiments, the somatic cells are epithelial cells. In yet further embodiments, the epithelial cells are thymic epithelial cells (TECs). In other embodiments, the somatic cells are immune cells. In certain embodiments, the immune cells are T cells. In specific embodiments, the T cells are CD4+ T cells. In other embodiments, the T cells are CD8+ T cells. In some embodiments, the T cells are chimeric antigen receptor (CAR) T cells. In other embodiments, the immune cells are phagocytic cells. In certain embodiments, the one or more mitochondria replaced cells are bone marrow cells. In specific embodiments, the bone marrow cells are a hematopoietic stem cell (HSC), or a mesenchymal stem cell (MSC).

In some embodiments of the compositions provided herein, the one or more mitochondria replaced cells are more viable than an isogenic cell having homoplasmic endogenous mtDNA. In other embodiments, the one or more mitochondria replaced cells are efficacious in killing a cancer cell, treating an age-related disease, treating a mitochondrial disease or disorder, treating a neurodegenerative disease, treating diabetes, or a genetic disease.

In certain embodiments of the compositions provided herein, the composition further comprises a small molecule, a peptide, or a protein.

Also provided herein is a composition for use in delaying senescence and/or extending lifespan in a cell comprising: (a) a senescent or near senescent cell having endogenous mitochondria; (b) isolated exogenous mitochondria from a non-senescent cell; and (c) an agent that reduces endogenous mtDNA copy number. In some embodiments the agent is a fusion protein. In certain embodiments, the fusion protein comprises an endonuclease that cleaves mtDNA and a mitochondrial target sequence (MTS). In specific embodiments, the endonuclease cleaves wild-type mtDNA. In some embodiments, the endonuclease is selected from the group consisting of XbaI, EcoRI, BamHI, HindIII, PstI, Cas9, zinc finger nuclease (ZEN), and transcription activator-like effector nuclease (TALEN). In further embodiments, the MTS targets a mitochondrial matrix protein. In yet further embodiments, the mitochondrial matrix protein is selected from the group consisting of cytochrome e oxidase subunit IV, cytochrome c oxidase subunit VIII, and cytochrome e oxidase subunit X. In certain embodiments, the fusion protein is transiently expressed in said senescent or near senescent cell.

The disclosure further provides a composition for use in delaying senescence and/or extending lifespan in a cell comprising: (a) a senescent or near senescent cell having endogenous mitochondria; (b) isolated exogenous mitochondria from a non-senescent cell; and (c) an agent that reduces mitochondrial function. In some embodiments, the agent that reduces mitochondrial function transiently reduces endogenous mitochondrial function. In other embodiments, the agent that reduces mitochondrial function permanently reduces endogenous mitochondrial function. In some embodiments, the exogenous mitochondria from the non-senescent cell has enhanced function relative to the endogenous mitochondria.

In some embodiments, the composition for use in delaying senescence and/or extending lifespan in a cell further comprises a second active agent. In specific embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In some embodiments, the activator of endocytosis is an activator of a clathrin-independent endocytosis pathway. In specific embodiments, the clathrin-independent endocytosis pathway is selected from the group consisting of a CLIC/GEEC endocytic pathway, Arf6-dependent endocytosis, flotillin-dependent endocytosis, macropinocytosis, circular doral ruffles, phagocytosis, and trans-endocytosis. In further embodiments, the clathrin-independent endocytosis pathway is macropinocytosis. In some embodiments, said activator of endocytosis comprises nutrient stress, and/or an mTOR inhibitor. In certain embodiments, said mTOR inhibitor comprises rapamycin or a derivative thereof.

In another aspect, the disclosure also provides a pharmaceutical composition comprising an isolated population of mitochondria replaced cells having an exogenous mitochondria from a healthy donor, wherein the cells are obtained by any of the methods provided herein for obtaining a mitochondrial replaced cell. In yet another aspect, the disclosure provides a pharmaceutical composition comprising an isolated population of mitochondria replaced cells having an exogenous mtDNA from a healthy donor, wherein the cells are obtained by any of the methods provided herein for obtaining a mitochondrial replaced cell. In some embodiments, the pharmaceutical composition comprising an isolated population of mitochondria replaced cells having an exogenous mtDNA from a healthy donor further comprises exogenous mitochondria.

For example, in some embodiments, a pharmaceutical composition comprising an exogenous mitochondria from a healthy donor are obtained by a method of generating a mitochondrial replaced cell that includes (a) contacting a recipient cell with an agent that reduces endogenous mtDNA copy number, (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mitochondria from a healthy donor, for a sufficient period of time to non-invasively transfer exogenous mitochondria into the recipient cell, thereby generating a mitochondria replaced cell. In certain embodiments, the cells are obtained by a method comprising (a) contacting a recipient cell with an agent that reduces mitochondrial function; (b) incubating the recipient cell for a sufficient period of time for the agent to partially reduce the endogenous mitochondrial function in the recipient cell; and (c) co-incubating (1) the recipient cell from step (b) in which the endogenous mitochondrial function has been partially reduced, and (2) exogenous mitochondria from a healthy donor, for a sufficient period of time to non-invasively transfer exogenous mitochondria into the recipient cell, thereby generating a mitochondria replaced cell.

In other embodiments, the cells are obtained by a method comprising (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mtDNA from a healthy donor, for a sufficient period of time to non-invasively transfer exogenous mtDNA into the recipient cell, thereby generating a mitochondria replaced cell. In other embodiments, the cells are obtained by a method comprising: (a) contacting a recipient cell with an agent that reduces mitochondrial function; (b) incubating the recipient cell for a sufficient period of time for the agent to partially reduce the endogenous mitochondrial function in the recipient cell; and (c) co-incubating (1) the recipient cell from step (b) in which the endogenous mitochondrial function has been partially reduced, and (2) exogenous mtDNA from a healthy donor, for a sufficient period of time to non-invasively transfer exogenous mtDNA into the recipient cell, thereby generating a mitochondria replaced cell.

In certain embodiments of the pharmaceutical compositions provided herein, the cells are obtained by a method further comprising further comprising contacting the recipient cell with a second active agent prior to co-incubating the recipient cell with exogenous mitochondria and/or exogenous mtDNA. In some embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In specific embodiments, the activator of endocytosis is a modulator of cellular metabolism. In other embodiments, the modulator of cellular metabolism comprises nutrient starvation, a chemical inhibitor, or a small molecule. In further embodiments, the chemical inhibitor or the small molecule is an mTOR inhibitor. In yet further embodiments, said mTOR inhibitor comprises rapamycin or a derivative thereof.

In certain embodiments of the pharmaceutical compositions provided herein, the pharmaceutical composition further comprises a pharmaceutically acceptable carrier.

In some embodiments of the pharmaceutical compositions provided herein, the cells are T cells. In other embodiments, the cells are hematopoietic stem cells.

4. BRIEF DESCRIPTION OF THE FIGURES

Figure 1A:
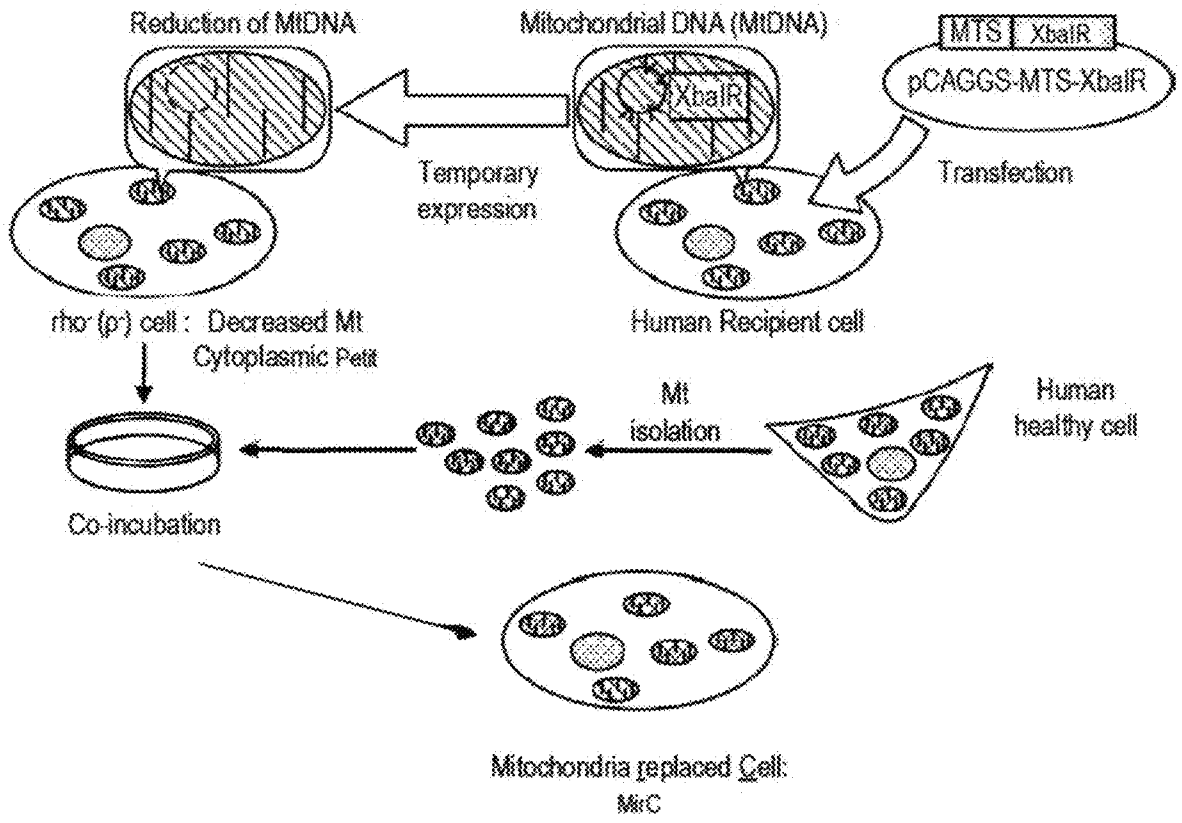
FIG. 1A depicts a scheme for generation of a Mitochondria replaced cell (MirC).
Figure 1B:
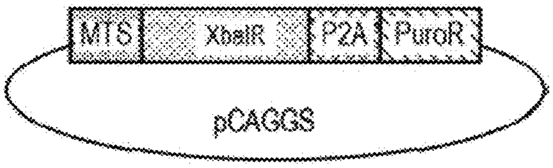
FIG. 1B depicts a plasmid construct for the Mitochondrial Targeting Sequence (MTS)-XbaI restriction enzyme (XbaIR) plasmid.
Figure 1C:
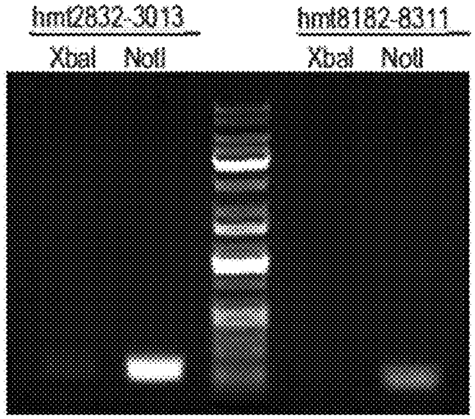
FIG. 1C depicts that isolated mitochondrial DNA is digested at multiple sites by the XbaI restriction enzyme, whereas NotI digestion of mitochondrial DNA resulted in a single fragment, as predicted by Cambridge Reference Sequence (CRS) of mitochondrial DNA.
Figure 1D:
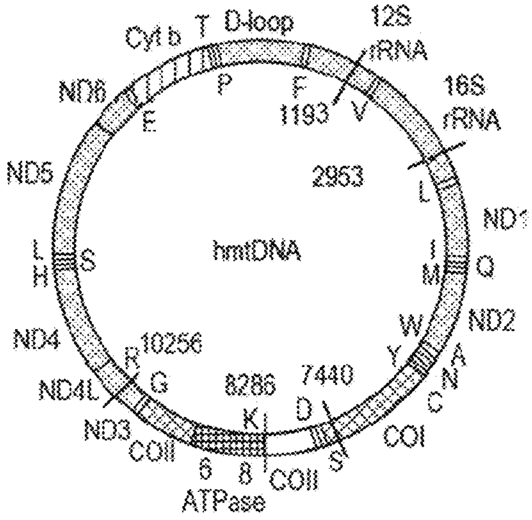
FIG. 1D depicts five XbaIR endonuclease sites (1193, 2953, 7440, 8286, 10256) on human mitochondrial DNA as predicted by Cambridge Reference Sequence (CRS).
Figure 1E:
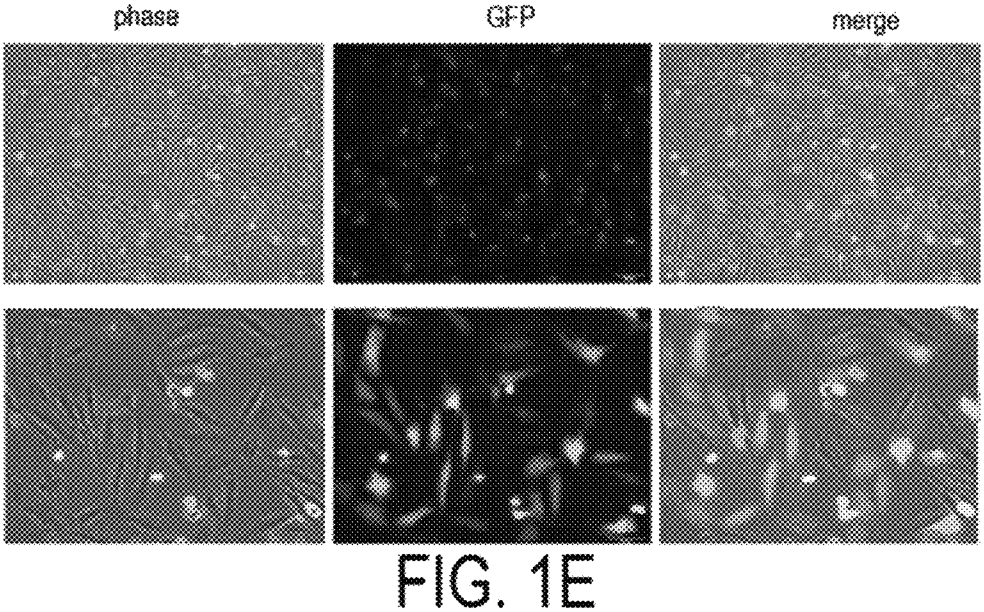

FIG. 1E depicts microscopy of human dermal fibroblasts under phase contrast (left), immunofluorescence of green fluorescence protein (middle), and merged fields (right) after uptake of a fusion MTS-green fluorescence protein (GFP) plasmid using electroporator (Nucleofector). Top, low magnification. Bottom, high magnification.

Figure 1F:
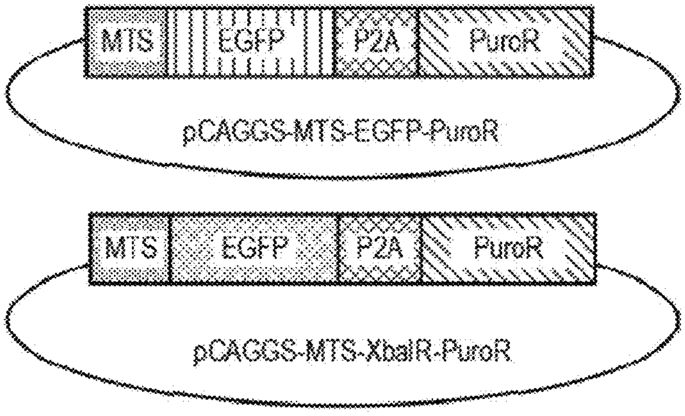

FIG. 1F depicts the construct for the pCAGGS-MTS-EGFP-PuroR and pCAGGS-MTS-XbaIR-PuroR plasmids.

Figure 1G:
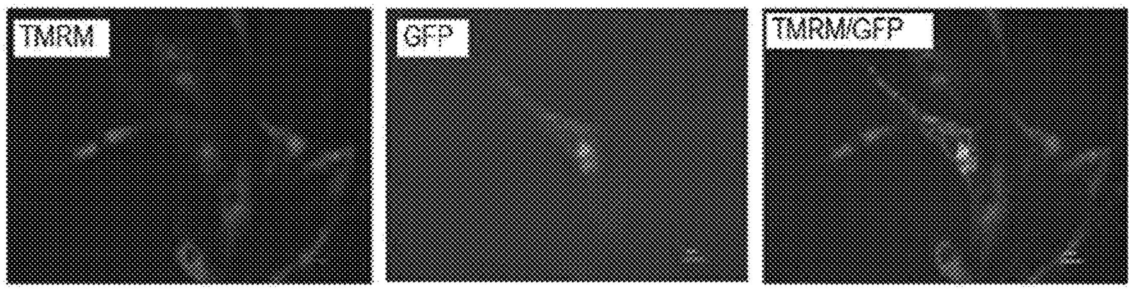

FIG. 1G depicts the localization of exogenous transgene products MTS-EGFP in mitochondria by mitochondria-specific staining with tetramethylrhodamine, methyl ester (TMRM).

Figure 2A:
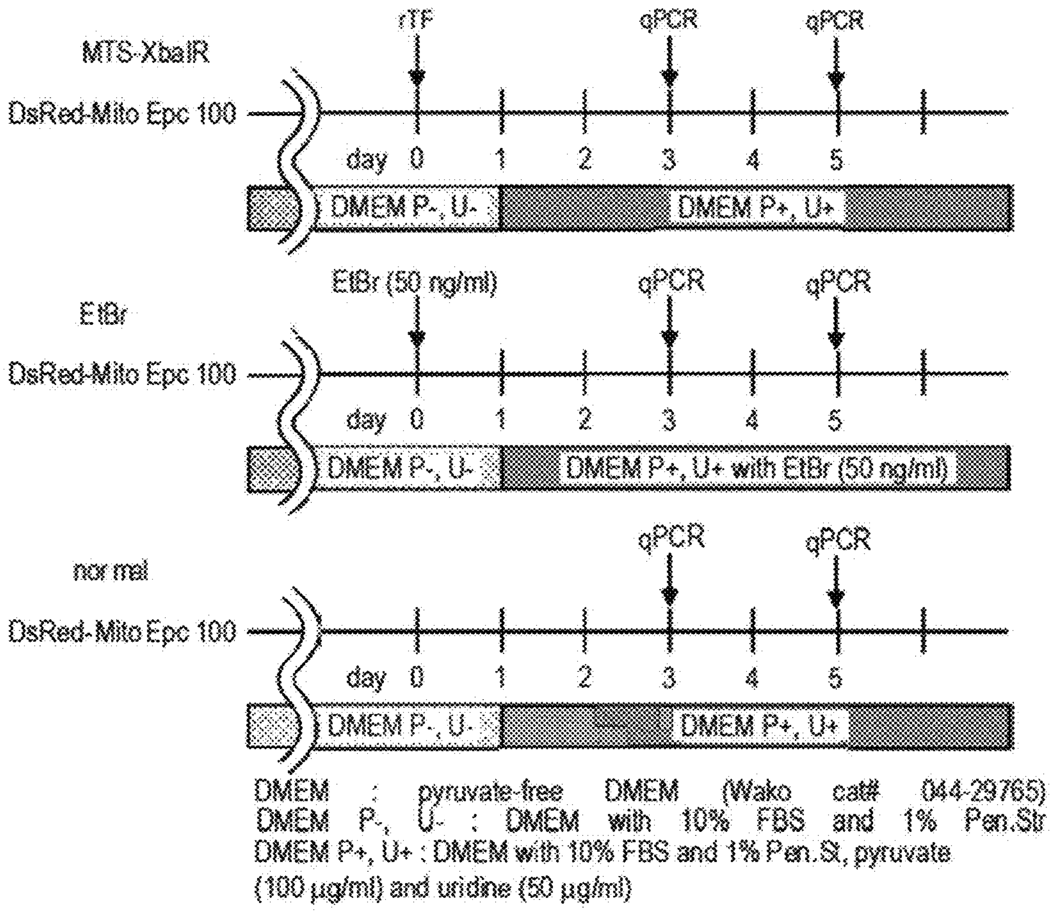

FIG. 2A depicts a scheme of the time schedule to compare the MTS-XbaIR endonuclease method (top) with the traditional method using ethidium bromide (EtBr) (middle), relative to non-contacted cells.

Figure 2B:
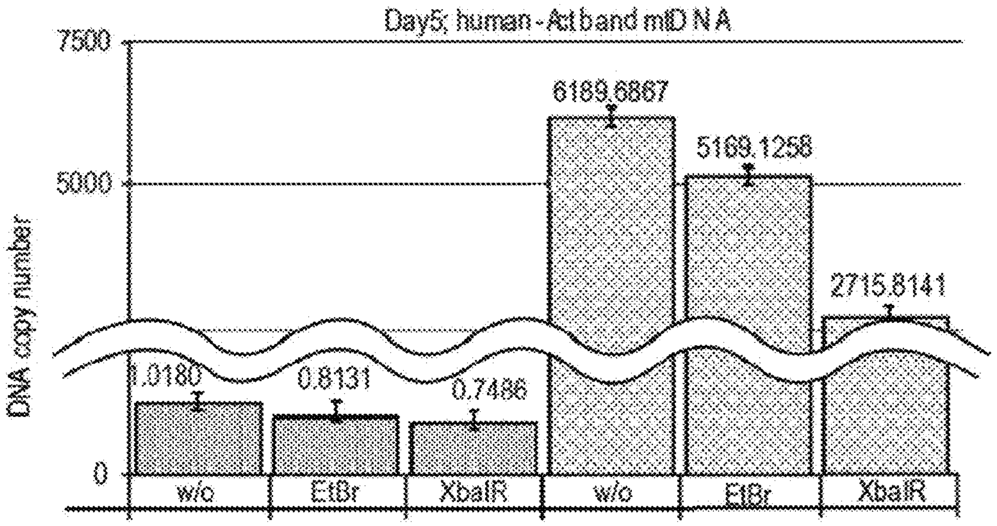

FIG. 2B depicts quantification of human β-actin (Actb), left columns, and mitochondria DNA (mtDNA), right columns, following contact with either the MTS-XbaIR endonuclease method or the ethidium bromide treatment, relative to non-contacted cells. XbaIR resulted in a greater reduction of mtDNA, compared to EtBr treatment. Actb was used as a housekeeping gene.

Figure 2C:
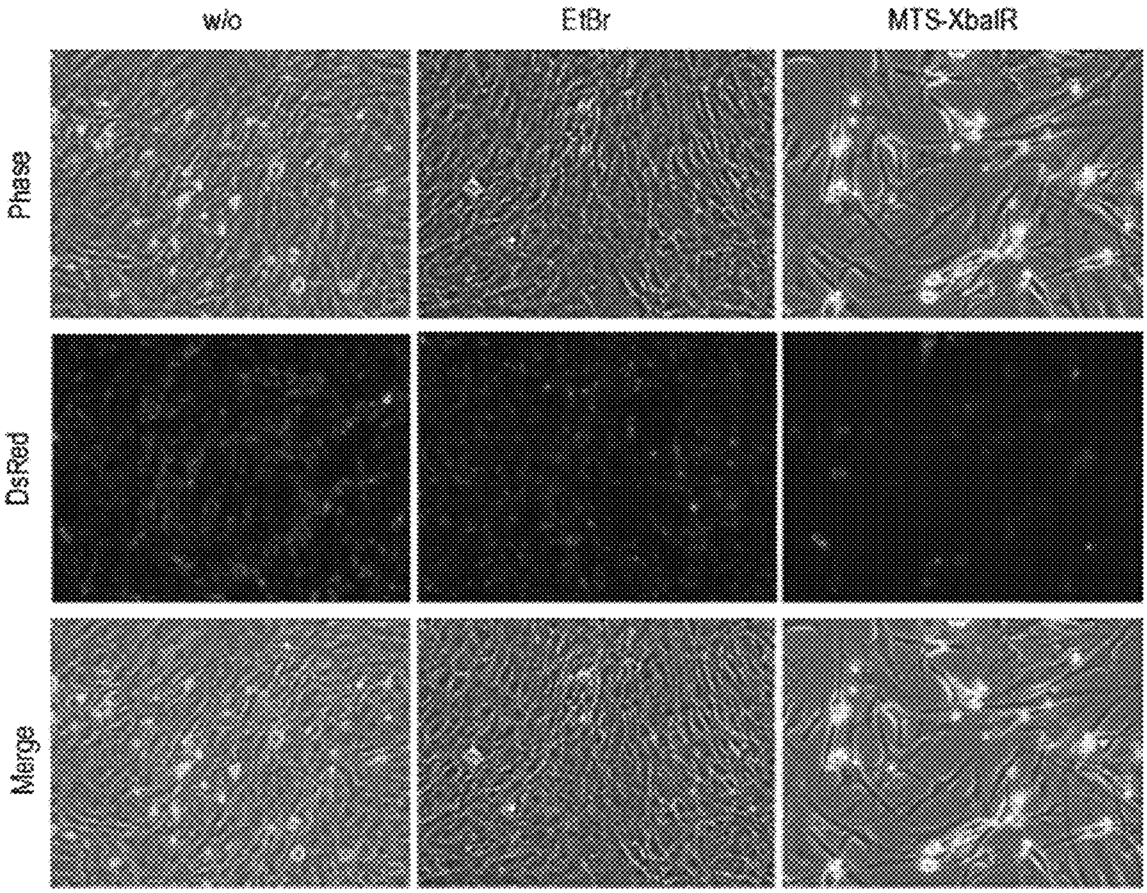

FIG. 2C depicts a greater reduction in mitochondria following exposure to the gene transfer of MTS-XbaIR, relative to EtBr treatment, based on DsRed fluorescence that had been expressed in mitochondria.

Figure 2D:
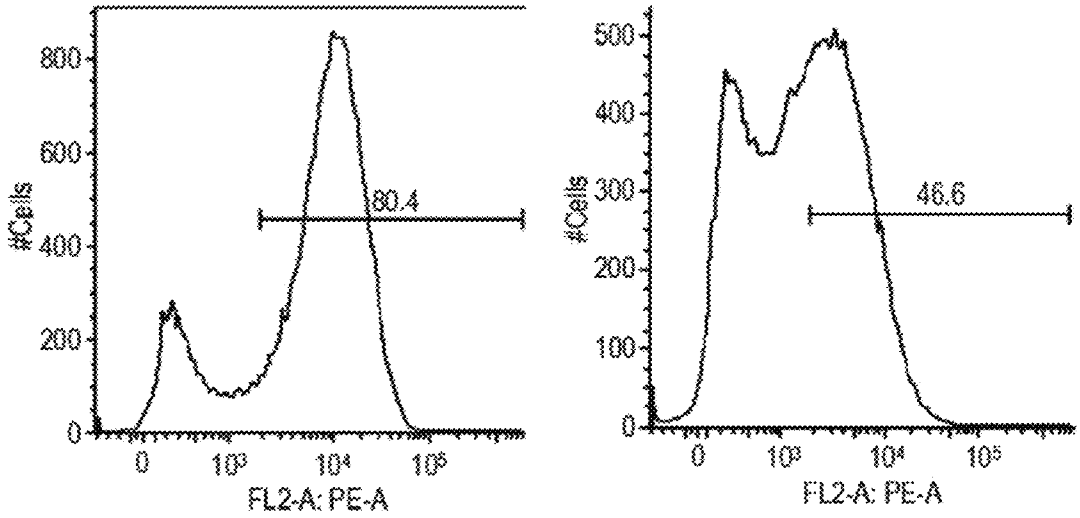

FIG. 2D depicts semi-quantification of mitochondrial membrane potentials (surrogate marker for mitochondrial content) in cells contacted with the gene transfer of MTS-XbaIR or EtBr using FACS analyses by using TMRM, and shows that MTS-XbaIR resulted in a greater reduction in mitochondria.

Figure 2E:
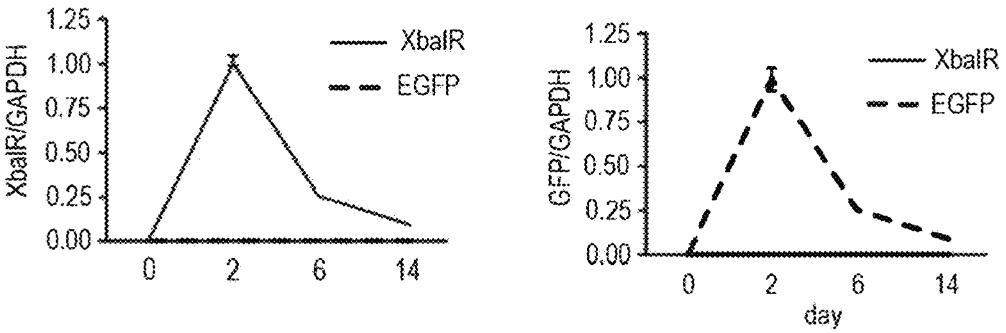

FIG. 2E depicts a time course quantification of transgene expression in the gene transfer system over fourteen days.

Figure 2F:
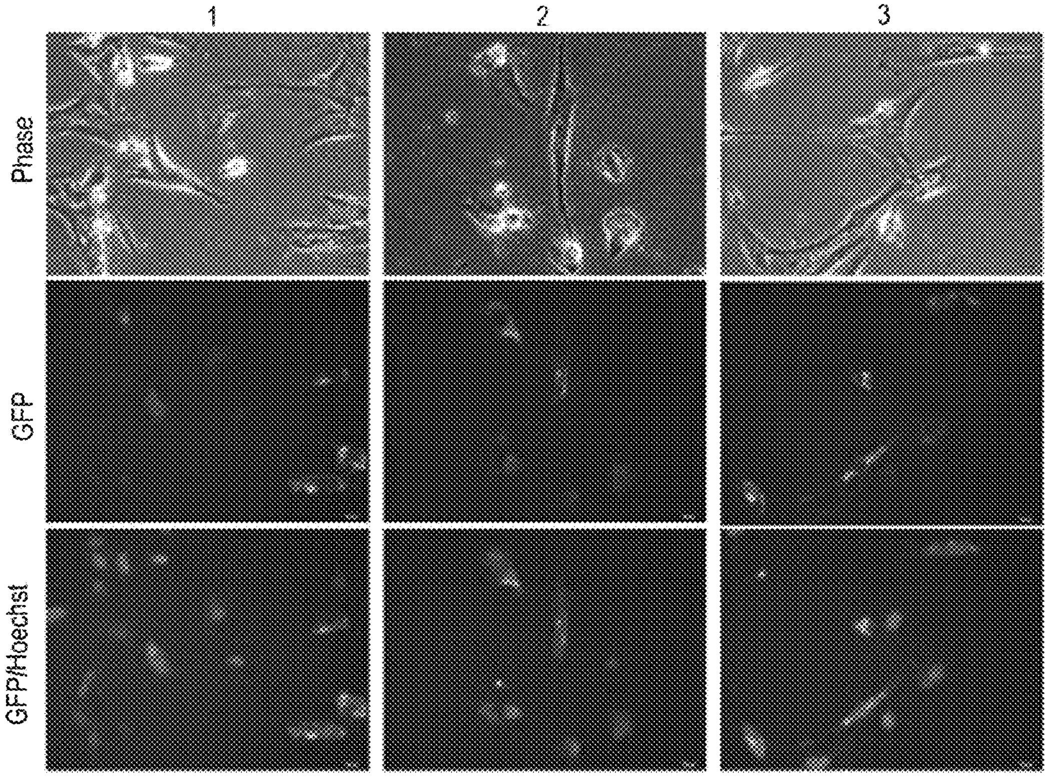
Figure 2G:
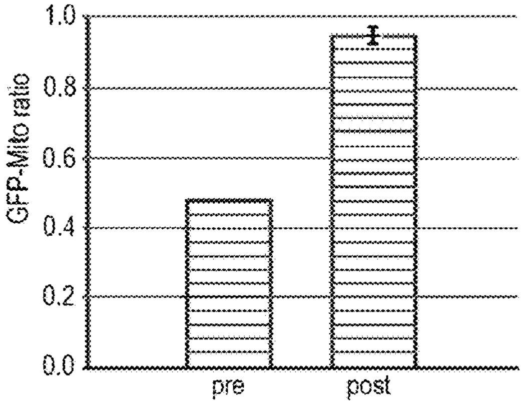

FIG. 2F and FIG. 2G depicts fluorescent images (FIG. 2F) following the transfer of the plasmid carrying GFP prior to ("pre") and after ("post") puromycin section, and quantification of the GFP/Mitochondria ratio (FIG. 2G) demonstrates enrichment of the GFP plasmid post-puromycin selection.

Figure 3A:
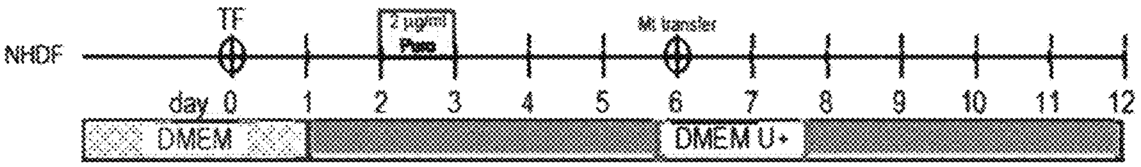

FIG. 3A depicts a scheme of the time schedule for mitochondria replacement. TF: Gene transfection of XbaIR or Mock; Puro: Puromycin for enrichment of gene transferred cells; U+: Addition of uridine to rescue ρ(−) cells devoid of mitochondrial ATP production; Mt Tx: Mitochondria transfer; NHDF: Normal Human Dermal Fibroblasts, EPC100: Placental venous endothelium-derived cell lines.

Figure 3B:
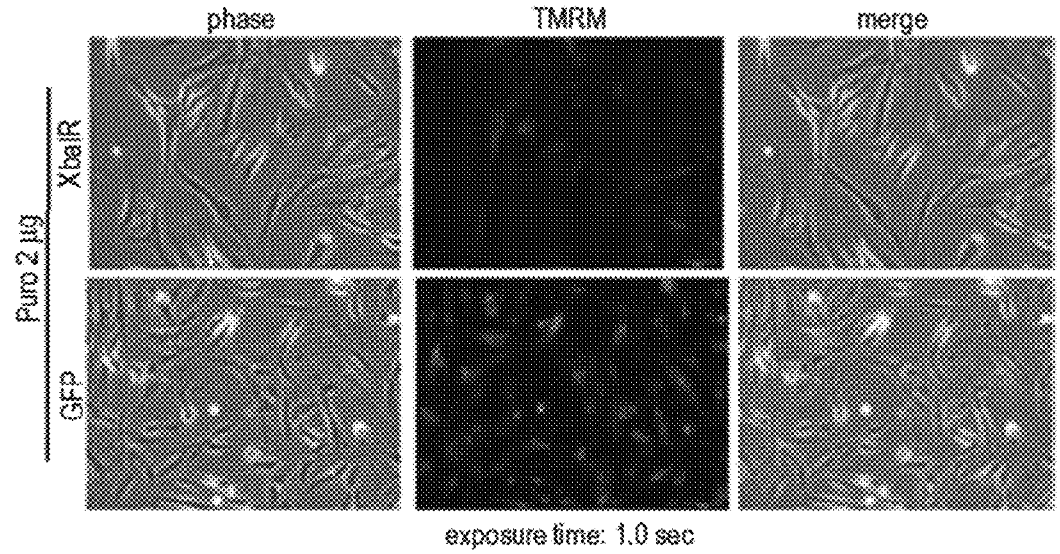

FIG. 3B depicts reduction in mitochondria on Day 6 following the gene transfer of XbaIR (top), but not following the transfer of the negative control vector expression GFP (bottom), as measured by TMRM staining.

Figure 3C:
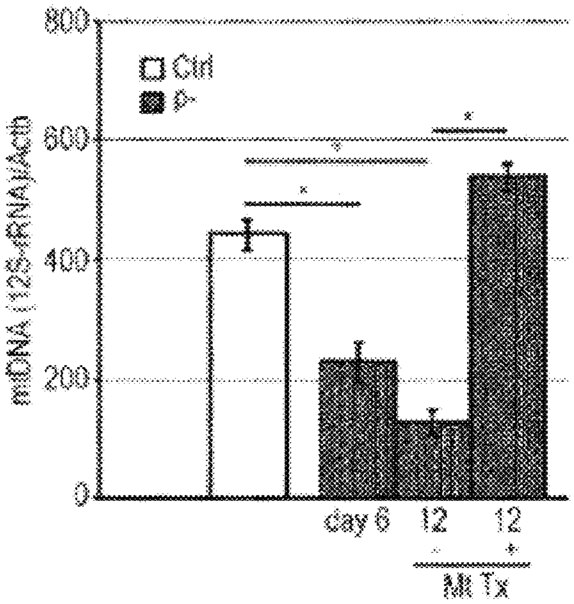

FIG. 3C depicts quantification of mitochondrial DNA copy numbers estimated by qPCR of human 12S rRNA relative to nuclear β-actin levels in NHDF cells after gene transfection of XbaIR or GFP transfection. Mitochondria were transferred to recipient cells where indicated ("Mt Tx"). XbaIR resulted in significant reduction of mitochondrial DNA, which could be rescued to levels equivalent to control treated cells after transfer of exogenous mitochondria. N=3, *$p<0.01$.

Figure 3D:
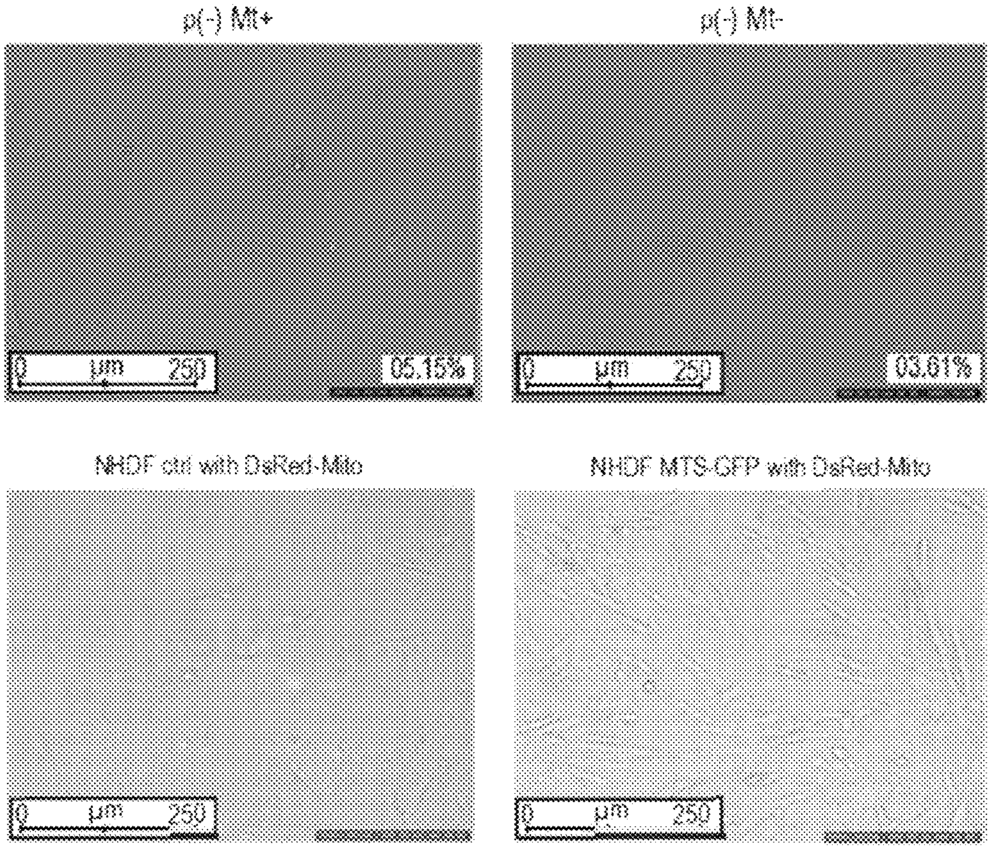
Figure 3E:
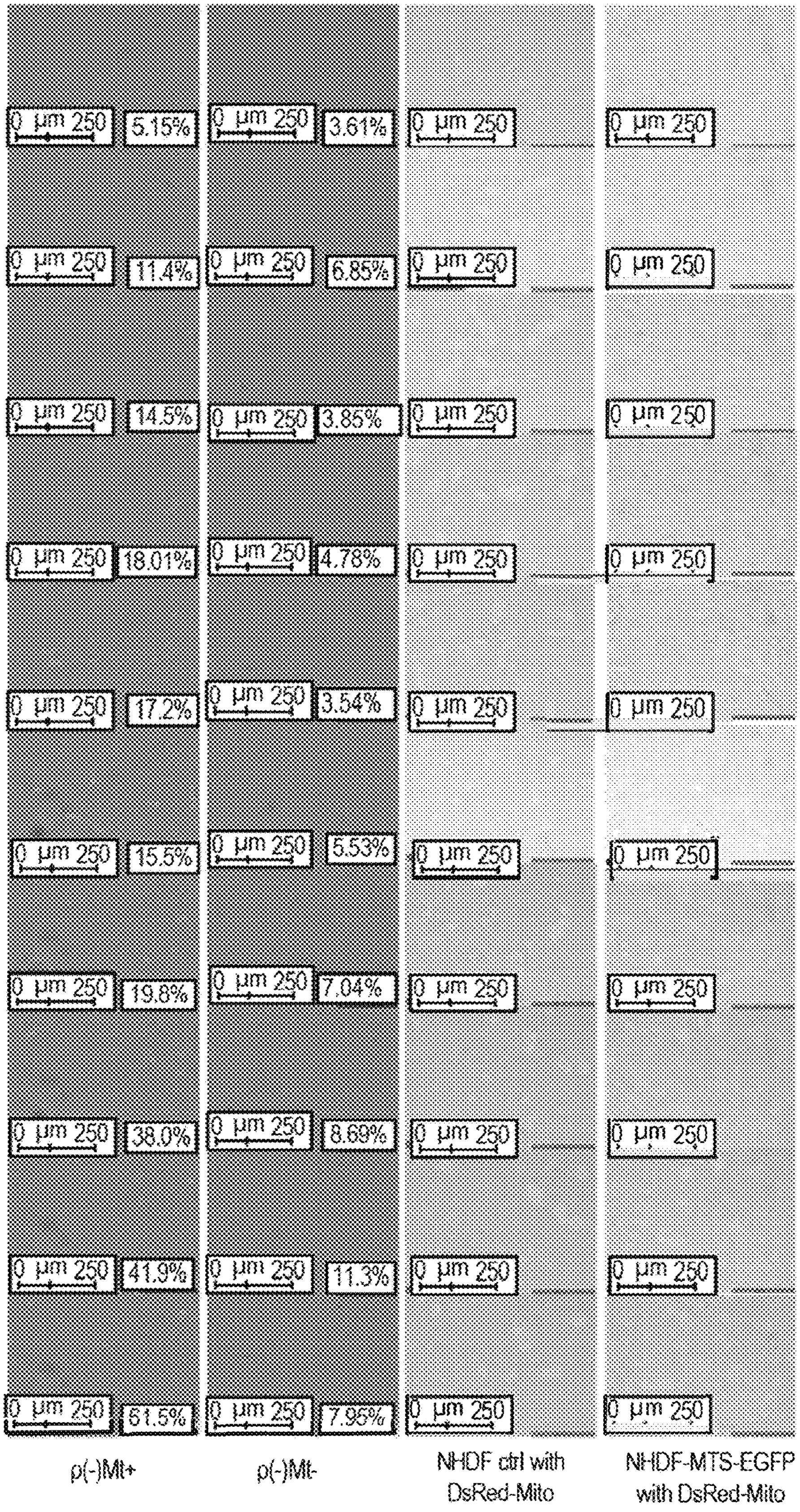
Figure 3F:
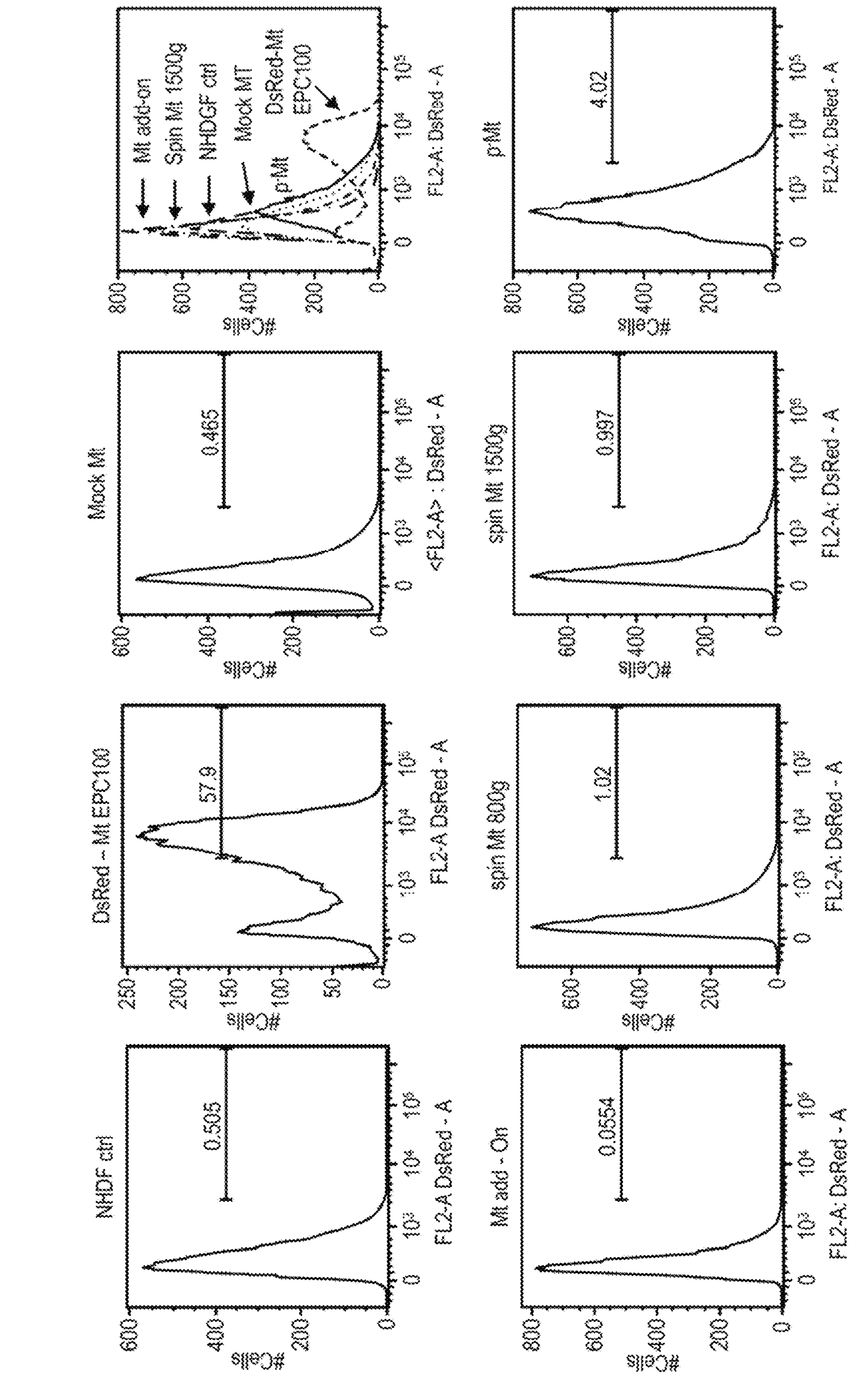

FIG. 3D depicts Photographs from time lapse movie: Upper left: Cocultivation of ρ (−) cells with isolated and DsRed-marked mitochondria; Upper right: ρ (−) cells as a control; Lower left: Cocultivation of NHDF with mitochondria; Lower right: Cocultivation of mock transfectant of NHDF with mitochondria;

FIG. 3E depicts a series of 10 still images from time lapse movie depicted in FIG. 3D, arranged chronologically, vertically;

FIG. 3F depicts measurement of DsRed labeled mitochondria by FACS analysis and revealed that the present invention ("DsRed-Mt EPC100") resulted in increased uptake of exogenous mitochondria compared to previously described methods.

Figure 3G:
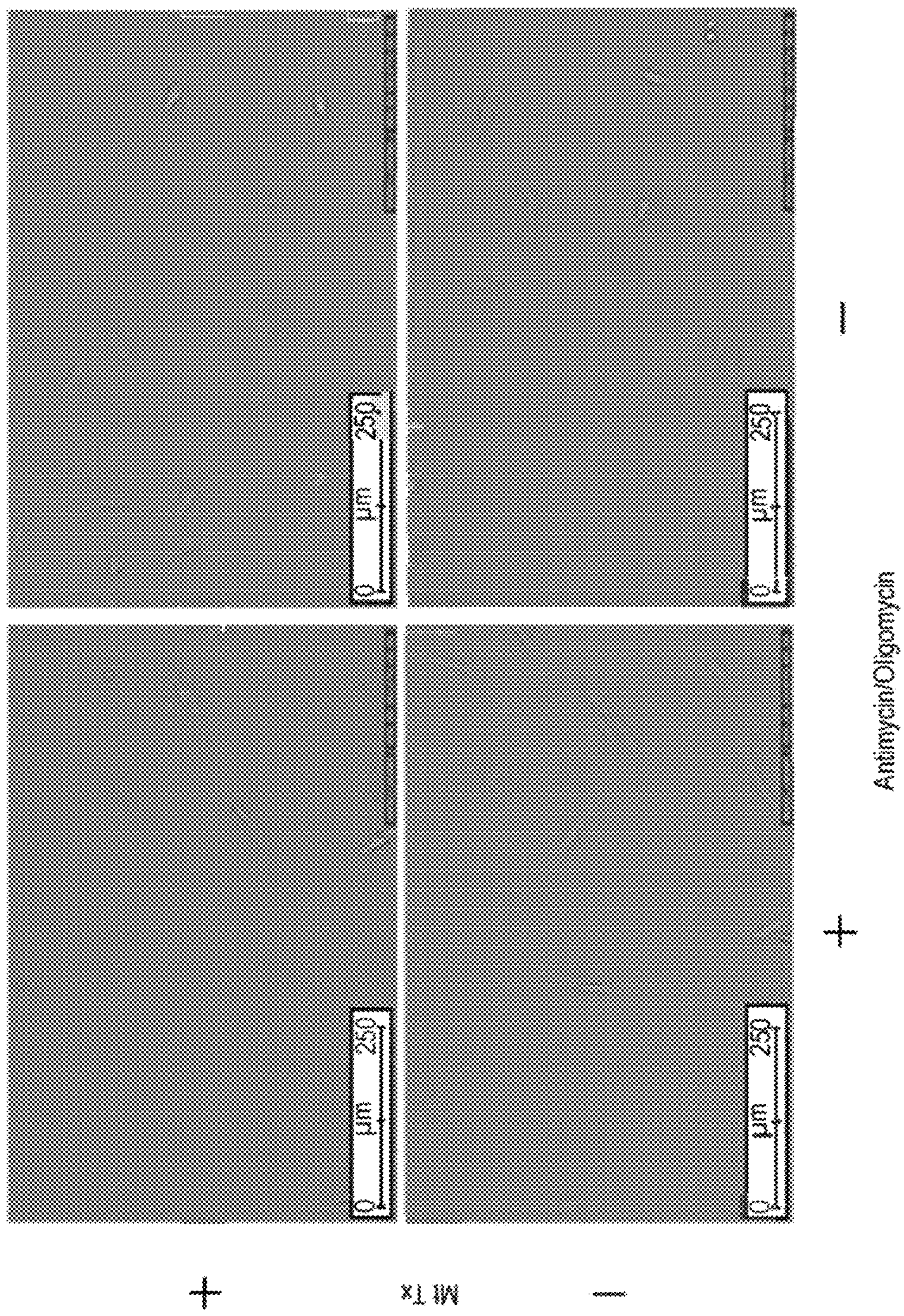
Figure 3H:
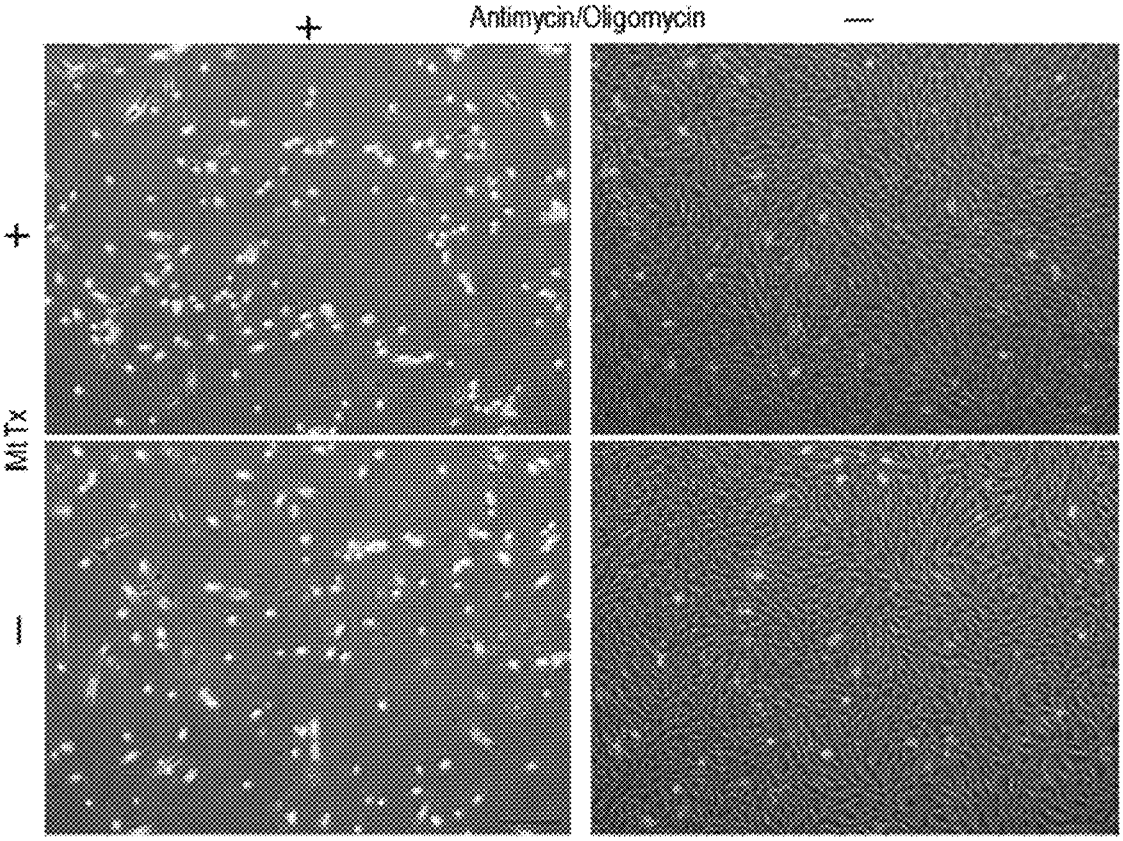
Figure 3I:
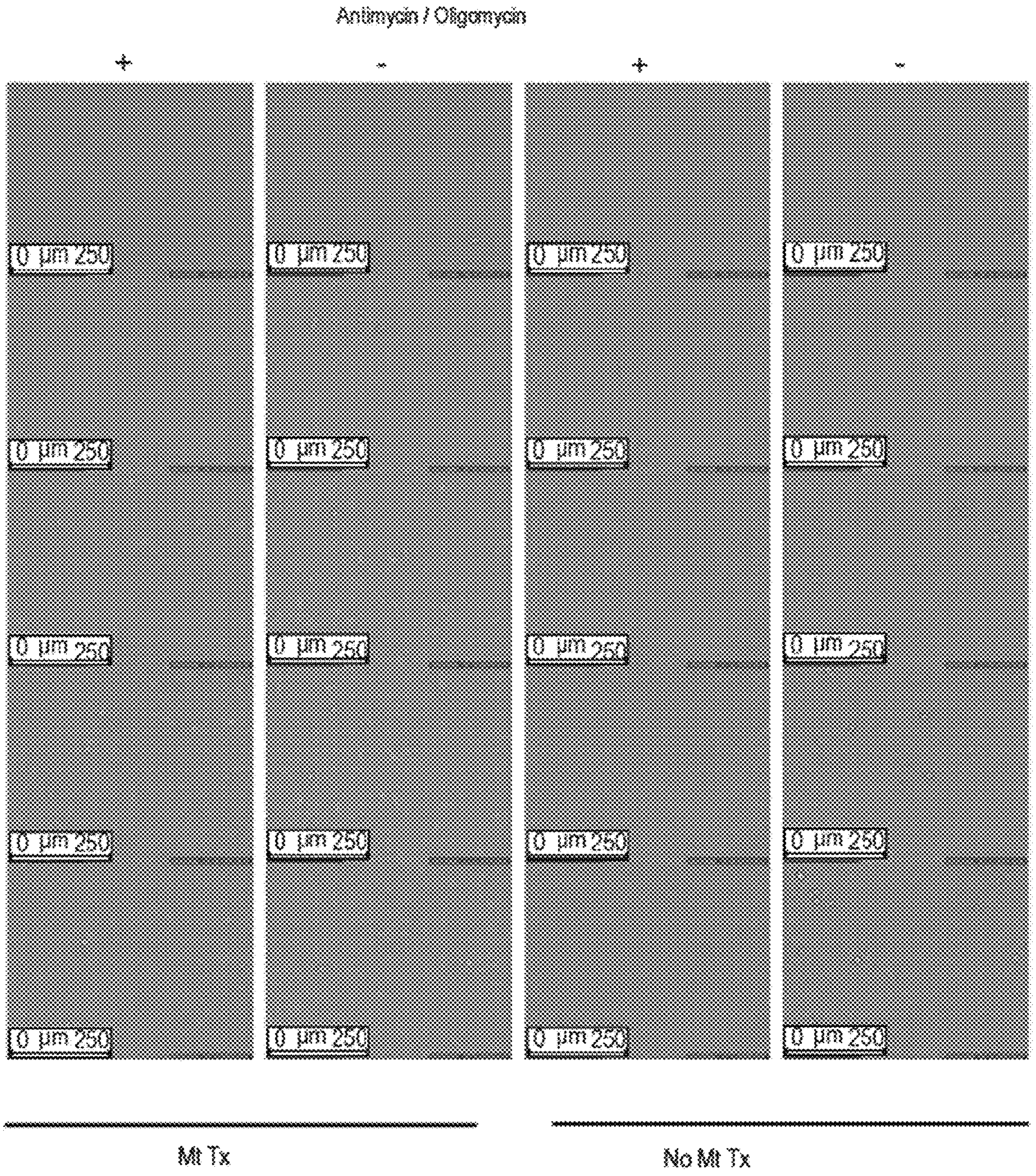
Figure 3J:
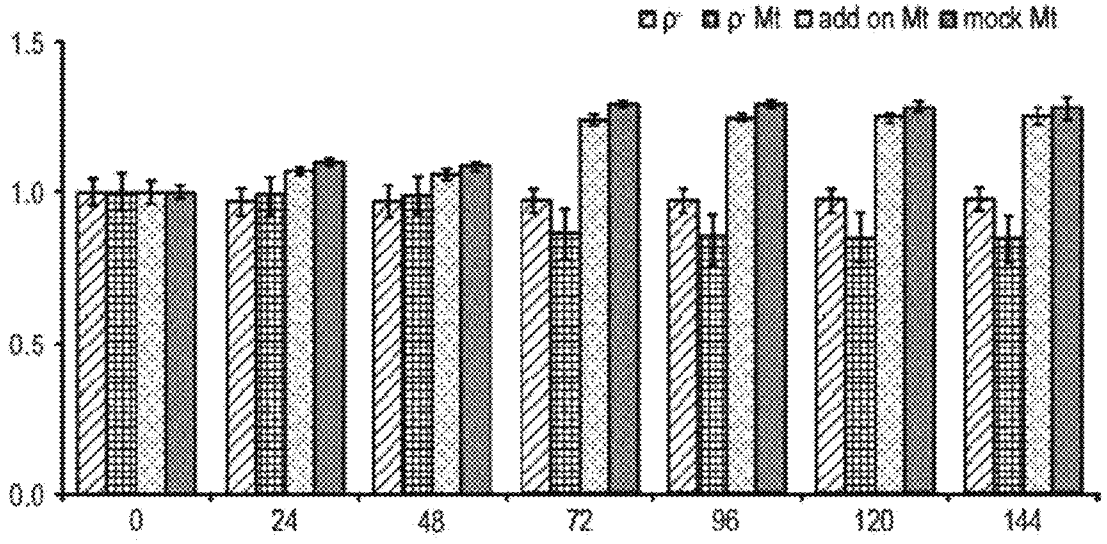

FIG. 3G and FIG. 3H depict microscopy images of DsRed labeled mitochondria (FIG. 3G) and phase contrast (FIG. 3H) after mitochondria transfer in ρ(0) cells treated with, or without, antimycin, and demonstrates that no engulfment of exogenous mitochondria occurred in cells with complete destruction of mitochondria;

FIG. 3I depicts a series of 5 still images from time lapse movie depicted in FIG. 3G, arranged chronologically, vertically FIG. 3J depicts quantification of fluorescent intensities of DsRed-labeled isolated exogenous mitochondria, measured every 24 hours in ρ (−) cells, or in ρ (−), mock transfected cells, or untreated cells (add on Mt) co-incubated with the Ds-Red mitochondria.

Figure 4A:
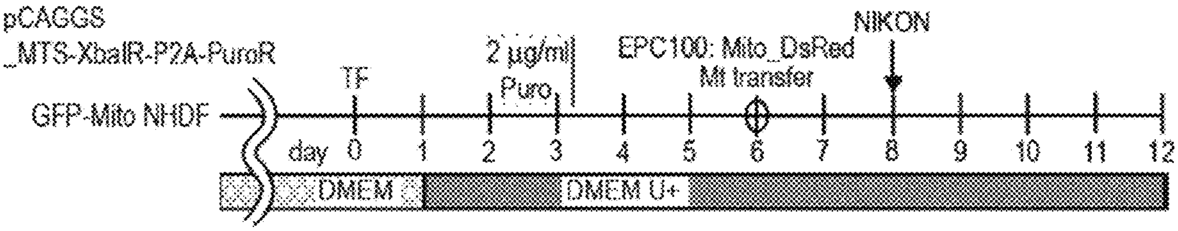

FIG. 4A depicts a scheme for measuring the fate of donor mitochondria following the engulfment by the recipient cells using DsRed marked mitochondria as donors and EGFP marked cells as recipients.

Figure 4B:
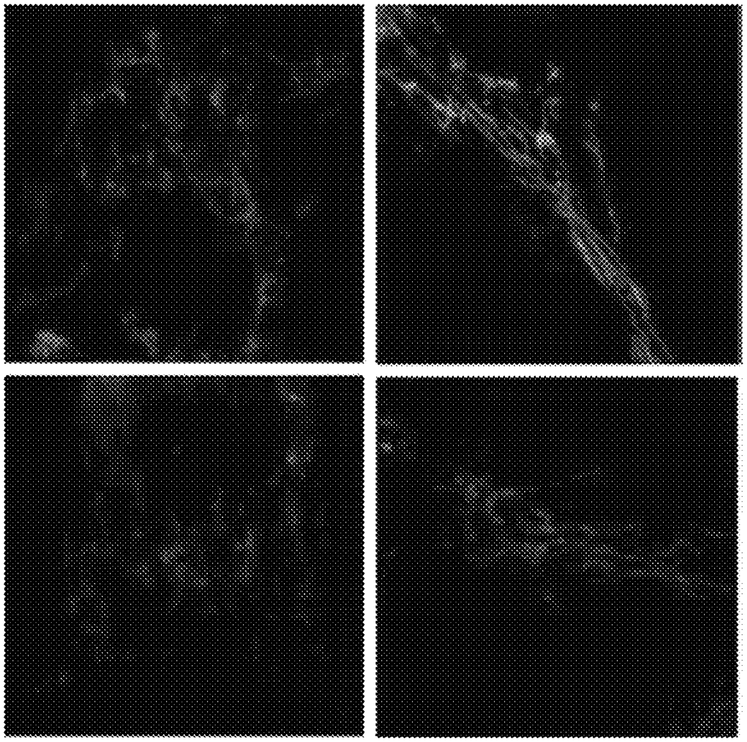

FIG. 4B depicts representative images from movies to observe engulfed exogenous mitochondria (indicated as red) in recipient cells with GFP marked mitochondria. Movies were recorded by using superfine microscopy, and few fusion images were recognized, and a major of the donor mitochondria separately exist to the pre-existing mitochondria.

Figure 4C:
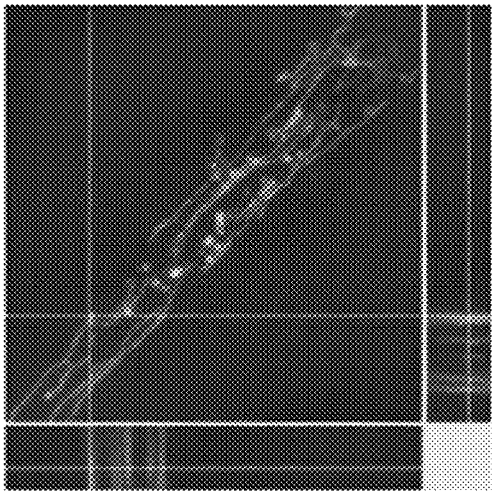

FIG. 4C depicts three dimensional reconstitutional photograph of the fusion.

Figure 4D:
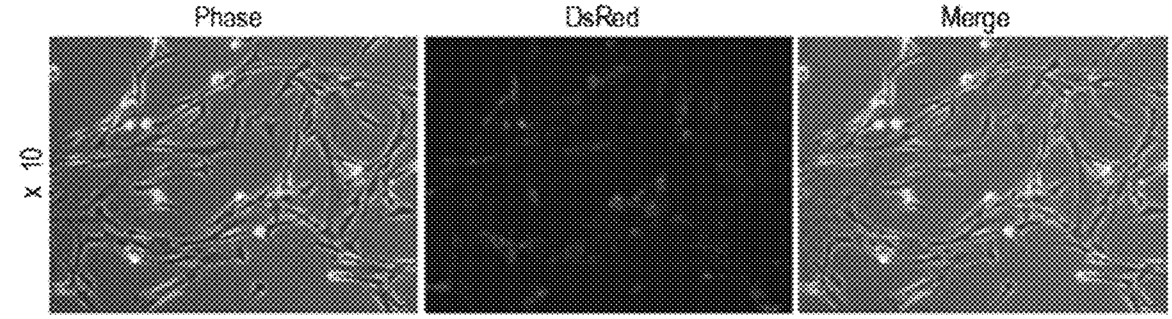

FIG. 4D depicts photos of NHDF transferred of gene coding DsRed fused with mitochondria transfer signal.

Figure 4E:
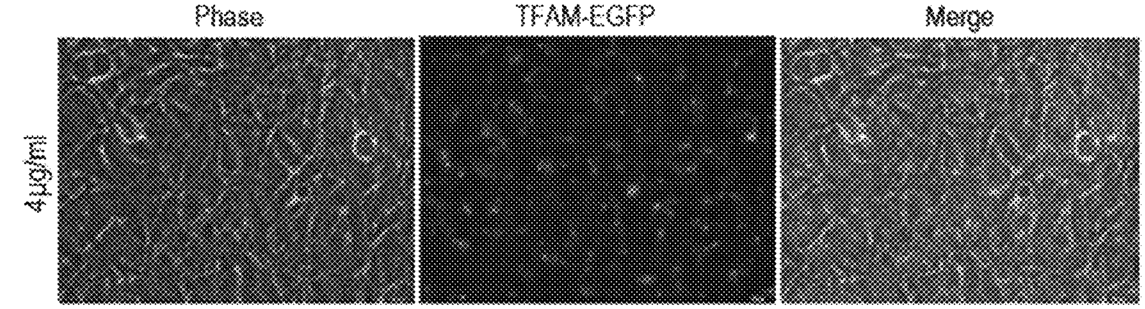

FIG. 4E depicts photos of EPC100 transferred of gene coding EGFP fused with TFAM.

Figure 4F:
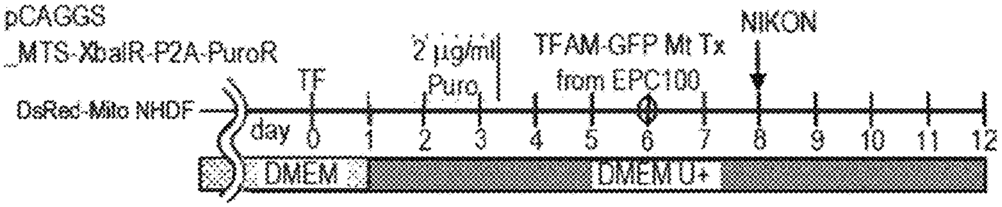

FIG. 4F depicts time course of mitochondria transfer using DsRed marked cells as recipients and TFAM targeted EGFP as donor mitochondria.

Figure 4G:

FIG. 4G depicts exogenous TFAMs were stably engrafted in the pre-existing mitochondria, after the exogenous mitochondria were transiently contacted with the recipient cell, suggesting that mitochondrial nucleoids including TFAMs were transferred to the pre-existing mitochondria via the transient contact, analogous to mouth-to-mouth feeding.

Figure 5A:
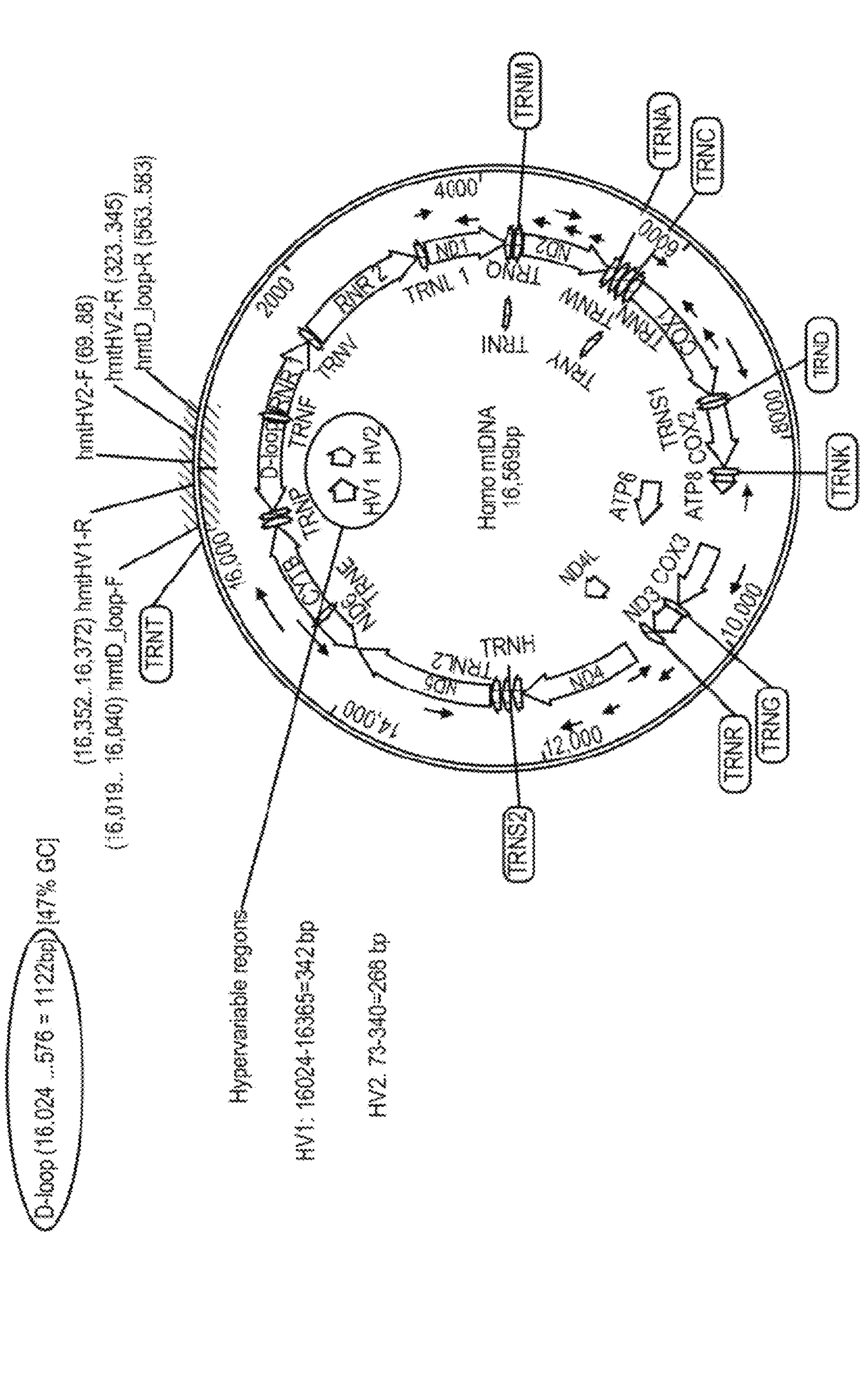
Figure 5B:
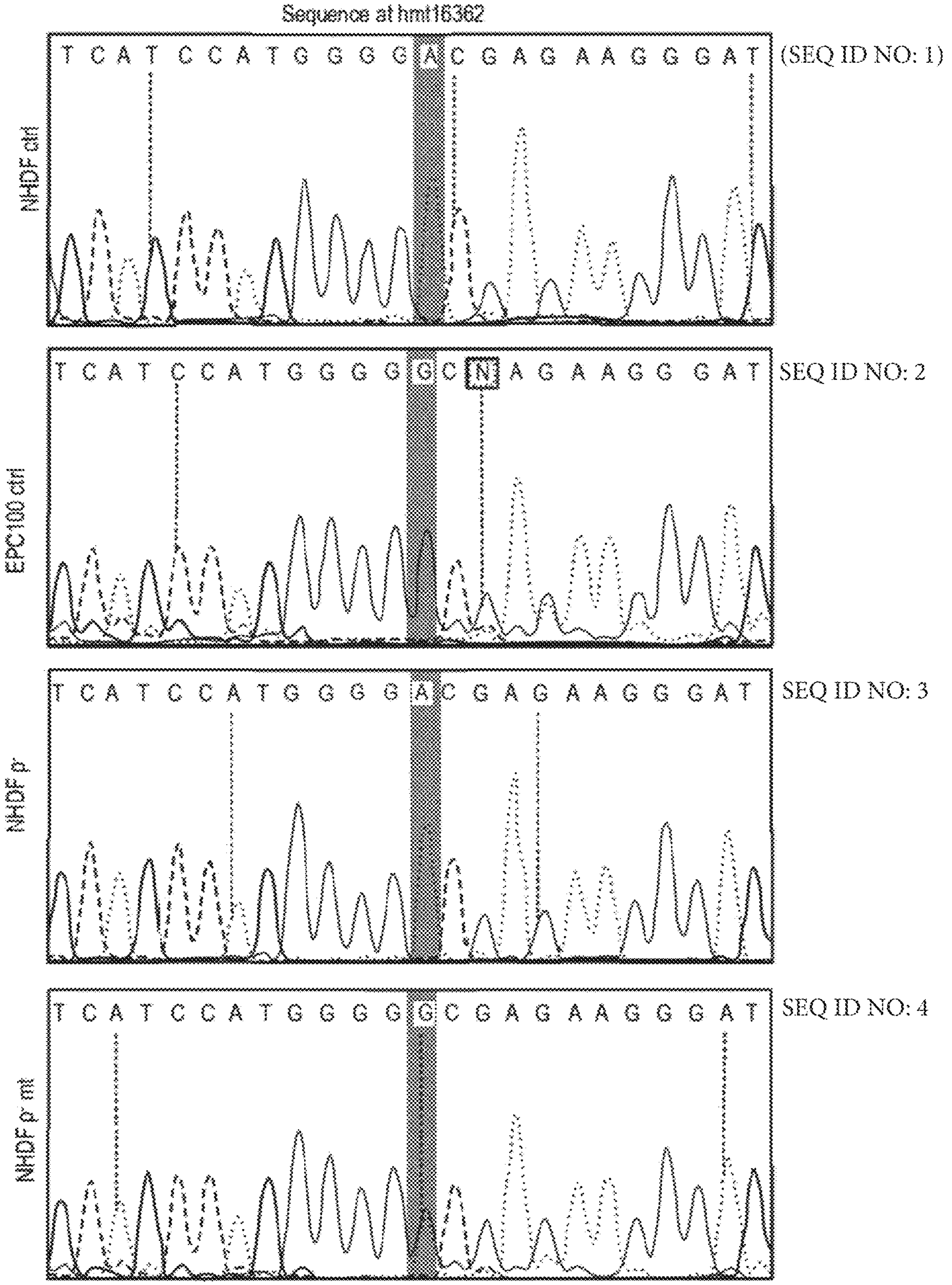

FIG. 5A depicts the whole circular mitochondrial DNA with the Cambridge reference sequence (CRS) of human mitochondrial DNA indicating hypervariable ("HV") regions 1/2, and 5 primers to identify the difference between NHDF and EPC100;

FIG. 5B depicts DNA sequencing data for the nucleotides surrounding hmt16362 in NHDF ctrl recipient cells (SEQ ID NO: 1), EPC100 ctrl donor cells (SEQ ID NO: 2), NHDF derived ρ(−) cells without mitochondria replacement (SEQ ID NO: 3), and NHDF derived ρ(−) cells with mitochondria replacement (SEQ ID NO: 4) and demonstrated that NHDF derived ρ(−) cells with mitochondria replacement (SEQ ID NO: 4) changed from A in the original recipient cells to G in the donor mtDNA at hmt16362.

Figure 5C:
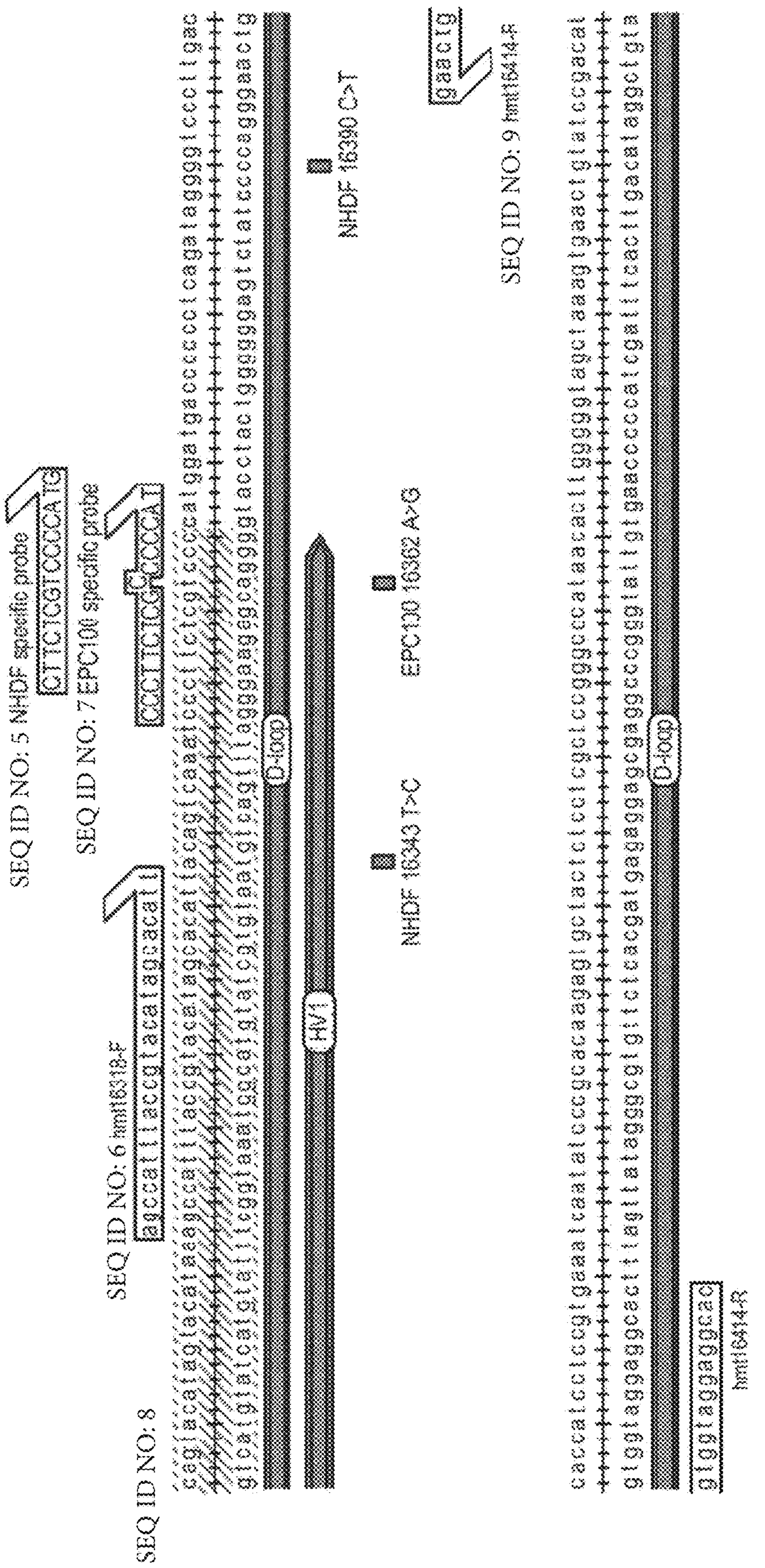

FIG. 5C depicts the hmt16318-F (SEQ ID) NO: 6) and hmt16414-R (SEQ ID NO: 9) set of primers used for amplification of the HV1 region of human mitochondrial DNA D-Loop (SEQ ID NO: 8) surrounding hmt16362 and the NHDF specific probe (SEQ ID NO: 5) and the EPC100 specific probe (SEQ ID NO: 7) that were designed for the TaqMan SNP genotyping assay.

Figure 5D:
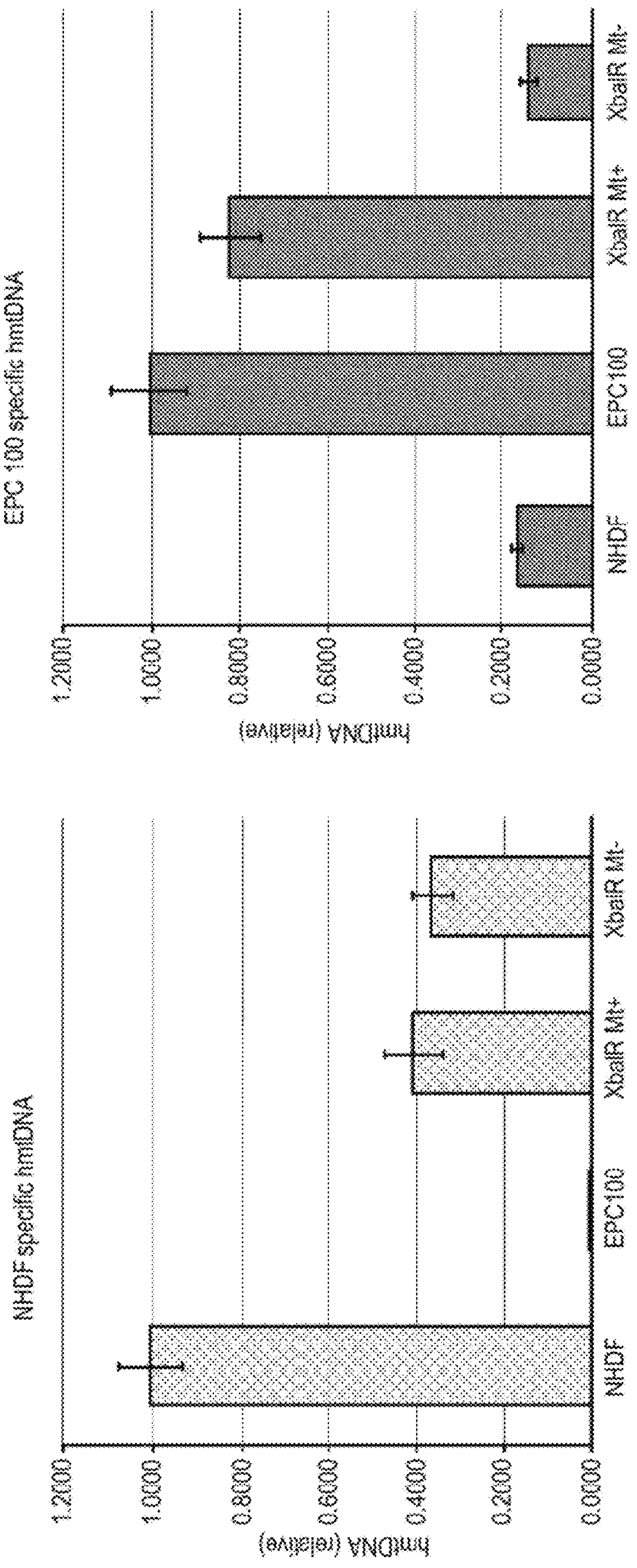

FIG. 5D depicts quantification of the NHDF specific hmtDNA (left) and EPC100 specific hmtDNA (right) in the parental NHDF and EPC100 cell lines, or in NHDF cells treated with XbaIR, with (XbaIR Mt+) or without mitochondria (XbaIR Mt−) from EPC100 cells, and revealed that EPC100 mitochondria was successfully transferred in XbaIR Mt+ cells, as evaluated by using single nucleotide polymorphism assay (SNP).

Figure 6A:
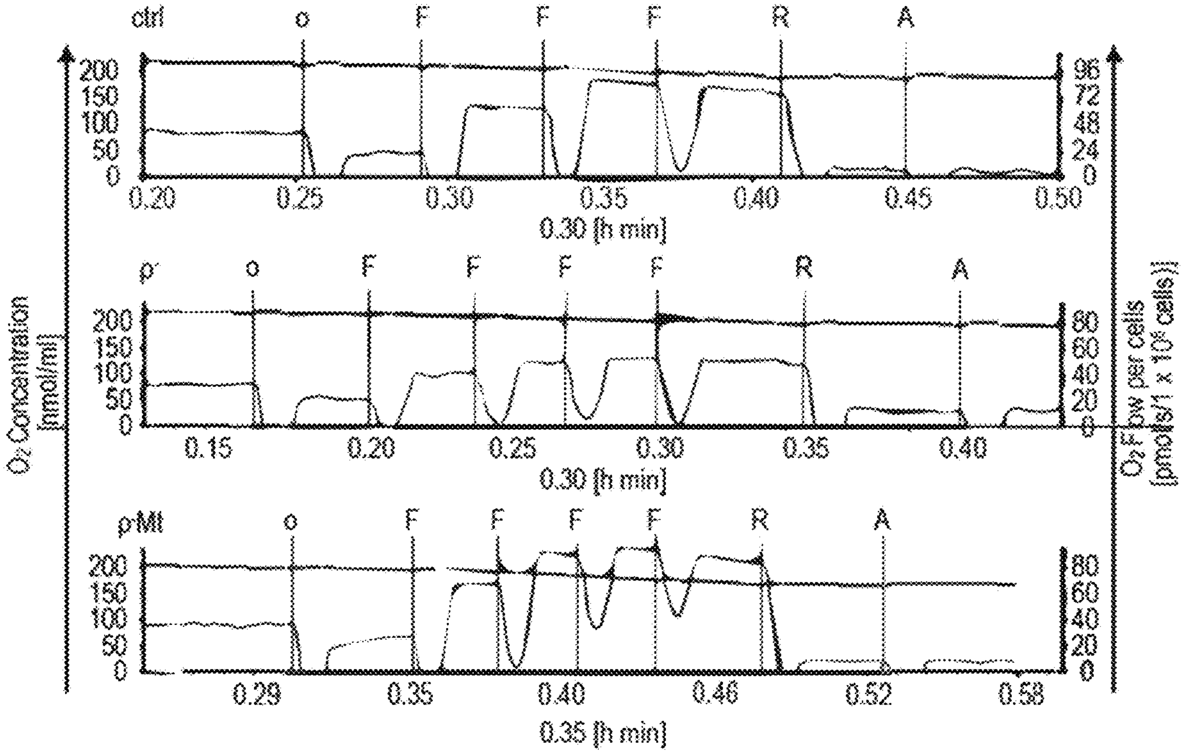

FIG. 6A depicts representative oxygraphies from a mitochondria functioning assay performed using Oroboros Oxygraph-2k, and demonstrated that NHDF cells with mitochondria replaced (ρ(−) Mt) (bottom) regained the mitochondrial function, relative to control NHDF cells (top), and ρ(−) NHDF cells without mitochondrial replacement (middle). The machine depicts respiratory flow in red line (pmol/sec/1×10$^6$ cells, right axis) and oxygen concentrations in blue line (μM, left axis).

Figure 6B:
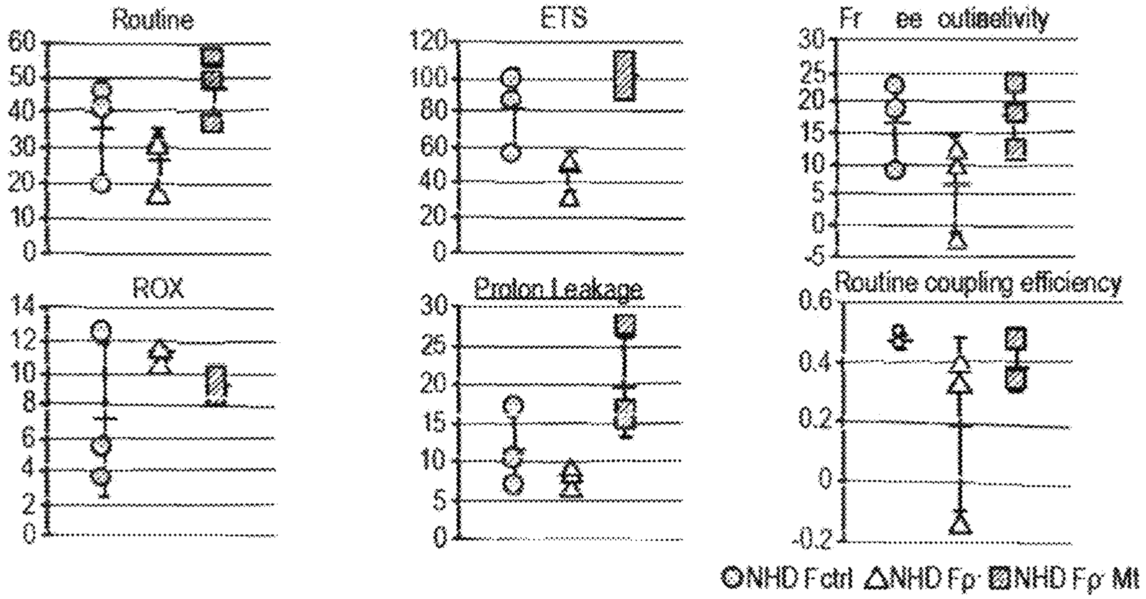

FIG. 6B depicts that the respiratory flows (routine, Electron Transfer System (ETS), ROX), free routine activities (mitochondrial ATP production), proton leakage, and coupling efficiency in each stage demonstrated that mitochondrial replacement in NHDF cells (ρ(−) Mt) regained the mitochondrial function, relative to NHDF control cells, and NHDF without mtDNA replacement (ρ(−)).

Figure 6C:
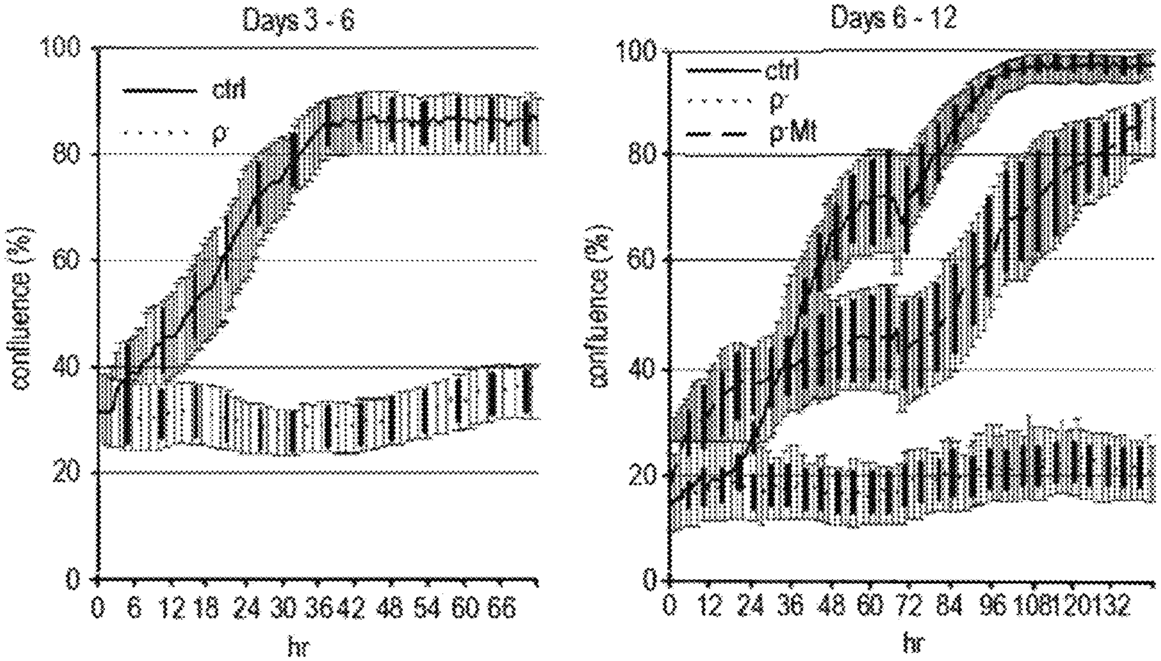

FIG. 6C depicts a time-lapse microphotograph, which enabled to estimate continuous cell number based on the surface area of cells, and demonstrated that ρ(−) cells were quiescent state between days 3 to 12, whereas mitochondria replaced cells regained the growth capability after day 6.

Figure 6D:
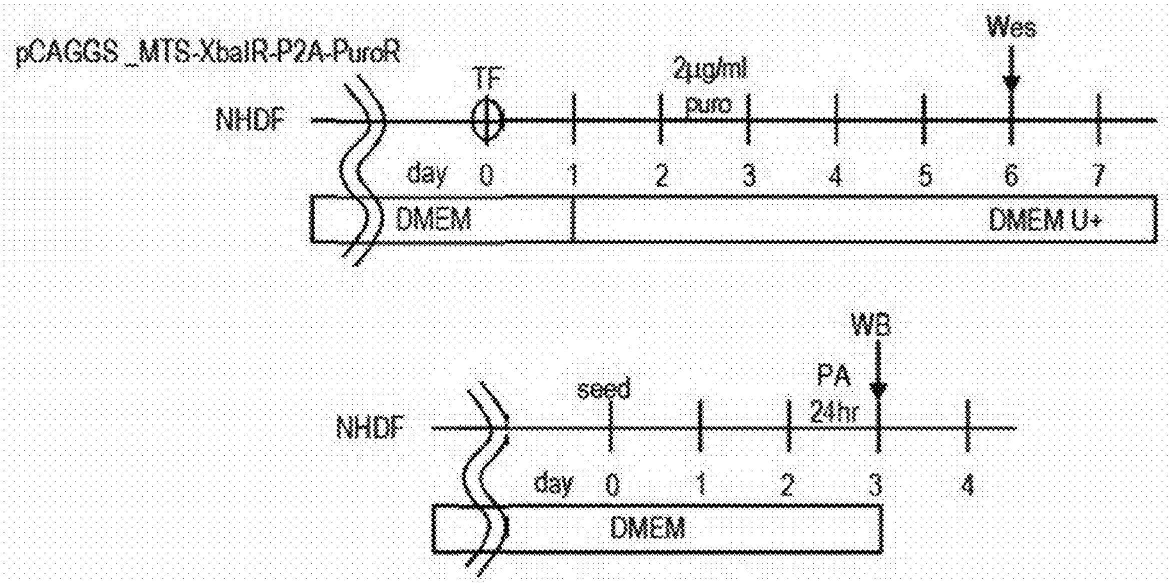

FIG. 6D depicts a scheme of the protocol used to examine the molecular mechanism for macropinocytosis, which involved transfecting NHDF cells with the MTS-XbaIR-P2A-PuroR plasmid, selecting with puromycin, and then serum starving the cells for 60 min, or treating the cells with palmitic acid (PA) or rapamycin for 24 hours.

FIG. 6E-FIG. 6H depict quantification of the WES™ analysis for phosphorylation of S6 kinase (FIG. 6E) and phosphorylation of AMPK (FIG. 6G), and corresponding WES™ blots (FIG. 6F) and (FIG. 6H), respectively, which demonstrated that AMPK is activated and mTOR is completely suppressed in ρ(−) cells. Rapa: Rapamycin, PA: Palmitic acid, EAA−: Essential amino acid-deficient.

Figure 6E:
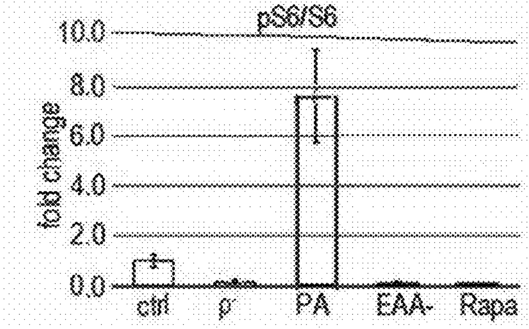
Figure 6F:
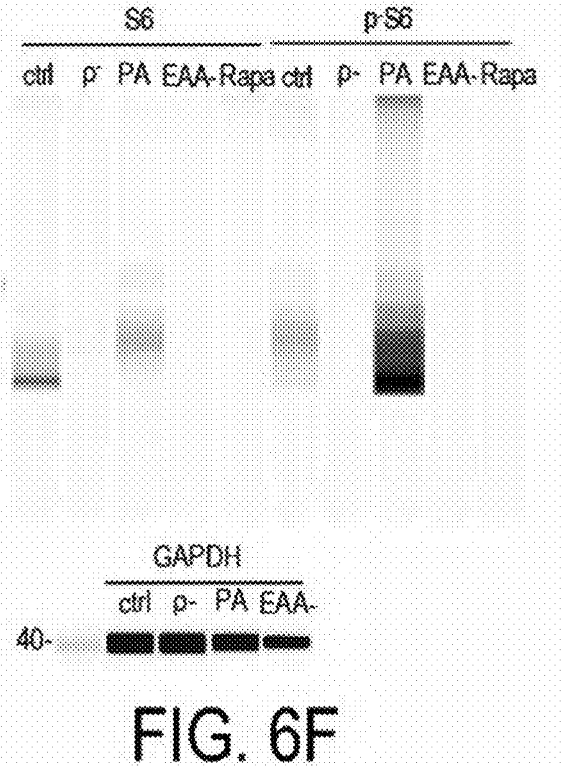
Figure 6G:
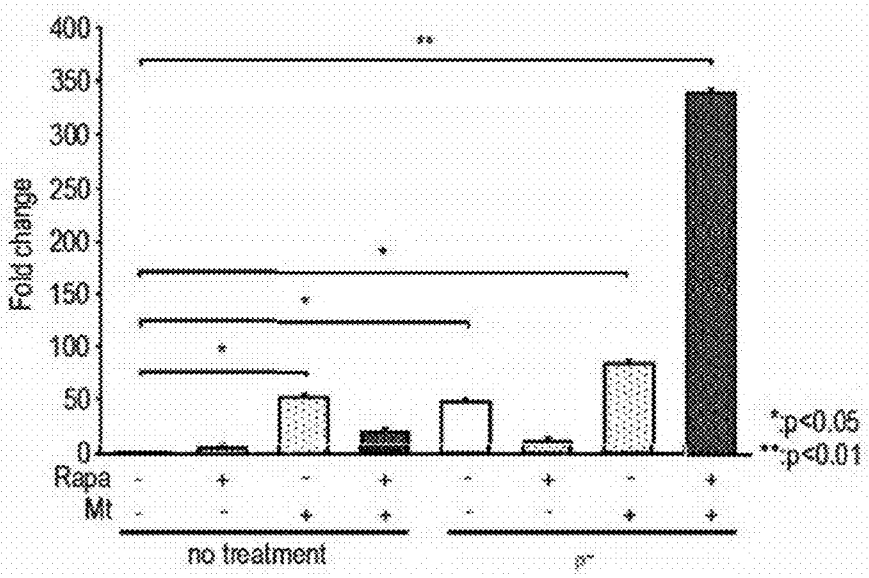
Figure 6H:
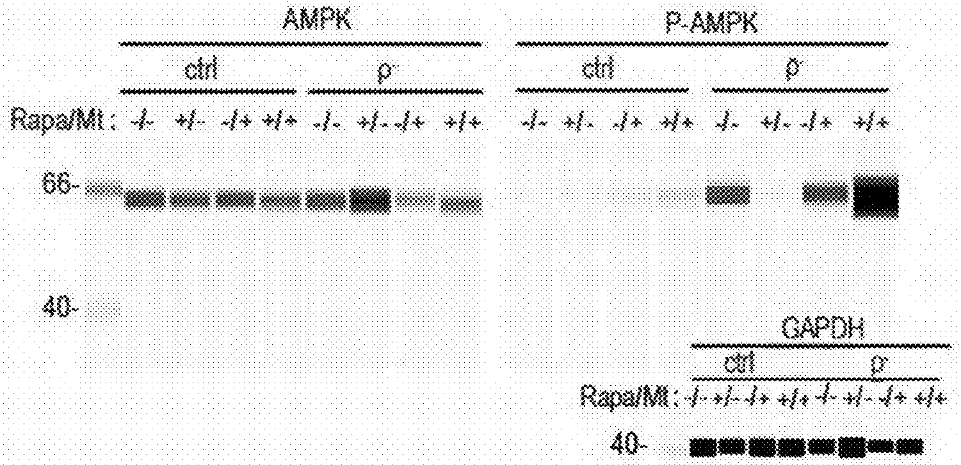
Figure 6I:
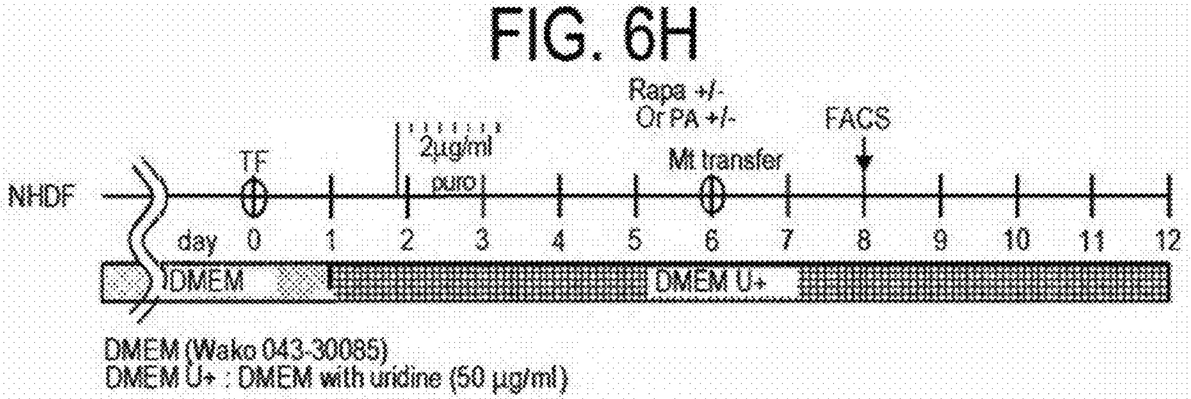

FIG. 6I depicts the protocol used to examine the effect of mTOR mediated macropinocytosis in the setting of MirC generation protocol.

Figure 6J:
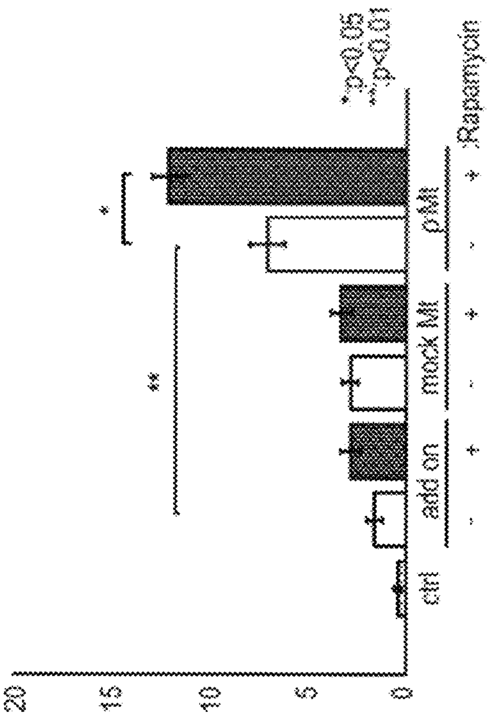
Figure 6K:
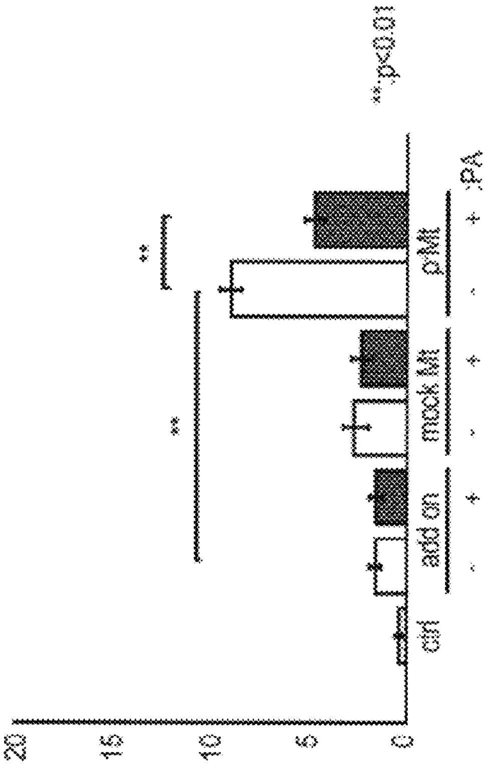
Figure 6L:
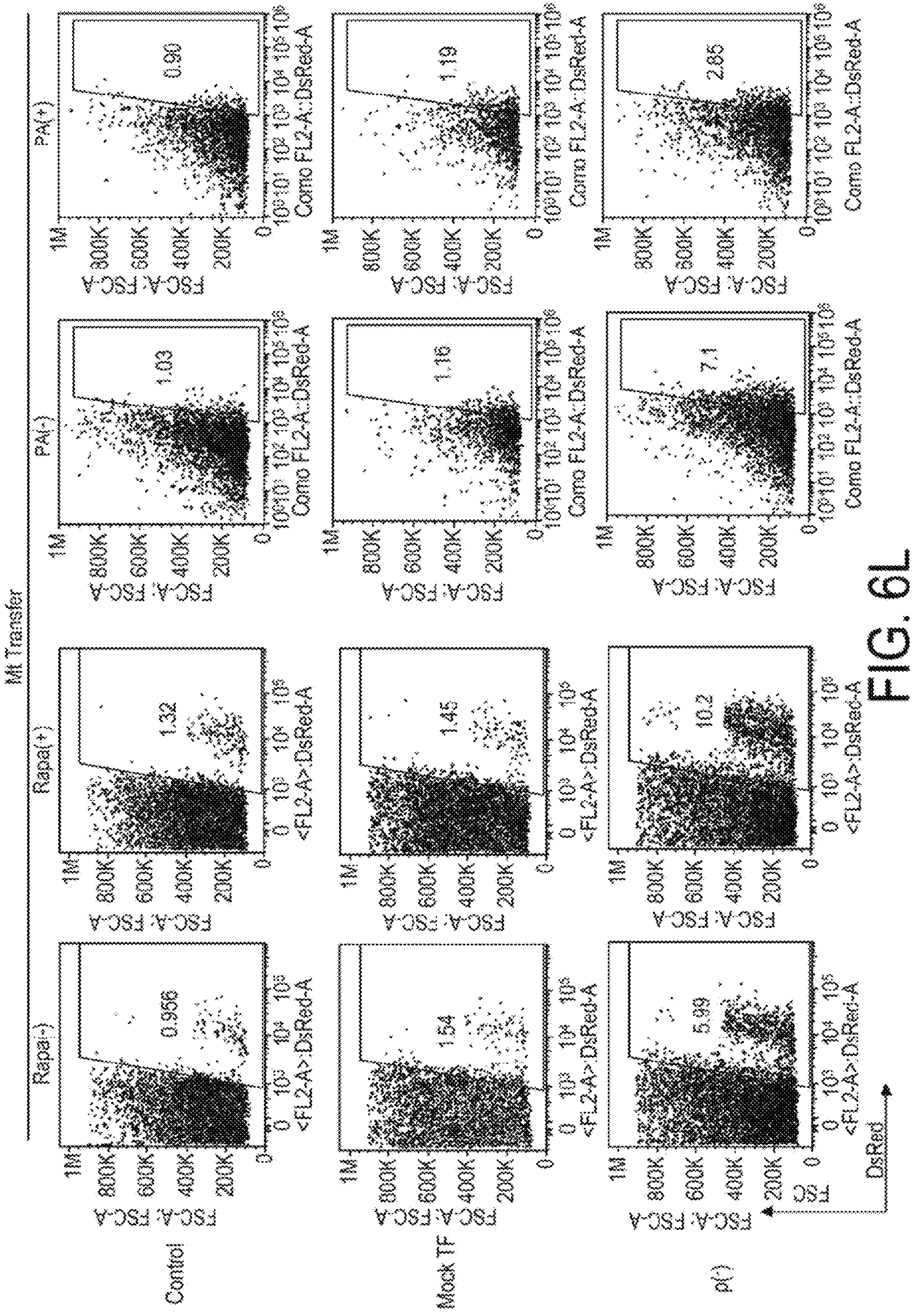

FIG. 6J-FIG. 6L depict quantification (FIG. 63 and FIG. 6K) AND FACS analysis (FIG. 6L) and of DsRed labeled mitochondrial uptake in control (top), mock transfected cells (middle), and ρ(−) cells, with or without rapamycin treatment, or with or without palmitic acid (PA) treatment. ρ(−) cells exhibited greater uptake of mitochondria, relative to control of mock TF cells, and the uptake of mitochondria was significantly increased after rapamycin treatment, whereas palmitic acid decreased mitochondria uptake in ρ(−) cells.

Figure 7A:
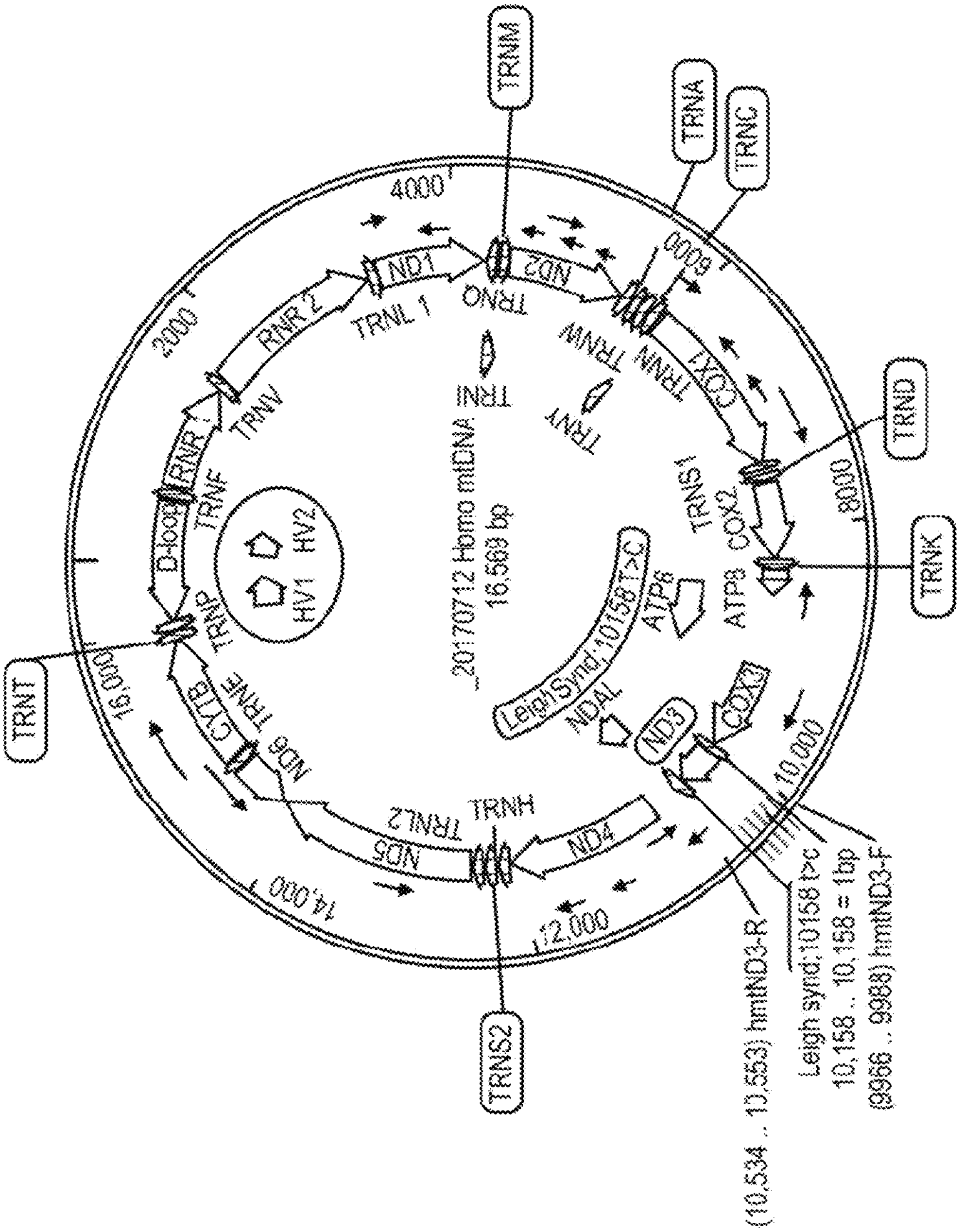

FIG. 7A depicts the whole mtDNA sequence showing the Leigh syndrome associated mutation of 10158T>C in the respiratory chain complex I (CD) subunit of the ND3 gene in mitochondrial DNA.

Figure 7B:
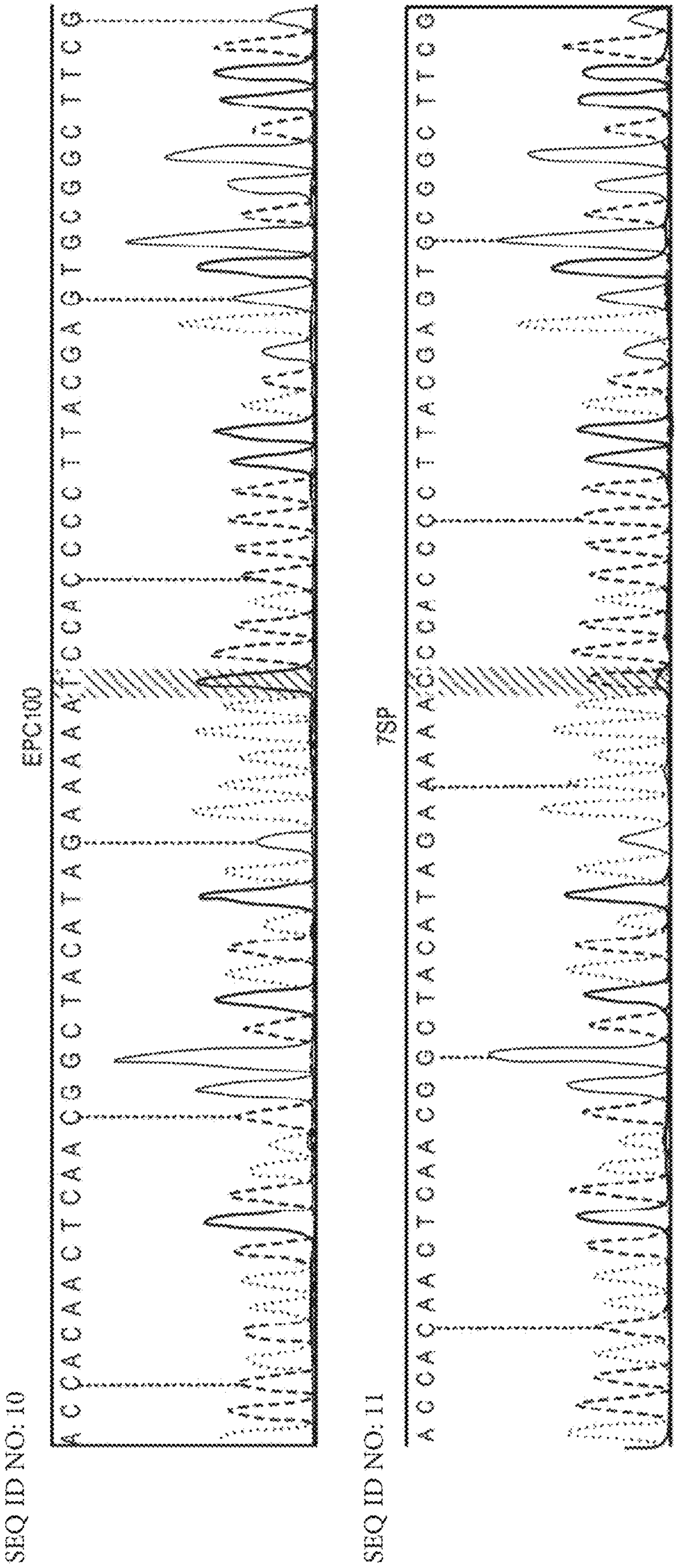

FIG. 7B depicts DNA sequencing data for the nucleotides surrounding hmt10158 within ND3 in EPC100 cells (top; SEQ ID NO: 10) and Leigh syndrome (7SP) fibroblasts (bottom; SEQ ID NO: 11), and revealed the mutation, 10158T>C, with a mosaic of C in the major wave and T in the minor wave, indicating the heteroplasmy.

Figure 7C:
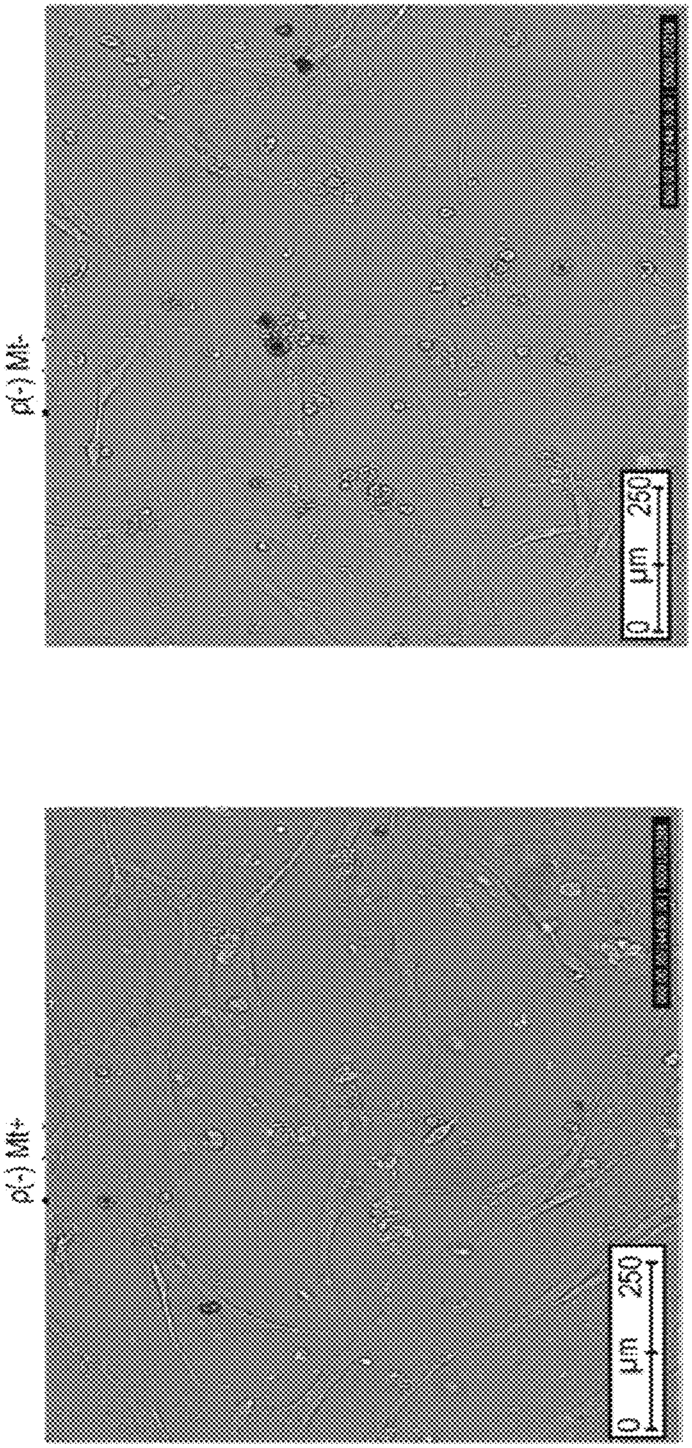

FIG. 7C depicts photographs from time lapse movies that demonstrated similar behavior in both ρ(−) 7SP fibroblasts, with and without exogenous mitochondria, as in NHDF experiments.

Figure 7D:
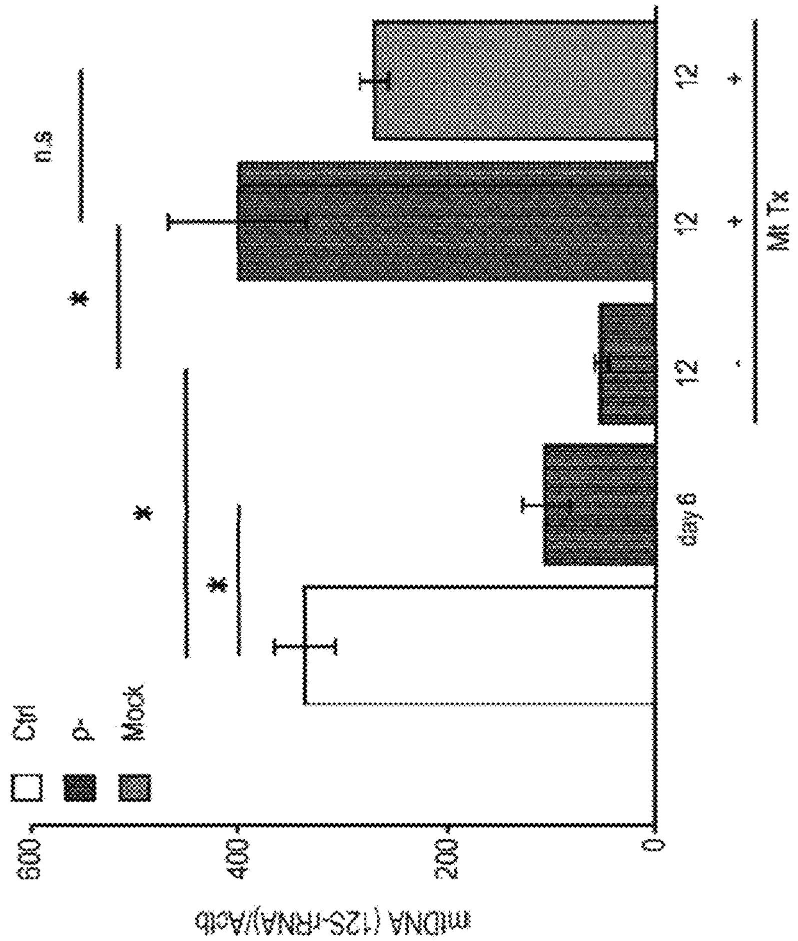

FIG. 7D depicts quantification of mitochondrial DNA copy numbers estimated by qPCR of human 12S rRNA relative to nuclear β-actin levels in NHDF cells after gene transfection of XbaIR or Mock transfection. Mitochondria were transferred to recipient cells where indicated. XbaIR resulted in significant reduction of mitochondrial DNA, which could be rescued by transfer of exogenous mitochondria. (n=3)

Figure 7E:
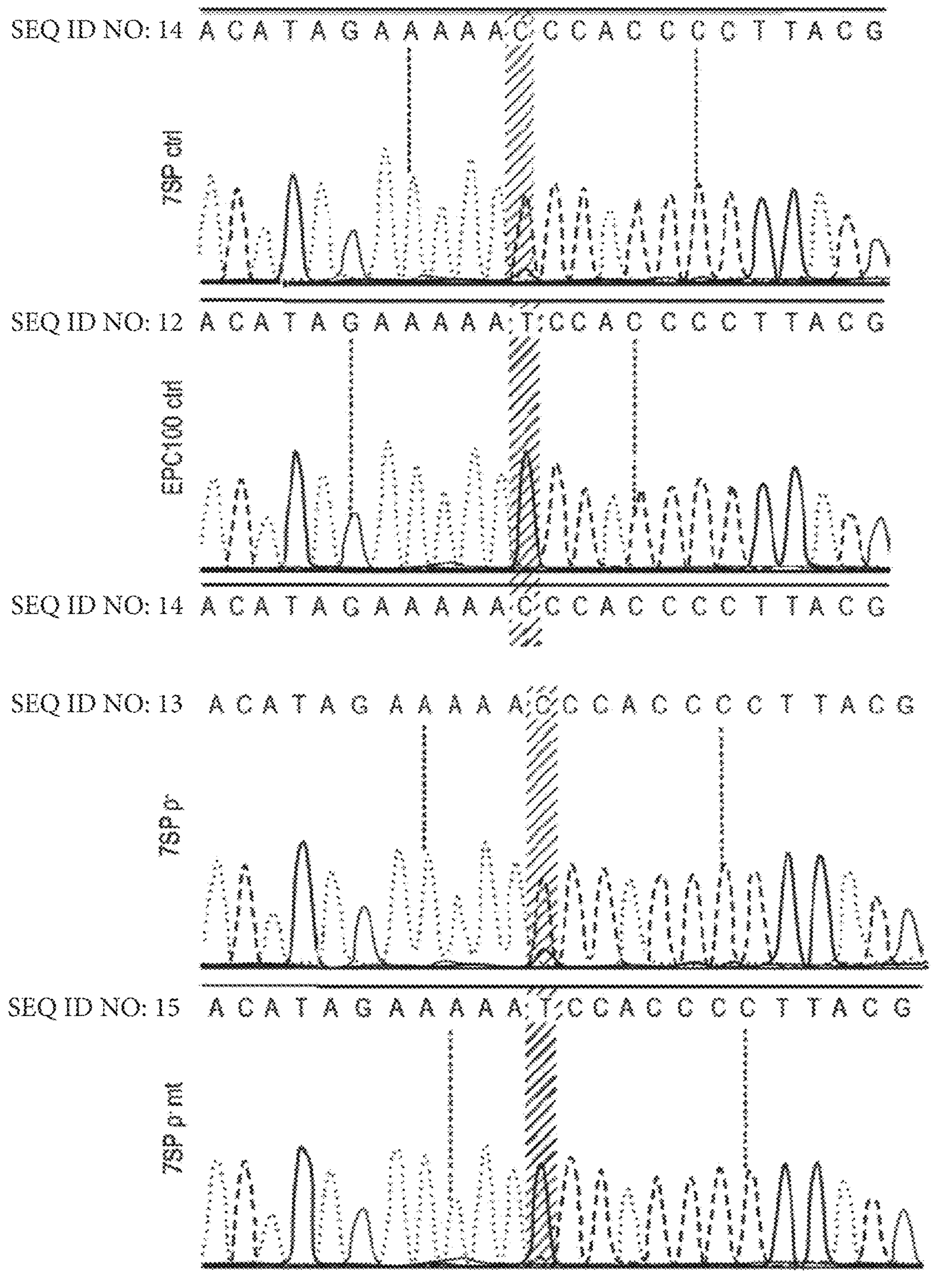

FIG. 7E depicts DNA sequencing data for the nucleotides surrounding hmt10158 in 7SP ctrl recipient cells (SEQ ID NO: 14), EPC100 ctrl donor cells (SEQ ID NO: 12), 7SP derived ρ(−) cells without mitochondria replacement (SEQ ID NO: 13), and 7SP derived ρ(−) cells with mitochondria replacement (SEQ ID NO: 15), and revealed that 7SP ctrl cells are heteroplasmic (majority 10158C; SEQ ID NO: 14), whereas EPC100 has only T in the same site in mitochondrial DNA (SEQ ID NO: 12). The ρ(−) cells stem from 7SP cells expressed the same wave as the original (SEQ ID NO: 13), whereas mitochondria replaced 7SP cells demonstrated T as major wave (SEQ ID NO: 15).

Figure 7F:
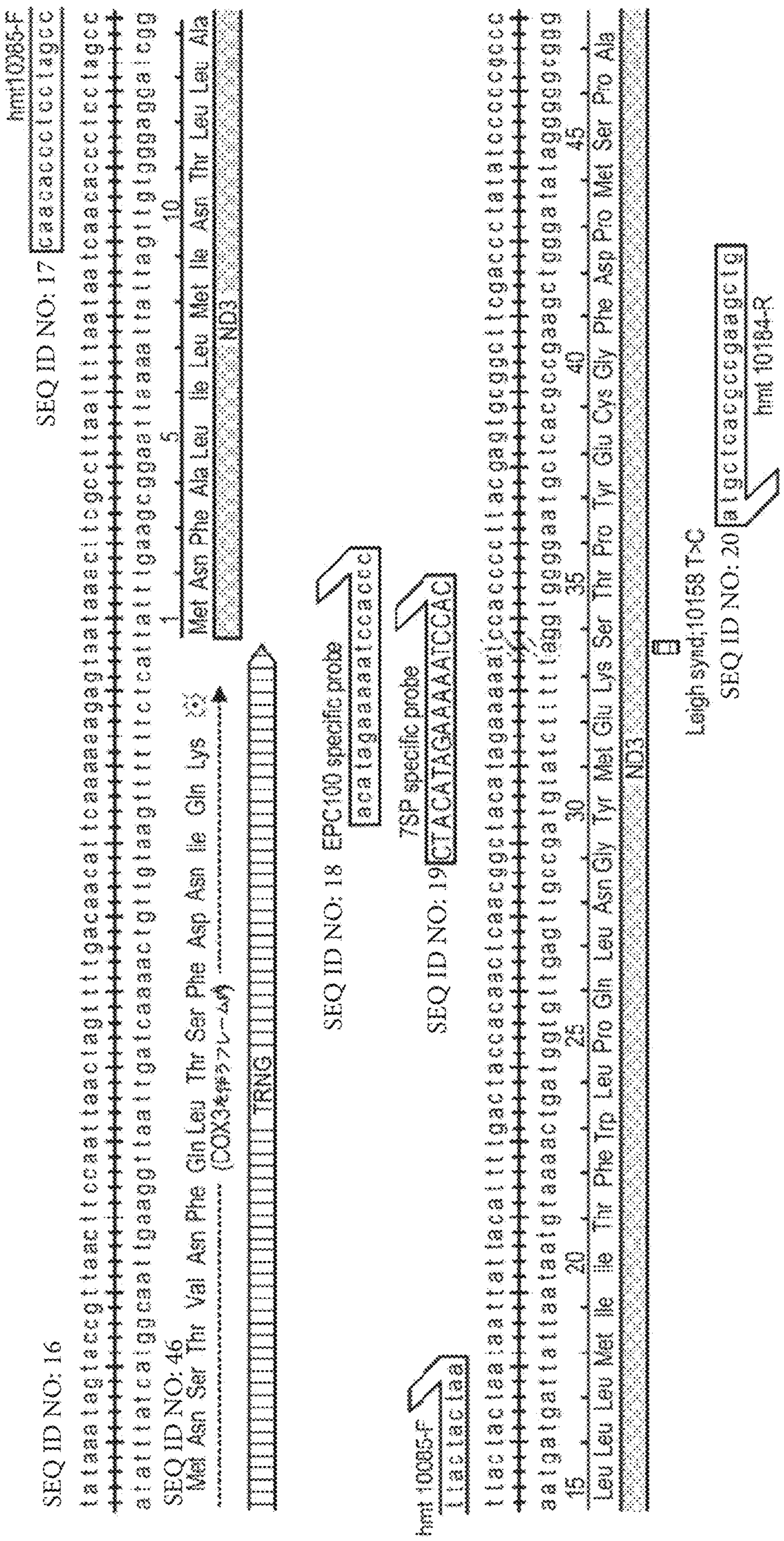

FIG. 7F depicts the hmt10085-F (SEQ ID NO: 17) and hmt10184-R (SEQ ID NO: 20) set of primers used for amplification of ND3 of human mitochondrial DNA (SEQ ID NO: 16) surrounding the Leigh syndrome associated SNP at hmt10158, and the EPC100 specific probe (SEQ ID NO: 18) and the 7SP specific probe (SEQ ID NO: 19) that were designed for the TaqMan SNP genotyping assay. The ND3 peptide sequence is also depicted (SEQ ID NO: 46).

Figure 7G:
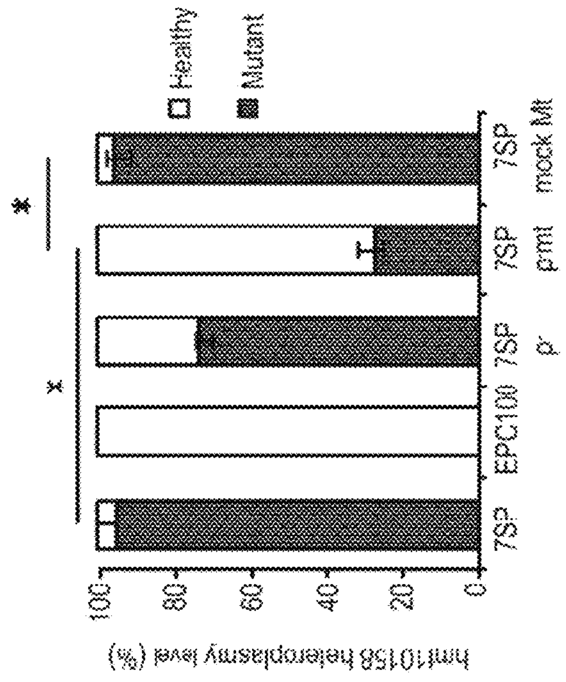

FIG. 7G depicts quantification of the percentage of hmt10158 heteroplasmy in each cell group evaluated by SNP assay, and revealed that exogenous normal sequence ("healthy") dominated up to 80% in mitochondria replaced 7SP cells, in spite that the original heteroplasmy of mutant sequence was over 90%. In case of mock transfectant, the heteroplasmy did not significantly change, and maintained the almost same ratio.

Figure 7H:
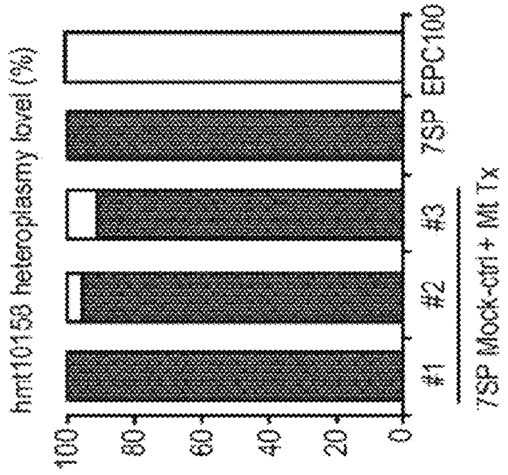
Figure 7I:
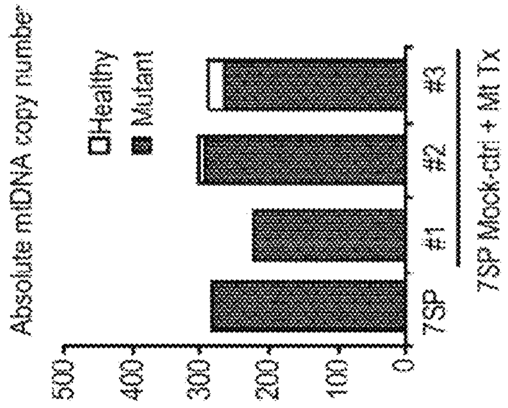

FIG. 7H and FIG. 7I depict quantification of heteroplasmy level percentage (FIG. 7H) and absolute mtDNA copy number (FIG. 7I) in three independent experiments in 7SP cells treated with mock control and subjected to mitochondrial transfer.

Figure 7J:
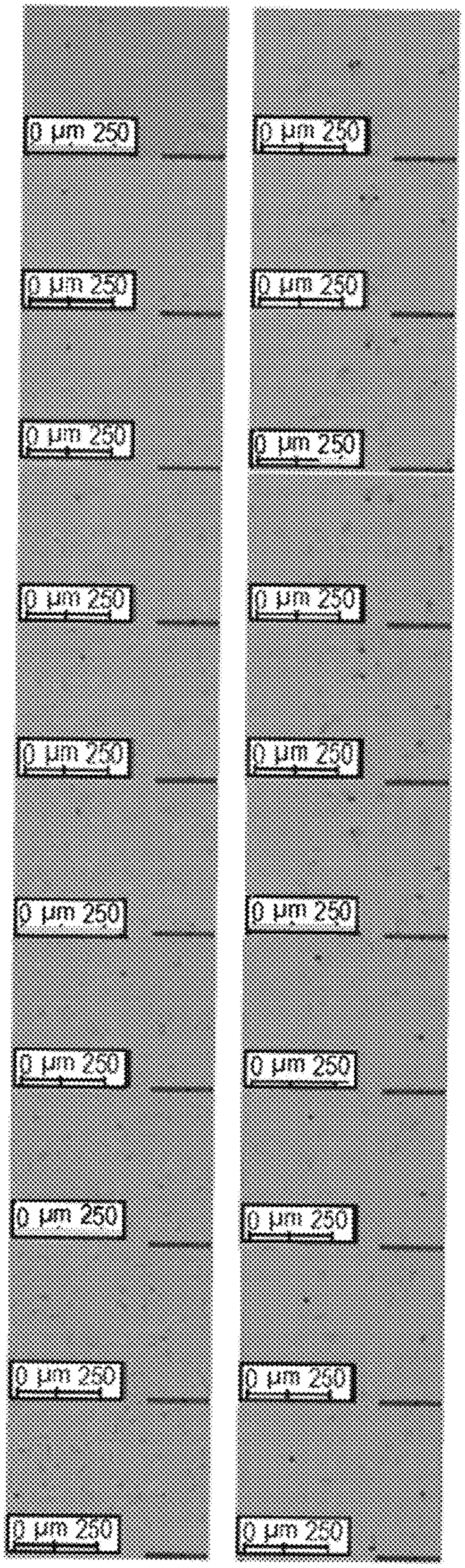

FIG. 7J depicts a series of 10 still images from the time lapse movie depicted in FIG. 7C, arranged chronologically, vertically.

Figure 8A:
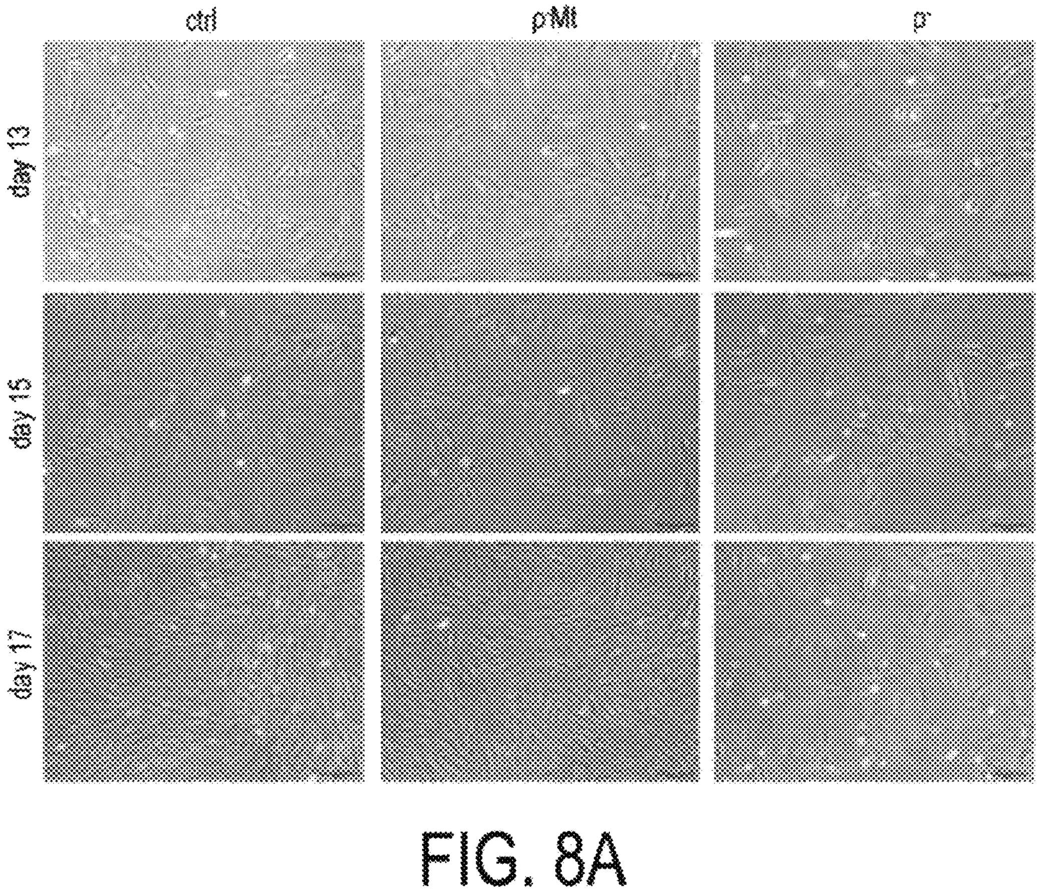

FIG. 8A depicts microscopic photos in ρ(−) mitochondria replaced 7SP fibroblasts with time, compared with the original 7SP fibroblasts and ρ(−) 7SP fibroblasts, and revealed that the growth of mitochondria replaced cells recovered to near control level.

Figure 8B:
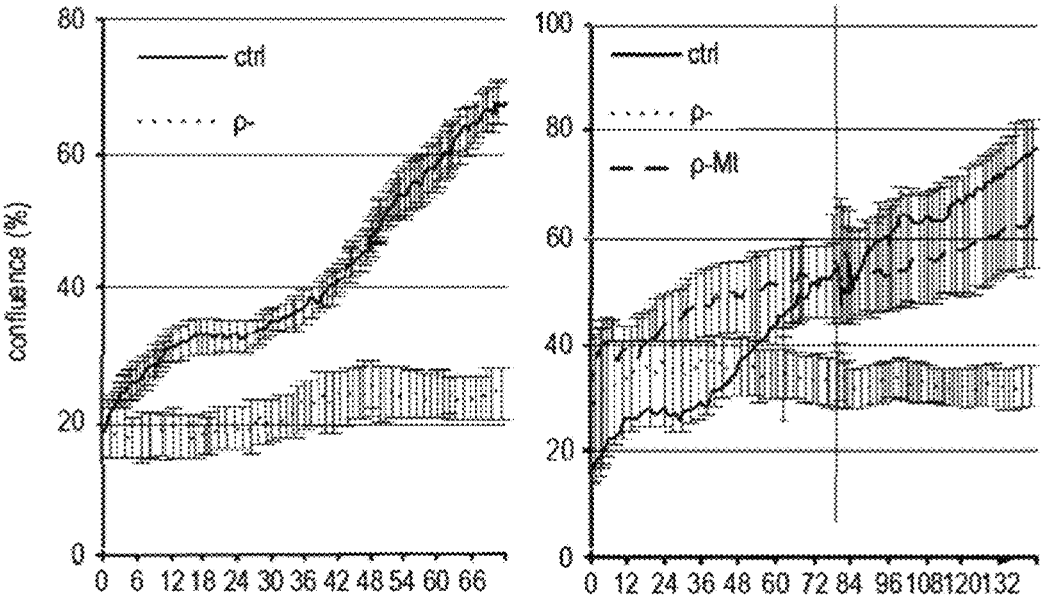

FIG. 8B depicts time-lapse-estimated cellular growth in 7SP fibroblasts, ρ(−) 7SP fibroblast, and ρ(−) 7SP fibroblasts with mitochondria replacement, and revealed that ρ(−) 7SP fibroblasts were quiescent, whereas mitochondria replaced 7SP cells recovered cellular growth to levels equivalent to the original 7SP fibroblasts around day 12.

Figure 8C:
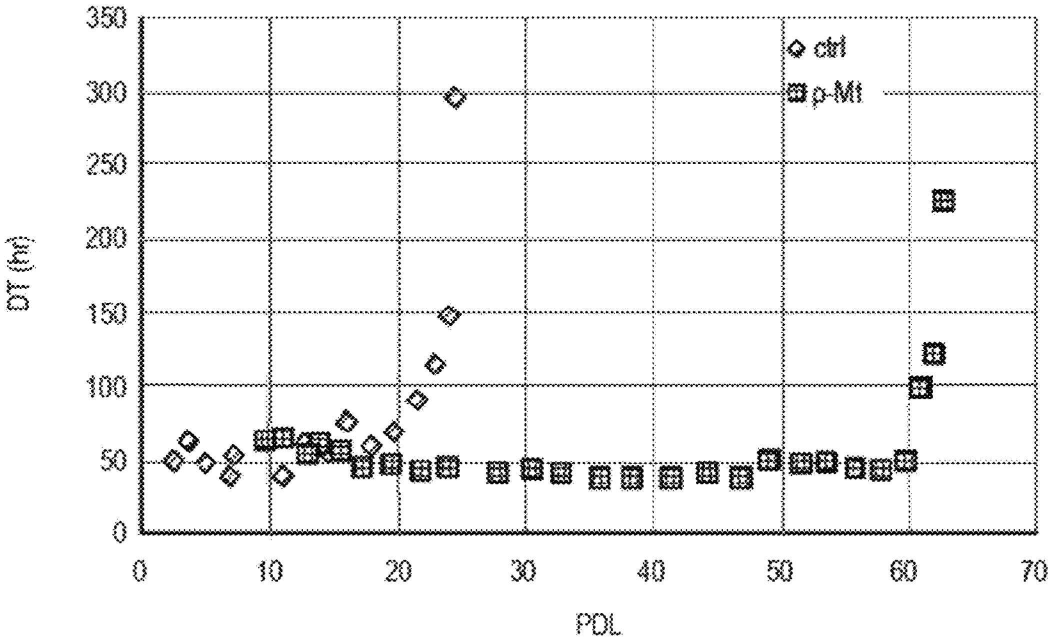

FIG. 8C depicts senescence in 7SP fibroblasts around population doubling levels (PDL) 25, which was extended to about PDL 63 in ρ(−) 7SP fibroblasts with healthy mitochondria replacement performed at PDL 8, indicating the lifespan extension of ρ(−) 7SP fibroblasts with healthy mitochondria replacement.

Figure 8D:
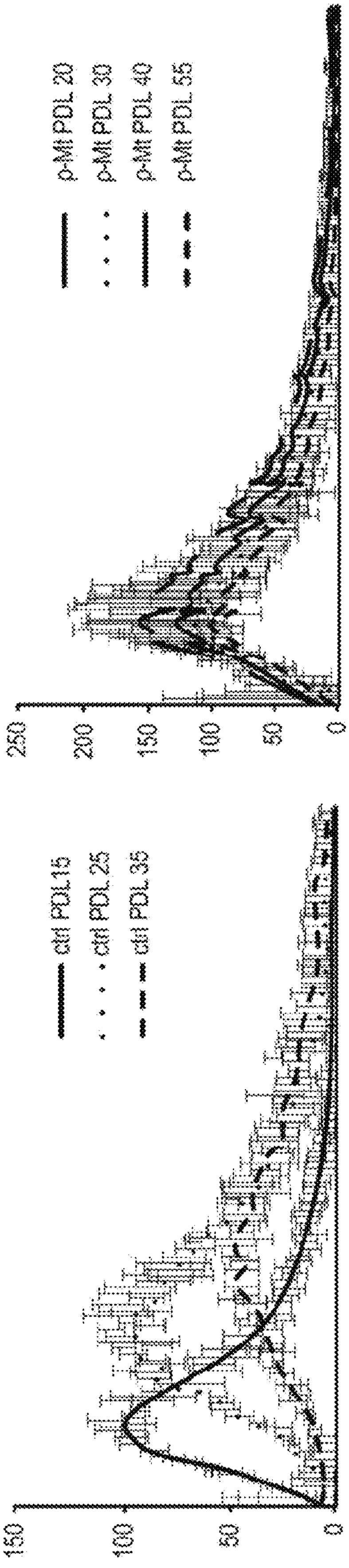

FIG. 8D depicts the increase in PDL produces an increase in cell size (left), which is reverted following mitochondria replacement, and is maintained even past PDL 50 (right).

Figure 8E:
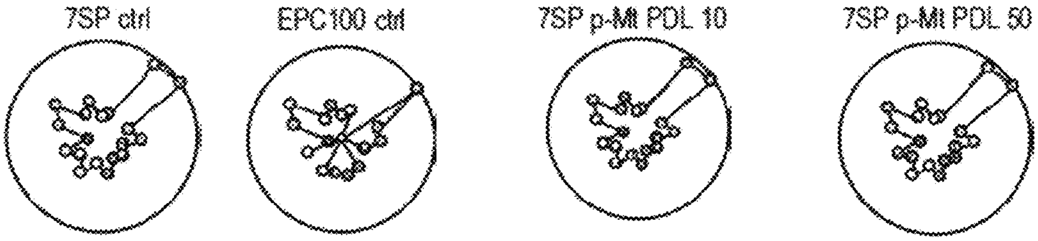

FIG. 8E depicts short tandem repeat (STR) assay, which discriminates cells with different origins and identifies contamination of different type of cells. The patterns of STR in mitochondria replaced cells in different time point were completely identical to that in the original 7SP fibroblasts.

Figure 8F:
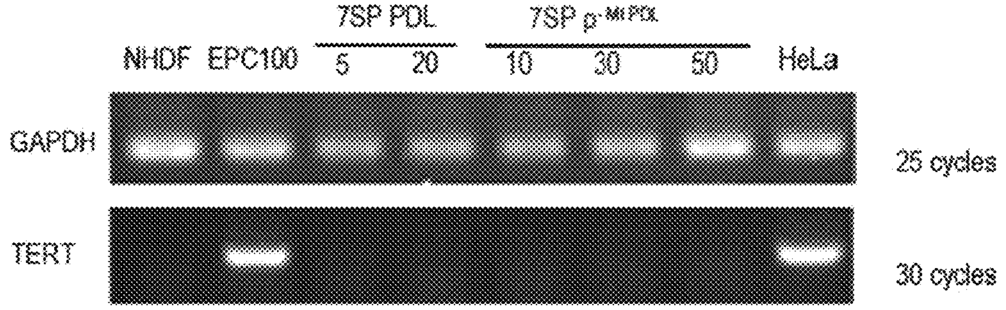

FIG. 8F depicts RT-PCR quantification of telomerase in 7SP fibroblasts and mitochondria replaced cells for different PDLs, relative to HeLa and EPC100, indicating that the cells were not transformed into cancer cells.

Figure 9A:
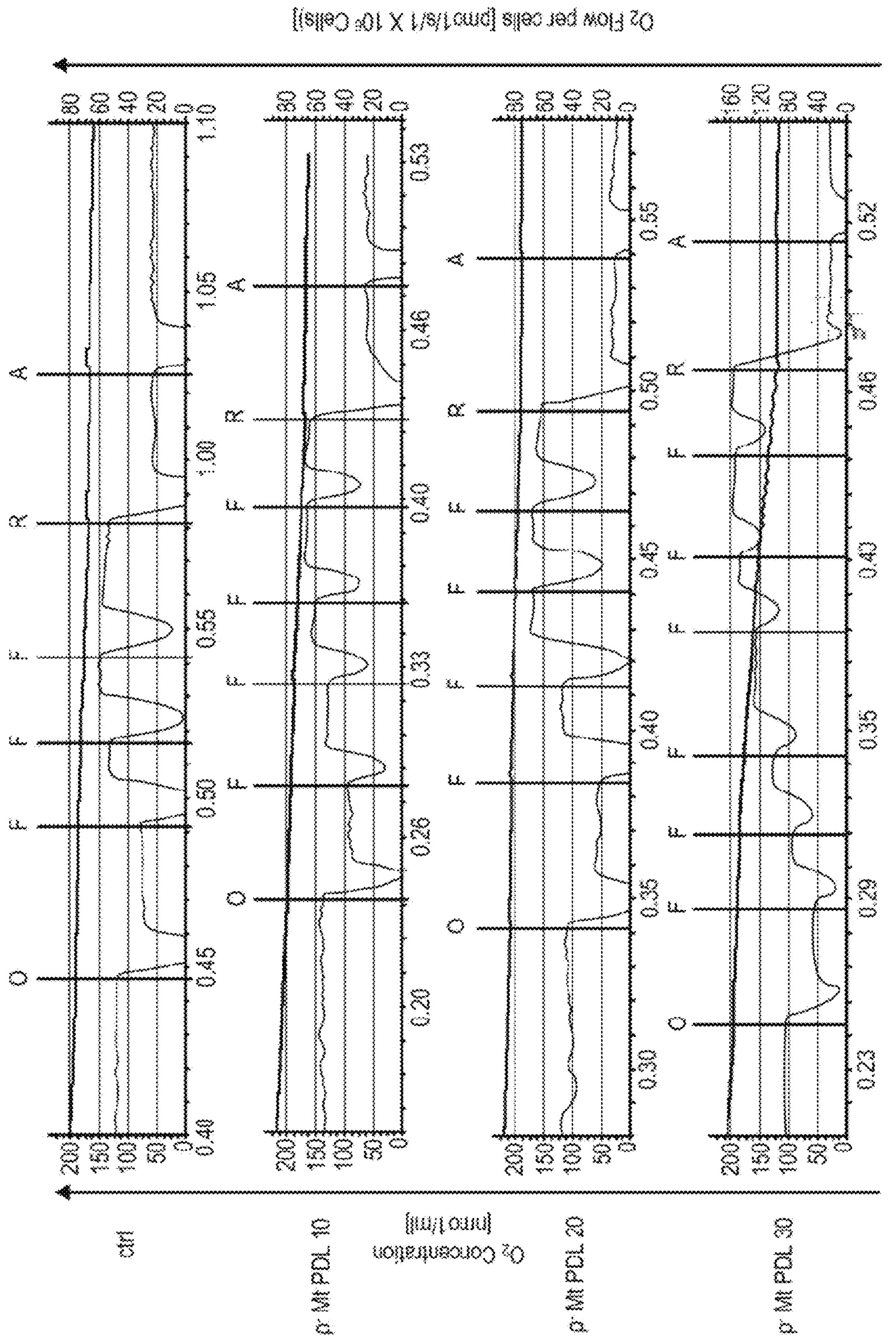

FIG. 9A depicts oxygraphies in 7SP fibroblasts at different PDLs following mitochondria replacement using Oroboros O2k according to coupling-control protocol (CCP), and the kinetics demonstrated that mitochondria function dropped at early PDL followed by a gradual recovery that eventually surpassed the original capability, relative to the original 7SP fibroblasts as control.

Figure 9B:
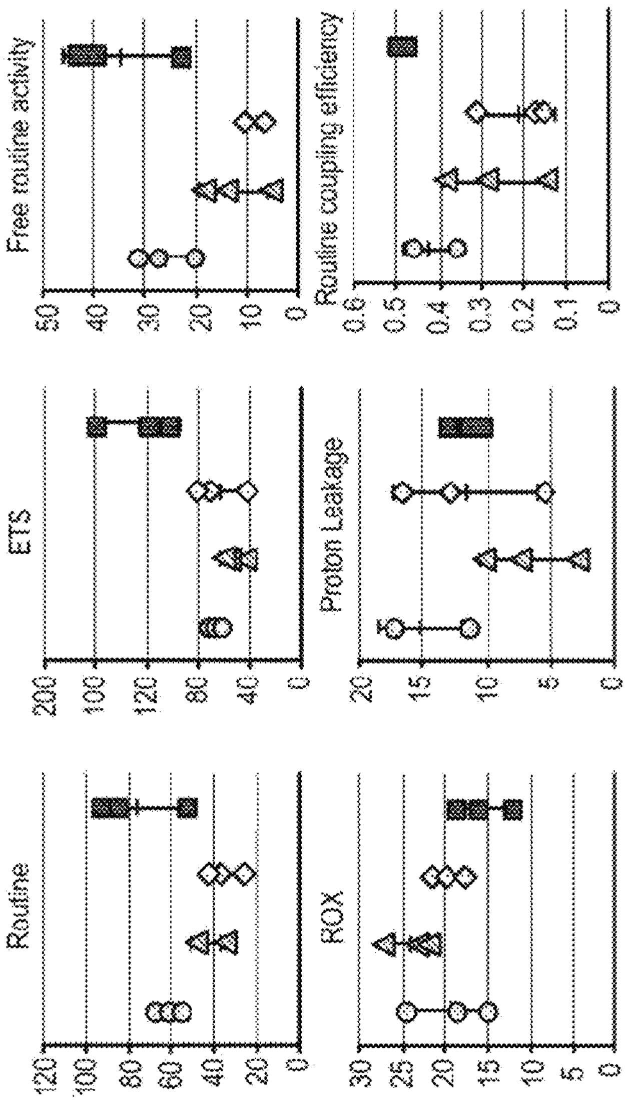
Figure 9C:
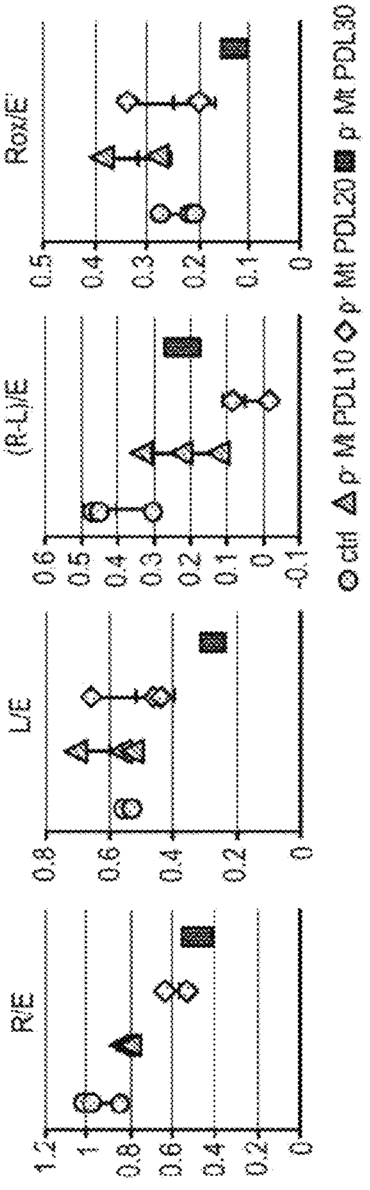

FIG. 9B and FIG. 9C depict that the respiratory flows (routine, Electron Transfer System (ETS), ROX), free routine activities (mitochondrial ATP production), proton leakage, and coupling efficiency (FIG. 9B), as well as the flux control ratios (FCRs), ROX/E, L/E, R/E, and (R−L)/E (FIG. 9C) regained to near control levels in mitochondrial replaced cells (ρ(−) Mt) after approximately PDL30.

Figure 10A:
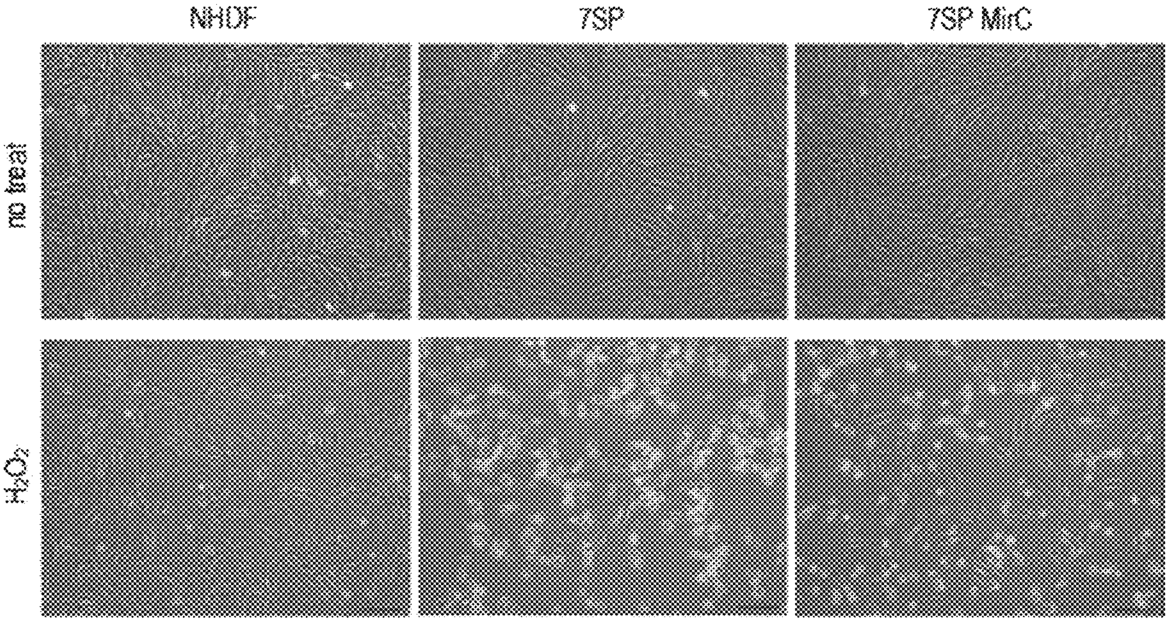

FIG. 10A depicts microscopy images of NHDF, 7SP, an 7SP MirC cells under basal conditions or following reperfusion using $H_2O_7$, and show that 7SP cells are highly sensitive to $H_2O_2$ relative to NHDF cells, whereas the 7SP MirC are not.

Figure 10B:
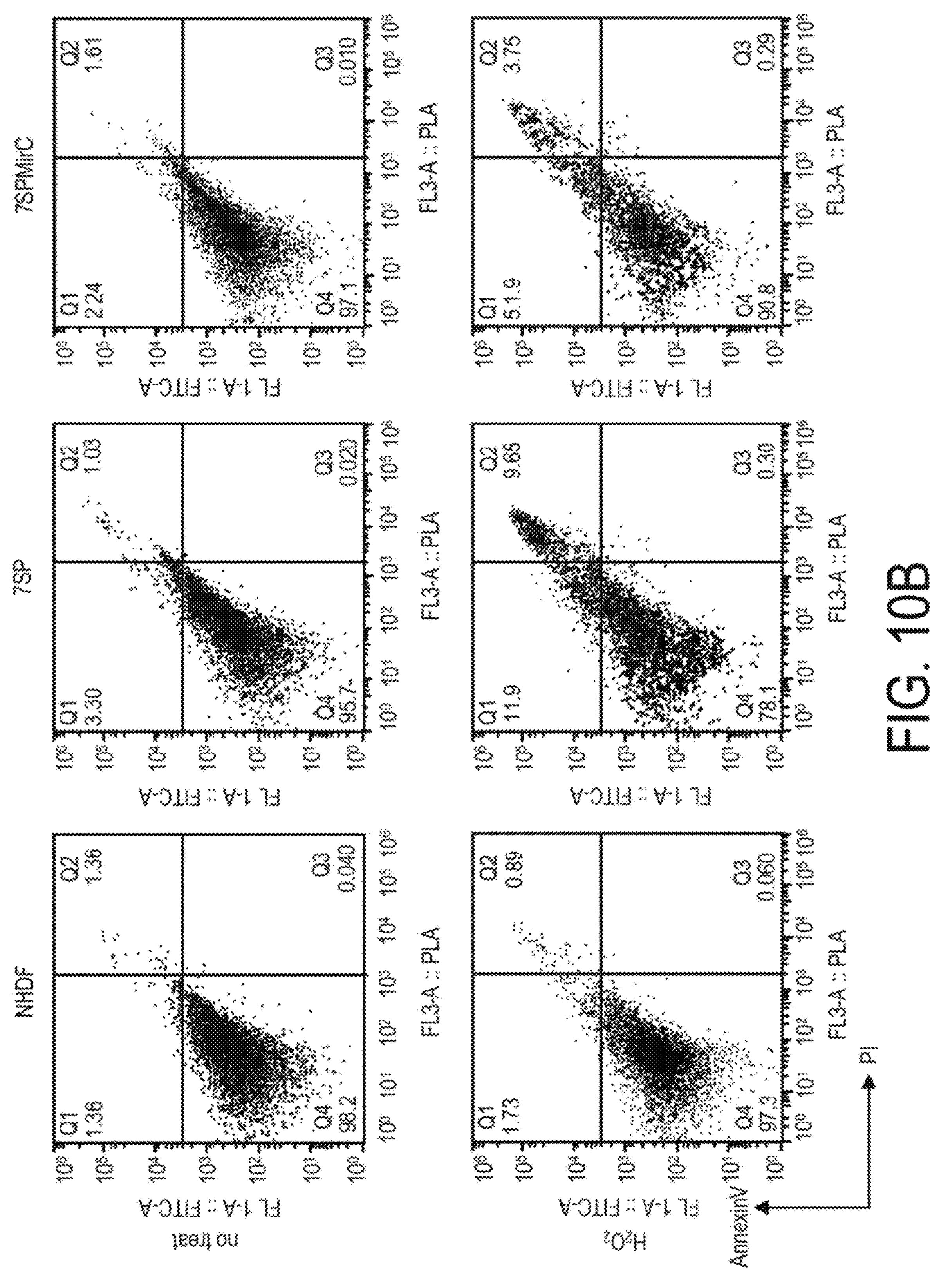
Figure 10C:
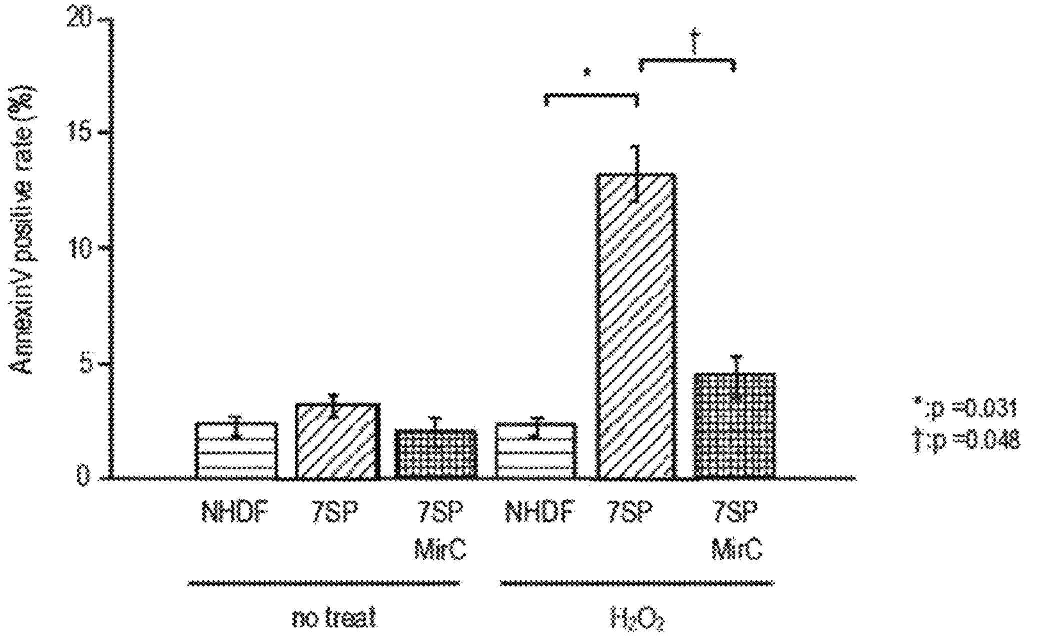
Figure 10D:
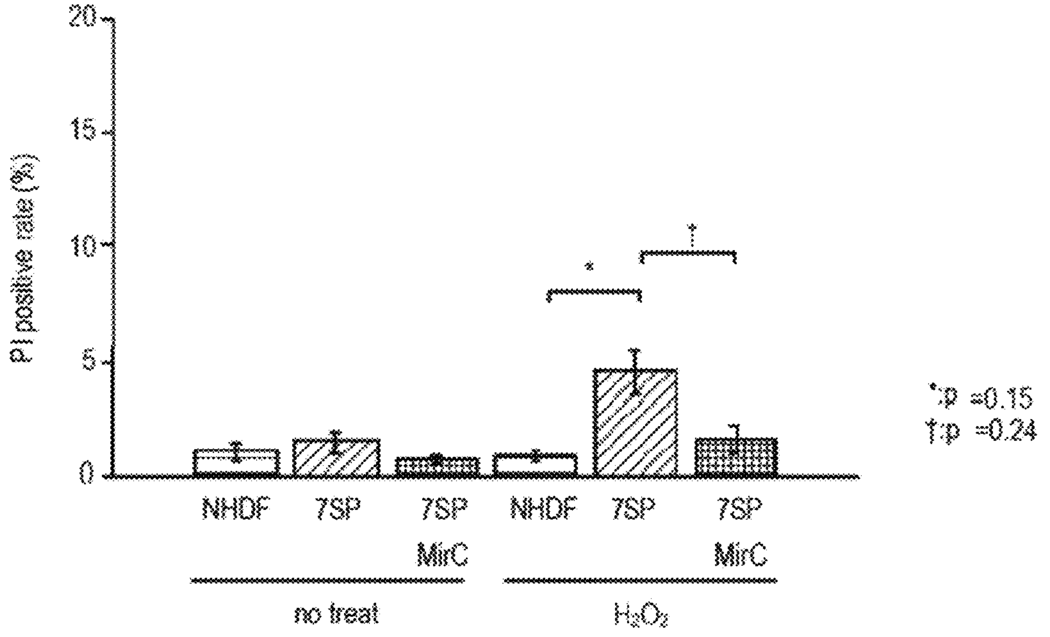

FIG. 10B-FIG. 10D depict FACS analysis (FIG. 10B) and quantification of Annexin V (FIG. 10C) and propidium iodine (PI; FIG. 10D) positive cells following no treatment or treatment with $H_2O_2$, and demonstrate that 7SP cells are highly sensitive to $H_2O_2$ relative to NHDF cells, whereas the 7SP MirC are not.

Figure 10E:
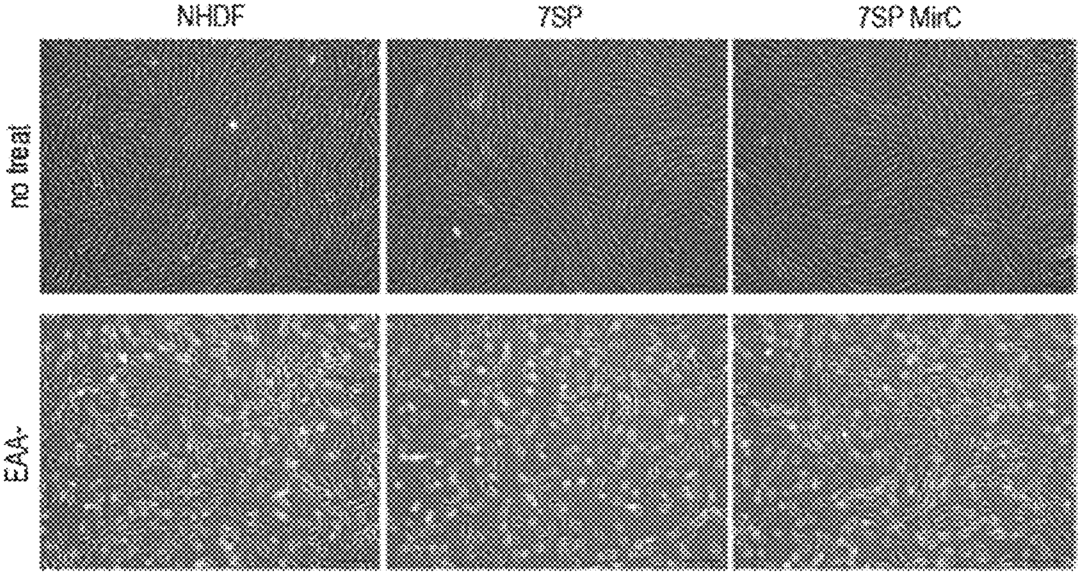

FIG. 10E depicts microscopy images of NHDF, 7SP, an 7SP MirC cells under basal conditions or following starvation conditions (EAA−), and show that 7SP cells are highly sensitive to starvation conditions relative to NHDF cells whereas the 7SP MirC are not.

Figure 10F:
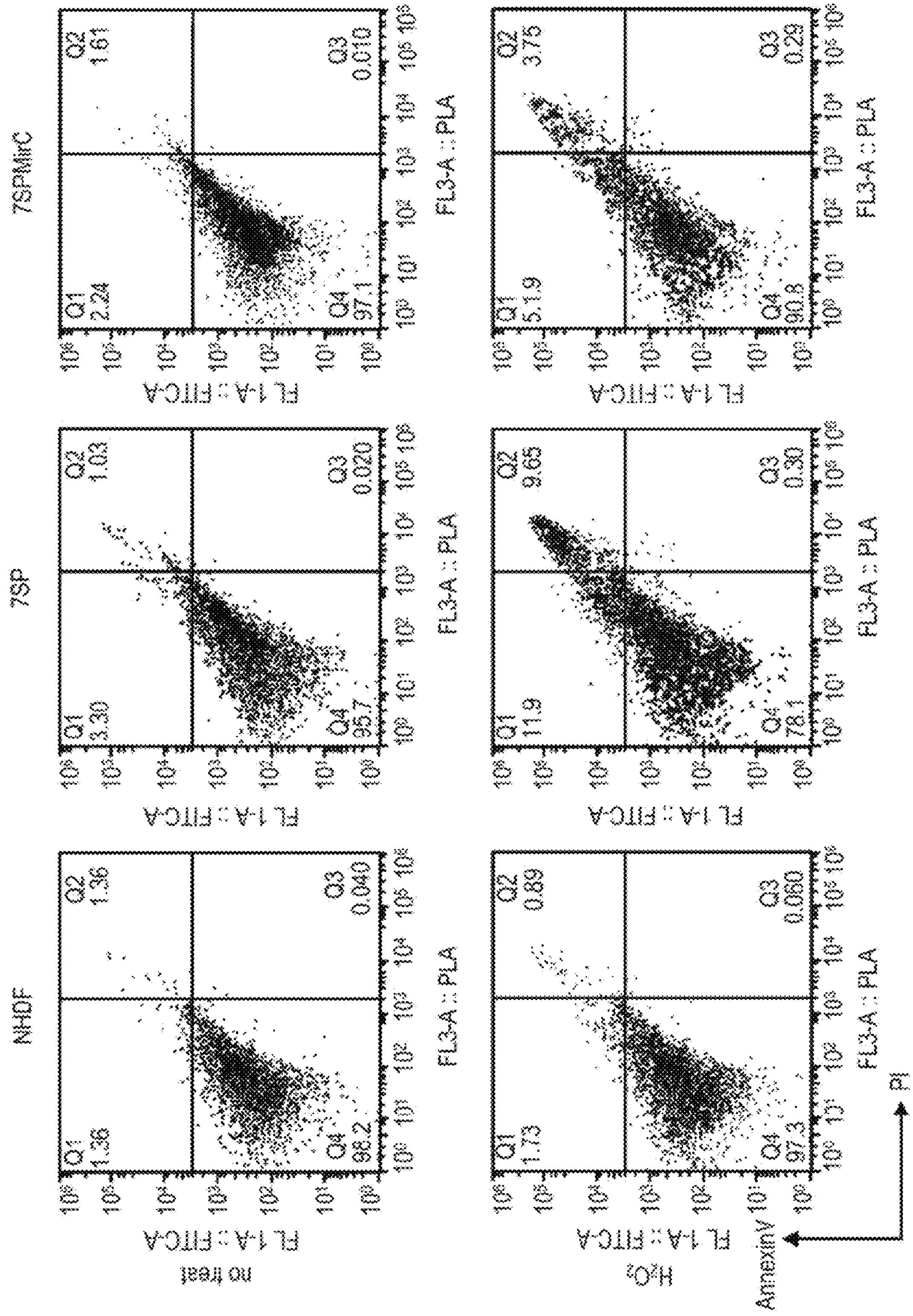
Figure 10G:
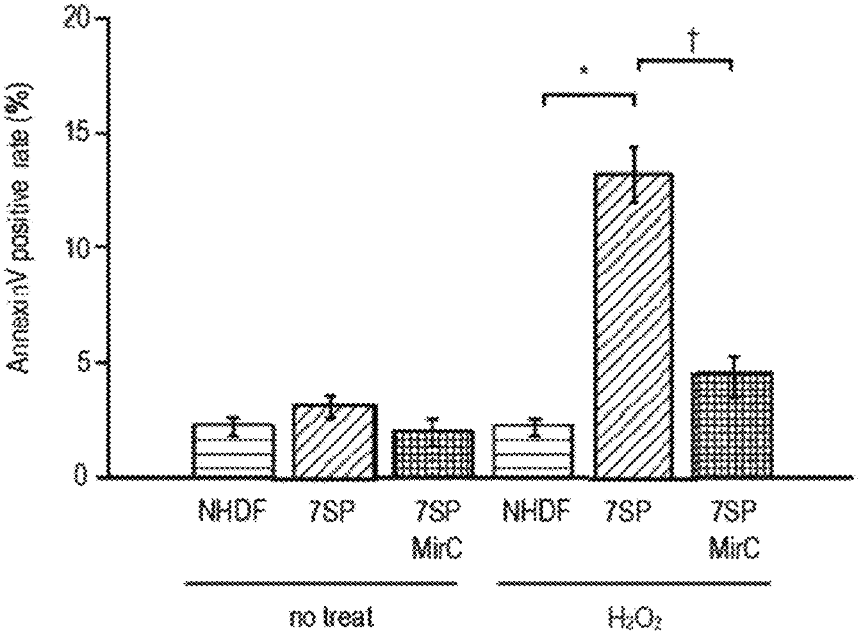
Figure 10H:
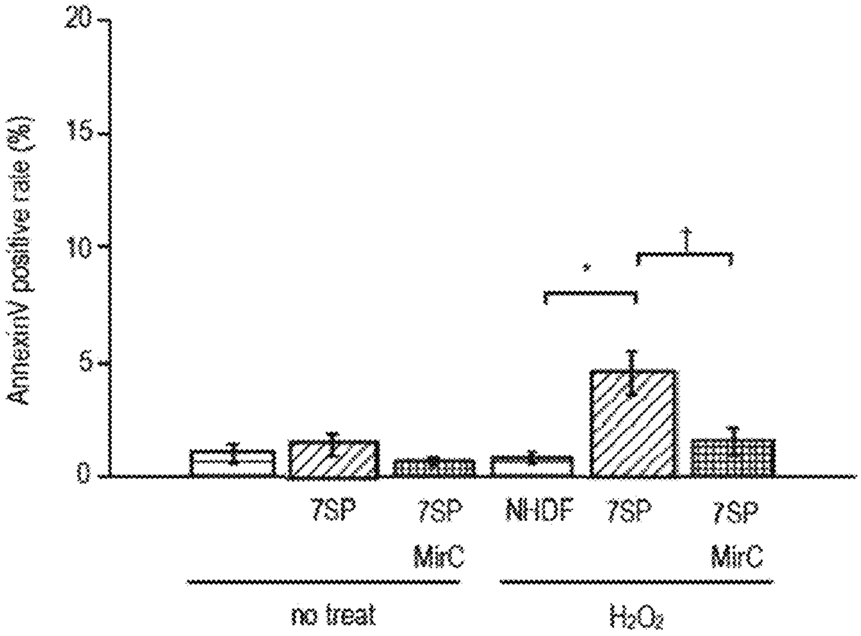

FIG. 10F-FIG. 10H depict FACS analysis (FIG. 10F) and quantification of Annexin V (FIG. 10G) and PI (FIG. 10H) positive cells following no treatment or starvation, and demonstrate that 7SP cells are highly sensitive to starvation conditions relative to NHDF cells, whereas the 7SP MirC are not.

Figure 11:
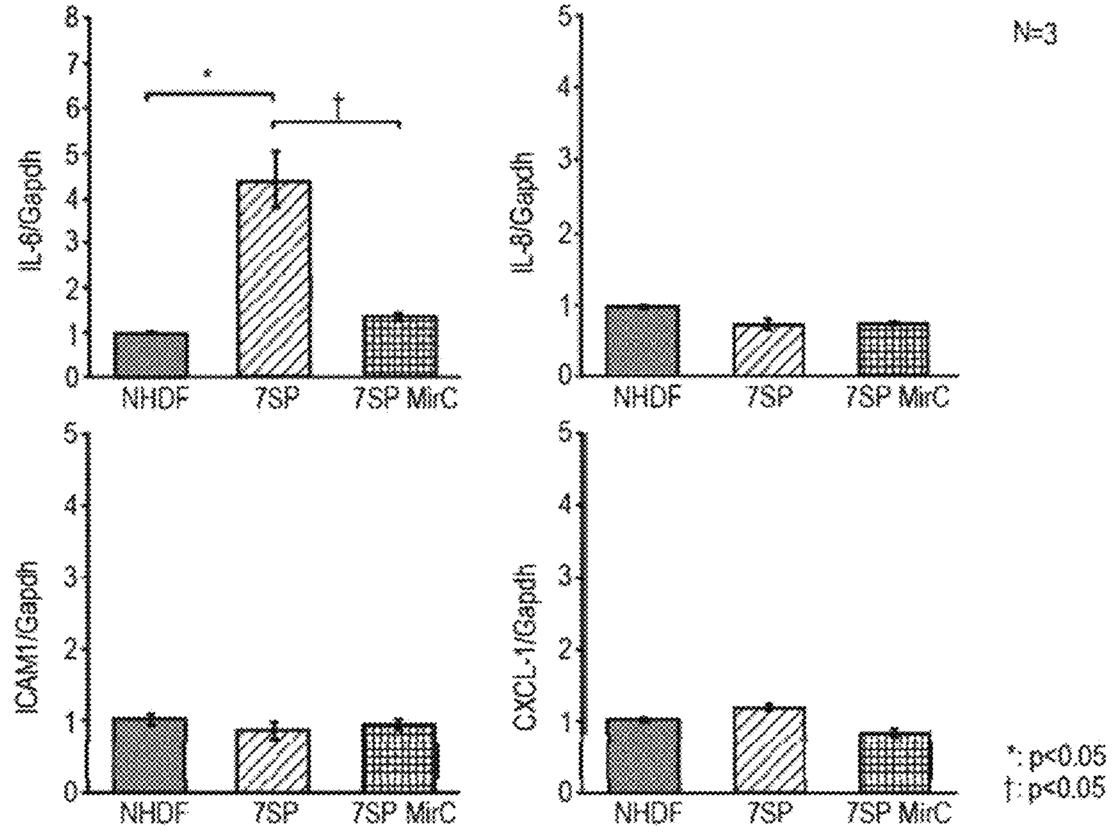

FIG. 11 depicts quantification of the expression levels of representative SASP cytokines, IL-6 and IL-8, chemokine, CXCL-1, and growth factor, ICAM1 for NHDF, 7SP fibroblast, and 7SP fibroblast-derived MirC cells, whose PDLs were almost the same, about 15 to 20, which demonstrated a significant reduction in IL-6, indicating a reversal of SASP in the MirC. GAPDH was used for normalization.

Figure 12A:
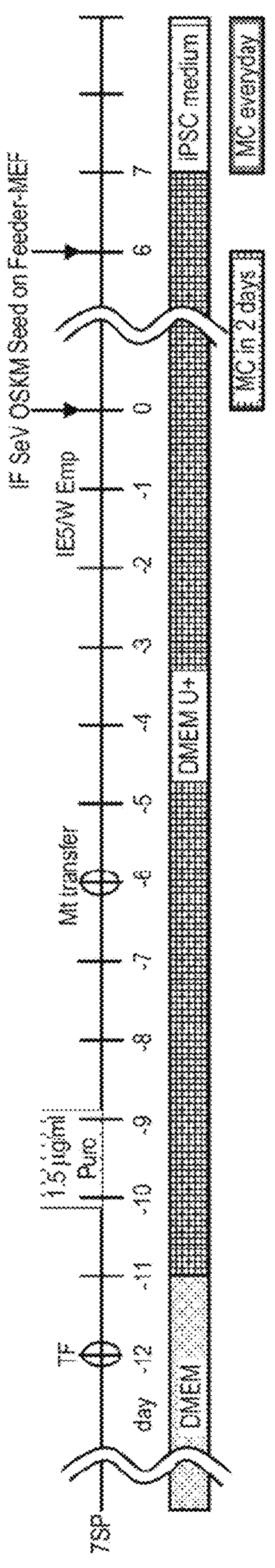

FIG. 12A depicts the scheme for generation of induced pluripotent stem cells (iPSCs) from mitochondria replaced 7SP fibroblasts.

Figure 12B:
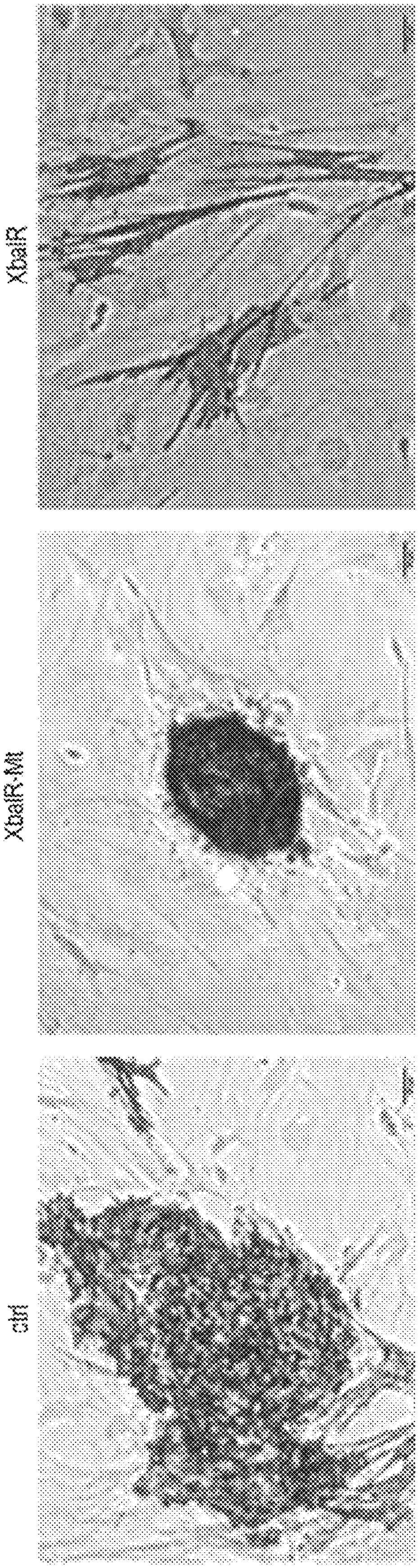
Figure 12C:
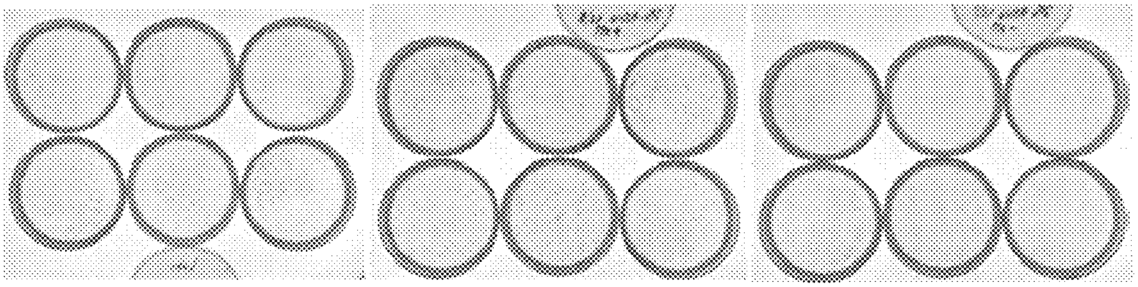
Figure 12D:
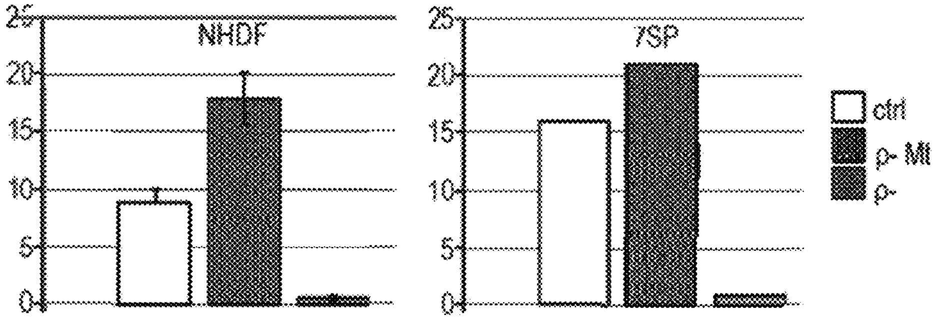

FIG. 12B-FIG. 12D depicts alkaline phosphatase (AP) staining and quantification as an indicator of iPSCs, which were generated from either 7SP fibroblasts, 7SP fibroblast-derived MirC, or mock transfectants originated from 7SP fibroblasts. Microscopic (FIG. 12B left panel; 7SP fibroblasts, middle panel; 7SP fibroblast-derived MirC, right panel: Mock transfectant of 7SP fibroblast) and macroscopic (FIG. 12C left panel; 7SP fibroblasts, middle panel; 7SP fibroblast-derived MirC, right panel. Mock transfectant of 7SP fibroblast) microscopy of AP stained cells, as well as quantification of the AP stained cells (FIG. 12D), revealed that mitochondrial replacement in cither NHDF or 7SP fibroblasts following XbaIR treatment resulted in increased AP staining.

Figure 12E:
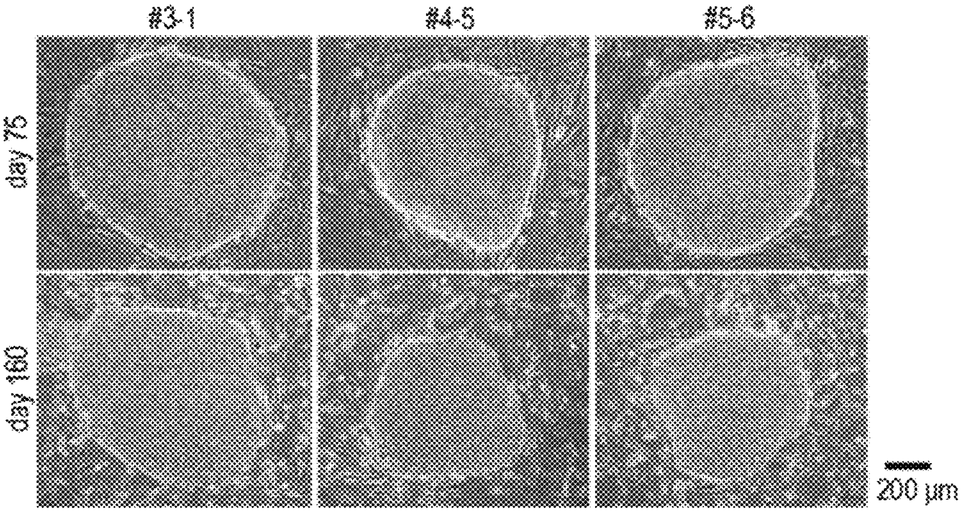

FIG. 12E depicts colony formation of iPSCs derived from mitochondria replaced 7SP fibroblasts. Photos of 3 representative colonies in 75 days and 170 days after gene transfer of reprogramming factors.

Figure 12F:
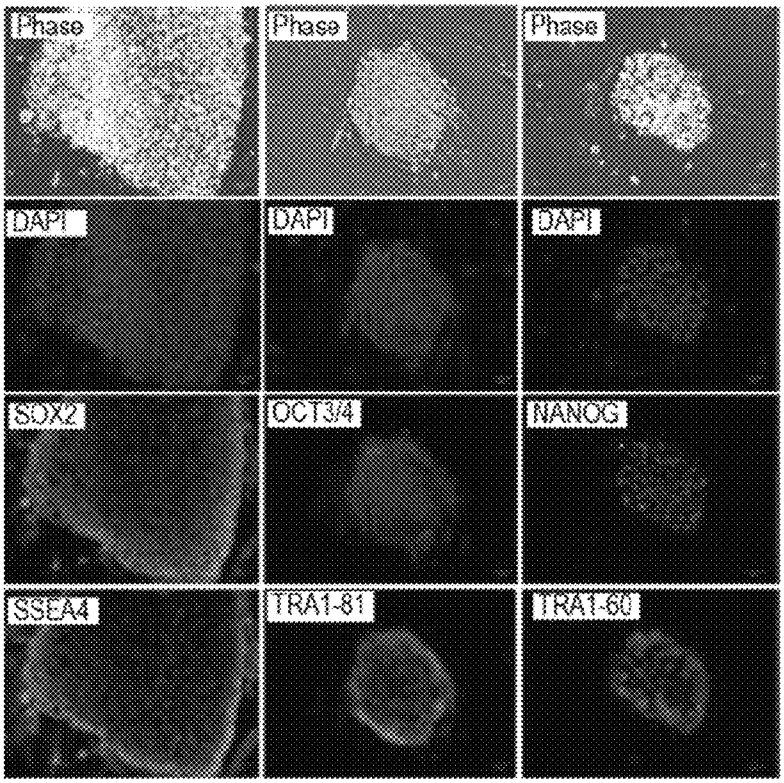
Figure 12G:
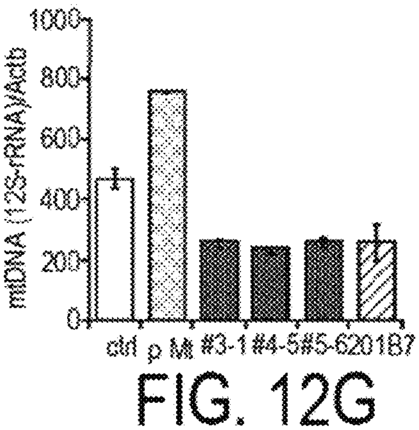

FIG. 12F depicts immunohistochemical staining for OCT3/4, NANOG, TRAI-80, and TRA-160 in iPSC's generated from 7SP fibroblasts following mitochondrial replacement, which are representative markers for pluripotent stem cells;

FIG. 12G depicts mitochondrial DNA copy number in iPSC's derived from 7SP fibroblast derived MirC, compared with the original 7SP fibroblasts and the standard human iPSCs (20187) as references, and revealed that iPSCs had limited number of mitochondrial DNA that was similar that of the standard human iPSCs (201B7).

Figure 12H:
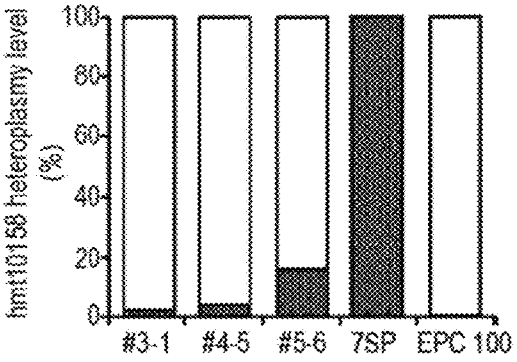
Figure 12I:
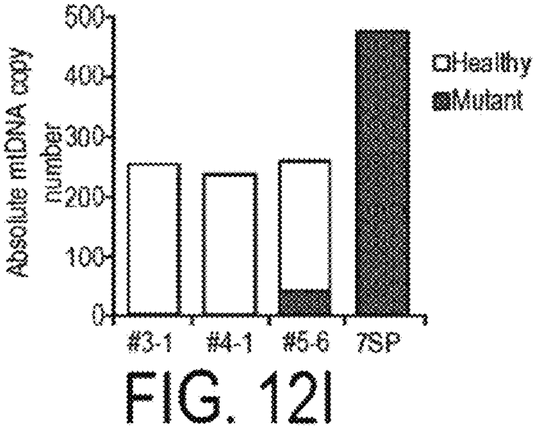

FIG. 12H and FIG. 12I depict the percentage of heteroplasmy (FIG. 12H) and absolute mtDNA copy number (FIG. 12I) in iPSCs derived from 7SP fibroblast-derived MirC in 170 days after the reprogramming procedure, and revealed that 7SP fibroblast-derived MirC that formed iPSC showed negligible levels of mutated genome sequence, reduced total mtDNA, and nearly 100% donor mtDNA in at least three clones, suggesting that the change of the heteroplasmy in MirC could be reverted into the original state, and different from the mitochondrial replacement therapy in IVF.

Figure 13A:
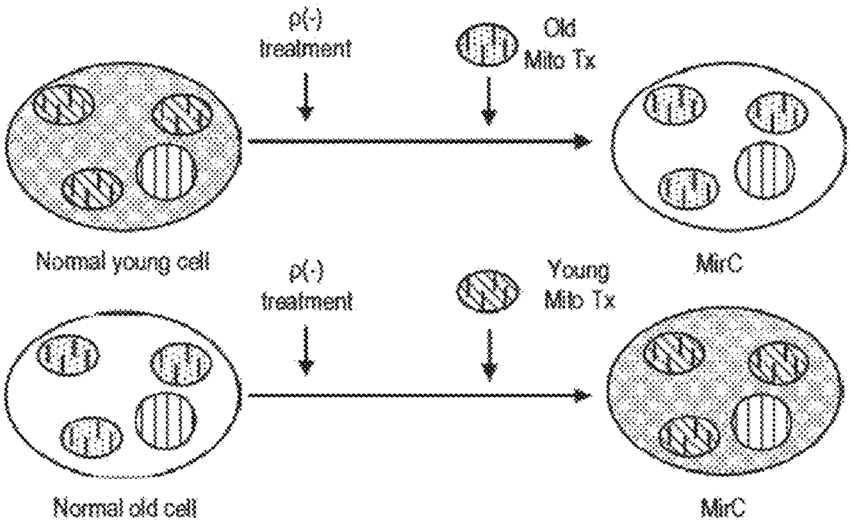

FIG. 13A depicts a scheme of the protocol for mitochondrial transfer from a donor cell to a recipient cell, where the donor cell and recipient cell are from different stages of a lifespan.

Figure 13B:
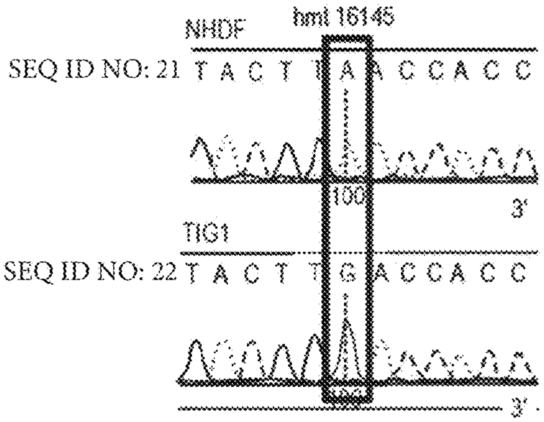

FIG. 13B depicts DNA sequencing data for the nucleotides surrounding hmt16145 in NHDF ctrl recipient cells (SEQ ID NO: 21) which have the genotype hmt16145 A, and TIG1 ctrl donor cells (SEQ ID NO: 22) which have the genotype hmt16145 G.

Figure 13C:
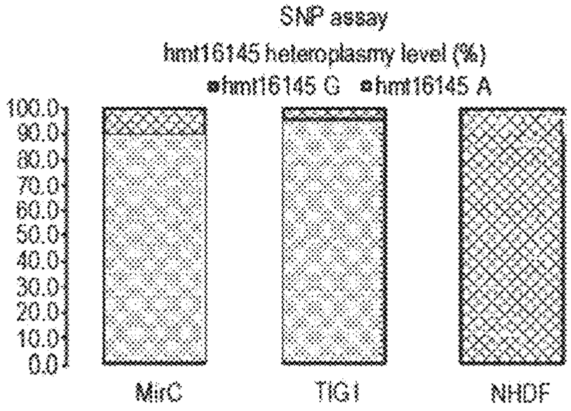

FIG. 13C depicts quantitation of hmt16145 heteroplasmy level (%) by SNP assay of the cells from mitochondria replaced cells (MirC) ("old" NHDF recipient cells with mitochondrial transfer of mitochondria from "young" TIG1 donor cells) and indicated that greater than 90% of the mtDNA in the NHDF derived MirC cells with mitochondria replacement from TIG1 derived mitochondria donor cells was hmt16145 G (i.e., from TIG1 mtDNA), whereas 100% of the NHDF ctrl cell's mtDNA was hmt16145 A.

Figure 13D:
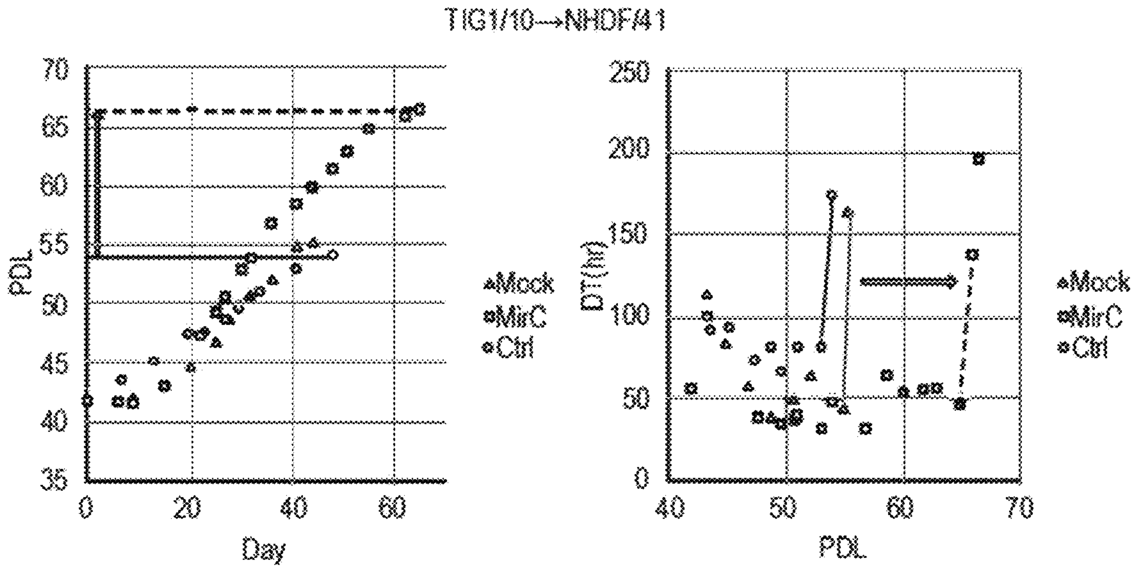

FIG. 13D depicts quantification of the population doubling level (PDL) versus time (days) (left), and doubling time (hours) versus population doubling level (right) in recipient NHDF cells transfected with MTS-GFP ("mock"), or MTS-XbaIR ("MirC") and coincubated with exogenous mitochondria from TIG1 donor cells, or untransfected ("Ctrl"). MirC with "young" donor TIG1 embryonic lung cell (PDL 10) to an "old" normal human dermal fibroblasts (NHDF) recipient cell (PDL 41) showed an extension in lifespan, as indicated by the upward shift in PDL (left) and rightward shift in PDL (right).

Figure 13E:
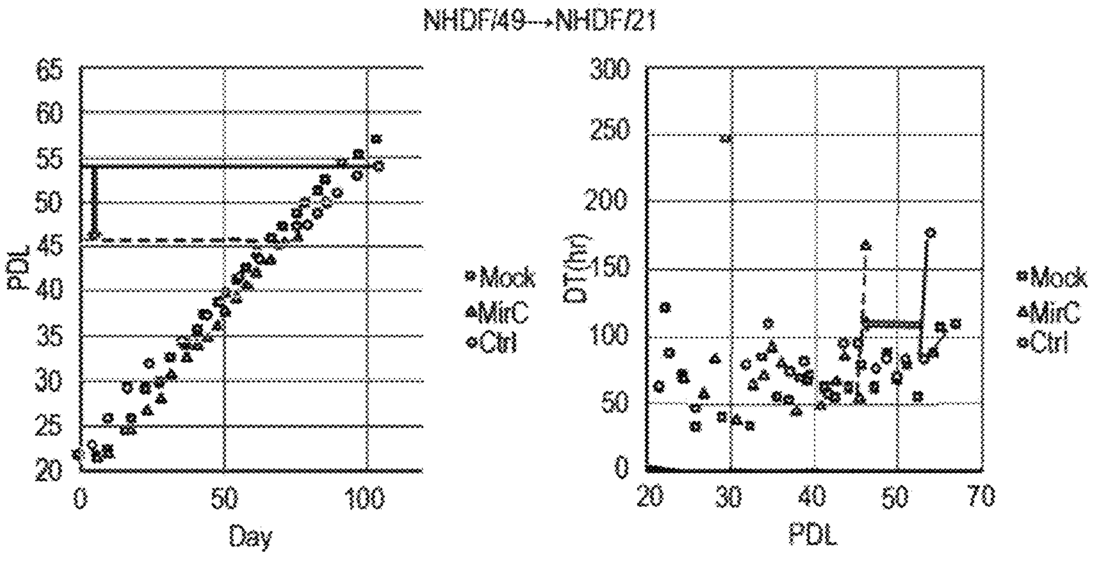

FIG. 13E depicts quantification of the population doubling level (PDL) versus time (days) (left), and doubling time (hours) versus population doubling level (right) in normal human dermal fibroblasts transfected with MTS-GFP plus mitochondrial transfer ("mock"), MTS-XbaIR plus mitochondrial transfer ("MirC"), or untransfected ("Ctrl"). Mitochondrial transfer from an "old" donor cell (PDL 49) to a "young" recipient cell (PDL<21) showed reduction in lifespan, as indicated by the downward shift in PDL (left), and leftward shift in PFL (right).

Figure 14A:
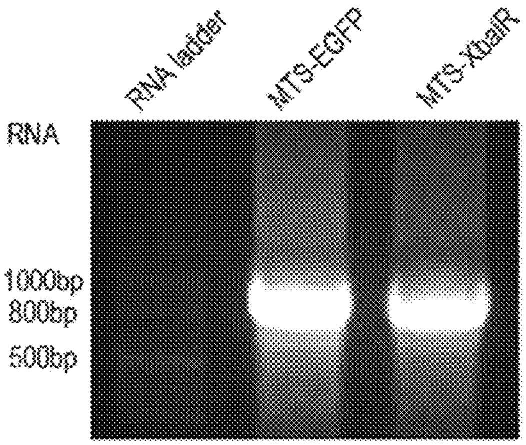

FIG. 14A depicts quality assessment of mRNA generated by in vitro transcription, as measured by electrophoresis of mRNA for MTS-EGFP and MTS-XbaIR.

Figure 14B:
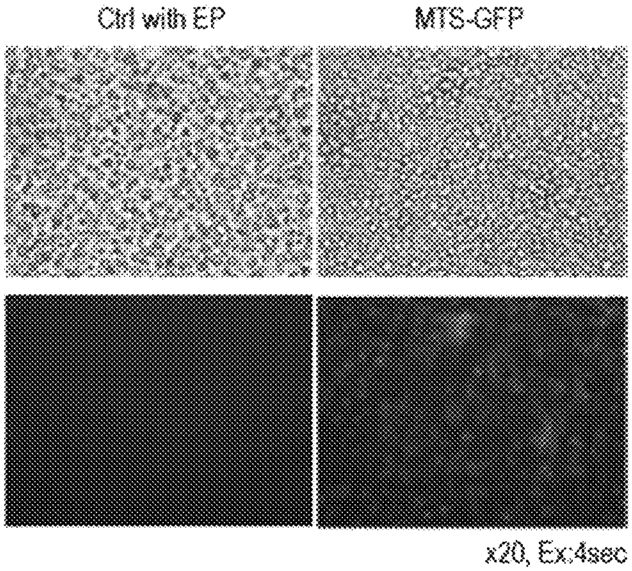

FIG. 14B depicts strong expression of the MTS-GFP transgene in mitochondria of T cells 24 hours following electroporation.

Figure 14C:
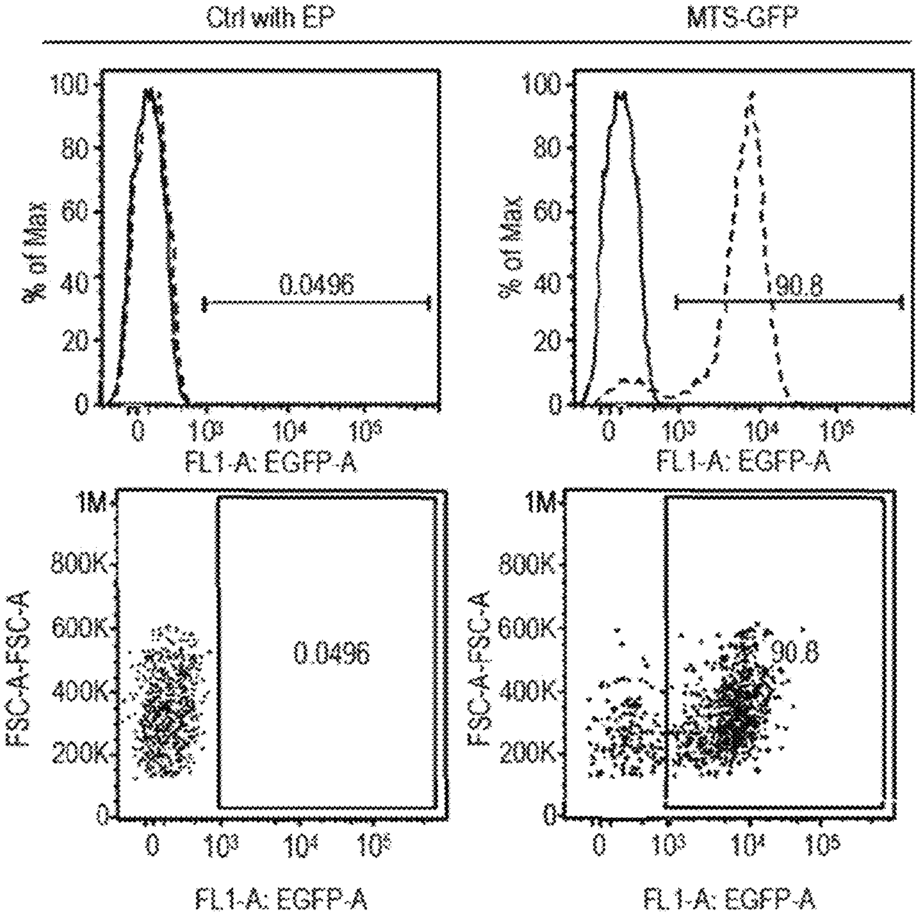

FIG. 14C depicts FACS analysis of GFP expression in T cells following transfection of the MTS-GFP mRNA by electroporation, and revealed that GFP expression is present in nearly all T cells.

Figure 14D:
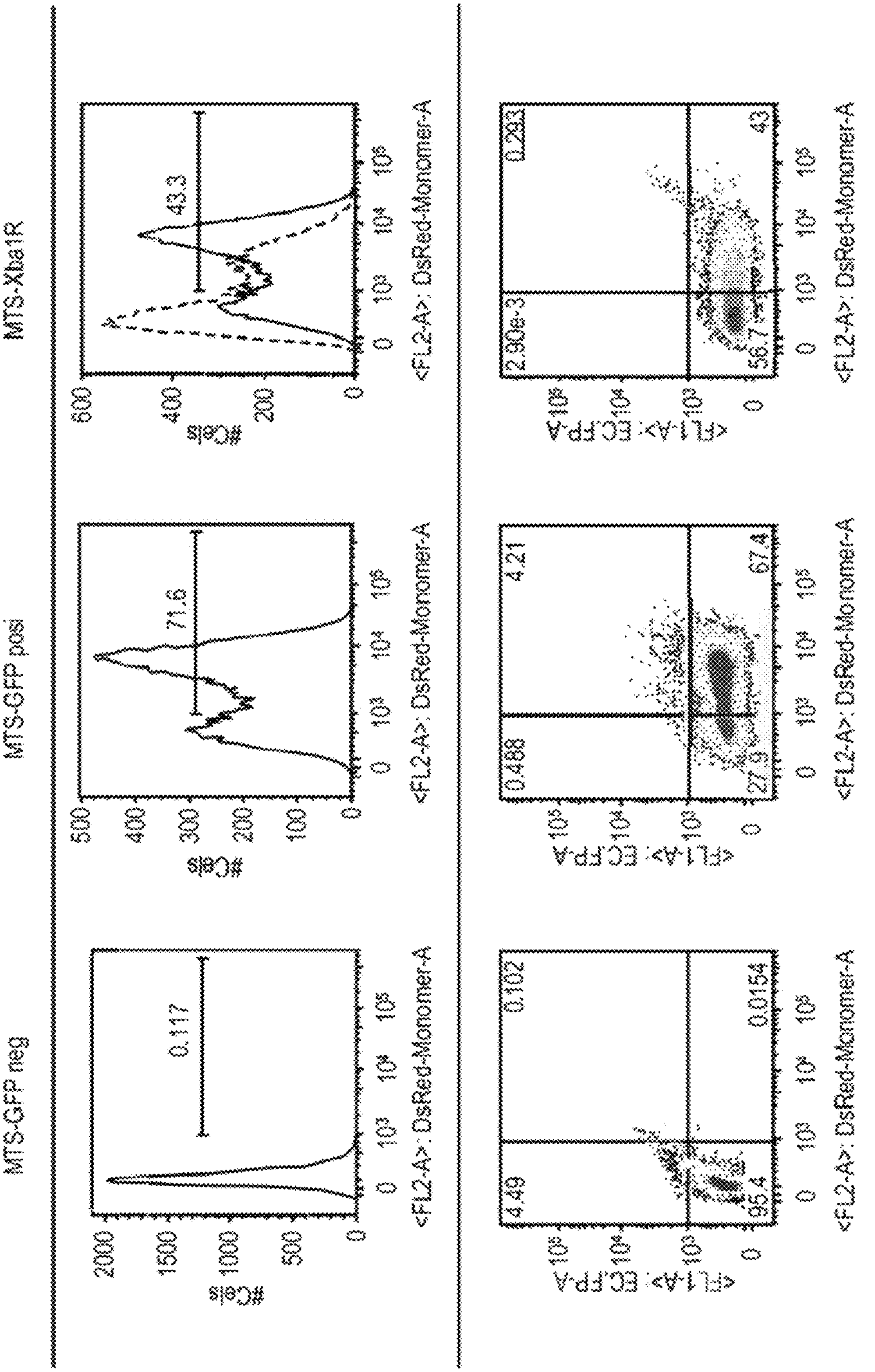

FIG. 14D depicts FACS analysis of DsRed labeled mitochondria and demonstrates that the MTS-XbaIR construct robustly degraded the endogenous mitochondria, whereas the MTS-GFP did not.

Figure 14E:
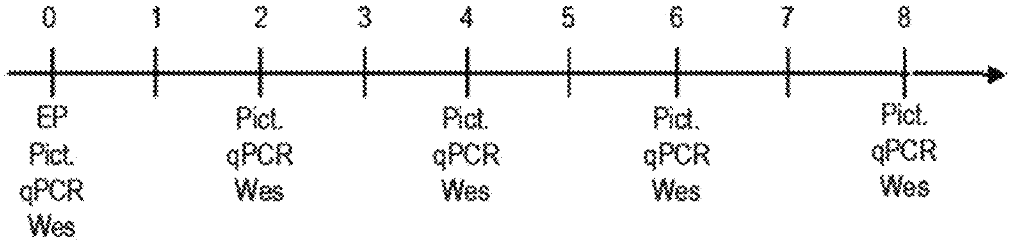

FIG. 14E depicts a scheme of the protocol design for determining the optimal time period of mitochondrial co-incubation.

Figure 14F:
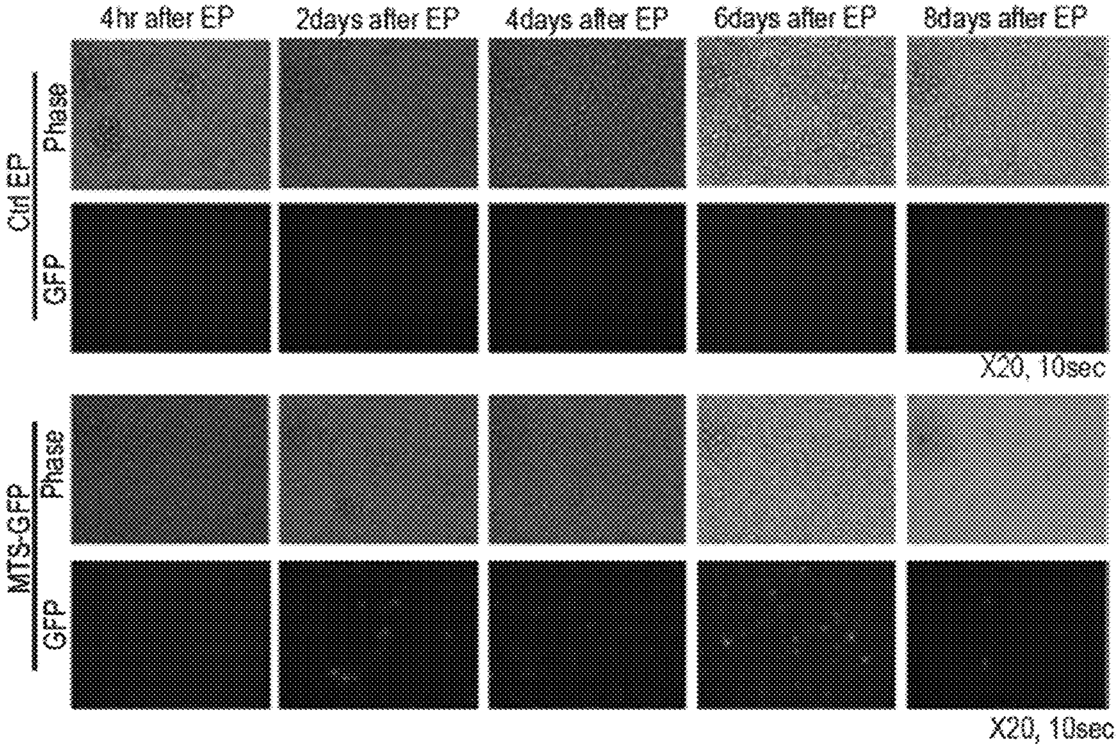

FIG. 14F depicts fluorescent images of control electroporated cells (upper panels) and MTS-GFP electroporated cells (lower panels) at 4 hr, 2 days, 4 days, 6 days, and 8 days after electroporation (EP), and indicated the MTS-GFP construct displayed high expression within 4 hours post-electroporation and was nearly absent by day 6.

Figure 14G:
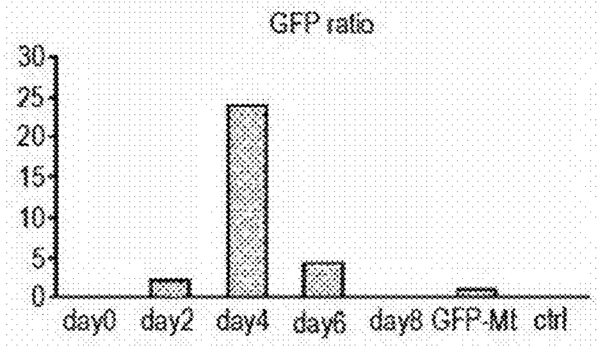
Figure 14H:
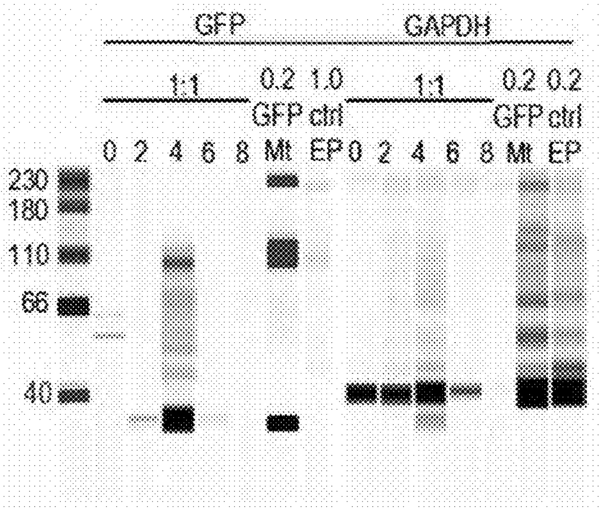

FIG. 14G and FIG. 14H depict electrophoresis (FIG. 14H) and quantification (FIG. 14G) of GFP in cells receiving the MTS-GFP mRNA, relative to GAPDH. The peak expression occurred at day4, and expression was lost by day6.

Figure 14I:
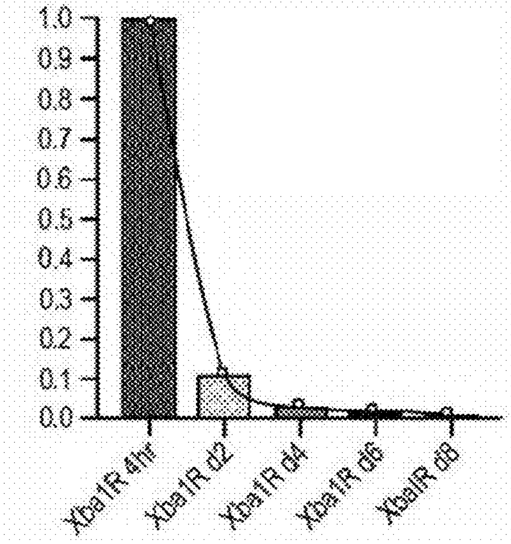

FIG. 14I depicts quantification of XbaIR transcript levels, at 4 hr, day 2 (d2), day 4 (d4), day 6 (d6) and day 8 (d8), indicating that the transcript expressions of the endonuclease were quite highest at 4 hours post-gene transfer.

Figure 14J:
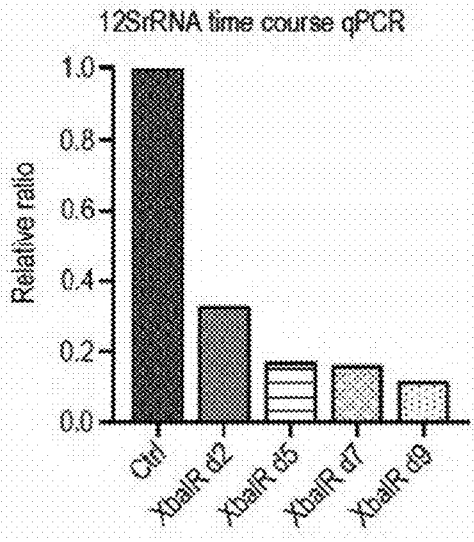

FIG. 14J depicts quantification of mitochondrial contents (12S rRNA) in cells subjected to MTS-XbaI, and demonstrated that mitochondria decreased to about 30% by day2, and was maintained at less than 20% throughout the length of the experiment.

Figure 15A:
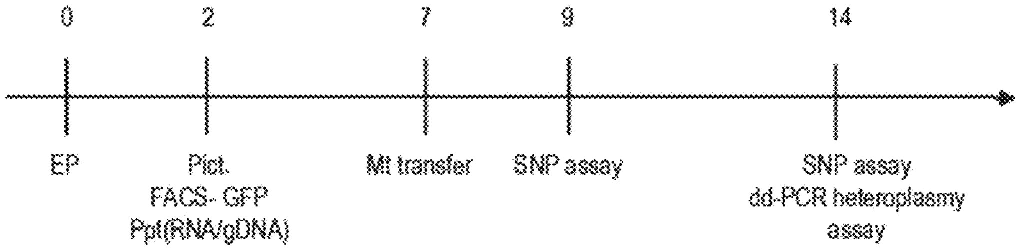

FIG. 15A depicts a scheme of the MirC protocol for human primary T cells, with electroporation at day 0, analysis at day 2, mitochondria (mt) transfer at day 7, SNP assays at day 9 and 14, and ddPCR heteroplasmy assay at day 14.

Figure 15B:
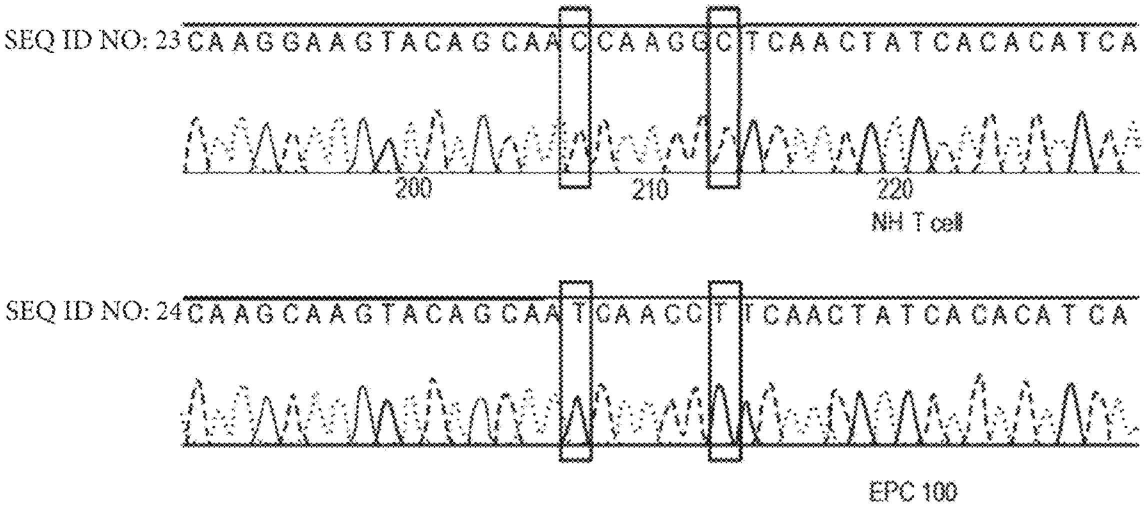

FIG. 15B depicts DNA sequencing data for the nucleotides surrounding hmtDNA 218 and hmtDNA 224 of the HV1 region of the human mitochondrial DNA D-loop in human primary NH T cell control recipient cells (top; SEQ ID NO: 23) and EPC100 control donor cells (bottom; SEQ ID NO: 24). hmtDNA 218 and hmtDNA 224 were C/C (SEQ ID NO: 23) and T/T (SEQ ID NO: 24) for T cells and EPC100 cells, respectively.

Figure 15C:
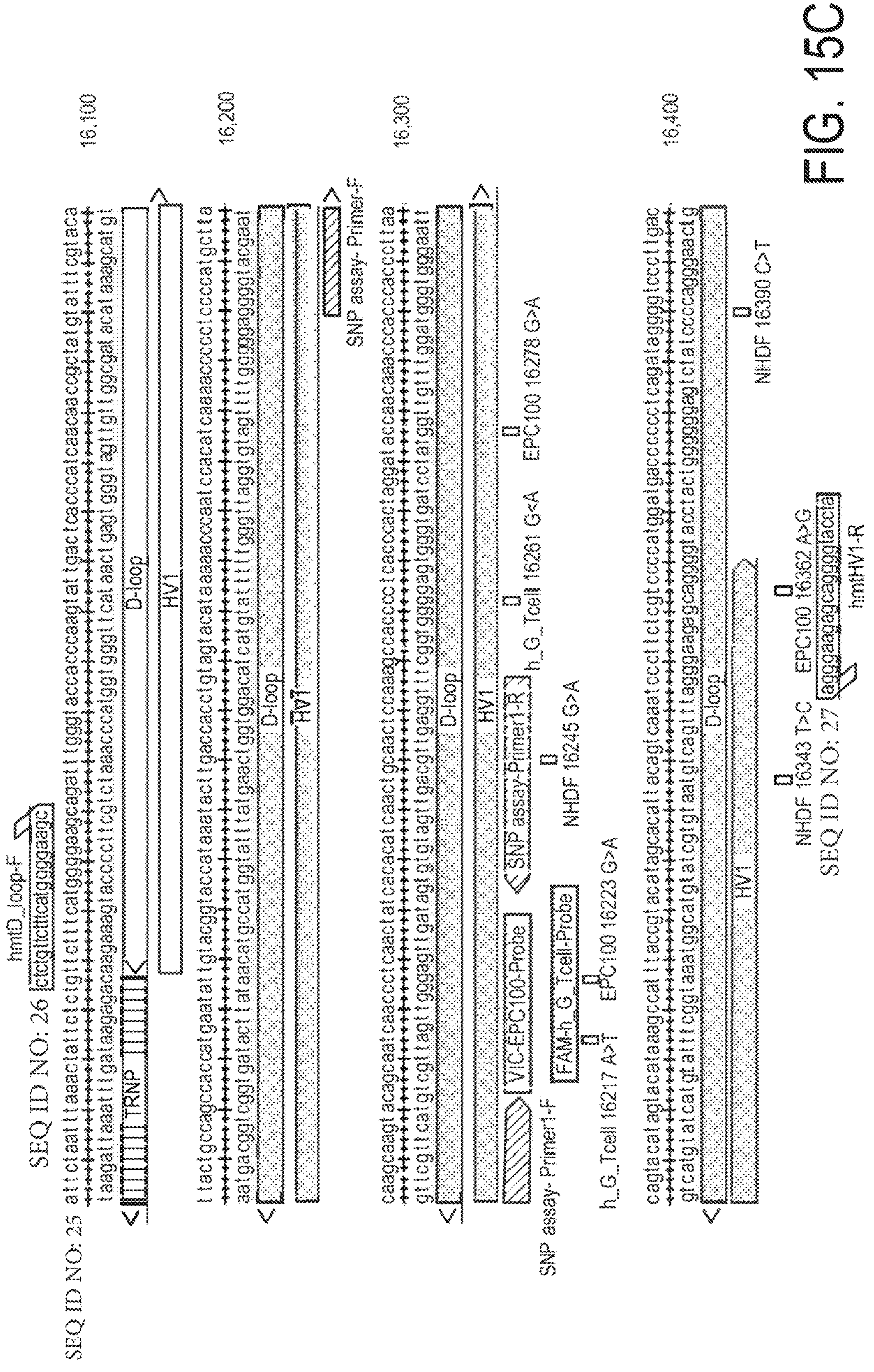

FIG. 15C depicts the hmtHV1-F (SEQ ID NO: 26) and hmtHV1-R (SEQ ID NO: 27) set of primers used for amplification of the HV1 region of human mitochondrial DNA D-loop (SEQ ID NO: 25) surrounding the SNPs at hmtDNA 218 and hmtDNA 224, as well as the SNP assay Primer1-F (SEQ ID NO: 40), the SNP assay-Primer1-R (SEQ ID NO: 41), the N-terminal VIC labeled EPC100 specific probe (SEQ ID NO: 38), and the N-terminal FAM labeled T cell specific probe (SEQ ID NO: 39) that were designed for the TaqMan SNP genotyping assay.

Figure 15D:
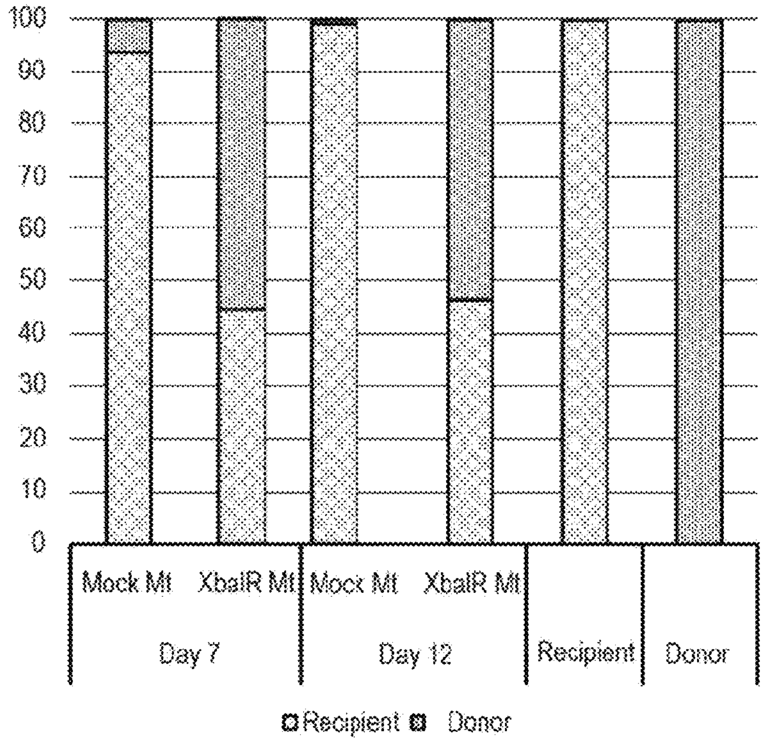

FIG. 15D depicts quantification of the amount of exogenous mtDNA present in the recipient cells at day 7 and day 12 for mock (MTS-GFP) or MTS-XbaIR (XbaIR) treated cells following coincubation with exogenous mitochondria from donor EPC100 cells. Quantification of recipient and donor cells was performed as positive controls.

Figure 15E:
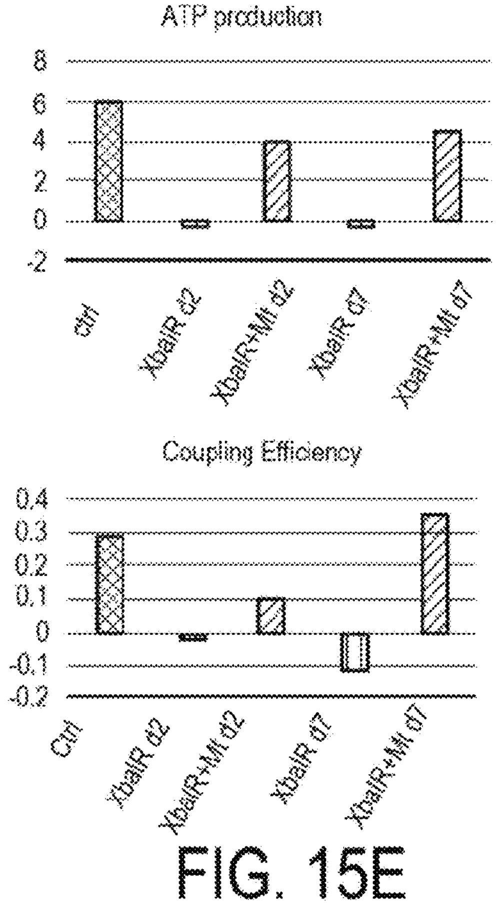

FIG. 15E depicts quantification of respirometry experiments performed using Oroboros O2k, and demonstrated a recovery of ATP production and coupling efficiency in human T cell-derived MirC, whereas ρ(−) human T cells that were generated by XbaIR mRNA transfer with electroporation maintained the loss of ATP production throughout the experiment.

Figure 15F:
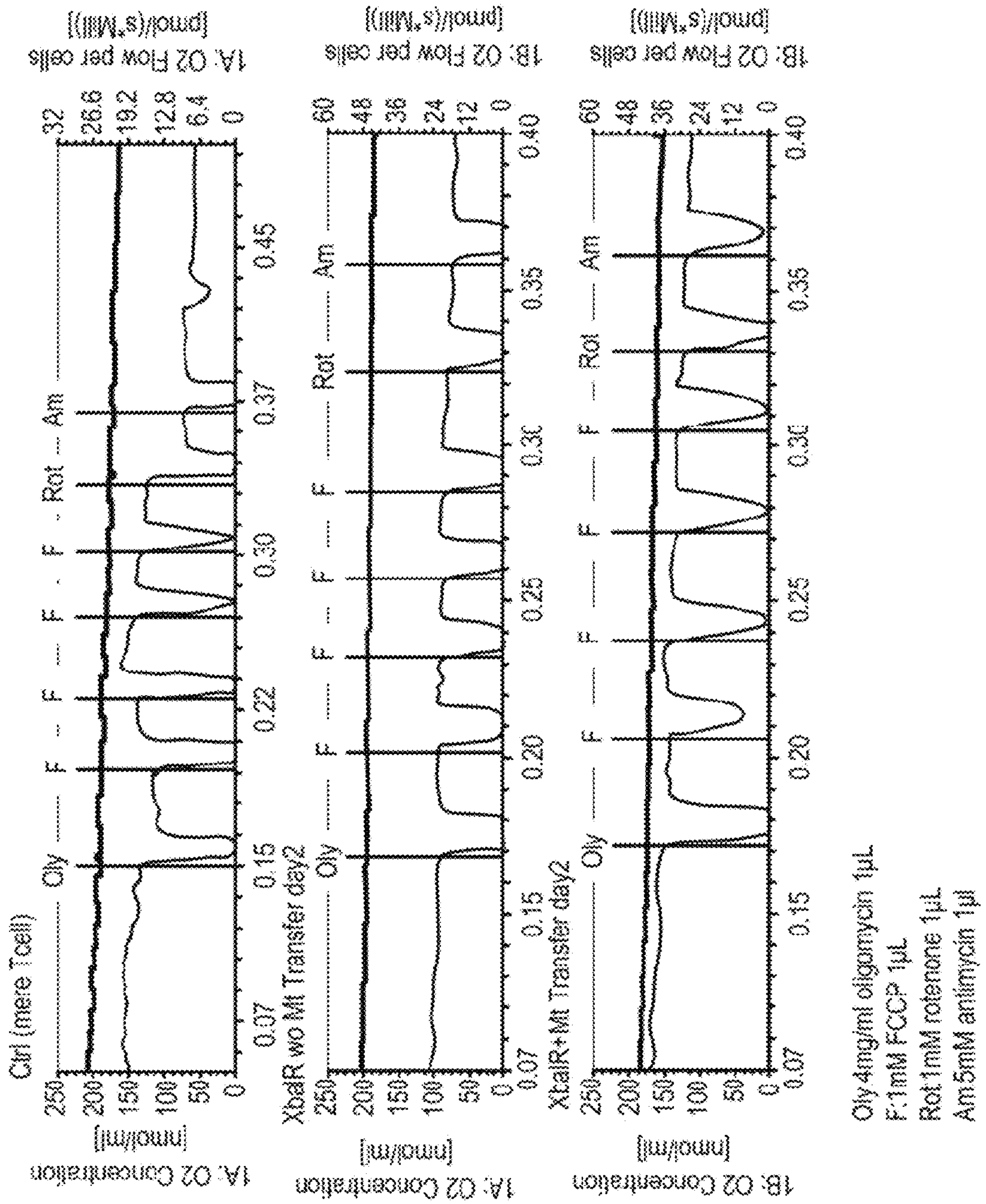
Figure 15G:
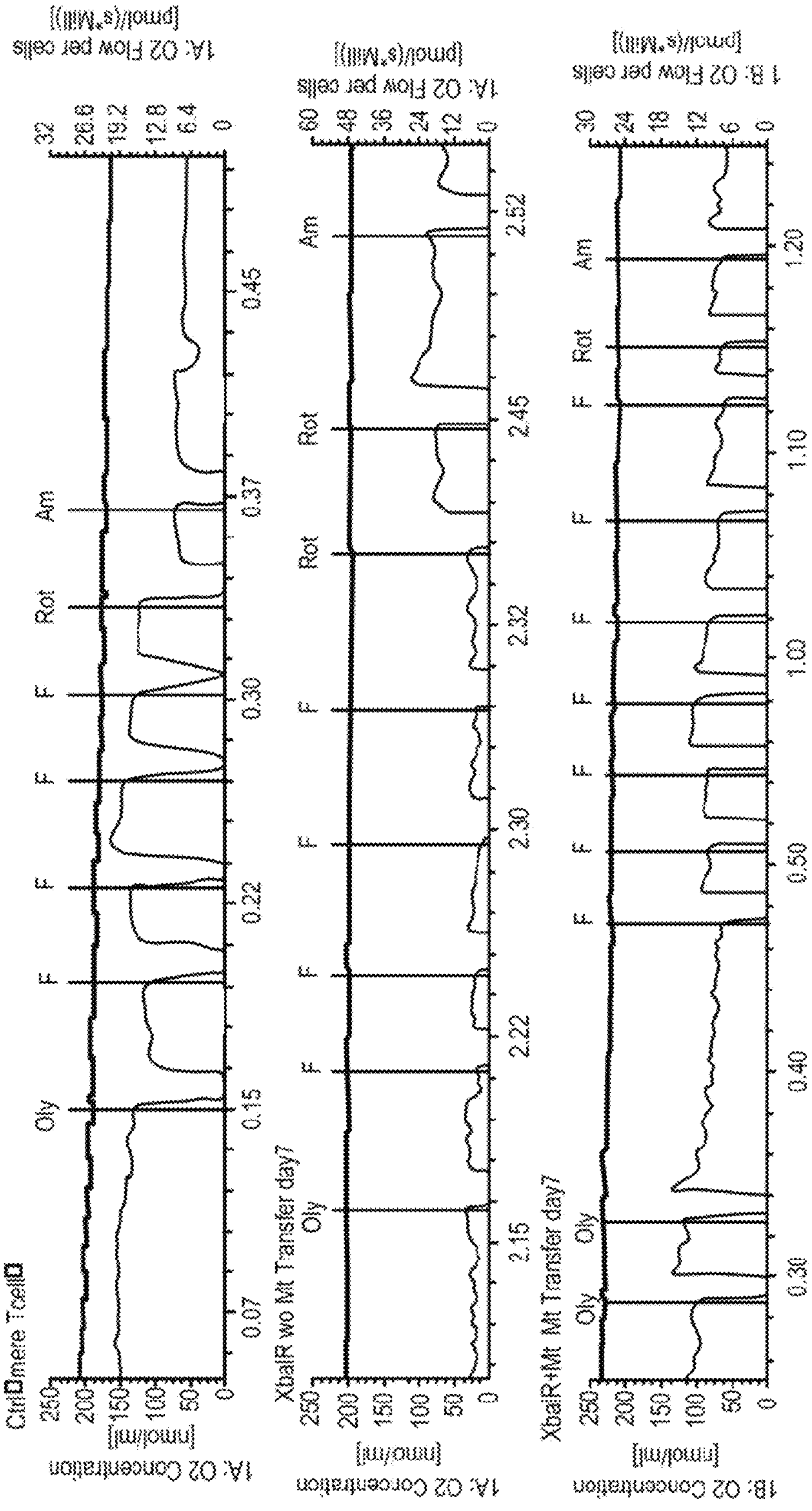

FIG. 15F and FIG. 15G depict representative raw data using coupling-control protocol (CCP), and show that MirC T cells are able to restore mitochondrial respiration.

Figure 16A:
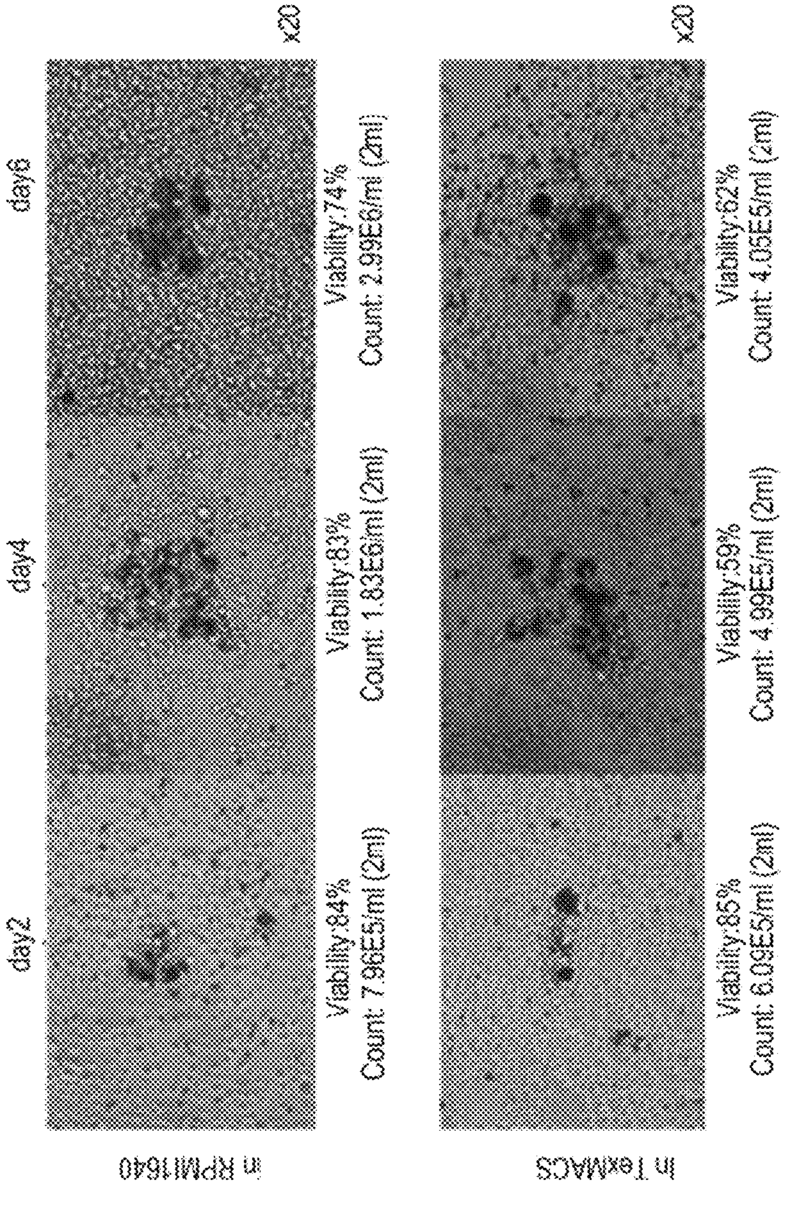

FIG. 16A depicts comparison viability (left panel) of mouse primary T cells cultured in RPMI1640 (top) or TexMACS (bottom) at day 2 (left side of left panel), day 4 (middle of left panel), and day 6 (right side of left panel), or CD3 expression (tight panel), and demonstrated that RPMI1640 produced greater viability and higher cell count, as well as a slight increase in CD3 expression, relative to TexMACS culture medium.

Figure 16B:
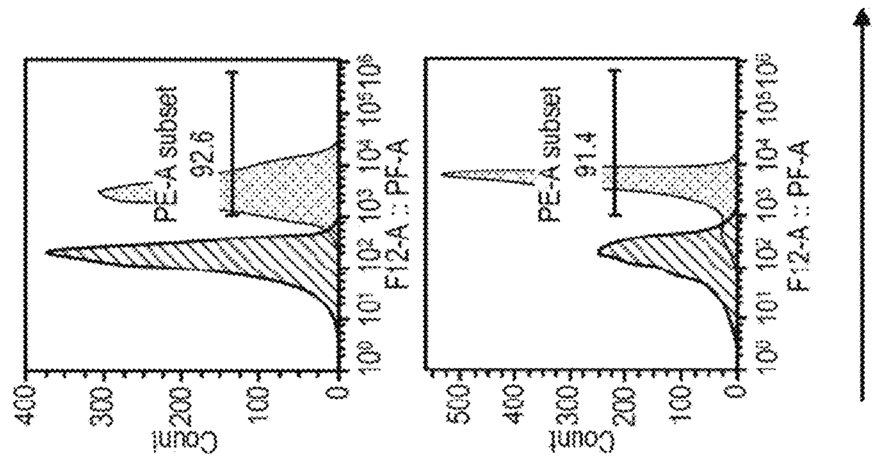

FIG. 16B depicts qualitative analysis of GFP expression in T cells following electroporation (EP) with pmax GFP (middle), or MTS-GFP (right), or without electroporation (left), at 6 hours after EP (top left panel), day 2 after EP (top right panel), day 4 after EP (bottom left panel), and day 6 after EP (bottom right panel). Viability was not significantly affected following EP with MTS-GFP at day 2 or day 4.

Figure 16C:
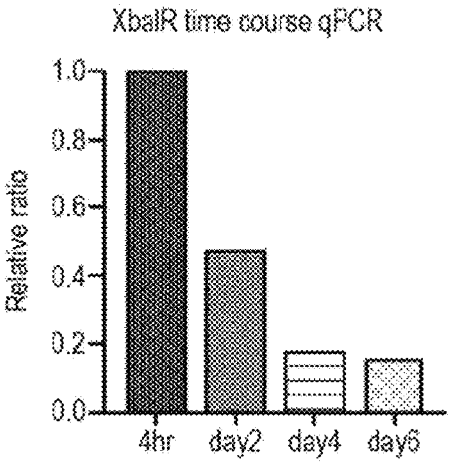

FIG. 16C depicts qPCR quantification of XbaIR levels in T cells electroporated with the MTS-XbaIR vector at 4 hr, day2, day4, and day 6 following electroporation and indicated that the XbaIR expression slowly decreased.

Figure 16D:
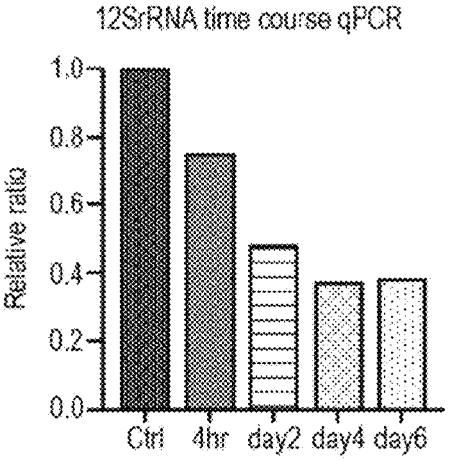

FIG. 16D depicts quantification of 12S rRNA levels in T cells electroporated with MTS-XbaIR and indicated that the murine mtDNA was decreased by approximately 60% by day 4.

Figure 16E:
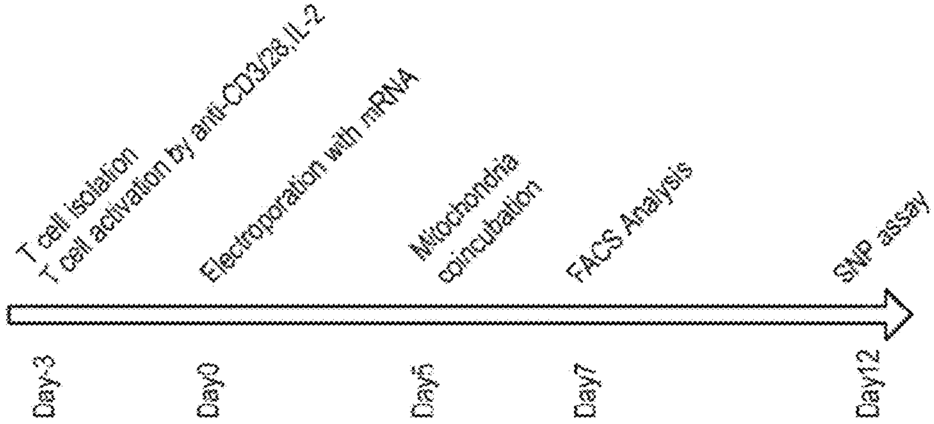

FIG. 16E depicts a scheme of the protocol used for MirC generation in T cells using mitochondrial coincubation on day 5.

Figure 16F:
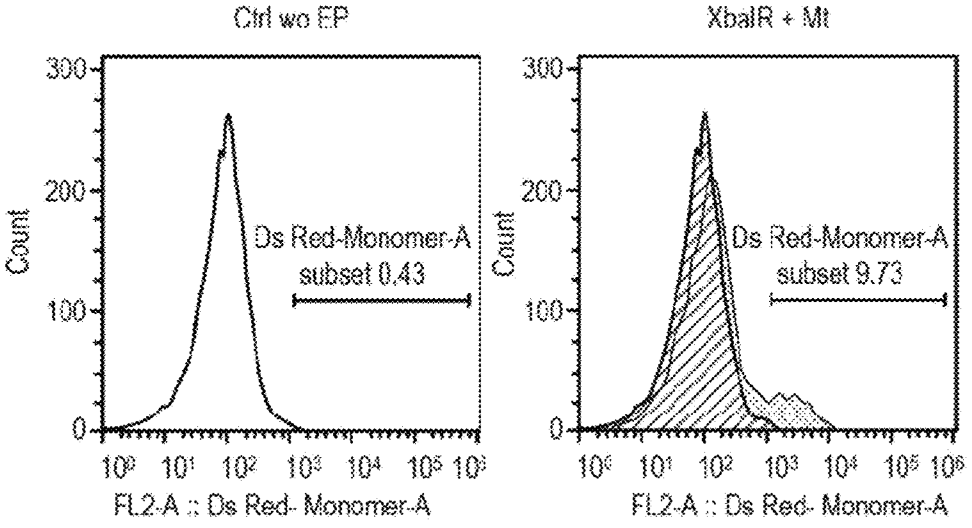

FIG. 16F depicts FACS analysis of engulfed DsRed-labeled mitochondria 48 hours in the recipient T cells, following the co-incubation with isolated DsRed-labeled mitochondria and revealed a significant positive fraction (9.73%) of T cells expressing exogenous mitochondria in MTS-XbaIR (right), compared with 0.43% in control cells without electroporation (i.e., "add-on").

Figure 17A:
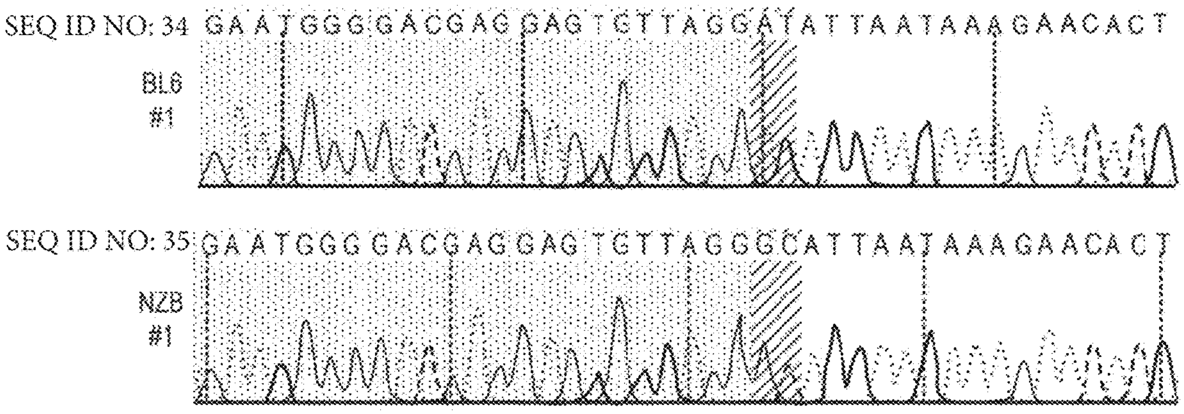

FIG. 17A depicts DNA sequencing data for the nucleotides surrounding ND1 in mouse mtDNA C57BL6 recipient cells ("BL6": top; SEQ ID NO: 34) which have the genotype mmt2766-A and mmt2767-T, and NZB donor cells (bottom; SEQ ID NO: 35), which have the genotype mmt2766-G and mmt2767-C.

Figure 17B:
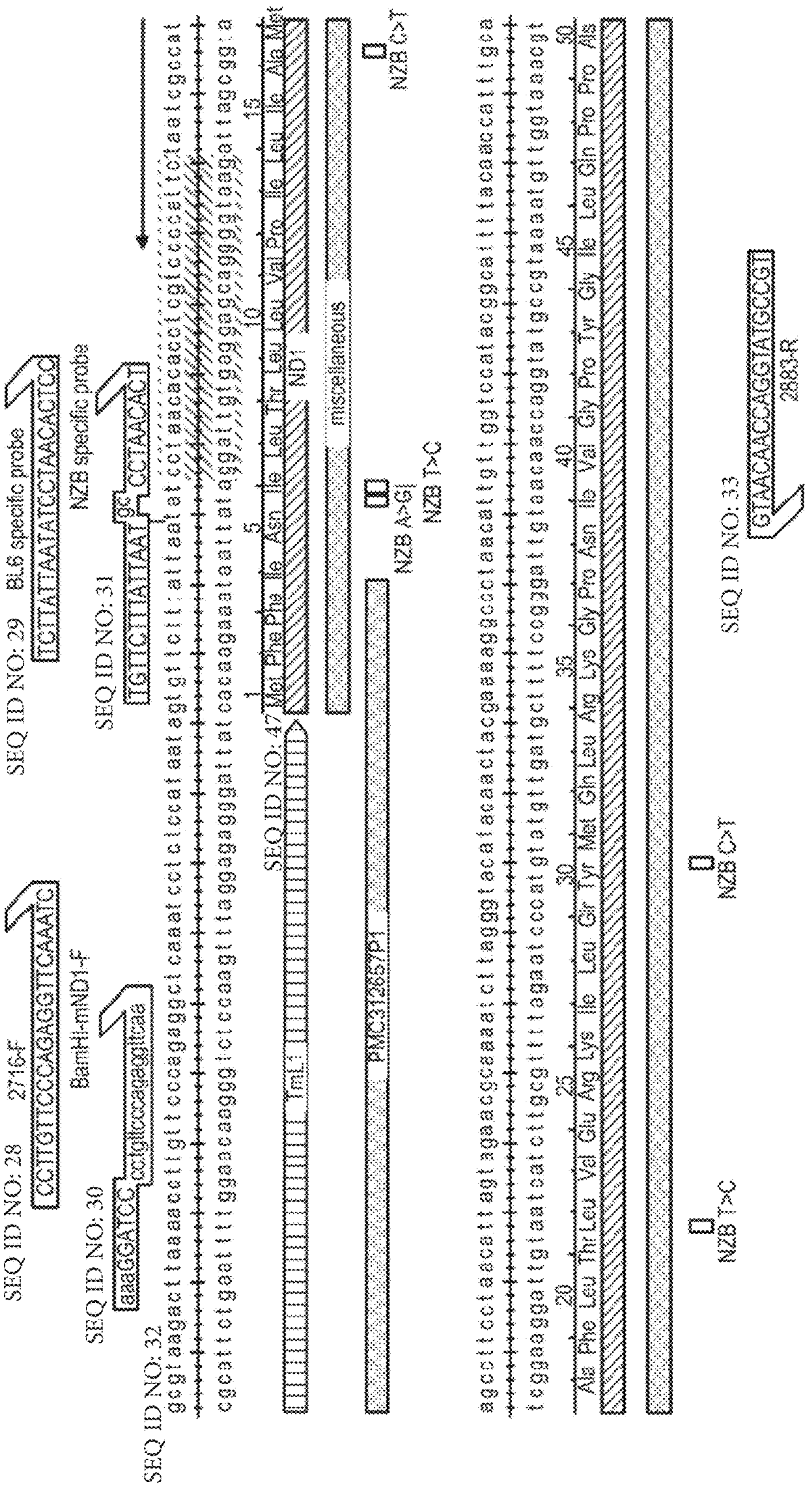

FIG. 17B depicts the 2716-F (SEQ ID NO: 28) and 2883-R (SEQ ID NO: 33) set of primers used for amplification of ND1 of mouse mitochondrial DNA (SEQ ID NO: 32) surrounding the polymorphic nucleotides mmt2766 and mmt2767, and the BL6 specific probe (SEQ ID NO: 29) and the NZB specific probe (SEQ ID NO: 31), that were designed for the TaqMan SNP genotyping assay, as well as the BamH1-mND1-F primer (SEQ ID NO: 30) used to clone the nucleotide sequence in a plasmid for generation of a standard curve to enable absolute quantification. The ND1 peptide sequence is also depicted (SEQ ID NO: 47).

Figure 17C:
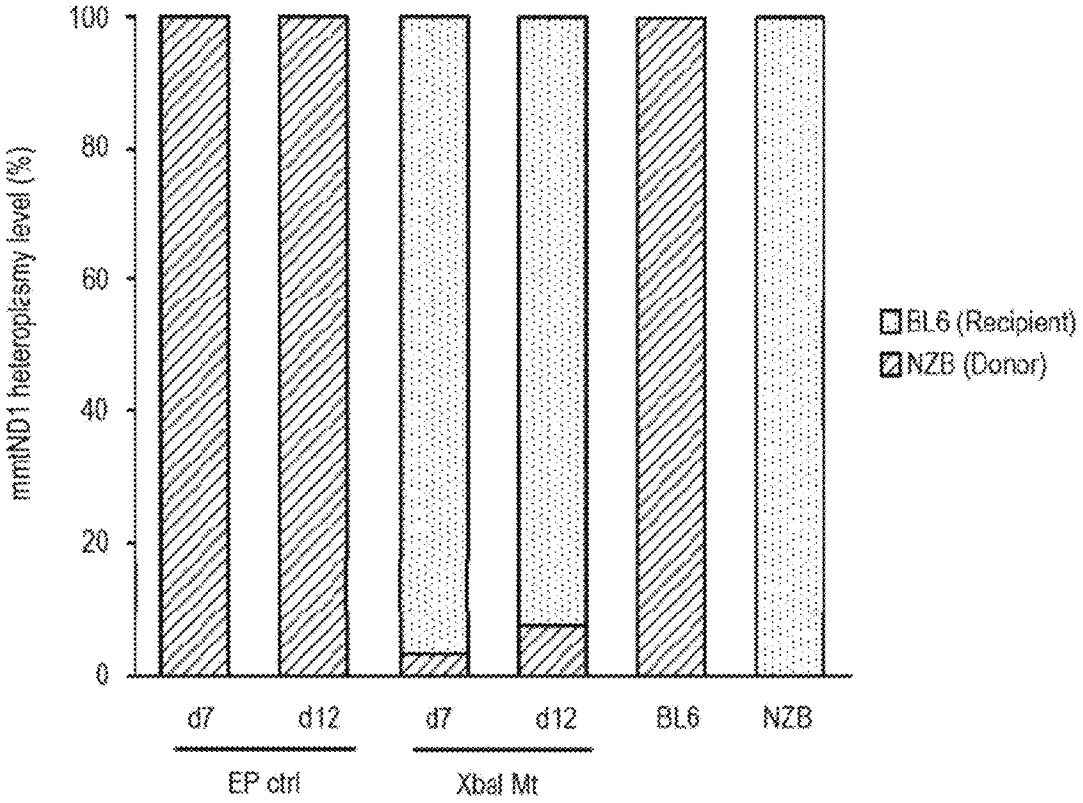

FIG. 17C depicts quantification of mouse mtND1 heteroplasmy levels in BL6 recipient cells at day 7 and day 12 following control electroporation (columns 1 and 2, respectively) or MTS-XbaI electroporation and coincubation with isolated mitochondria from NZB cells (columns 3 and 4, respectively). Basal levels of BL6 (column 5) and NZB (column 6) cells were measured as controls.

Figure 17D:
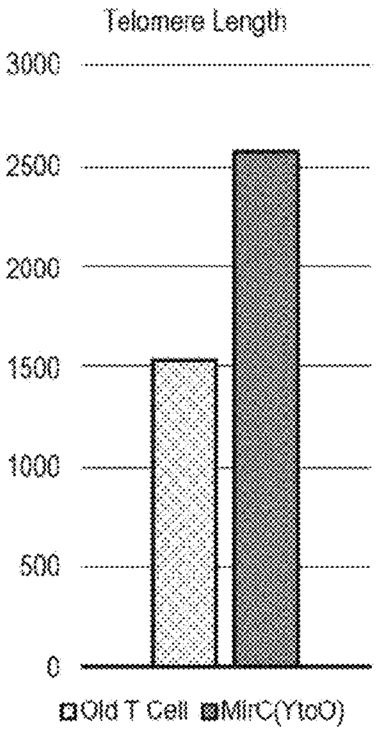

FIG. 17D depicts measurement of telomere length following the treatment of old murine cells with the MTS-XbaIR mRNA and co-incubation with exogenous mitochondria from the young donor cells to generate the MirC (Young to Old: YtoO) and revealed an increase in the length of telomeres in MirC compared to the parental "Old" cells.

Figure 17E:
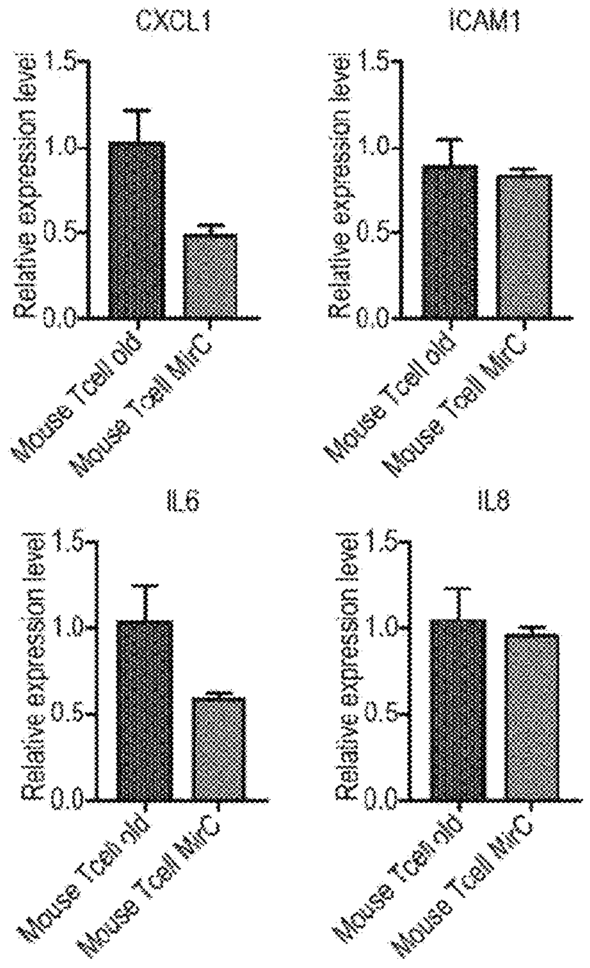

FIG. 17E depicts measurement of SASP associated cytokines CXCL1, ICAM1, IL-6, and IL-8 in the parental old T cell, or the MirC-derived T cell, and indicated that CXCL1 and IL6 were lower in the MirC-derived T cells.

Figure 17F:
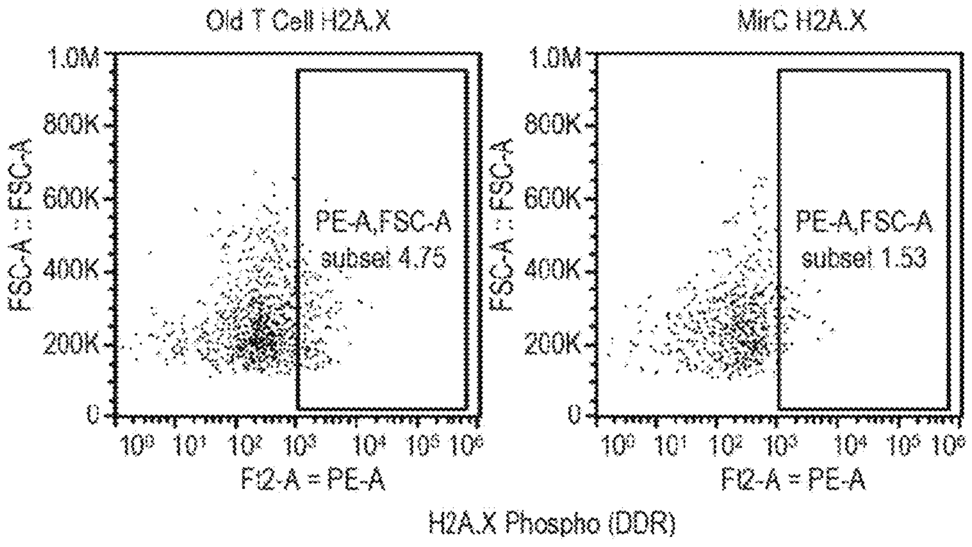

FIG. 17F depicts measurement of DNA damage response in the MirC and the original T cells using the histone 2 A (H2A) phosphorylation antibody, which indicated that the positive fraction for DDR was lower in the MirC (1.53%), compared with the original T cells (4.75%).

Figure 18A:
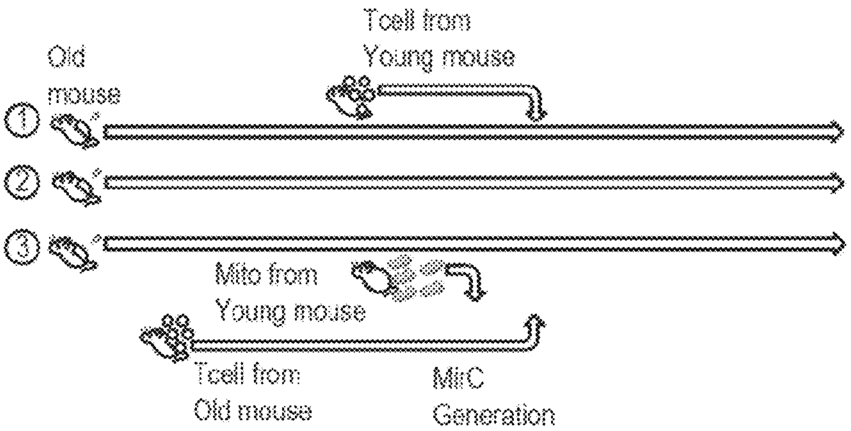

FIG. 18A depicts a scheme of the in vivo ACT experiment using old mice with ACT of T cells from young mouse (Group 1), old mice with ACT (Group 2) or old mice with ACT of MirC derived from a T cell of an old mouse transferred with exogenous mitochondria from a young mouse (Group 3).

Figure 18B:
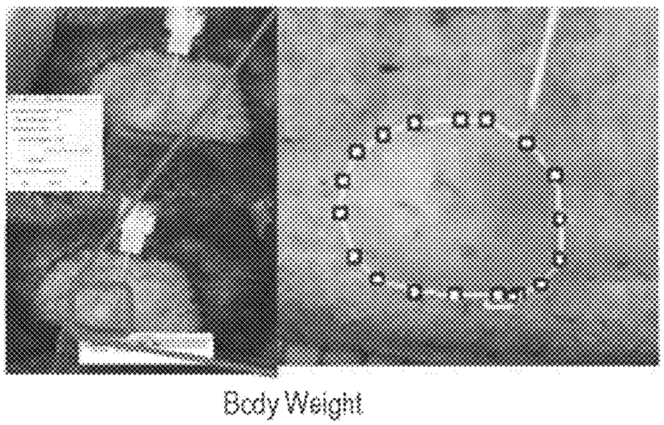

FIG. 18B depicts a representative image of tumor growth imaging performed during the experimental protocol.

Figure 18C:
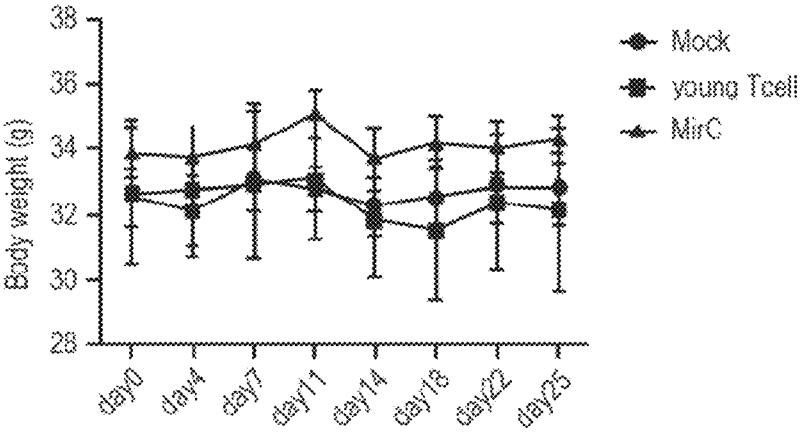

FIG. 18C depicts the body weight of the mock, young T cell, or MirC groups, and reveals that no significant difference between the three groups was observed during the 25 days experiment.

Figure 18D:
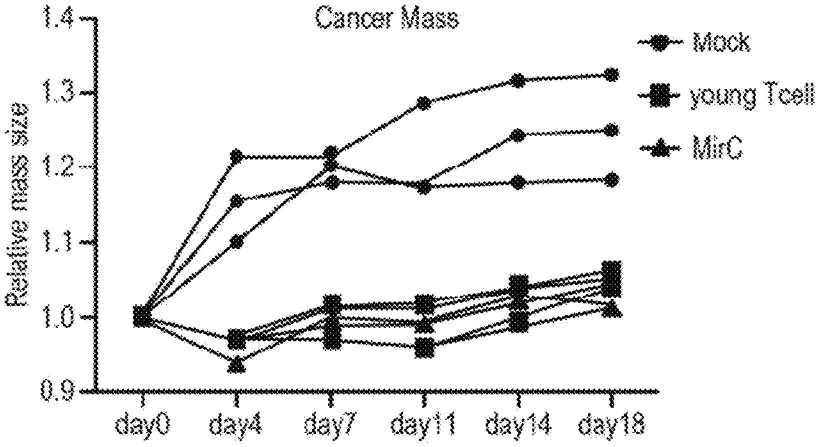
Figure 18E:
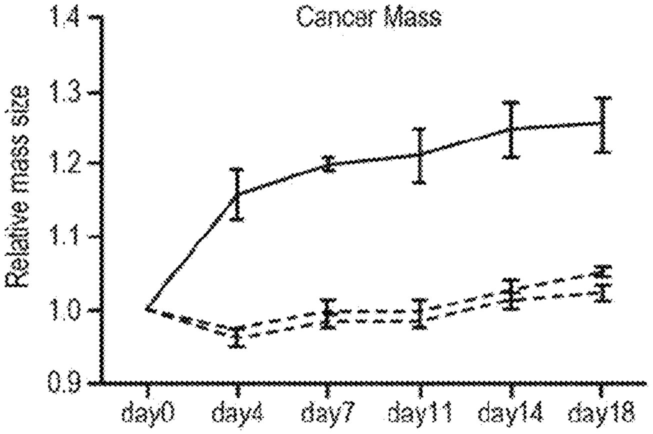

FIG. 18D and FIG. 18E depict quantification of the individual (FIG. 18D) and mean (FIG. 18E) cancer mass size, and revealed that the MirC group reduced cancer mass size to levels equivalent to the Young T cell group (lower lines), whereas the mock group increased in cancer mass throughout the length of the experiment (top lines).

Figure 18F:
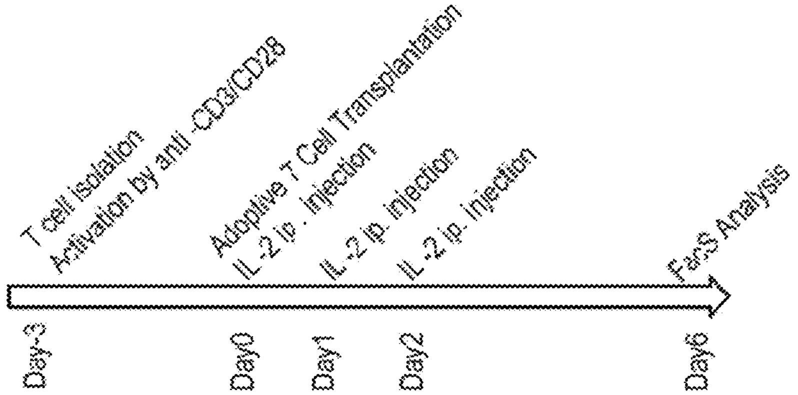

FIG. 18F depicts a scheme of the protocol used to analyze the present of infused T cells in the animals.

Figure 18G:
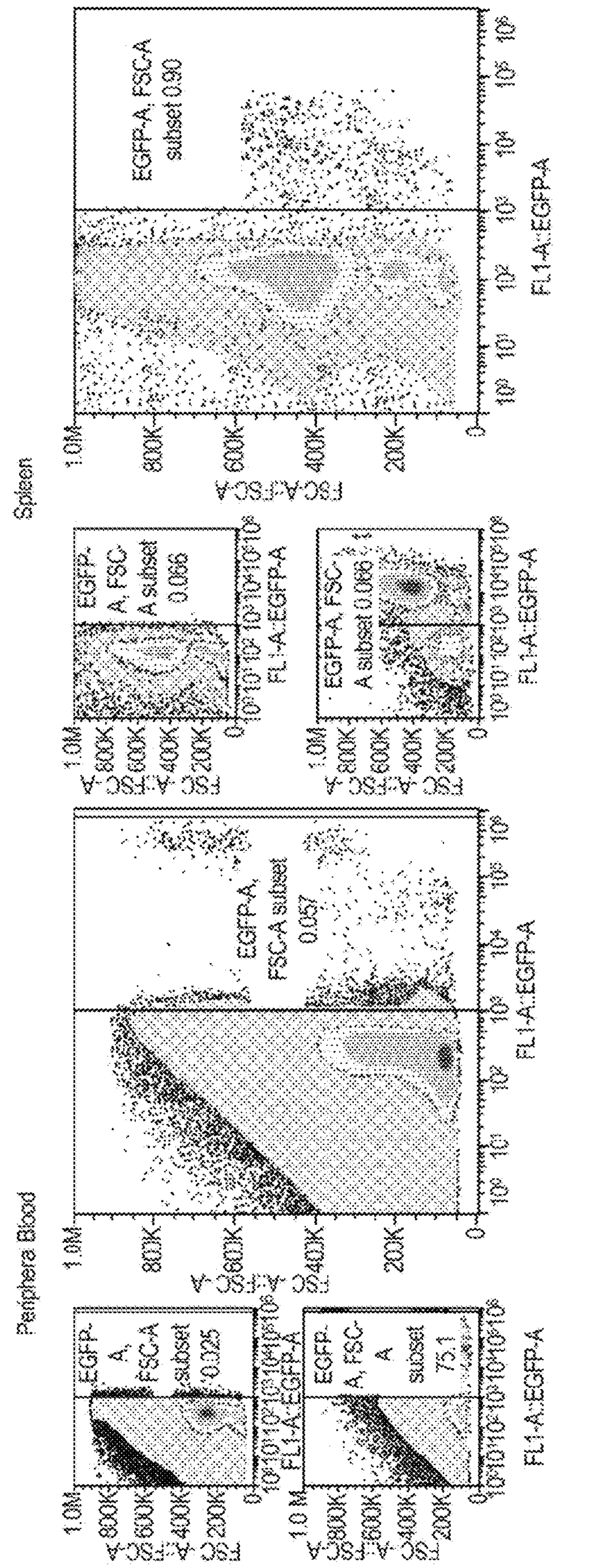

FIG. 18G depicts FACS analysis of peripheral blood (left panels) or spleen (right panels). Negative controls using C57BL/6 mice (left upper panel), and positive controls using GFP transgenic mice (left lower panel) were generated for both the peripheral blood and the spleen. Positive fractions of T cells expressing GFP fluorescence were recognized in both the peripheral blood and spleen, 0.057% and 0.9%, respectively.

Figure 18H:
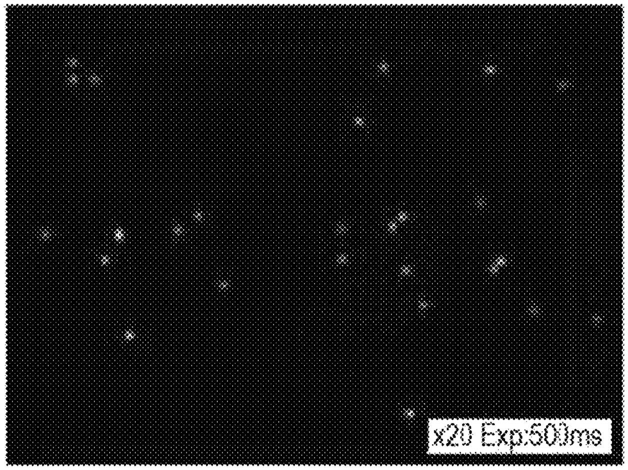

FIG. 18H depicts immunofluorescence images of the transferred T cells detected in the mice on day 6 following transplantation.

Figure 18I:
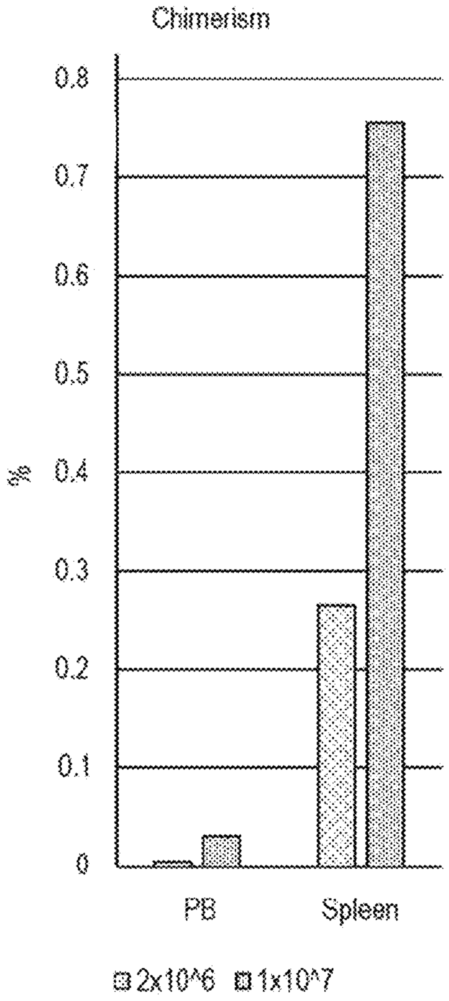

FIG. 18I depicts the percentage of chimerism following infusion of the exogenous T cells in peripheral blood (PB) or the spleen after injection of $1\times10^7$ or $2\times10^7$ cells.

Figure 19A:
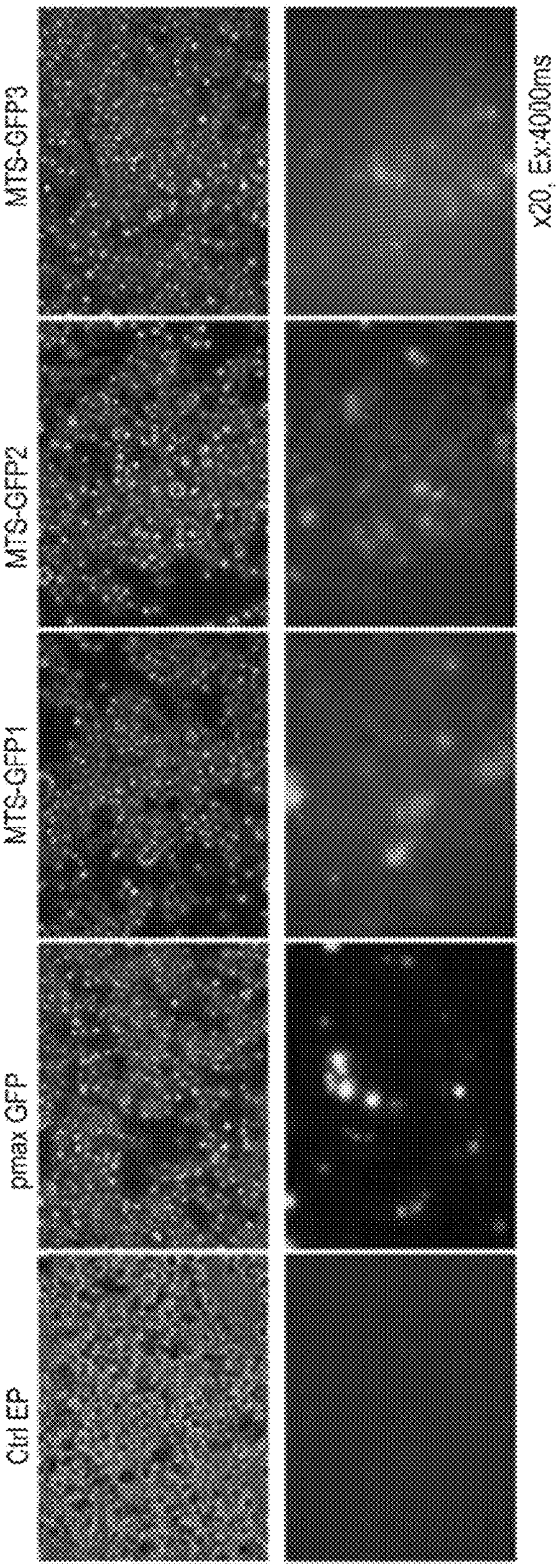
Figure 19B:
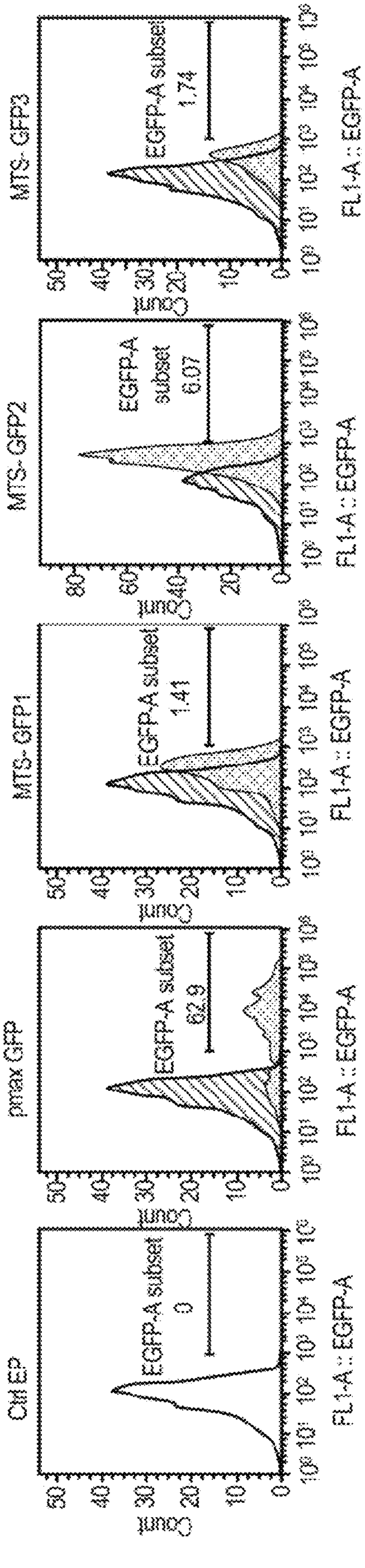

FIG. 19A and FIG. 19B depict evaluation of MTS-GFP transfection into hematopoietic cells (HSCs) using the X-001, Y-001, and T-030 programs (MTS-GFP1, 2, and 3, respectively) or pmax GFP as a positive control or Ctl EP as a negative control by microscopy (FIG. 19A) or FACS (FIG. 19B), and show that MTS-GFP1 was the optimal protocol for electroporating HSCs.

Figure 19C:
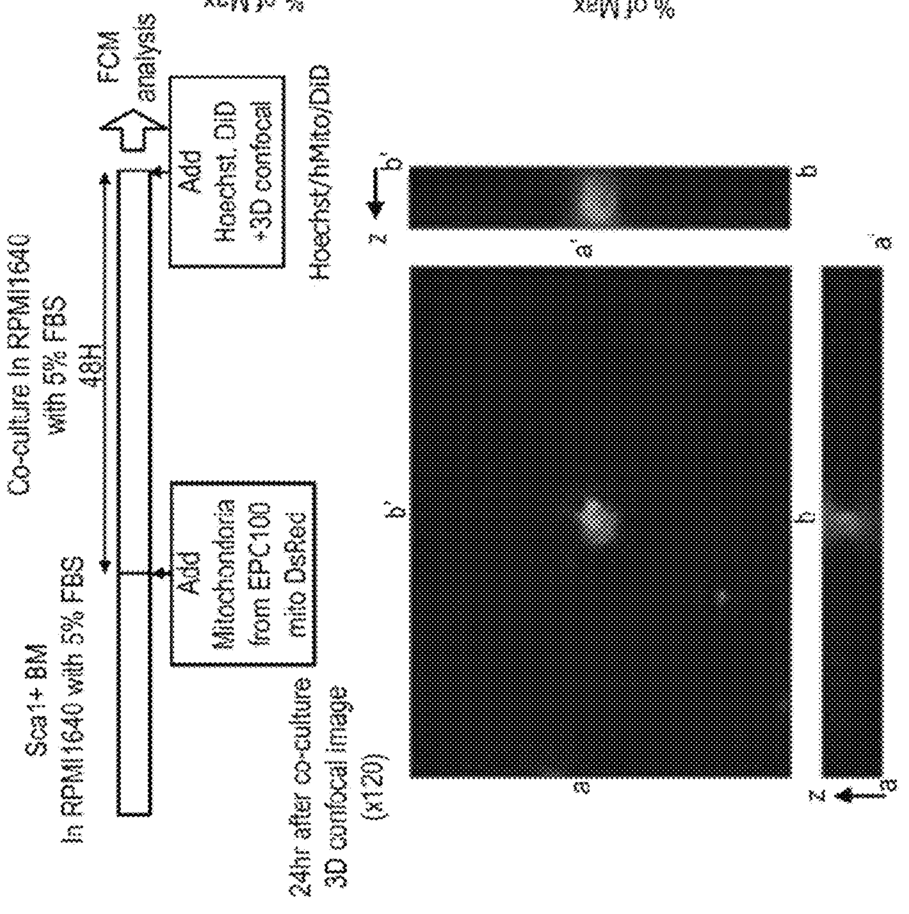

FIG. 19C depicts 3-D confocal fluorescent imaging of the bone marrow-derived Sca-1 cells 48 hours after the co-incubation with DsRed-labeled mitochondria from EPC100 cells, and showed that the exogenous mitochondria were engulfed.

Figure 19D:
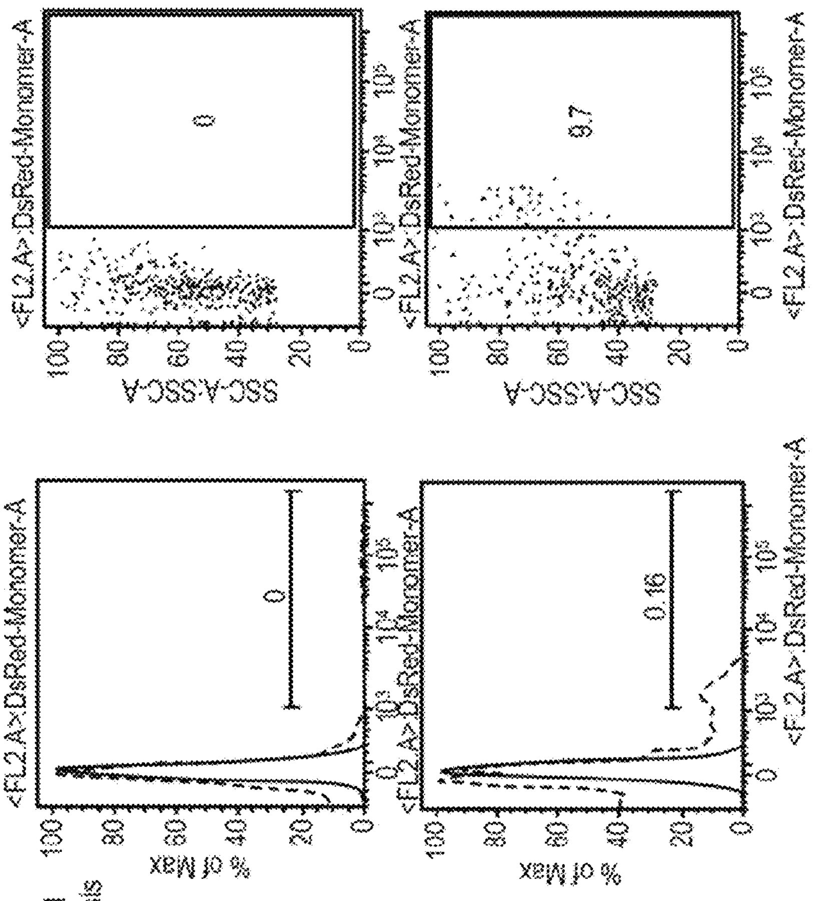

FIG. 19D depicts quantification of the mitochondrial transfer efficiency by FACS analysis of DsRed fluorescence, and revealed that a subpopulation of about 10% of the Sca-1 exhibited a right ward shift of the fluorescent.

Figure 19E:
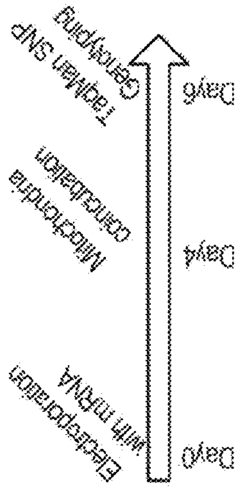

FIG. 19E depicts the scheme used to generate HSC derived MirC by coincubating with exogenous mitochondria on day 4 and analyzing the MirC on day 6 by SNP assay.

Figure 19F:
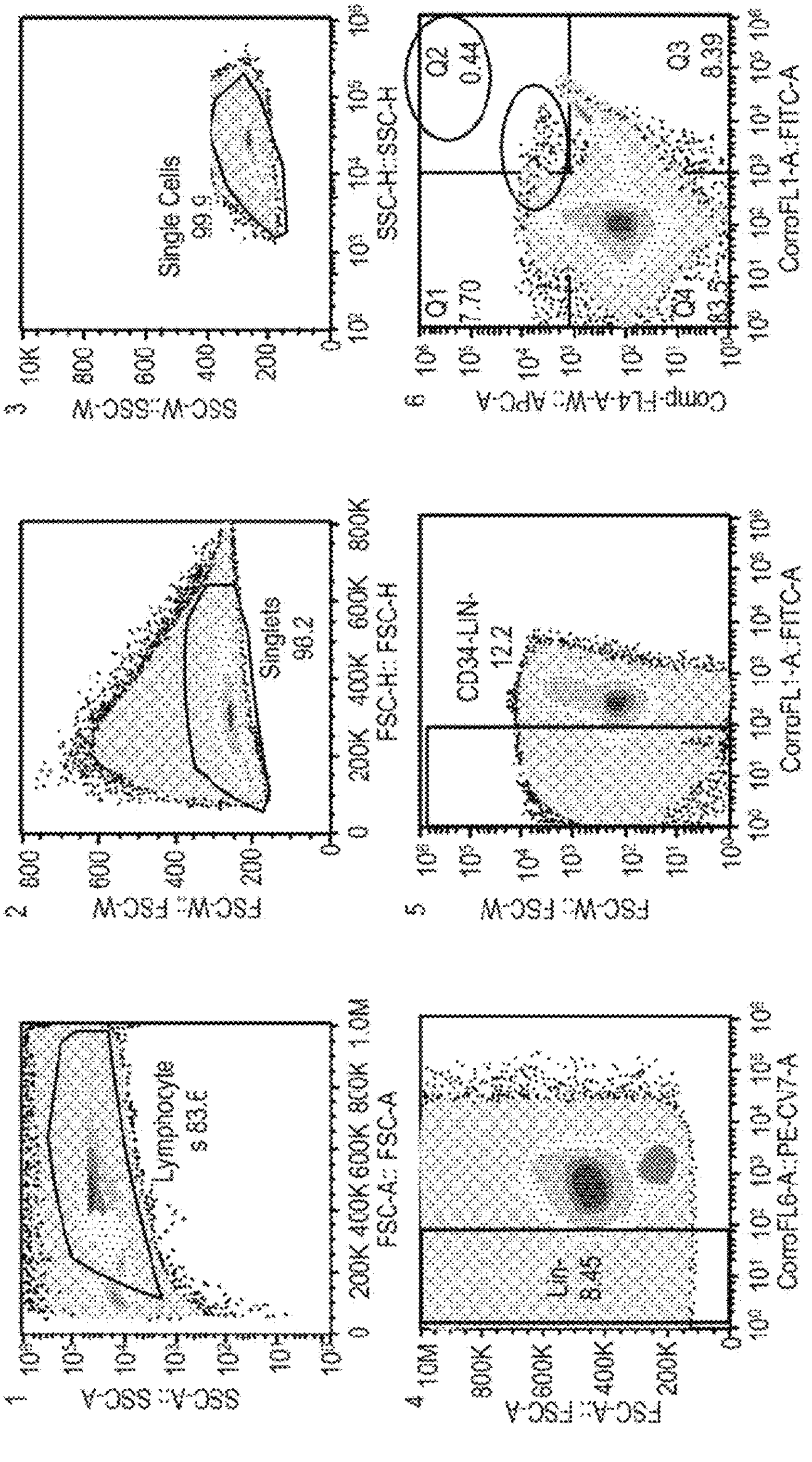

FIG. 19F depicts the FACS sorting for the c-kit+, Sca-1+, Lineage−, CD34− (called as KSLC) fraction of cells.

Figure 19G:
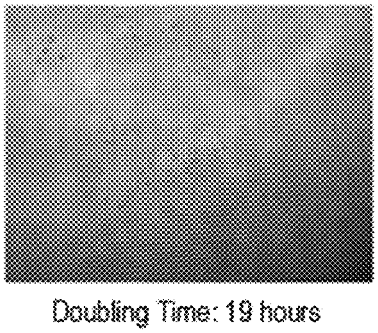

FIG. 19G depicts that the doubling time of the KSLC fraction was 19 hours.

Figure 19H:
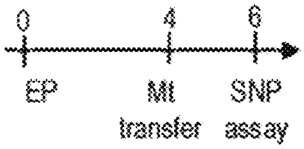

FIG. 19H depicts the scheme used to evaluate HSC derived MirC.

Figure 19I:
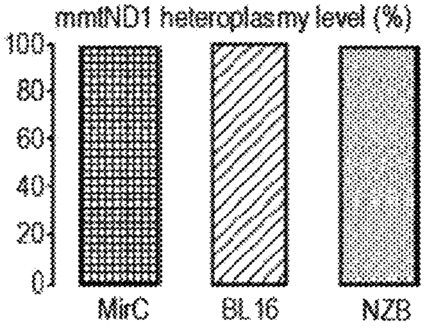

FIG. 19I depicts quantification of the murine mtND1 heteroplasmy level percentage in murine KSLC-derived MirC or the parental recipient BL6 cells or NZB donor cells, and demonstrated that the MirC derived HSC expressed 99.9% of the polymorphism genotype of the donor cells on day6 following the MTS-XbaI mRNA transfer with electroporation.

Figure 20A:
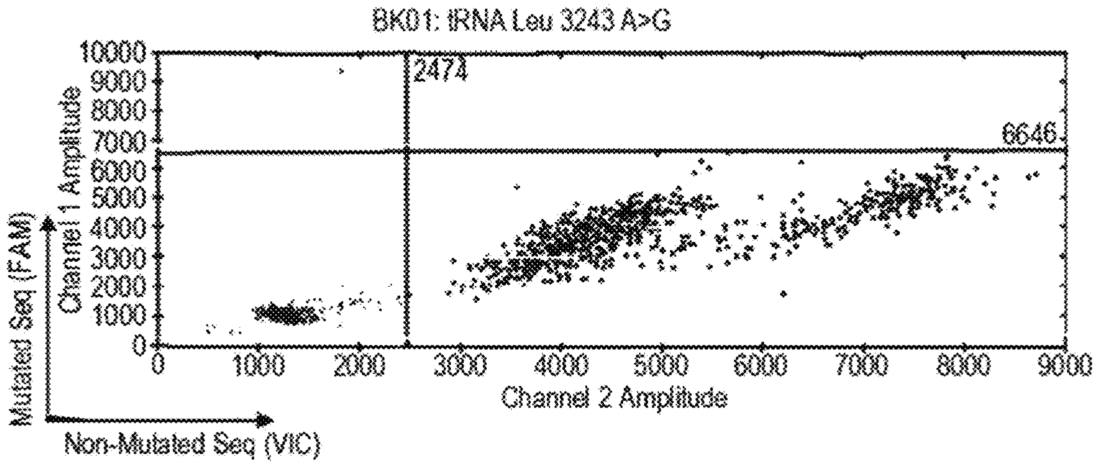

FIG. 20A depicts a 2-D plot of droplet digital PCR results in which sequences for mutated mtDNA and non-mutated mtDNA were analyzed in normal human dermal fibroblasts for tRNA Leu 3243 A>G, and show only detection of the non-mutant sequence (lower right quadrant) and no detection of the mutant sequence (upper left quadrant).

Figure 20B:
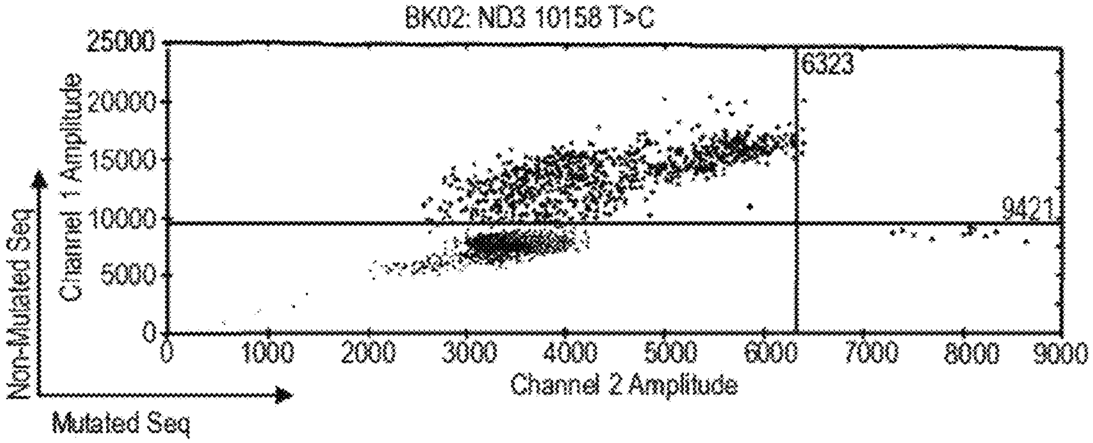

FIG. 20B depicts a 2-D plot of droplet digital PCR results in which sequences for mutated mtDNA and non-mutated mtDNA were analyzed in normal human dermal fibroblasts for ND3 10158 T>C, and show only detection of the non-mutant sequence (lower right quadrant) and no detection of the mutant sequence (upper left quadrant).

Figure 20C:
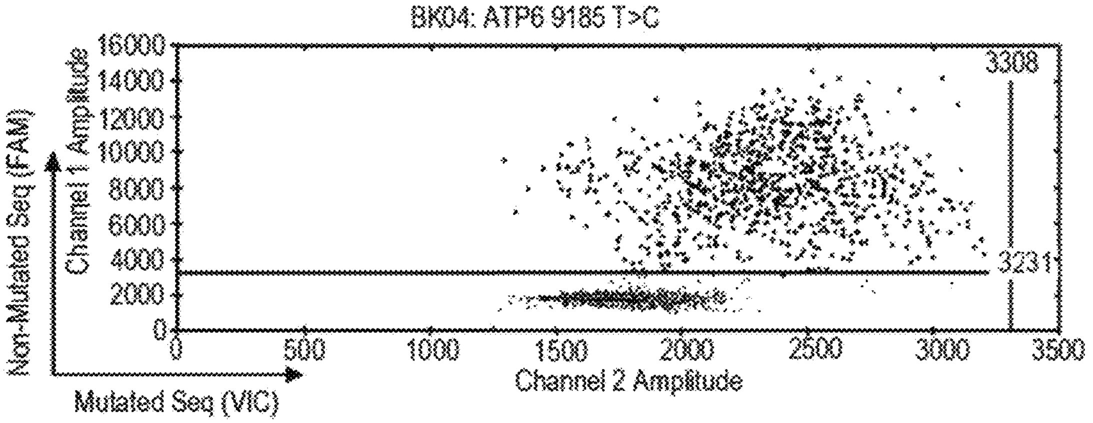

FIG. 20C depicts a 2-D plot of droplet digital PCR results in which sequences for mutated mtDNA and non-mutated mtDNA were analyzed in normal human dermal fibroblasts for ATP6 9185 T>C, and show only detection of the non-mutant sequence (lower right quadrant) and no detection of the mutant sequence (upper left quadrant).

Figure 20D:
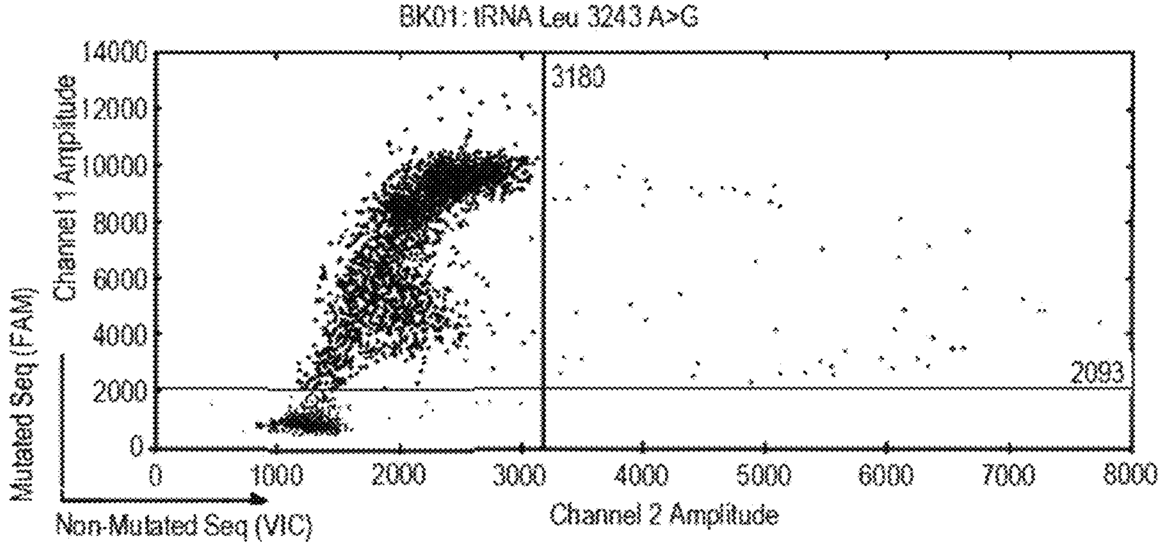

FIG. 20D depicts a 2-D plot of droplet digital PCR results in which sequences for mutated mtDNA and non-mutated mtDNA were analyzed in primary skin fibroblasts from a patient with MELAS having an mtDNA A3243G mutation, and show the majority of cells had homoplasmy of mutated mtDNA (upper left quadrant).

Figure 20E:
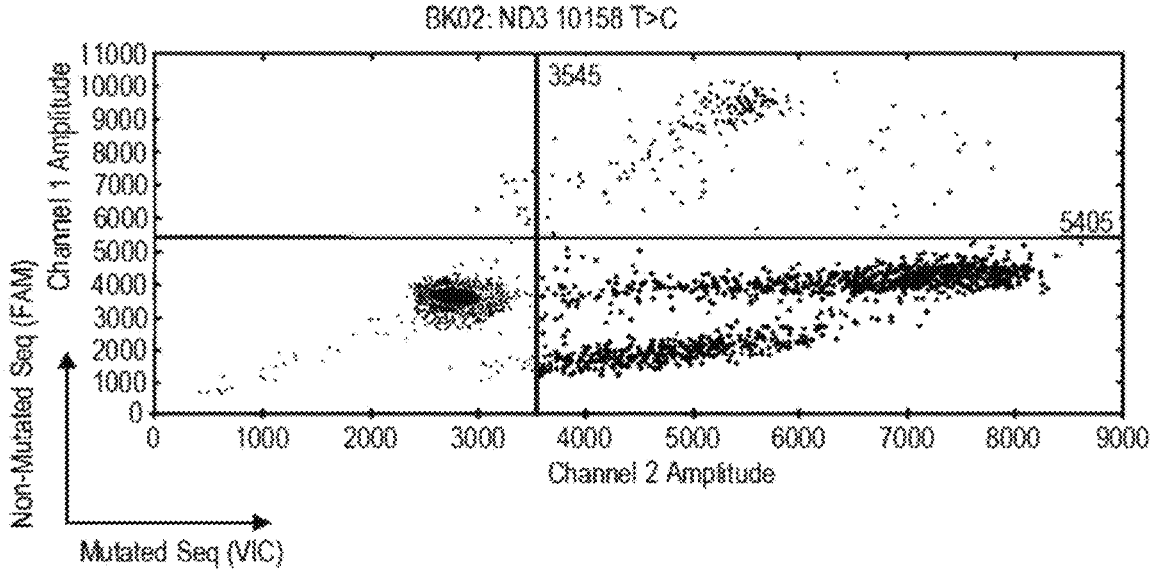

FIG. 20E depicts a 2-D plot of droplet digital PCR results in which sequences for mutated mtDNA and non-mutated mtDNA were analyzed in primary skin fibroblasts from a patient with Leigh Syndrome having a mtDNA T10158C mutation of Complex I, ND3 gene, and showed a minor portion of double positive cells with heteroplasmy in a single cell level (upper right quadrant), a major population of homoplasmy of mutated mtDNA (lower right), and no population with homoplasmy of non-mutated mtDNA (upper left).

5. DETAILED DESCRIPTION OF THE INVENTION

Provided herein are novel and enhanced methods of generating a mitochondria replaced cell (MirC) that do not require complete removal of endogenous mtDNA, and can optionally be performed using reagents that are compatible with clinical use. In addition, in certain embodiments provided herein are methods of treatment involving administering a therapeutically effective amount of the MirC generated using the methods provided herein.

Also provided are compositions that include one or more mitochondria replaced cells obtained by the methods provided herein. In certain embodiments, the compositions can also include a second active agent that enhances the uptake of exogenous mitochondria, exogenous mtDNA, or a combination thereof, and/or an agent that reduces endogenous mtDNA copy number or reduces endogenous mitochondrial function. In further embodiments, the compositions can also include exogenous mitochondria and/or exogenous mtDNA, one or more recipient cells, or a combination thereof. In one specific embodiment, provided herein are methods and compositions for use in the treatment of a disease or disorder associated with dysfunctional mitochondria. However, it is understood that the methods and compositions provided herein can also be used to delay senescence, extend the lifespan, or enhance the function of a cell that has functional mitochondria, and is not limited to replacement of dysfunctional mitochondria. Furthermore, the methods and compositions provided herein can also be used to replace functional mitochondria with exogenous mitochondria that is dysfunctional or exhausted, for example, to generate a disease model.

5.1 Definitions

Unless particularly defined otherwise, all terms including technical and scientific terms used in this application have the same meaning as commonly understood by one of ordinary skill in the art to which this invention belongs. In general, the nomenclatures used in this specification and the experimental methods described below are widely known and generally used in the related art.

As used herein, the term "mitochondria replaced cell" or MirC is intended to mean a cell having the substitution of endogenous mitochondria and/or mtDNA with exogenous mitochondria and/or mtDNA. For example, an exemplary mitochondria replaced cell (MirC) involves the substitution of endogenous mtDNA that encodes dysfunctional mitochondria, such as mtDNA originating from a subject having a mitochondrial disease or disorder, with exogenous mtDNA that encodes functional mitochondria, such as mtDNA originating from a healthy subject. Exemplary MirC can also include a cell with endogenous mitochondria substituted with exogenous mitochondria. However, it is understood that the substitution of the endogenous mitochondria and/or mtDNA can also include, for example, functional endogenous mtDNA from one cell, such as from an old cell, that is substituted with functional exogenous mtDNA from a different cell, such as from a healthier cell that is from a young subject. It is further understood that healthy endogenous mitochondria and/or mtDNA can also be substituted with dysfunctional exogenous mitochondria and/or exogenous mtDNA such as, for example, to mimic a mitochondrial disease or disorder. Replacement need not result in a complete substitution of all the endogenous mitochondria in a cell, and that exemplary mitochondria and/or mtDNA replacement involves substitution of about 5% of more, about 10% or more, about 20% or more, about 30% or more, about 40% or more, about 50% or more, about 60% or more, about 70% or more, about 80% or more, about 90% or more, or about 95% or more of the endogenous mitochondria and/or mtDNA.

As used herein, the term "recipient cell," "acceptor cell," and "host cell" are interchangeable and refer to a cell receiving the exogenous mitochondria and/or mtDNA. In some embodiments, the exogenous mitochondria and/or mtDNA is from isolated mitochondria from a donor cell. In some embodiments, the donor cells and the recipient cells may be different or identical. In some embodiments, the donor cells and the recipient cells come from different or the same species. In some embodiments, the donor cells and the recipient cells come from different or the same tissues.

As used herein, the term "healthy donor" is intended to mean a donor that does not have a mitochondrial disease or disorder, age-related disease, or otherwise dysfunctional mitochondria. In preferred embodiments, a healthy donor has a wild-type mtDNA sequence, relative to the Cambridge Reference Sequence of the mitochondrial genome.

As used herein, the terms "treat," "treating," and "treatment" refer to reduction in severity, progression, spread, and/or frequency of symptoms, elimination of symptoms and/or underlying cause, prevention of the occurrence of symptoms and/or their underlying cause, and improvement or remediation of damage "Treatment" is meant to include therapeutic treatment as well as prophylactic, or suppressive measures for the condition, disease or disorder.

As used herein, the term "agent" when used in reference to depleting reducing mtDNA refers to an enzyme or compound that is capable of reducing mtDNA. Preferred agents include restriction enzymes, such as XbaI, that cleave mtDNA at one or more sites, without producing toxicity in the recipient cell. However, agents can also include an enzyme or compound that inhibit mtDNA synthesis or selectively promote degradation of the mitochondria.

As used herein, the terms "reduce," or "decrease" generally means a decrease of at least 5%, for example a decrease by at least about 10%, or at least about 20%, or at least about 30%, or at least about 40%, or at least about 50%, or at least about 60%, or at least about 70%, or at least about 80%, or at least about 90%, or any decrease between 5%-99% as compared to a reference level, as that term is defined herein. It is understood that a partial reduction or an agent that partially reduces endogenous mtDNA or decrease, as used herein, does not result in a complete depletion of all endogenous mtDNA (i.e., ρ0 cells). The term "increase" as used herein generally means an increase of at least 5%, for example an increase by at least about 10%, or at least about 20%, or at least about 30%, or at least about 40%, or at least about 50%, or at least about 60%, or at least about 70%, or at least about 80%, or at least about 90%, or more than 90%.

As used herein, the term "endogenous" refers to originating or derived internally. For example, endogenous mitochondria are mitochondria that are native to a cell.

As used herein, the term "exogenous" refers to cellular material (e.g., mitochondria or mtDNA) that is non-native to the host, such as cellular material that is derived externally. "Externally" typically means from a different source. For example, mitochondrial genomes are exogenous to host cells or host mitochondria when the mitochondrial genomes originate from different cell types or different species than the host cells or host mitochondria. In addition. "exogenous" can also refer to mitochondrial genomes that are removed from mitochondria, manipulated, and returned to the same mitochondria.

As used herein, the term "sufficient period of time" refers to an amount of time that produces the desired results. It is understood that the sufficient period of time will vary according to the experimental conditions, including but not limited to, the temperature, the amount of reagent used, and the cell type. Exemplary protocols are provided throughout as guidelines for the "sufficient period of time," and a person skilled in the art would be able to identify the period of time that is sufficient without undue experimentation.

As used herein, the term "majority" is intended to mean the greatest amount, relative to the other amounts being compared. An exemplary majority when comparing two groups, is an amount that is any integer greater than about 50% or more, about 60% or more, about 70% or more, about 80% or more, or about 90% or more, or about 95% or more, of the total population, including any integer in-between. It is understood that the majority will depend on the total population being compared, and can be amounts lower than 50% when there are three or more groups being compared.

As used herein, the term "non-invasively" when used in reference to the transfer of exogenous material is intended to mean without the use of invasive instruments (e.g., nanoblade or electroporation), physical force (e.g., centrifugation), or harmful culture conditions (e.g., thermal shock). In preferred embodiments, the non-invasive transfer procedure involves co-incubation of a recipient cell and donor mitochondria.

As used herein, the term "subject in need of mitochondrial replacement," is intended to mean a subject that has or is predisposed to having a dysfunctional mitochondria. The subject in need of mitochondrial replacement may be asymptomatic and in need of preventative care. The subject in need of mitochondrial replacement may also be symptomatic and in need of treatment. In certain embodiments, the subject in need of mitochondrial replacement has dysfunctional mitochondria that is not the result of an age-related disease or a mitochondrial disease or disorder.

As used herein, the term "subject" is intended to mean a mammal. A subject can be a human or a non-human mammal, such as a dog, cat, bovid, equine, mouse, rat, rabbit, or transgenic species thereof. It is understood that a "subject" can also refer to a "patient," such as a human patient.

As used herein, the term "effective amount" refers to the amount of a composition of the invention effective to modulate, treat, or ameliorate any disease or disorder associated with heteroplasmy and/or dysfunctional mitochondria. As such, an effective amount can include, for example, a therapeutically effective amount, which refers to an effective amount in a therapy, or a biologically effective amount, which refers to an effective amount for a biological effect. The terms "therapeutically effective amount" and "effective amount" can encompass an amount that improves overall therapy, reduces or avoids symptoms or causes of disease or disorder, or enhances the therapeutic efficacy of another therapeutic agent. The amount of a given composition that will correspond to such an amount will vary depending upon various factors, such as the given composition, the pharmaceutical formulation, the route of administration, the type of condition, disease or disorder, the identity of the subject or host being treated, and the like, but can nevertheless be routinely determined by one skilled in the art. As defined herein, a therapeutically effective amount of an agent may be readily determined by one of ordinary skill by routine methods known in the art.

As used herein, the term "age-related disease" refers to any number of conditions attributable to advancement in age. These conditions include, without limitation, osteoporosis, bone loss, arthritis, stiffening joints, cataracts, macular degeneration, metabolic diseases including diabetes mellitus, neurodegenerative diseases including Alzheimer's Disease and Parkinson's Disease, immunosenescence, and heart disease including atherosclerosis and dyslipidemia. The phrase "age related disease" further encompasses neurodegenerative diseases, such as Alzheimer's Disease and related disorders, ALS, Huntington's disease, Parkinson's Disease, and cancer.

As used herein, the term "autoimmune disease" is intended to mean a disease or disorder arising from immune reactions directed against an individual's own tissues, organs or a manifestation thereof or a resulting condition therefrom. An autoimmune disease can refer to a condition that results from, or is aggravated by, the production of autoantibodies that are reactive with an autoimmune antigen or epitope thereof. An autoimmune disease can be tissue- or organ-specific, or it can be a systemic autoimmune disease. Systemic autoimmune diseases include connective tissue diseases (CTD), such as systemic lupus erythematosus (lupus; SLE), mixed connective tissue disease systemic sclerosis, polymyositis (PM), dermatomyositis (DM), and Sjögren's syndrome (SS). Additional exemplary autoimmune diseases further include rheumatoid arthritis, and anti-neutrophil cytoplasmic antibody (ANCA) polyangiitis.

As used herein, the term "genetic disease" refers to a disease caused by an abnormality, such as a mutation, in the nuclear genome. Exemplary genetic diseases include, but are not limited to, Hutchinson-Gilford Progeria Syndrome, Werner Syndrome, and Huntington's disease.

As used herein, the term "cancer" includes but is not limited to, solid cancer and blood borne cancer. The terms "cancer" and "cancerous" refer to or describe the physiological condition in mammals that is typically characterized by unregulated cell growth.

As used herein, the terms "mitochondrial disease or disorder" and "mitochondrial disorder" are interchangeable and refer to a group of conditions caused by inherited or acquired damage to the mitochondria causing an energy shortage within those areas of the body. Exemplary organs effected by mitochondrial disease or disorder include those that consume large amounts of energy such as the liver, muscles, brain, eye, ear, and the heart. The result is often liver failure, muscle weakness, fatigue, and problems with the heart, eyes, and various other systems.

As used herein, the term "mitochondrial DNA abnormalities" refer to mutations in mitochondrial genes whose products localize to the mitochondrion, and not observed in the cells of healthy subjects. Exemplary diseases associated with mitochondrial DNA abnormalities include, for example, chronic progressive external ophthalmoplegia (CPEO), Pearson syndrome, Kearns-Sayre syndrome (KSS), diabetes and deafness (DAD), leber hereditary optic neuropathy (LHON), LHON-plus, neuropathy, ataxia, and retinitis pigmentosa syndrome (NARP), maternally-inherited Leigh syndrome (MILS) also known as Leigh syndrome caused by mutant mtDNA, mitochondrial encephalomyopathy, lactic acidosis, and stroke-like episodes (MELAS), myoclonic epilepsy and ragged-red fiber disease (MERRF), familial bilateral striatal necrosis/striatonigral degeneration (FBSN), Luft disease, aminoglycoside-induced Deafness (AID), and multiple deletions of mitochondrial DNA syndrome.

As used herein, the term "nuclear DNA abnormalities" within the context of mitochondrial disease or disorder refer to mutations or changes in the coding sequence of nuclear genes whose products localize to the mitochondrion. Exemplary mitochondrial disease or disorders associated with nuclear mutations include Mitochondrial DNA depletion syndrome-4A, mitochondrial recessive ataxia syndrome (MIRAS), mitochondrial neurogastrointestinal encephalomyopathy (MNGIE), mitochondrial DNA depletion syndrome (MTDPS), DNA polymerase gamma (POLG)-related disorders, sensory ataxia neuropathy dysarthria ophthalmoplegia (SANDO), leukoencephalopathy with brainstem and spinal cord involvement and lactate elevation (LBSL), co-enzyme Q10 deficiency, Leigh syndrome (caused by nuclear mutations), mitochondrial complex abnormalities, fumarase deficiency, α-ketoglutarate dehydrogenase complex (KGDHC) deficiency, succinyl-CoA ligase deficiency, pyruvate dehydrogenase complex deficiency (PDHC), pyruvate carboxylase deficiency (PCD), carnitine palmitoyltransferase I (CPT I) deficiency, carnitine palmitoyltransferase II (CPT II) deficiency, carnitine-acyl-carnitine (CACT) deficiency, autosomal dominant-/autosomal recessive-progressive external ophthalmoplegia (ad-/ar-PEO), infantile onset spinal cerebellar atrophy (IOSCA), mitochondrial myopathy (MM) spinal muscular atrophy (SMA), growth retardation, aminoaciduria, cholestasis, iron overload, early death (GRACILE), and Charcot-Marie-Tooth disease type 2A (CMT2A).

As used herein, the term "dysfunctional mitochondria" refer to mitochondria that are in opposition to functional mitochondria. Exemplary dysfunctional mitochondria include mitochondria that are incapable of synthesizing or synthesize insufficient amounts of ATP by oxidative phosphorylation. As used herein, the term "functional mitochondria" refers to mitochondria that consume oxygen and produce ATP.

As used herein, the term "mutation" refers to any changing of the structure of a gene, resulting in a variant (also called "mutant") form. Mutations in a gene may be caused by the alternation of single base in DNA, or the deletion, insertion, or rearrangement of larger sections of genes or chromosomes. In some embodiments, the mutation can affect the function or the resulting protein. For example, a mutation in a single nucleotide of DNA (i.e., point mutation) in the coding region of a protein can result in a codon that encodes for a different amino acid (i.e., missense mutation). It is understood that this different amino acid can alter the structure of the protein, and that in certain circumstances, as described herein, can alter the function of the organelle, such as the mitochondrion.

As used herein, the terms "heteroplasmy" and "heteroplasmic" refer to the occurrence of more than one type of mitochondrial DNA genome in an individual or sample. Varying degrees of heteroplasmy are associated with varying degrees of the physiological conditions described herein. Heteroplasmy may be identified by means known to the art, and the severity of the physiological condition associated with specific nucleotide alleles is expected to vary with the percentage of such associated alleles within the individual.

As used herein, the term "wild-type" when used in the context of mitochondrial DNA refers to the genotype of the typical form of a species as it occurs in nature. An exemplary reference genome for the wild-type human mtDNA genome includes the Cambridge Reference Sequence (CRS).

As used herein, the term "old" or "older" is intended to mean that the source of the mtDNA is from a subject that is greater in age than the recipient cell, or from a cell in a population of cells that have doubled their population a greater number of times since their culture in vitro (i.e., population doubling level, PDL) relative to the recipient cell.

As used herein, the term "young" or "younger" is intended to mean that the source of the mtDNA is from a subject that is lower in age than the recipient cell, or from a cell in a population of cells that have doubled their population a fewer number of times since their culture in vitro (i.e., population doubling level, PDL) relative to the recipient cell.

As used herein, the term "isolated" when used in reference to mitochondria refers to mitochondria that have been physically separated or removed from the other cellular components of its natural biological environment.

As used herein, the terms "intact" and "intact mitochondria" refers to mitochondria comprising an outer and an inner membrane, an inter-membrane space, the cristae (formed by the inner membrane) and the matrix. Exemplary intact mitochondria contain mtDNA. In preferred embodiments, intact mitochondria are functional mitochondria. However, it is understood that intact dysfunctional mitochondria can also be used in the present invention.

As used herein, the term "autologous" is intended to mean biological compositions obtained from the same subject.

As used herein, the term "allogeneic" is intended to mean biological compositions obtained from the same species, but a different genotype than that of the subject receiving the biological composition.

As used herein, the term "animal cell" is intended to mean any cell from a eukaryotic organism. It is understood that an animal cell can include mammalian and non-mammalian species, such as amphibians, fish, insects (e.g., *Drosophila*), and worms (e.g., *Caenorhabditis elegans*).

As used herein, the term "fusion protein" refers to a sequence of amino acids, predominantly, but not necessarily, connected to each other by peptidic bonds, wherein a part of the sequence is derived (i.e., has sequence similarity to sequences) from one origin (native or synthetic) and another part of the sequence is derived from one or more other origin Exemplary fusion proteins can be prepared by construction of an expression vector that codes for the whole of the fusion protein (coding for both sections, such as a mitochondrial-targeted sequence and an endonuclease) so that essentially all the bonds are peptidic bonds. It is also understood that the fusion may be made by chemical conjugation, such as by using any of the known methodologies used for conjugating peptides.

As used herein, the terms "mitochondrial-targeted sequence (MTS)" and "mitochondrial targeting sequence (MTS)" are interchangeable and refer to any amino acid sequence capable of causing the transport of an enzyme, peptide, sequence, or compound attached to it into the mitochondria. In certain embodiments, the MTS is a human MTS. In another embodiment, the MTS is from another species. Non-limiting examples of such sequences are the cytochrome c oxidase subunit X (COX10) MTS (MAAS-PHTLSSRLLTGCVGGSVWYLERRT, SEQ ID NO: 36), and the cytochrome c oxidase subunit VIII (COX8) MTS (MSVLTPLLLRSLIGSARRLMVPRA, SEQ ID NO: 37) Additional non-limiting examples of MTS sequences are the natural MTS of each individual mitochondrial protein that is encoded by the nuclear DNA, translated (produced) in the cytoplasm and transported into the mitochondria, as well as citrate synthase (cs), lipoamide deydrogenase (LAD), and C6ORF66 (ORF). The various MTS may be exchangeable for each mitochondrial enzyme among themselves. Each possibility represents a separate embodiment of the fusion protein for use of the present invention.

As used herein, the term "small molecule" refers to a compound that affects a biological process and has molecular weight of about 900 Daltons or lower. An exemplary small molecule had a molecular weight between about 300 and about 700 daltons.

As used herein, the terms "about" or "approximately" when used in conjunction with a number refer to any number within 1, 5, 10, 15 or 20% of the referenced number.

As used herein, the term "somatic cell" refers to any differentiated cell forming the body of an organism, apart from stem cells, progenitor cells, and germline cells (i.e., ovogonies and spermatogonies) and the cells derived therefrom (e.g., oocyte, spermatozoa). For instance, internal organs, skin, bones, blood, and connective tissue are all made up of somatic cells. Somatic cells are obtained from animals, preferably human subjects, and cultured according to standard cell culture protocols available to those of ordinary skill in the art.

As used herein, the term "endocytosis pathway" refers to the cellular process in which cells take in molecules from their surroundings. The endocytosis pathway can be "clathrin-dependent," which requires the recruitment of clathrin to help curve the plasma membrane into the vesicle which absorbs the molecules, or "clathrin-independent," which does not require the recruitment of clathrin. An exemplary type of clathrin-independent endocytosis includes, for example, macropinocytosis. The term "activator of endocytosis," as used herein, refers to agents that, e.g., induce or activate the endocytosis pathway, or process, such that the endocytosis pathway is increased. An exemplary "activator of endocytosis" increases mitochondrial uptake from the extracellular environment.

As used herein, the term "macropinocytosis" refers to a clathrin-independent form of endocytosis that mediates the non-selective uptake of solute molecules, nutrients and antigens.

As used herein, the term "compound" refers to a compound capable of effecting a desired biological function. The term includes, but is not limited to, DNA, RNA, protein, polypeptides, and other compounds including growth factors, cytokines, hormones or small molecules.

As used herein, the term "peptide" the terms "peptide," "polypeptide" and "protein" are used interchangeably and in their broadest sense to refer to constrained (that is, having some element of structure as, for example, the presence of amino acids which initiate a β turn or β pleated sheet, or for example, cyclized by the presence of disulfide bonded Cys residues) or unconstrained (e.g., linear or unstructured) amino acid sequences. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

As used herein, the terms "modulate," "modulation," "modulator," and "modulating" are intended to mean a change in the character or composition of the basal, homeostatic state. An exemplary modulation includes altering cellular metabolism by disrupting the homeostasis, such that cellular metabolism is significantly reduced. The term "modulator" includes inhibitors and activators. Inhibitors are agents that, e.g., inhibit expression or modification of a desired protein, pathway, or process, or bind to, partially or totally block stimulation, decrease, prevent, delay activation, inactivate, desensitize, or down regulate the activity of the described target protein, pathway, or process. In certain embodiments, inhibitors are antagonists of the target protein, pathway, or process. Activators are agents that, e.g., induce or activate the expression or modification of a described target protein, pathway, or process, or bind to, stimulate, increase, open, activate, facilitate, enhance activation of inhibitor activity, sensitize or up regulate the activity of described target protein (or encoding polynucleotide), pathway, or process. In certain embodiments, an activator is an agonist of the target protein, pathway, or process. Modulators include naturally occurring and synthetic ligands, antagonists and agonists (e.g., small chemical molecules, antibodies and the like that function as either agonists or antagonists). It is further understood that modulators can be biological (e.g., antibodies), or chemical.

As used herein, the term "prior to" is intended to mean a period of time preceding the initiation of an event, such that it is a sufficient length of time to achieve and sustain a desired result (e.g., antibiotic selection) or effect (e.g., biological effect) without the desired result or effect completely dissipating before the intended event is initiated. For instance, in an exemplary situation, it is understood that modulating cellular metabolism prior to transfer of an exogenous mitochondria and/or exogenous mtDNA would involve a sufficient period of time to, for example, exhibit a desired biological effect (e.g., increase phosphorylation of S6 kinase), without the biological effect reverting back to the homeostatic state before the transfer of exogenous mitochondria and/or exogenous mtDNA occurs.

As used herein, the term "nutrient stress" refers to nutrient deficiency or nutrient starvation conditions sufficient to produce perturbations in the cellular homeostasis, such as induction of autophagy, AMPK signaling, and/or mTOR signaling pathways. Exemplary nutrient stress conditions include serum starvation, removal of essential amino acids, and/or disruption of metabolic pathways.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The abbreviation "A," when used in reference to a nucleotide is intended to mean adenine (A). The abbreviation "G," when used in reference to a nucleotide is intended to mean Guanine (G). The abbreviation "C," when used in reference to a nucleotide is intended to mean Cytosine (C). The abbreviation "T," when used in reference to a nucleotide is intended to mean Thymine (T).

The term "pharmaceutically acceptable" when used in reference to a carrier, is intended to mean that the carrier, diluent or excipient must be compatible with the other ingredients of the formulation and not deleterious to the recipient thereof.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., Molecular Cloning: A Laboratory Manual, Third Ed., Cold Spring Harbor Laboratory, New York (2001); Ausubel et al., Current Protocols in Molecular Biology, John Wiley and Sons, Baltimore, MD (1999); Glover, ed., DNA Cloning, Volumes I and II (1985); Gait, ed., Oligonucleotide Synthesis (1984); Hames & Higgins, eds., Nucleic Acid Hybridization (1984); Hames & Higgins, eds., Transcription and Translation (1984); Freshney, ed., Animal Cell Culture: Immobilized Cells and Enzymes (IRL Press, 1986); Kallen et al, Plant Molecular Biology—A Laboratory Manual (Ed. by Melody S. Clark: Springer-Verlag, 1997); Immunochemical Methods in Cell and Molecular Biology (Academic Press, London); Scopes, Protein Purification: Principles and Practice (Springer Verlag, N.Y., 2d ed. 1987), and Weir & Blackwell, eds., Handbook of Experimental Immunology, Volumes I-IV (1986).

5.2 Methods of Generating a Mitochondria Replaced Cell (MirC)

The present invention is based, in part, on the discovery that any agent that reduces the function of endogenous mitochondria, including an agent that reduces endogenous mitochondrial DNA (mtDNA), may enhance the non-invasive transfer of exogenous mitochondria. However, the complete depletion of the endogenous mtDNA, such as with ρ(0) cells, prevents this enhancement. This is because the non-invasive transfer of exogenous mitochondria is energy dependent, and a complete depletion of the endogenous mtDNA greatly limits the energy available to facilitate the non-invasive transfer process. Similarly, the non-invasive transfer of exogenous mitochondria is also inefficient when the mitochondria function and/or mtDNA is unperturbed, for example, when mitochondria is merely co-incubated (i.e., "add-on") or added by centrifugation.

Thus, provided herein are methods of generating a mitochondria replaced cell (MirC), that can include (a) contacting a recipient cell with an agent that reduces endogenous mtDNA copy number or an agent that reduces mitochondrial function; (b) incubating the recipient cell for a sufficient period of time for the agent to partially reduce the endogenous mtDNA copy number or partially reduce the endogenous mitochondrial function in the recipient cell, respectively; and (c) co-incubating (1) the recipient cell from step (b) in which the endogenous mtDNA, or the endogenous mitochondrial function, respectively, has been partially reduced, and (2) exogenous mitochondria from a healthy donor, for a sufficient period of time to non-invasively transfer exogenous mitochondria into the recipient cell, thereby generating a mitochondria replaced cell. Also provided herein, is a method of generating a mitochondria replaced cell, that includes performing steps (a) and (b) as described above, and then (c) co-incubating (1) the recipient cell from step (b) in which the endogenous mtDNA or the endogenous mitochondrial function, respectively, has been partially reduced, and (2) exogenous mtDNA from a healthy donor, for a sufficient period of time to non-invasively transfer exogenous mtDNA into the recipient cell, thereby generating a mitochondria replaced cell. In certain embodiments, the exogenous mtDNA is transferred via exogenous mitochondria.

The generation of a MirC can be a useful strategy for a variety of applications. By way of example, the transfer of exogenous mitochondria, exogenous mtDNA, or a combination thereof into a recipient cell can be useful in, for example, replacing endogenous mitochondria that is dysfunctional and/or comprised of mutant mtDNA with functional mitochondria, such as mitochondria comprised of wild-type mtDNA. In certain embodiments, the methods provided herein are performed in a recipient cell that has endogenous mtDNA that encodes for dysfunctional mitochondria. In specific embodiments, the endogenous mtDNA is mutant mtDNA. In certain embodiments, the endogenous mtDNA is heteroplasmic and comprised of both wild-type mtDNA and mutant mtDNA.

As described above, in certain applications, the transfer of exogenous mitochondria, exogenous mtDNA, or a combination thereof can involve the transfer of functional mitochondria or wild-type mtDNA to replace endogenous mitochondria that is, for example, dysfunctional or comprised of mutant mtDNA. Accordingly, in certain embodiments, the exogenous mtDNA is wild-type mtDNA. In other embodiments, the endogenous mitochondria of the recipient cell has wild-type mtDNA, and dysfunctional endogenous mitochondria. For example, exemplary dysfunctional mitochondria of the recipient cell with wild-type mtDNA can include mutant nuclear DNA that encode for mitochondrial proteins, or dysfunctional mitochondria that arises due to a secondary effect, such as aging or disease.

The endogenous mitochondria that is dysfunctional, comprised of mutant mtDNA, or a combination thereof can therefore be replaced using the methods described herein. Mitochondrial dysfunction can occur as a result of many factors. Non-limiting examples include mitochondrial dysfunction due to a disease (e.g., an age-related disease, a mitochondrial disease or disorder, a neurodegenerative disease, a retinal disease, a genetic disease), diabetes, a hearing disorder, or any combination thereof. Mitochondrial dysfunction can involve the function of the endogenous mitochondria being reduced by greater than 5%, greater than 10%, greater than 20%, greater than 30%, greater than 40%, greater than 50%, greater than 60%, greater than 70%, greater than 80%, or greater than 90%. Therefore, in some embodiments, the endogenous mitochondria includes mitochondria with reduced function of about 5%, about 10%, about 15%, about 20%, about 25%, about 30%, about 40%, about 50%, about 60%, about 70%, about 80%, about 90%, or about 100%.

The methods provided herein are applicable to both homoplasmic and heteroplasmic mtDNA. In specific embodiments, the endogenous mtDNA is a single type of mtDNA (i.e., the endogenous mtDNA is homoplastic). In other specific embodiments, the endogenous mtDNA includes more than one type of mtDNA (i.e., the endogenous mtDNA is heteroplasmic). In some embodiments, the heteroplasmic mtDNA includes both wild-type mtDNA and mutant mtDNA. Generally, the proportion of mutant mtDNA determines the severity of the phenotype and can influence the degree to which mitochondrial function is reduced. For example, in some embodiments the heteroplasmic mtDNA is 5% mutant mtDNA and 95% wild-type mtDNA, and the mitochondrial function is reduced 5%. In other embodiments, the heteroplasmic mtDNA is 55% mutant mtDNA and 45% wild-type mtDNA, and the mitochondrial function is reduced 55%. However, it is understood that the percentage of mutant mtDNA need not be proportional to the mitochondrial function.

Dysfunctional mitochondria is generally characterized by a loss of efficiency in the electron transport chain and reductions in the synthesis of high-energy molecules, such as adenosine-5'-triphosphate (ATP), the leakage of deleterious reactive oxygen species (ROS), and/or disrupted cellular respiration. A person skilled in the art would understand how to evaluate mitochondrial function. For example, cell-based assays, such as the Seahorse Bioscience XF Extracellular Flux Analyzer, can used performed for the determination of basal oxygen consumption, glycolysis rates, ATP production, and respiratory capacity in a single experiment to assess mitochondrial dysfunction. Similarly, the Oroboros 02K respirometer can also be used to establish quantitative functional mitochondrial diagnosis. It is understood that the assay examples described above are exemplary and are not inclusive of all methods to evaluate mitochondrial function.

In some embodiments, functional mitochondria have an intact outer membrane. In some embodiments, functional mitochondria are intact mitochondria. In another embodiment, functional mitochondria consume oxygen at an increasing rate over time. In another embodiment, the functionality of mitochondria is measured by oxygen consumption. In another embodiment, oxygen consumption of mitochondria may be measured by any method known in the art such as, but not limited to, the MitoXpress fluorescence probe (Luxcel). In some embodiments, functional mitochondria are mitochondria which display an increase in the rate of oxygen consumption in the presence of ADP and a substrate such as, but not limited to, glutamate, malate or succinate. Each possibility represents a separate embodiment of the present invention. In another embodiment, functional mitochondria are mitochondria that produce ATP.

While the methods provided herein can be useful in generating a MirC from a recipient cell that has dysfunctional mitochondrial, mutant mtDNA, or a combination thereof, it is also understood that the MirC generation need not be performed in a recipient cell with dysfunctional mitochondria. In some embodiments, a MirC is generated using a recipient cell with functional endogenous mitochondria, wild-type mtDNA, or a combination thereof, and the exogenous mitochondria is also functional, contains wild-type mtDNA, or a combination thereof. For example, endogenous wild-type mtDNA can be reduced using the methods provided herein and exogenous wild-type mtDNA can be transferred into the recipient cell, such as mitochondrial replacement in an "old" recipient cell (e.g., a cell from an aged subject or a cell with relatively high population doubling level (PDL)) with exogenous mtDNA from a healthy donor cell (e.g., a young cell with relatively low PDL). Thus, in certain embodiments, the exogenous mtDNA is from a donor cell that is a healthy donor cell, for example a donor cell that is younger than the recipient cell. In certain embodiments, the donor and recipient cell have a difference in PDL of about 1.5 fold, about 2 fold, about 2.5 fold, about 3 fold, about 4 fold, about 5 fold, or greater than 5 fold. In other embodiments, the donor and recipient cells are from subjects that are separated in age by about 1.5 fold, about 2 fold, about 2.5 fold, about 3 fold, about 4 fold, about 5 fold, or greater than 5 fold. However, it is understood that a difference in age between the donor cell and the recipient cell is not a requirement. In some embodiments, the donor and recipient cell are the same age, and the donor cell is a heathy cell.

In yet other embodiments, the generation of a MirC is performed in a recipient cell with functional endogenous mitochondria, such as wild-type endogenous mtDNA, and the exogenous mtDNA is mutant, encodes for dysfunctional mitochondria, the exogenous mitochondria is dysfunctional, or a combination thereof. In other embodiments, the exogenous mitochondria, exogenous mtDNA, or a combination thereof is from a donor cell that is older than the recipient cell. For example, in some embodiments, a model of a mitochondrial disease or disorder can be created by replacement of functional mitochondria in a recipient cell with exogenous mtDNA from a donor cell that is mutant and/or encodes for dysfunctional mitochondria. It is understood that the examples described herein are exemplary and are not inclusive of all combinations involving mtDNA replacement.

As provided herein, the methods of generating a MirC can be practiced using either an agent that reduces endogenous mtDNA, or an agent that reduces endogenous mitochondrial function. In certain circumstances, a combination of the two agents can be used. Agents that are capable of reducing mitochondrial function are well known in the field, and are within the skillset of a person skilled in the art. Exemplary agents include inhibitors of the mitochondrial respiratory chain that block respiration in the presence of either ADP or uncouplers, such as an inhibitor of complex III (e.g., myxothiazol), an inhibitor of complex IV (e.g., sodium azide, potassium cyanide (KCN)), or an inhibitor of complex V (e.g., oligomycin); inhibitors of phosphorylation that abolish the burst of oxygen consumption after adding ADP, but have no effect on uncoupler-stimulated respiration; uncoupling agents that abolish the obligatory linkage between the respiratory chain and the phosphorylation system which is observed with intact mitochondria (e.g., dinitrophenol, CCCP, FCCP); ATP/ADP transport inhibitor, such as an adenine nucleotide translocase inhibitor (e.g., atractyloside) that either prevent the export of ATP, or the import of raw materials across the mitochondrial inner membrane, ionophores (e.g. valinomycin, nigericin) which make the inner membrane permeable to compounds which are ordinarily unable to cross; or a Krebs cycle inhibitor (e.g. arsenite, aminooxyacetate) which block one or more of the TCA cycle enzymes, or an ancillary reaction. It is understood that the agents that are capable of reducing mitochondrial function described above are non-limiting, and that a person skilled in the art can readily identify suitable agents that are capable of reducing mitochondrial function using techniques known in the art.

In specific embodiments, the agent that reduces endogenous mitochondrial function transiently reduces the endogenous mitochondrial function. In other embodiments, the agent that reduces endogenous mitochondrial function permanently reduces the endogenous mitochondrial function. In preferred embodiments, the agent that reduces endogenous mitochondrial function partially reduces the endogenous mitochondrial function.

Various agents can be used to reduce mtDNA. In certain embodiments, the agent that reduces mtDNA is selected from a nucleic acid encoding a fusion protein comprising a mitochondrial-targeted sequence (MTS) and an endonuclease, an endonuclease, or a small molecule. In certain embodiments, the small molecule is a nucleoside reverse transcriptase inhibitor (NRTI). The nucleic acid can be a messenger ribonucleic acid (mRNA) or a deoxyribonucleic acid (DNA). In certain embodiments, the agent that reduces mtDNA is a plasmid DNA expression vector cassette encoding an endonuclease. In preferred embodiments, the agent is a plasmid DNA expression vector cassette encoding an endonuclease with a MTS. Various expression vector cassettes can be used, and a person skilled in the art would understand the necessary considerations required to enable successful expression of the endonuclease depending on the host cell. For example, a mammalian expression vector, such as a vector having a cytomegalovirus (CMV) promoter, SV40 promoter, or CAG promoter, would be suitable for expression of the endonuclease in a mammalian cell, but not a non-mammalian cell. Similarly, it is understood that viral expression vectors can also be used and a person skilled in the art would understand that such viral expression vectors may require helper plasmids (i.e., envelope and packaging plasmids) to be used in tandem with the transfer plasmid. In other embodiments, the agent is an mRNA encoding an endonuclease. In other preferred embodiments, the agent is an mRNA encoding an endonuclease with a MTS. In yet further embodiments, the agent is an endonuclease that is a recombinant protein. In other embodiments, the agent is a small molecule, such as, for example, a small molecule that disrupts synthesis of mtDNA. Techniques for generating any of the expression methods are known to those skilled in the art, and can be readily performed without undue experimentation. In preferred embodiments, the agent is suitable for clinical use.

In specific embodiments, the endonuclease can be a restriction enzyme that cleaves DNA double helices into fragments at specific sites, such as XbaI, of which the cut site is T/CTAGA.

The endonuclease can also include, for example, restriction enzymes other than XbaI, such as EcoRI, BamHI, HindIII, or PstI, which all digest mtDNA at multiple sites. Endonucleases have defined recognition sites, which allows prediction of their sensitivity on mtDNA. The defined recognition sites of restriction enzymes, such as, for example, XbaI, EcoRI and SmaI, are specific to a given nucleic acid sequence. Accordingly, in some embodiments, the reduction of endogenous mtDNA can be performed using zinc fingers and transcription activator-like effectors (TALEs) that have been combined to DNA nucleases. These two types of DNA-binding proteins can be engineered to have specificities for new DNA sequences of interest. Similarly, clustered regularly interspaced short palindromic repeats (CRISPR)/Cas9 proteins can be also introduced into cells through the addition of the corresponding encoding genes. Therefore, in some embodiments, the endonuclease can be a programmable nuclease, such as a RNA-guided DNA endonuclease (e.g., Cas9), zinc finger nuclease (ZFN), or transcription activator-like effector nuclease (TALEN). It is understood that the nucleases described above are non-limiting, and that a person skilled in the art can readily identify suitable endonucleases using techniques known in the art. For example, the Cambridge Reference Sequence or similar consensus sequence can be used to identify suitable endonucleases that recognize the mtDNA sequence by, for example, an in silico analysis. In specific embodiments, the endonuclease cleaves a wild-type sequence of mtDNA. In other embodiments, the endonuclease cleaves a mutant sequence of mtDNA. It is also understood that the agent that reduces endogenous mtDNA need not be an endonuclease and that any agent capable of reducing mtDNA can be employed, including an agent that inhibits the biosynthesis of mtDNA, such as ethidium bromide. Also contemplated herein, are agents, such as, for example, Urolithin A or the small molecule p62-mediated mitophagy inducer (PMI), that induce autophagy in order to promote the selective degradation of endogenous mitochondria (i.e., mitophagy agonist). The present invention can also be practiced using a nucleoside reverse transcriptase inhibitor (NRTI) as an agent that reduces mtDNA.

In addition, in some embodiments, the expression vector cassette can include one or more antibiotic resistance genes to enable selection of a population of cells that express the expression vector cassette. For example, in some embodiments, the expression vector can include the puromycin N-acetyl-transferase gene (pac) from *Streptomyces*, and cells can be selected using puromycin. In circumstances where selection is performed using antibiotics, e.g., puromycin, the selection can be brief (e.g., 24-48 hours) to limit long term exposure to the drug. However, it is understood that the example provided above is merely exemplary, and that the expression vector cassette can include other antibiotics resistance genes, such as, for example, the bsr, bls, or BSD gene for selection with Blasticidin, or the hph gene for selection with hydromycin B. It is generally understood that the concentration of antibiotic used for selection will depend on the type of antibiotic and the cell type, and would be readily obtainable to one skilled in the art without undue experimentation. It is further understood that selection can be produced by any means known in the art, and need not involve antibiotic resistance. For example, in some embodiments, selection of the cells can be performed by, for example, fluorescence-activated cell sorting (FACS) of a cell surface marker or expression of a fluorescent protein encoded by the expression. In yet further embodiments, selection can be performed according to the cell's phenotype. For example, in some embodiments, the successful deletion of mutant endogenous mtDNA in a cell with heteroplasmy can result in a phenotypic response that is selectable, such as, for example, cell survival.

Accordingly, in some embodiments, the cells are selected after introducing an expression vector cassette that contains an endonuclease that degrades mtDNA. In some embodiments, the cells are selected to obtain a homogenous population of cells that express an endonuclease that degrades mtDNA. In specific embodiments, the cells are selected after introducing an expression vector cassette that contains an endonuclease that degrades mtDNA, and a homogenous, stable cell line is generated. In other embodiments, the cells are selected to enrich for a population of cells that express an endonuclease that degrades mtDNA. As described above, this enrichment by selection can involve a brief exposure to an antibiotic. The enriched cells can stably express the endonuclease or transiently express the endonuclease depending on the extent and/or manner of the selection pressure. It is understood that an enriched population need not be homogenous, and that an enriched population of cells that express an endonuclease that degrades mtDNA contains a higher percentage of cells with the endonuclease, relative to an unselected population of cells, but may also contain some cells that do not express the endonuclease.

In other embodiments, the cells are not selected after introducing an expression vector that contains an endonuclease that degrades mtDNA. In specific embodiments, the cells are not selected after introducing an expression vector that contains an endonuclease that degrades mtDNA, and the endonuclease is transiently expressed.

Various methods for introducing the plasmid DNA expression vector cassette, mRNA, and/or recombinant protein are known in the art. In some embodiments, the plasmid DNA expression vector cassette is introduced by electroporation. In specific embodiments, the electroporation method is flow electroporation, such as MaxCyte Flow Electroporation. In other specific embodiments, the electroporation method includes the nucleofection technology, such as Lonza's Nucleofector™ technology. In other embodiments, the plasmid DNA expression vector cassette is introduced by cationic lipid transfection. In yet further embodiments, the plasmid DNA expression vector cassette is introduced by viral transduction. It is understood that the methods described above for introducing the expression vector cassette are non-limiting and merely intended to be exemplary methods, and that any method known in the art can be used for introducing the DNA expression vector cassette.

Where the agent for reducing endogenous mitochondria comprises an endonuclease, expression of the endonuclease can also involve introduction of mRNA encoding the endonuclease or introducing the endonuclease as a recombinant protein. In certain embodiments, the MaxCyte electroporator can be used for mRNA transfection, particularly in the clinical setting, which has cleared the standards of Good Manufacturing Practice and Good Clinical Practice. The transfection can be performed using the MaxCyte electroporator according to the manufacturer's protocol. It is further understood that the methods described above are merely exemplary and that any means of introducing mRNA and/or recombinant protein can be used.

The specific targeting of the endonuclease to the mitochondria can be performed by incorporating a mitochondrial targeting sequence (MTS) adjacent to the endonuclease coding sequence, which will result in a fusion protein that targets the mitochondria. Strong MTSs have been identified and shown capable of targeting proteins to specific compartments when fused on their N-termini, and are termed mitochondrial targeting sequences. MTS suitable for the methods of the present invention are well known to the person skilled in the art (see, e.g., U.S. Pat. No. 8,039, 587B2, which is hereby incorporated by reference in its entirety). For example, MTS to the mitochondrial matrix can be used, such as the MT'S that is a targeting peptide from the cytochrome c oxidase subunit IV (CO)×4), subunit VIII (COX 8), or subunit X (COX 10). In principle, any target sequence derived from any nuclear encoded mitochondrial matrix or inner membrane enzyme or an artificial sequence that is capable of rendering the fusion protein into a mitochondrial imported protein (hydrophobic moment greater than 5.5, at least two basic residues, amphiphilic alpha-helical conformation; see. e.g., Bedwell et al., Mol Cell Biol. 9(3) (1989), 1014-1025) is useful for the purposes of the present invention.

In certain embodiments, the MTS is a human MTS. In another embodiment, the MTS is from another species. Non-limiting examples of such sequences are the cytochrome c oxidase subunit X (COX 10) MTS (MAASPHTLSSRLLTGCVGGSVWYLERRT, SEQ ID NO: 36), and the cytochrome c oxidase subunit VIII (COX 8) MTS (MSVLTPLLLRSLTGSARRLMVPRA, SEQ ID NO: 37). Additional non-limiting examples of MTS sequences are the natural MTS of each individual mitochondrial protein that is encoded by the nuclear DNA, translated (produced) in the cytoplasm and transported into the mitochondria, as well as citrate synthase (cs), lipoamide deydrogenase (LAD), and C6ORF66 (ORF). The various MTS may be exchangeable for each mitochondrial enzyme among themselves. Accordingly, in some embodiments, the MTS targets a mitochondrial matrix protein. In specific embodiments, the mitochondrial matrix protein is subunit VIII of human cytochrome C oxidase. Each possibility represents a separate embodiment of the fusion protein for use of the present invention.

Upon contacting a recipient cell with an agent that reduces endogenous mtDNA copy number or an agent that reduces endogenous mitochondrial function, the recipient cell is incubated for a sufficient period of time for the agent to partially reduce the endogenous mtDNA copy number in the recipient cell or partially reduce the endogenous mitochondrial function in the recipient cell, respectively. Identifying the "sufficient period of time" to allow the agent to reduce partially reduce the endogenous mtDNA copy number or partially reduce the endogenous mitochondrial function is within the skill of those in the art. The sufficient or proper time period will vary according to various factors, including but not limited to, the particular type of cells, the amount of starting material (e.g., the number of recipient cells and/or amount of mtDNA to be reduced), the amount and type of agent(s), the plasmid promoter regulator(s), and/or the culture conditions. In various embodiments the sufficient period of time to allow a partial reduction of the endogenous mtDNA copy number in a recipient cell is about 1 day, about 2 days, about 3 days, about 4 days, about 5 days, about 6 days, about 7 days, about 8 days, about 9 days, about 10 days, about 1-2 weeks, about 2-3 weeks or about 3-4 weeks. In preferred embodiments, the sufficient period of time will be long enough that the resulting recipient cell has a reduction in a majority of the endogenous mtDNA copy number or a reduction in the function of a majority of the endogenous mitochondria and is also substantially free of the agent that reduces endogenous mtDNA or the agent that reduces endogenous mitochondrial function before incubating the recipient cell with an exogenous mtDNA and/or exogenous mitochondria.

An important and novel aspect of the present invention is the finding that mitochondrial transfer efficiency is severely reduced in cells with a complete depletion of endogenous mitochondria (i.e., (p) 0 cells), but can be greatly improved when the endogenous mtDNA copy number is reduced but not completely depleted (i.e., (p) cells). Furthermore, the present invention also demonstrates that simple add-on or centrifugation protocols are inefficient without partial reduction in the endogenous mtDNA copy number. Accordingly, in preferred embodiments, the reduction of the endogenous mtDNA copy number in the recipient cell is less than a 100% depletion of the endogenous mtDNA. In some embodiments, the endogenous mtDNA copy number in the recipient cell is reduced by about 5% to about 99%. In specific embodiments, the agent that reduces endogenous mtDNA copy number reduces about 30% to about 70% of the endogenous mtDNA copy number. In other embodiments, the agent that reduces endogenous m (D) NA copy number reduces about 50% or more, about 60% or more, about 70% or more, about 80% or more, or about 90% or more, or about 95% or more of the endogenous mtDNA copy number. In yet further embodiments, the agent that reduces endogenous mtDNA copy number reduces about 60% to about 90% of the endogenous mtDNA copy number. It is also understood that in some embodiments, the agent that reduces endogenous mtDNA copy number reduces mitochondrial mass.

In certain embodiments, the exogenous mtDNA is contained in isolated exogenous mitochondria from a donor cell. Mitochondrial isolation may be accomplished by any of a number of well-known techniques including but not limited to those described herein, and in the cited references. In certain embodiments, the exogenous mitochondria for use in mitochondrial transfer is isolated using a commercial kit, such as, for example, the Qproteum mitochondria isolation kit (Qiagen, USA), the MITOISO2 mitochondria isolation kit (Sigma, USA), or Mitochondria Isolation Kit for Cultured Cells (Thermo Scientific). In other embodiments, the exogenous mitochondria for use in mitochondrial transfer is isolated manually. For example, an exemplary manual isolation of mitochondria includes isolating the mitochondria from donor cells by pelleting the donor cells, washing the cell pellet of 1-2 mL derived from approximately $10^9$ cells grown in culture, swelling the cells in a hypotonic buffer, rupturing the cells with a Dounce or Potter-Elvehjem homogenizer using a tight-fitting pestle, and isolating the mitochondria by differential centrifugation. Manual isolation can also include, for example, sucrose density gradient ultracentrifugation, or free-flow electrophoresis. Without wishing to be bound by any particular method, it is understood that the kits and manual methods described herein are exemplary, and that any mitochondrial isolation method can be used, and would be within the skill set of a person skilled in the art.

In some embodiments, the isolated donor mitochondria is substantially pure of other organelles. In other embodiments, the isolated mitochondria can contain impurities and is enriched for mitochondria. For example, in some embodiments, the isolated mitochondria are about 90% pure, about 80% pure, about 70% pure, about 60%, pure, about 50%, pure, or any integer in-between. In general, it is understood that any impurities contained with the isolated donor mitochondria will not affect the viability or function of the recipient cell upon mitochondrial transfer. In specific embodiments, the transfer of the exogenous mitochondria, exogenous mtDNA, or a combination thereof does not involve transfer of non-mitochondrial organelles.

The quantity and quality of isolated mitochondria can easily be determined by a number of well-known techniques including but not limited to those described herein, and in the cited references. For example, in some embodiments, the quantity of isolated mitochondria is determined by assessment of total protein content. Various methods are available for measurement of total protein content, such as the Biuret and Lowry procedures (see, e.g., Hartwig et al., *Proteomics,* 2009 June; 9(11):3209-14). In other embodiments, the quantity of isolated mitochondria is determined by mtDNA copy number.

In some embodiments, the isolated mitochondria are functional mitochondria. In further embodiments, the isolated mitochondria are dysfunctional mitochondria. In some embodiments, the mitochondrial function can be assessed in the donor cell prior to isolation. In other embodiments, the mitochondrial function can be assayed from the isolated mitochondria.

The preservation of mitochondrial membrane integrity is another important factor during mitochondria isolation. In some embodiments, the mtDNA used in the methods provided herein is from intact mitochondria. In specific embodiments, about 10%, about 20%, about 30%, about 40%, about 50%, about 60%, about 70%, about 80%, about 90%, or greater than 90% of the isolated mitochondria are intact. Mitochondrial membrane integrity can be accomplished by any of a number of well-known techniques including but not limited to those described herein, and in the cited references. For example, TMRM, Rhod123, JC-1 and DiOC6 are typical probes for measurement of mitochondrial membrane potential (see, e.g., Perry et al., *Biotechniques,* 2011 February; 50(2):98-115). JC-1 is a widely used dye for measurement of inner-membrane potential of isolated mitochondria, and is based on electrochemical proton gradient of mitochondrial inner membrane.

In certain embodiments of the methods provided herein, the recipient having a partial reduction of endogenous mtDNA in co-incubated with exogenous mitochondria from a healthy donor for a sufficient period of time to non-invasively transfer exogenous mitochondria into the recipient cell, thereby generating a mitochondria replaced cell. In other embodiments, the recipient having a partial reduction of endogenous mtDNA in co-incubated with exogenous mtDNA from a healthy donor for a sufficient period of time to non-invasively transfer exogenous mitochondria into the recipient cell, thereby generating a mitochondria replaced cell. Identifying the "sufficient period of time" to non-invasively transfer exogenous mitochondria and/or exogenous mtDNA into the recipient cell is within the skill of those in the art. The sufficient or proper time period will vary according to various factors, including but not limited to, the particular type of cells, the amount of starting material (e.g., the number of recipient cells and/or amount of endogenous mtDNA to be replaced), the amount of donor material (e.g., the quantity, quality, and/or purity of exogenous mtDNA) and/or the culture conditions. In various embodiments the sufficient period of time to non-invasively transfer exogenous mitochondria and/or exogenous mtDNA into a recipient cell is about 1 day, about 2 days, about 3 days, about 4 days, about 5 days, about 6 days, about 7 days, about 8 days, about 9 days, about 10 days, about 1-2 weeks, about 2-3 weeks or about 3-4 weeks. In certain embodiments, at the end of the co-incubation period, the recipient cells will have a majority of the exogenous mtDNA and be substantially free of any exogenous mitochondria organelles.

Another feature of the current invention is the finding that the total mtDNA copy number in the MirC does not substantially increase, relative to the original recipient cell. In contrast, other less efficient methods have attempted to add on mitochondria without modulating the recipient cell before the co-incubation step, or transfer exogenous mitochondria using centrifugation without modulating the recipient cell prior to the centrifugation. Consequently, the resultant cell populations using the inefficient methods tend to have large increase in the total mtDNA copy number. Thus, in certain embodiments, the mitochondria replaced cell has a total mtDNA copy number no greater than about 1.1 fold, about 1.2 fold, about 1.3 fold, about 1.4 fold, about 1.5 fold, or more, relative to the total mtDNA copy number of the recipient cell prior to contacting with the agent that reduces endogenous mtDNA copy number.

The use of non-invasive transfer is another unique aspect of the present invention Previous methods have employed invasive instruments to inject exogenous mitochondria, physically force the mitochondria into the cells by centrifugation, or similar harsh conditions that are harmful to the recipient cells. In clinical settings, particularly when the recipient cell number may be limited, such as with hematopoietic stem cells or T cells, harsh manipulation of the cells in undesirable. Therefore, the use of the non-invasive transfer is a beneficial feature of this invention, which lends itself to use in the clinical setting.

As provided herein, the exogenous mitochondria, exogenous mtDNA, or a combination thereof can be autologous or allogeneic to the recipient cell. In some embodiments, the exogenous mtDNA is allogeneic, relative to the recipient cell. For example, the exogenous mtDNA can be obtained from the same species as the recipient cell, and have a different genotype than that of the recipient cell. In other embodiments, the exogenous mitochondria, exogenous mtDNA, or a combination thereof is autologous. By way of example, an exemplary autologous exogenous mtDNA can include mtDNA from a healthy donor cell, for example a "young" donor cell such as from umbilical cord blood, and the recipient cell can be from the same subject, and be an "old" recipient cell, where the terms "young" and "old" refer to the total number of times the cells in the population have doubled or the age of the subject from which the cells are taken. Another exemplary autologous exogenous mtDNA can include, for example, donor mtDNA that has been isolated from the same subject as the recipient cell and modified prior to replacing it with the recipient cell. In certain embodiments, only the mtDNA and/or mitochondria are allogenic and the recipient cell is autogenic to the subject in need of an exogenous mtDNA and/or exogenous mitochondria.

In certain embodiments, the replacement of mtDNA in the recipient cell can be evaluated by sequencing the DNA sequences of hyper variable region (HVR) of mtDNA, for example, the HV1 and/or HV2 of the D-loop, and comparing it to the sequence of both the donor mitochondria and the recipient cells. In specific embodiments, the differences in sequences between the recipient cell and the donor mitochondria can be identified by a Single Nucleotide Polymorphism assay. For example, the amplified sequences of the mtDNA from the recipient cell and the donor mitochondria can be cloned into a plasmid for use as a standard for quantification.

In some embodiments, the cells (i.e. donor cells and recipient cells) are animal cells or plant cells. In specific embodiments, the cells are mammalian cells. In some embodiments, the cells are isolated from a mammalian subject who is selected from a group consisting of: a human, a horse, a dog, a cat, a mouse, a rat, a cow and a sheep. In some embodiments, the cells are human cells. In some embodiments, the cells are cells in culture. The cells may be obtained directly from a mammal (preferably human), or from a commercial source, or from tissue, or in the form for instance of cultured cells, prepared on site or purchased from a commercial cell source and the like. In certain embodiments, the cells are primary cells (i.e., cells obtained directly from living tissue, for example, biopsy material). The cells may come from any organ including, but not limited to, the blood or lymph system, from muscles, any organ, gland, the skin, or the brain. In certain embodiments, the cells are somatic cells. In some embodiments, the cells are selected from the group consisting of epithelial cells, neural cells, epidermal cells, keratinocytes, hematopoietic cells (e.g., bone marrow cells), melanocytes, chondrocytes, hepatocytes, B-cells, T cells, erythrocytes, macrophages, monocytes, fibroblasts, muscle cells, vascular smooth muscle cells, hepatocytes, splenocytes, and pancreatic β cells.

As provided herein, in specific embodiments, the donor cells are commercially available cells cultured under Current Good Manufacturing Practices (eGMP). For example, the donor cells can be obtained from a cell repository, such as Waisman Biomanufacturing, or similar commercial resource, such as a commercial source that generates cGMP compliant cells. In some embodiments, the donor cells are cGMP manufactured bone-marrow derived Mesenchymal Stromal Cells (BM-MSCs). In other embodiments, the cells are cGMP grade human hepatocytes. As such, it is also understood that the donor cells can be frozen cells that are thawed prior to isolating the mitochondria. However, the mitochondria need not be isolated after freezing the cells, and can be isolated from fresh cells and used immediately, or, in certain embodiments, the mitochondria can be isolated and then frozen before transferring into the recipient cell.

In some embodiments, the cells are cancer cells. Typically, the cancer cells are isolated from a cancer selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In some embodiment, the cells are stem cells. As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type. Stem cells include pluripotent stem cells, which can form cells of any of the body's tissue lineages: mesoderm, endoderm and ectoderm. Therefore, for example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiment, the stem cell is a mesenchymal stem cell. The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage, e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. In some embodiments, the stem cell is a partially differentiated or differentiating cell. In some embodiments, the stem cell is an induced pluripotent stem cell (iPSC), which has been reprogrammed or de-differentiated. In specific embodiments, the recipient cell is an iPSC. In other embodiments, the recipient cell is a hematopoietic stem cell (HSC) or a MSC. Stem cells can be obtained from embryonic, fetal or adult tissues.

In other embodiments, the cells are immune cells. In specific embodiments, the recipient cell is an immune cell. In some embodiments, the immune cell is selected from the group consisting of a T cell, a phagocyte, a microglial cell, and a macrophage. In specific embodiments, the T cell is a CD4+ T cell. In other embodiments, the T cell is a CD8+ T cell. In yet further embodiments, the T cell is a chimeric antigen receptor (CAR) T cell. In specific embodiments, the recipient cell is an exhausted or near exhausted T cell in a state or near a state of T cell dysfunction.

5.3 Method of Enhanced Mitochondrial Transfer

Also provided herein are methods for the transfer of mtDNA and/or mitochondria that involve the use of a second active agent in combination with any of the methods described in Section 5.2 The transfer of mitochondria has been reported to involve the endocytosis pathway, which is an ATP-dependent process. For example, under certain cell culture conditions, mitochondria have been observed to be engulfed via macropinocytosis (see, e.g., Kitani et al, *J Cell Mol Med.,* 2014, 18(8):1694-1703). Accordingly, the present invention also relates to the novel findings that the use of a second active agent prior to co-incubating the recipient cell with exogenous mitochondria and/or exogenous mtDNA can promote the uptake of the exogenous mitochondria and/or exogenous mtDNA.

Various types of agents can be used to promote the uptake of the exogenous mitochondria and/or exogenous mtDNA. In some embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In specific embodiments, the activator of endocytosis is a modulator of cellular metabolism. Cellular metabolism can be modulated using various methods known to one skilled in the art. In certain embodiments, modulation of cellular metabolism comprises nutrient starvation, a chemical inhibitor, or a small molecule.

As described above, transfer of intact mitochondria has been reported to occur by an endocytosis pathway. For example, the exogenous mitochondria and/or exogenous mtDNA can be transferred by uptake of intact mitochondria via the endocytosis pathway. The endocytosis pathways can be subdivided into four categories: 1) clathrin-mediated endocytosis, 2) caveolae, 3) macropinocytosis, and 4) phagocytosis. Clathrin-mediated endocytosis is mediated by small (approx. 100 nm in diameter) vesicles that have a morphologically characteristic coat made up of a complex of proteins that are mainly associated with the cytosolic protein clathrin. Accordingly, in certain embodiments, the endocytosis pathway for mitochondrial transfer is a clathrin-dependent endocytosis pathway. In other embodiments, the endocytosis pathway for mitochondrial transfer is a clathrin-independent pathway. In specific embodiments, the endocytosis pathway is macropinocytosis.

Macropinocytosis has been suggested to be an important process in nutrient-deprived environments. As a result, it was hypothesized that a shortage of cellular nutrients or an inhibition of the pathways or target molecules that are activated with sufficient nutrition such as mTOR could be a strategy to augment the cellular engulfment of intact mitochondria into the cytosol. Specifically, as provided herein, it was discovered that a suppression of mTOR can enhance the uptake of exogenous mitochondria. mTOR is an essential sensor of amino acids, energy, oxygen, and growth factors, and a key regulator of protein, lipid, and nucleotide synthesis that is involved in uptake of extracellular nutrients. Accordingly, in some embodiments, the methods provided herein further comprise contacting a recipient cell with a small compound, a peptide, or a protein that can increase macropinocytosis. In specific embodiments, the methods provided herein further comprise modulating cellular metabolism of a recipient cell prior to transfer of the exogenous mitochondria and/or exogenous mtDNA. In certain embodiments, the modulating cellular metabolism is performed using the same small compound, a peptide, or a protein that can increase macropinocytosis.

Modulating cellular metabolism may be accomplished by any of a number of well-known techniques including but not limited to those described herein, and in the cited references. For example, in some embodiments, modulating cellular metabolism is performed by nutrient starvation or nutrient deprivation. In other embodiments, modulating cellular metabolism is performed by a chemical inhibitor or small molecule. In specific embodiments, the chemical inhibitor or small molecule is an mTOR inhibitor.

Various compounds are known to inhibit mTOR, including rapamycin, also known as sirolimus (CAS Number 53123-88-9; $C_{51}H_{79}NO_{13}$), and rapamycin derivatives (e.g., rapamycin analogs, also known as "rapalogs"). Rapamycin derivatives include, for example, temsirolimus (CAS Number 162635-04-3; $C_{56}H_{87}NO_{16}$), everolimus (CAS Number 159351-69-6; $C_{53}H_{83}NO_{14}$), and ridaforolimus (CAS Number 572924-54-0; $C_{53}H_{84}NO_{14}P$). Accordingly, in some embodiments, the methods provided herein for mitochondrial transfer further comprise modulating cellular metabolism of a recipient cell prior to transfer of the exogenous mitochondria and/or exogenous mtDNA using rapamycin or a derivative thereof. It is understood that the embodiments described above for modulating cellular metabolism are non-limiting, and modulating cellular metabolism need not involve a chemical compound or small molecule.

Accordingly, in some embodiments, rapamycin or a derivative thereof, which include clinically approved drugs, can be utilized to increase the transfer efficiency of exogenous mitochondria, either as a stand-alone method or in combination with any of the methods provided herein, such as methods involving the partial reduction in the endogenous mitochondria of the recipient cells.

One skilled in the art would understand that additional methods of delivery can also be used to introduce the exogenous mitochondria and/or exogenous mtDNA, and that macropinocytosis is an exemplary pathway. In some embodiments, the mtDNA can be delivered by clathrin-dependent endocytosis, or clathrin-independent endocytosis In specific embodiments, the clathrin-independent pathway can be, for example, CLIC/GEEC endocytic pathway, Arf6-dependent endocytosis, flotillin-dependent endocytosis, macropinocytosis, circular doral ruffles, phagocytosis, or trans-endocytosis. It is further understood that delivery of exogenous mitochondria and/or exogenous mtDNA can be enhanced by the use of any compound that stimulates mitochondrial delivery, such as an activator of endocytosis. Non-limiting exemplary compounds suitable for activating endocytosis include, for example, phorbol-12-myristate-13-acetate (PMA) ($C_{36}H_{56}O_8$), 12-O-tetradecanoylphorbol 13-acetate (TPA) ($C_{36}H_{56}O_8$), tanshinone IIA sodium sulfonate (TSN-SS) ($C_{19}H_{17}O_6S{\cdot}Na$), and phorbol-12,13-dibutyrate, or derivatives thereof. Furthermore, it is also understood that non-endocytosis mediated transfer of mtDNA and/or mitochondria can be used, including methods that bypass endocytosis and/or cell fusion.

5.4 Methods of Treatment

Provided herein are various methods for the treatment of conditions associated with mutant mtDNA and/or dysfunctional mitochondria, uses of compositions for the treatment of conditions associated with mutant mtDNA and/or dysfunctional mitochondria, and uses of compositions in the manufacture of medicaments for the treatment of conditions associated with mutant mtDNA and/or dysfunctional mitochondria. Also provided are methods of treatment involving the use of exogenous mitochondria and/or exogenous mtDNA to restore or enhance the function of endogenous mitochondria, uses of compositions to restore or enhance the function of endogenous mitochondria, and uses of compositions in the manufacture of medicaments for the treatment of a subject in need of mitochondrial replacement. In certain embodiments, the treatment involves prevention of mitochondrial dysfunction.

5.4.1 Methods of Treating an Age-Related Disease

In certain embodiments, provided herein are methods of treating a subject having or suspected of having an age-related disease involving any of methods described in Section 5.2 and/or Section 5.3. In some embodiments, provided herein are methods of treating a subject having or suspected of having an age-related disease involving generating a mitochondria replaced cell ex vivo or in vitro by contacting a recipient cell with an agent that reduces endogenous mtDNA or reduces endogenous mitochondrial function, incubating the recipient cell for a sufficient period of time for the agent to partially reduce the mtDNA copy number in the recipient cell or partially reduce the endogenous mitochondrial function, co-incubating (1) the recipient cell in which the endogenous mtDNA or endogenous mitochondrial function has been partially reduced, and (2) exogenous mitochondria and/or exogenous mtDNA from a healthy donor, for a sufficient period of time to non-invasively transfer exogenous mitochondria into the recipient cell, thereby generating a mitochondria replaced cell, and then administering a therapeutically effective amount of the mitochondria replaced recipient cell to the subject having or suspected of having an age-related.

In certain embodiments, the age-related disease includes an autoimmune disease, a metabolic disease, a genetic disease, cancer, a neurodegenerative disease, and immunosenescence. The metabolic disease can include diabetes. Non-limiting examples of neurodegenerative diseases that can be treated by the methods provided herein include Alzheimer's disease, or Parkinson's disease. In addition, the genetic disease capable of being treated include Hutchinson-Gilford Progeria Syndrome, Werner Syndrome, and Huntington's disease. Additional age-related diseases that involve dysfunctional mitochondria are also contemplated.

In certain embodiments, the methods of treating a subject having or suspected of having an age-related disease involves generating a MirC, where the recipient cell used to generate the MirC is a T cell or a hematopoietic stem cell (HSC). For example, endogenous mtDNA, endogenous mitochondria, or a combination thereof in a senescent T cell or hematopoietic stem cell (HSC) can be replaced for rejuvenation. The in vitro or ex vivo mitochondrial replacement can be a feasible option for the treatment using human T cells and/or hematopoietic stem cells with diseased patients. Thus in some embodiments, the methods provided herein can be used to delay senescence and/or extending lifespan in a cell by non-invasively transferring isolated exogenous mitochondria from a healthy, non-senescent cell into a senescent or near senescent cell to rejuvenate the recipient cell, and the resulting rejuvenated MirC can then be administered to a patient having or suspected of having an age-related disease.

As demonstrated herein, the rejuvenation of senescent T cells is one possible embodiment by which the present invention can be used to treat a subject having an age-related disease, such as cancer. By way of example, an old T cell, exhibiting a Senescence Associated Secretory Phenotype (SASP) consisting of inflammatory cytokines, growth factors, and proteases, reduced and/or slower rates of cell population doublings, shortened telomeres, increased DNA damage response (DDR), or a combination thereof can be rejuvenated by using the methods provided herein to non-invasively transfer, for example, isolated mitochondria from a young, healthy T cell that is autologous to a subject having an age-related disease, such as cancer. The T cell-derived MirC with characteristics of a young, non-senescent cell can then be administered to the subject for treatment of the age-related disease.

Thus, in specific embodiments, the methods of treating a subject having or suspected of having an age-related disease involves generation of a MirC where the recipient cell is a T cell. T cell fate is regulated by the metabolic pathway, with either glycolysis or oxidative phosphorylation (OXPHOS) being responsible for providing a majority of the energy to T cells. Glycolysis dominant T cells select to differentiate into effector T cells, whereas OXPHOS dominant T cells for memory T cells. Thus, exogenous mitochondria and/or mtDNA can be used to modulate T cell fate. For example, in the case of allergy, exogenous mitochondria and/or mtDNA could be used to calm hyper-activated T cells. In other situations, such as in cancer immunotherapy, exogenous mitochondria and/or mtDNA could empower anti-tumor T cells to allow the T cells to persist for a longer time, or facilitate T cell lytic capacity and/or reduce tumor burden. Moreover, emerging treatments using chimeric antigen receptor T cells (CAR T) utilize autologous T cells. Those CAR T cells might be in fatigue due to aging or malnutrition such as cachexia which is frequently seen in a severe pathologic stage of cancer. The mitochondrial replacement technology may energize and rejuvenate CAR T to provide more ATP leading to better outcomes.

Accordingly, in certain embodiments, the methods of treating a subject involve a recipient cell that is a T cell. The T cell can be a CD4+ T cell, a CD8+ T cell, or a CAR T cell. In specific embodiments, the mitochondrial replacement in the recipient I cell results in a T cell with a prolonged lifespan. For example, the lifespan can be increased about 1.5 fold, about 2 fold, about 3 fold, about 4 fold, about 5 fold, or greater than 5 fold. In specific embodiments, the mitochondrial replacement in the recipient T cell inhibits or delays senescence of the recipient T cells, as compared to a T cell without mitochondrial replacement. As described in Section 5.2, lifespan can be prolonged by performing mtDNA replacement using exogenous mitochondria and/or exogenous mtDNA from a donor cell that is younger than the recipient cell. In certain embodiments, the donor and recipient cell have a difference in PDL of about 1.5 fold, about 2 fold, about 2.5 fold, about 3 fold, about 4 fold, about 5 fold, or greater than 5 fold. In other embodiments, the donor and recipient cells are from subjects that are separated in age by about 5 years, about 10 years, about 15 years, about 20 years, or greater than 20 years. In other specific embodiments, the mitochondrial replacement in the recipient T cell results in T cells having increased lytic capacity, relative to T cells not having mitochondrial replacement. In yet further embodiments, the mitochondrial replacement in the T cells results in reduced tumor burden.

Although in certain embodiments plasmid-based gene transfection can be used to generate a T cell with exogenous mitochondria and/or exogenous mtDNA, in other embodiments mRNA transfection can be used. The use of mRNA transfection can decrease the chance of the RNA sequence being integrated into the host genome, and can also have minimal long-term gene expression that would cause the endogenous mtDNA reduction.

In certain embodiments, the MaxCyte electroporator can be used for mRNA transfection, particularly in the clinical setting, which has cleared the standards of Good Manufacturing Practice and Good Clinical Practice. The transfection can be performed using the MaxCyte electroporator according to the manufacturer's protocol.

The methods of treating a subject having or suspected of having an age-related disease can also involve the generation of a MirC using the methods provided herein, where the recipient cell is a hematopoietic stem cell (HSC). Hematopoietic stem cells (HSC) supply not only blood cells, but also, for example, the endothelium which fixes damaged resident cells in the remote organs via trans-differentiation. Moreover, malfunctions of HSCs have been reported to be involved in senescence throughout the whole body. Therefore, it is contemplated that HSC-derived MirC can be used as a method of treatment in any age-related disease.

In addition, allogenic HSC transplantation can result in rejection of the transplant or even graft-versus-host disease. Autologous HSC transplantation is often a safer and more practical measure for disease intervention. For example, autologous HSC transplantation typically does not require the preconditioning with immunosuppressive agents, such as radiation and chemicals. Accordingly, in vitro or ex vivo generation of a MirC using exogenous mtDNA from a healthy young mitochondria in an autologous HSC that is then returned back to the patients' bodies is envisioned using the methods provided herein.

In certain embodiments, the HSC is autologous to the subject in need of mitochondrial and/or mtDNA replacement, and the exogenous mtDNA is allogenic. As provided herein, the mtDNA replacement in an HSC can result in a differentiated cell with functional mitochondria and/or a differentiated cell with improved function. Accordingly, the methods provided herein can be used in the setting of HSC transplantation.

Aging alters the biological processes and leads to development of degenerative disorders, such as Alzheimer's disease, atherosclerosis, osteoporosis, type 2 diabetes mellitus, and tissue fibrosis which is causative for chronic kidney disease and chronic obstructive pulmonary disease. Mitochondria can play a role in senescence, via reactive oxygen species generated by mitochondria, which can impact the ageing process. Mitochondrial dysfunction in aging is in a vicious cycle related to a deregulated nutrient sensing where a shortage of nicotinamide adenine dinucleotide ($NAD^+$), caused by downregulation of nicotinamide phosphoribosyltransferase (NAMPT) and hyperactivation of poly (ADP-ribose) polymerase 1 (PARP1), leads to an inhibition of $NAD^+$-dependent deacetylase sirtuin 1 (SIRT1). It then relays to the acetylation-dependent inactivation of PGC1α consequently resulting in a depressed mitochondrial biogenesis that exaggerates the $NAD^+$ availability. The low activity of PGC1α yields downregulated the expressions not only of mitochondrial proteins encoded in nucleus but also of the mitochondrial transcription factor TEAM neighboring the mitochondrial DNA.

In addition to the two core senescence-regulating pathways including p53 and p16/Rb, senescence-associated secretory phenotype (SASP), where an array of inflammatory cytokines, chemokines, and proteases such as IL-1, IL-6/VEGF, IL-8, and CXCL9/MMP are released, is one of the most characterized phenomena in senescence. The transcription factor GATA4 is degraded with the association of the autophagic adaptor p62 by selective autophagy under normal condition, whereas DNA damage response (DDR) kinases ATM (ataxia telangiectasia mutated) and ATR (ataxia telangiectasia and Rad3-related) received senescence signals facilitate the dissociation between GATA4 and p62 and stabilize GATA4, in turn activate NF-kB through TRAF3IP2 (tumor necrosis factor receptor-associated factor interacting protein 2) and ILIA and support SASP. SASP is completely hampered in rho0 cells (mtDNA free cells established by a forced mitophagy). Mitochondrial replacement of oocytes derived from the old in an experimental IVF surely promoted the success rate for zygote formation, development and embedding of embryo, and bearing offspring.

Impaired proteostasis (protein homeostasis) is another characteristics in aging. The integrity of proteostasis is strictly maintained by translational regulation, protein folding chaperon, ubiquitin-proteasome system (UPS), and the autophagy-lysosome system. Because chaperones depend upon ATP, decrease of bioenergy with aging jeopardize the function to correct protein folding. Both UPS and the autophagy-lysosome system, including mitophagy, decline with time. The alterations of these three systems generate aggregates which are not recycled in cytosol leading to degenerative disorders. In mitochondrial matrices, the accumulation of aberrant proteins not only actuates the system to degrade them but also offers an opportunity to recover the mitochondrial function communicating to nucleus termed as mitochondrial unfolded protein response ($UPR^{mt}$). All the above mentioned pathways involve mitochondria. The mitochondrial replacement in somatic cells could break the deleterious worsening cycle of aging, slow the senescent process, and even rejuvenate cells.

Thus, the methods provided herein offer clinically viable methods to treat heteroplasmy, and/or treat various diseases, such as diseases associated with senescence, by replacing endogenous dysfunctional mitochondria, such as endogenous mitochondria with mutant mtDNA, with young and/or healthy mitochondria that can have either an autologous or allogeneic origin.

In some embodiments, the methods provided herein for mitochondria replacement can be used for the treatment of mitochondrial disease or disorder, as well as senescence, cancer, and immune system deficiencies.

5.4.2 Methods of Treating a Mitochondrial Disease or Disorder

Also provided herein, are methods of treating a subject having or suspected of having mitochondrial disease or disorder according to any of methods described in Section 5.2 and/or Section 5.3. In some embodiments, the methods of treating a subject having or suspected of having a mitochondrial disease or disorder include generating a MirC according to any of the methods described in Section 5.2 and/or Section 5.3, and then administering a therapeutically effective amount of the mitochondria replaced recipient cell to the subject having or suspected of having a mitochondrial disease or disorder.

Various mitochondrial diseases or disorders are known, and all are capable of being treated using the methods provided herein. For example, the mitochondrial disease or disorder capable of being treated using the methods provided herein can be a Complex I deficiency (OMIM: 252010). Complex I deficiency can be caused by a mutation in any of the subunits thereof. In another embodiment, the Complex I deficiency is caused by a mutation in a gene selected from the group consisting of NDUFV1 (OMIM: 161015), NDUFV2 (OMIM:600532), NDUFS1 (OMIM: 157655), NDUFS2 (OMIM:602985), NDUFS3 (OMIM: 603846), NDUFS4 (OMIM:602694), NDUFS6 (OMIM: 603848), NDUFS7 (OMIM:601825), NDUFS8 (OMIM: 602141), and NDUFA2 (OMIM:602137).

In addition, the mitochondrial disease or disorder capable of being treated using the methods provided herein can be a Complex IV deficiency (cytochrome c oxidase; OMIM: 220110). Complex IV deficiency can be caused by a mutation in any of the subunits thereof. In certain circumstances the Complex IV deficiency is caused by a mutation in a gene selected from the group consisting of MTCO1 (OMIM: 516030), MTCO2 (OMIM:516040), MTC03 (OMIM: 516050), COX10 (OMIM:602125), COX6B1 (OMIM: 124089), SCO1 (OMIM:603644), FASTKD2 (OMIM: 612322), and SCO2 (OMIM:604272).

Mitochondrial diseases or disorders can be caused by or associated with a mutation. The mutation can be a point mutation, a missense mutation, a deletion, and an insertion It is understood that the identification of mutations in mtDNA or nDNA is within the skill of those in the art, and exemplary methods are provided herein, such as, for example, a single nucleotide polymorphism (SNP) assay or a droplet digital PCR.

Non-limiting examples of specific types of mitochondrial diseases or disorders capable of being treated using the methods provided herein include Ornithine Transcarbamylase deficiency (hyperammonemia) (OTCD), Carnitine O-palmitoyltransferase II deficiency (CPT2), Fumarase deficiency, Cytochrome c oxidase deficiency associated with Leigh syndrome, Maple Syrup Urine Disease (MSUD), Medium-Chain Acyl-CoA Dehydrogenase deficiency (MCAD), Acyl-CoA Dehydrogenase Very Long-Chain deficiency (LCAD), Trifunctional Protein deficiency, Progressive External Ophthalmoplegia with Mitochondrial DNA Deletions (POLG), DGUOK, TK2, Pyruvate Decarboxylase deficiency, and Leigh Syndrome (LS). In another embodiment, the mitochondrial disease or disorder is selected from the group consisting of Alpers Disease; Barth syndrome; β-oxidation defects; carnitine-acyl-camitine deficiency; carnitine deficiency; co-enzyme Q10 deficiency; Complex II deficiency (OMIM:252011), Complex III deficiency (OMIM:124000), Complex V deficiency (OMIM:604273), LHON-Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease, FICP—Fatal Infantile Cardiomyopathy Plus, a MELAS—associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+Deafness; CIPO—Chronic Intestinal Pseudoobstruction with myopathy and Ophthalmoplegia, DEAF—Maternally inherited DEAFness; PEM—Progressive encephalopathy, SNHL—SensoriNeural Hearing Loss, Encephalomyopathy; Mitochondrial cytopathy: DEMCHO—Dementia and Chorea; AMDF—Ataxia, Myoclonus, ESOC Epilepsy; Optic atrophy; FBSN Familial Bilateral Striatal Necrosis; FSGS Focal Segmental Glomerulosclerosis; LIMM Lethal Infantile Mitochondrial Myopathy: MDM Myopathy and Diabetes Mellitus; MEPR Myoclonic Epilepsy and Psychomotor Regression; MERME MERRF/MELAS overlap disease: MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; PEM Progressive Encephalopathy; PME Progressive Myoclonus Epilepsy: RTT Rett Syndrome; SIDS Sudden Infant Death Syndrome; and MIDD Maternally Inherited Diabetes and Deafness.

The methods provided herein for treating a mitochondrial disease or disorder can also include, in specific embodiments, a mitochondrial disease or disorder caused by mitochondrial DNA abnormalities, where the mitochondrial DNA abnormalities are selected from the group consisting of chronic progressive external ophthalmoplegia (CPEO), Pearson syndrome, Kearns-Sayre syndrome (KSS), diabetes and deafness (DAD), leber hereditary optic neuropathy (LHON), LHON-plus, neuropathy, ataxia, and retinitis pigmentosa syndrome (NARP), maternally-inherited Leigh syndrome (MILS), mitochondrial encephalomyopathy, lactic acidosis, and stroke-like episodes (MELAS), myoclonic epilepsy and ragged-red fiber disease (MERRF), familial bilateral striatal necrosis/striatonigral degeneration (FBSN), Luft disease, aminoglycoside-induced Deafness (AID), and multiple deletions of mitochondrial DNA syndrome.

Mutations in mtDNA are thought to be associated with numerous clinical disorders. In adults, these include neurological diseases (e.g., migraine, strokes, epilepsy, dementia, myopathy, peripheral neuropathy, diplopia, ataxia, speech disturbances, and sensorineural deafness), gastrointestinal diseases (e.g., constipation, irritable bowel, and dysphagia), cardiac diseases (e.g., heart failure, heart block, and cardiomyopathy), respiratory diseases (e.g., respiratory failure, nocturnal hypoventilation, recurrent aspiration, and pneumonia), endocrine diseases (e.g., diabetes, thyroid disease, parathyroid disease, and ovarian failure), ophthalmological diseases (e.g., optic atrophy, cataract, ophthalmoplegia, and ptosis). In children, disorders thought to be associated with mtDNA mutations include neurological diseases (e.g., epilepsy, myopathy, psychomotor retardation, ataxia, spasticity, dystonia, and sensorineural deafness), gastrointestinal diseases (e.g., vomiting, failure to thrive, and dysphagia), cardiac diseases (e.g., biventricular hypertrophic cardiomyopathy and rhythm abnormalities), respiratory diseases (e.g., central hypoventilation and apnea), hematological diseases (e.g., anemia and pancytopenia), renal diseases (e.g., renal tubular defects), liver diseases (e.g., hepatic failure), endocrine diseases (e.g., diabetes and adrenal failure), and ophthalmological diseases (e.g., optic atrophy). Accordingly, the methods and compositions provided herein are contemplated for use in treating or preventing diseases and disorders associated with mutations in mtDNA.

In other specific embodiments, the methods provided herein allow for treating a mitochondrial disease or disorder where the mitochondrial disease or disorder is caused by nuclear DNA abnormalities, and the nuclear DNA abnormalities are selected from the group consisting of Mitochondrial DNA depletion syndrome-4A, mitochondrial recessive ataxia syndrome (MIRAS), mitochondrial neurogastrointestinal encephalomyopathy (MNGIE), mitochondrial DNA depletion syndrome (MTDPS), DNA polymerase gamma (POLG)-related disorders, sensory ataxia neuropathy dysarthria ophthalmoplegia (SANDO), leukoencephalopathy with brainstem and spinal cord involvement and lactate elevation (LBSL), co-enzyme Q10 deficiency, Leigh syndrome, mitochondrial complex abnormalities, fumarase deficiency, α-ketoglutarate dehydrogenase complex (KGDHC) deficiency, succinyl-CoA ligase deficiency, pyruvate dehydrogenase complex deficiency (PDHC), pyruvate carboxylase deficiency (PCD), carnitine palmitoyltransferase I (CPT 1) deficiency, carnitine palmitoyltransferase II (CPT II) deficiency, camitine-acyl-carnitine (CACT) deficiency, autosomal dominant-/autosomal recessive-progressive external ophthalmoplegia (ad-/ar-PEO), infantile onset spinal cerebellar atrophy (IOSCA), mitochondrial myopathy (MM) spinal muscular atrophy (SMA), growth retardation, aminoaciduria, cholestasis, iron overload, early death (GRACILE), and Charcot-Marie-Tooth disease type 2A (CMT2A).

Many individuals with a mutation of mtDNA display a cluster of clinical features that fall into a discrete clinical syndrome, such as the Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), or Leigh syndrome (LS). However, considerable clinical variability exists and many individuals do not fit neatly into one particular category, which is well-illustrated by the overlapping spectrum of disease phenotypes (including mitochondrial recessive ataxia syndrome (MIRAS) resulting from mutation of the nuclear gene POLG, which has emerged as a major cause of mitochondrial disease or disorder.

Exemplary diseases where mitochondrial impairment is known to play an important role include, but are not limited to, the pathogenesis of many neurodegenerative diseases, including Alzheimer's disease, Parkinson's disease, Huntington's disease, and amyotrophic lateral sclerosis. In addition, mitochondrial disease or disorders are subtyped into a number of syndromes according to the symptoms rather than the types of mutations. For example, mitochondrial syndromes include Mitochondrial myopathy, Encephalomyopathy, Lactic acidosis, Stroke-like symptoms (MELAS), Myoclonic Epilepsy with Ragged Red Fibers (MERRF), and Leigh syndrome.

5.4.3 Methods of Treating a Subject in Need of Mitochondrial Replacement

Also provided herein, are methods of treating a subject in need of mitochondrial replacement according to any of methods described in Section 5.2 and/or Section 5.3. In some embodiments, the methods of treating a subject in need of mitochondrial replacement include generating a MirC according to any of the methods described in Section 5.2 and/or Section 5.3, and then administering a therapeutically effective amount of the mitochondria replaced recipient cell to the subject in need of mitochondrial replacement.

A subject in need of mitochondrial replacement includes any subject that has a dysfunctional mitochondria. In certain embodiments, the subject in need of mitochondrial replacement has an age-related disease, a mitochondrial disease or disorder, a neurodegenerative disease, a retinal disease, diabetes, a hearing disorder, a genetic disease, or a combination thereof. Neurodegenerative diseases that can benefit from mitochondrial replacement include, but are not limited to, amyotrophic lateral sclerosis (ALS), Huntington's disease, Alzheimer's disease, Parkinson's disease, Friedreich's ataxia, Charcot Marie Tooth disease and leukodystrophy. The retinal disease can be wet or dry age-related macular degeneration, macular edema, or glaucoma. Other exemplary diseases, such as age-related diseases, and/or mitochondrial disease or disorder are described in more detail in Section 5.4.1 and 5.4.2.

A subject in need of mitochondrial replacement can also include a subject that is predisposed to mitochondrial dysfunction, and is asymptomatic. For example, the subject may have mutant mtDNA, but be without manifestations of, for example, a mitochondrial disease because the disease is an adult-onset disease. Therefore, the methods provided herein can be used to also prevent any of the diseases described herein by treating a subject in need of mitochondrial replacement.

5.5 Methods to Produce an iPSC

The current invention also provides methods, as described in Section 5.2 and Section 5.3, for producing or enhancing the production of an induced pluripotent stem cell (iPSC) from a non-pluripotent cell. iPSCs have been demonstrated to be produced from non-pluripotent cells using exogenous expression of stemness factors, such as Oct3/4, Klf4, Sox2, and c-Myc. In addition, low amount of mitochondrial DNA (mtDNA) copies have been detected in undifferentiated ESCs, while this number increases upon differentiation together with the level of mitochondrial maturation (Facucho-Oliveira J M, et al, J Cell Sci 2007; 120(Pt 22):4025-4034). Thus, the present invention has also identified that the methods provided herein can be used to enhance the generation of iPSC by reducing endogenous mtDNA in a non-pluripotent by contacting a recipient non-pluripotent cell with an agent that reduces endogenous mtDNA, incubating the recipient non-pluripotent cell for a sufficient period of time for the agent to partially reduce the endogenous mtDNA in the non-pluripotent cell, and then introducing one or more expression cassettes for expression of Oct3/4, Klf4, Sox2, and c-Myc. In certain embodiments, exogenous mtDNA and/or exogenous mitochondria is non-invasively transferred into the recipient cells.

It is understood that the introduction of the one or more expression cassettes for expression of Oct3/4, Klf4, Sox2, and c-Myc can occur prior to, during, or after introduction of the agent that reduces endogenous mtDNA. Accordingly, in some embodiments, the methods for producing an iPSC includes introducing one or more expression cassettes for expression of Oct3/4, Klf4, Sox2, and c-Myc, contacting a recipient non-pluripotent cell with an agent that reduces endogenous mtDNA, and incubating the recipient non-pluripotent cell for a sufficient period of time for the agent to partially reduce the endogenous mtDNA in the recipient cell.

In certain embodiments, the method further comprises incubating the recipient cell with an exogenous mitochondria and/or exogenous mtDNA for a sufficient period of time to non-invasively transfer the exogenous mitochondria and/or exogenous mtDNA into a recipient cell. In specific embodiments, the method further comprises incubating the recipient cell with an exogenous mitochondria and/or exogenous mtDNA for a sufficient period of time to replace a majority of the endogenous mtDNA. The methods of producing an iPSC from a non-pluripotent cell that include transferring exogenous mitochondria and/or exogenous mtDNA and/or exogenous mitochondria can also include any of the embodiments described in Section 5.3.

Because low amounts of mitochondrial DNA (mtDNA) copies have been detected in undifferentiated embryonic stem cells (ESCs), the methods provided herein can also be used to promote pluripotency in non-pluripotent stem cells, and reduce the number of exogenous genes that are required to generate an iPSC. For example, in some embodiments, the methods provided herein can be used to generate an iPSC by reducing endogenous mtDNA in a non-pluripotent by contacting a recipient non-pluripotent cell with an agent that reduces endogenous mtDNA, incubating the recipient non-pluripotent cell for a sufficient period of time for the agent to partially reduce the endogenous mtDNA in the non-pluripotent cell, and then introducing one or more of Oct3/4, Klf4, Sox2, and c-Myc into the non-pluripotent cell, thereby generating a pluripotent stem cell. In some embodiments, the iPSC can even be generated using only small molecule agents and no exogenous factors.

In certain embodiments, the iPSC contains mutant mtDNA. For example, the mutant mtDNA can contain a point mutation, such as, for example, a point mutation in tRNA (e.g., MELAS). The mutant mtDNA can also include mtDNA with a long deletion of mtDNA. In other embodiments, the non-pluripotent cell for use in producing iPSC is heteroplasmic. The incorporation of mutant mtDNA can facilitate, for example, generation of disease models.

In some embodiments, the non-pluripotent recipient cells are somatic cells. In specific embodiments, the non-pluripotent cells are fibroblasts.

Culture conditions, identification, and establishment of iPSCs is within the skill of those in the art. For example, methods include those provided in U.S. Pat. Nos. 8,058,065, and 8,278,104, which are hereby incorporated by reference in their entireties.

5.6 Assays for Measuring Heteroplasmy

As disclosed previously, mutant mtDNA and/or heteroplasmy can result in dysfunctional mitochondria. Therefore, assays useful for assessing mitochondrial function and/or mtDNA mutations in connection with the methods provided herein for mtDNA replacement include any assays known to a person skilled in the art that can be used to determine or predict the functionality of mitochondria and/or mtDNA mutations.

By way of example, assays to determine mitochondrial function include, for example, measurement of any one of the following secretory factors associated with senescence (e.g., pro-inflammatory cytokines, proteases, and growth and angiogenesis factors, such as IL-1, IL-6/VEGF, IL-8, and CXCL9/MMP); mitochondria function by using Oroboros; Mitophagy by using Keima-Red; mitochondrial permeability; mitochondrial membrane potential; cytochrome c levels; reactive oxygen species; cell respiration; transcriptomics and proteomics for measurement of activated innate immunity, rescission of hyperactivated glycolysis, mitigation of ER stress, repression of m TOR-S6 pathway, and activation of cell cycle; mitochondria dynamics, such as fission and fusion, observed by superfine microscopy, and quantified by a specialized software; or any assay known in the art that measures mitochondrial function Various sequencing methods can be used in combination of any of the methods provided herein to (1) detect mutant mtDNA, (2) quantify heteroplasmy, and/or (3) evaluate or confirm transfer of exogenous mitochondria and/or exogenous mtDNA. A stretch of roughly 1, 100 nucleotides is gene-free that been called D-Loop, Displacement Loop, and Control Region. The D-Loop contains two regions within which mutations accumulate more frequently than anywhere else in the mitochondrial genome. The regions are called hypervariable regions HV1 and HV2, respectively. Accordingly, in some embodiments, mtDNA mutations can be identified in connection with the methods provided herein, by sequencing the hypervariable regions (HV) (i.e., HV1 and/or HIV2) of the D-loop of mtDNA. mtDNA sequencing can be performed using any sequencing method known in the art. In specific embodiments, the sequencing method comprises a single nucleotide polymorphism (SNP) assay. In other embodiments, the sequencing method comprises digital PCR. In specific embodiments, the digital PCR is droplet digital PCR.

5.7 Compositions

Also provided herein are compositions of cells obtained by any of the methods described in Sections 5.2-5.5. In certain embodiments, provided herein is a composition comprising one or more mitochondria replaced cells obtained by the method of (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mitochondria for a sufficient period of time to non-invasively transfer the exogenous mitochondria into the recipient cell, thereby generating a mitochondria replaced cell, wherein said mitochondria replaced cell comprises greater than 5% of exogenous mtDNA. In other aspects, provided herein is a composition comprising one or more mitochondria replaced cells obtained by the method of (a) contacting a recipient cell with an agent that reduces endogenous mtDNA copy number; (b) incubating the recipient cell for a sufficient period of time for the agent to partially reduce the endogenous mtDNA copy number in the recipient cell; and (c) co-incubating (1) the recipient cell from step (b) in which the endogenous mtDNA has been partially reduced, and (2) exogenous mtDNA from healthy donor, for a sufficient period of time to non-invasively transfer exogenous mtDNA into the recipient cell, thereby generating a mitochondria replaced cell, thereby generating a mitochondria replaced cell, wherein said mitochondria replaced cell comprises greater than 5% of exogenous mtDNA.

The compositions can also be obtained by a method that involves contacting a cell with an agent that reduces mitochondrial function, and then incubating the recipient cell for a sufficient period of time for the agent to partially reduce endogenous mitochondrial function in the recipient cell. In some embodiments, the recipient cell having partially reduced endogenous mitochondrial function can then be co-incubated with either exogenous mitochondria from a healthy donor, for a sufficient period of time to non-invasively transfer exogenous mitochondria into the recipient cell, thereby generating a mitochondria replaced cell. In other embodiments, the recipient cell having partially reduced endogenous mitochondrial function can then be co-incubated with either exogenous mtDNA from a healthy donor, for a sufficient period of time to non-invasively transfer exogenous mitochondria into the recipient cell, thereby generating a mitochondria replaced cell. In some embodiments, the mitochondria replaced cell generated by the methods described above comprises greater than 5% of exogenous mtDNA.

As described above, the exogenous mitochondria can be comprised of exogenous mtDNA. Therefore, in some embodiments both exogenous mitochondria and exogenous mtDNA are transferred to the recipient cell and the MirC has both exogenous mitochondria and exogenous mtDNA. In other embodiments, the exogenous mtDNA is transferred to the recipient cell via exogenous mitochondria, and then the exogenous mtDNA is delivered to the endogenous mitochondria. Under certain circumstances the exogenous mitochondria is removed from the cell after the exogenous mtDNA is delivered to the endogenous mitochondria. Accordingly, in some embodiments, the MirC have exogenous mtDNA and does not have exogenous mitochondria.

Because the endogenous mtDNA of the recipient cell is partially degraded, the MirC that includes exogenous mitochondria, exogenous mtDNA, or a combination thereof can contain both exogenous mtDNA and endogenous mtDNA. Similarly, in scenarios where the exogenous mitochondria is transferred to the recipient cell, the MirC can contain both exogenous mitochondria and endogenous mitochondria. Thus, in specific embodiments, the compositions of one or more mitochondria replaced cells obtained by the methods provided herein have a mixture of endogenous and exogenous mitochondria. In other embodiments, the compositions of one or more mitochondria replaced cells obtained by the methods provided herein have a mixture of endogenous mtDNA and exogenous mtDNA (i.e., heteroplasmic mtDNA). In yet further embodiments, the one or more mitochondria replaced cells have a total mtDNA copy number that is no greater than about 1.1 fold, about 1.2 fold, about 1.3 fold, about 1.4 fold, about 1.5 fold, or more, relative to the total mtDNA copy number of the recipient cell prior to contacting with the agent that reduces endogenous mtDNA copy number.

The present invention also includes compositions for use in a method of generating mitochondria replaced that includes an agent that reduces endogenous mtDNA or an agent that reduces mitochondrial function, and a second active agent. In certain embodiments, the composition can further include an exogenous mitochondria, one or more recipient cells, or a combination thereof. In yet further embodiments, the composition can further include exogenous mtDNA.

As described in Section 5.3, various second active agents can be used in the methods for generating one or more mitochondria replaced cells. For example, in some embodiments, the second active agent includes large molecules, small molecules, or cell therapies, and the second active agent is optionally selected from rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ). SkQ1 (Visomitin), resveratrol, curcumin, ketogenic treatment, hypoxia, and an activator of endocytosis.

The use of an activator of endocytosis was found to enhance the uptake of exogenous mitochondria in cells treated with the MTS-XbaIR plasmid, but had no effect on promoting uptake with "add on" or mock transfected cells, which indicated that this mechanism of transferring exogenous mitochondria was unique to the invention provided herein. Non-limiting exemplary compounds suitable for activating endocytosis include, for example, phorbol-12-myristate-13-acetate (PMA) ($C_{36}F_{56}O_8$), 12-O-tetradecanoylphorbol 13-acetate (TPA) ($C_{36}H_{56}O_8$), tanshinone IIA sodium sulfonate (TSN-SS) ($C_{19}H_{17}O_6S{\cdot}Na$), and phorbol-12,13-dibutyrate, or derivatives thereof. In some embodiments, the activator of endocytosis comprises a modulator of cellular metabolism.

Modulating cellular metabolism may be accomplished by any of a number of well-known techniques including but not limited to those described herein, and in the cited references. For example, in some embodiments, modulating cellular metabolism is performed by nutrient starvation or nutrient deprivation. In other embodiments, modulating cellular metabolism is performed by a chemical inhibitor or small molecule. In specific embodiments, the chemical inhibitor or small molecule is an mTOR inhibitor.

Various compounds are known to inhibit mTOR, including rapamycin, also known as sirolimus (CAS Number 53123-88-9, $C_{51}H_{79}NO_{13}$), and rapamycin derivatives (e.g., rapamycin analogs, also known as "rapalogs"). Rapamycin derivatives include, for example, temsirolimus (CAS Number 162635-04-3; $C_{56}H_{87}NO_{16}$), everolimus (CAS Number 159351-69-6; $C_{53}H_{83}NO_{14}$), and ridaforolimus (CAS Number 572924-54-0; $C_{53}H_{84}NO_{14}P$). Accordingly, in some embodiments, the compositions provided herein comprise rapamycin or a derivative thereof. It is understood that the embodiments described above for modulating cellular metabolism are non-limiting, and modulating cellular metabolism need not involve a chemical compound or small molecule, and can include modulation of other pathways beyond mTOR. It is also understood that the compositions can optionally comprise activators of endocytosis, and that it is not a required component. In addition, in some embodiments the invention provided herein can involve non-endocytosis mediated transfer of mtDNA and/or mitochondria, such as in non-clinical settings.

As described in Section 5.5, the present invention also provides, in certain embodiments, a composition for use in a method of producing an induced pluripotent stem cells (iPSC) from a non-pluripotent cell that includes an agent that reduces endogenous mtDNA, one or more expression cassettes for expression of Oct3/4, Klf4, Sox2, and c-Myc, and a recipient cell, wherein the recipient cell is a non-pluripotent cell, wherein the agent that reduces endogenous mtDNA is present in an amount effective to increase efficiency of producing an induced pluripotent stem cells (iPSC) from a non-pluripotent cell, as compared to a non-pluripotent cell not treated with an agent that reduces endogenous mtDNA. In some embodiments, the agent that reduces endogenous mtDNA is present in an amount effective to increase efficiency of producing an induced pluripotent stem cells (iPSC) from a non-pluripotent cell, as compared to a non-pluripotent cell not treated with an agent that reduces endogenous mtDNA. This is based in part on the observation that pluripotent cells have a reduction in mtDNA copy number. In specific embodiments, the composition for use in a method of producing an iPSC further comprises exogenous mitochondria and/or exogenous mtDNA.

The present invention also includes pharmaceutical compositions for use in the treatment of an age-related disease, a mitochondrial disease or disorder, a neurodegenerative disease, diabetes, a genetic disease, or any subject in need of mitochondrial replacement, as described in Section 5.4. In certain embodiments, provided herein are pharmaceutical compositions that include an isolated population of mitochondria replaced cells that have exogenous mitochondria from a healthy donor, and the cells are obtained by the methods described herein, such as in Sections 5.2-5.3. In other embodiments, the pharmaceutical composition includes an isolated population of mitochondria replaced cells with exogenous mitochondria and/or exogenous mtDNA from a healthy donor, and the cells are obtained by the methods described herein, such as in Sections 5.2-5.3. For example, in some embodiments, the mitochondria replaced cells that have exogenous mtDNA can optionally further include exogenous mitochondria. In other embodiments, the exogenous mtDNA is transferred into the cell via exogenous mitochondria, delivered to the endogenous mitochondria, and then the exogenous mitochondria is removed from the recipient cell.

The disclosure also provides a pharmaceutical composition comprising an isolated population of mitochondria replaced cells having an exogenous mitochondria from a healthy donor, wherein the cells are obtained by any of the methods provided herein for obtaining a mitochondrial replaced cell. In yet another aspect, the disclosure provides a pharmaceutical composition comprising an isolated population of mitochondria replaced cells having an exogenous mtDNA from a healthy donor, wherein the cells are obtained by any of the methods provided herein for obtaining a mitochondrial replaced cell. In some embodiments, the pharmaceutical composition comprising an isolated population of mitochondria replaced cells having an exogenous mtDNA from a healthy donor further comprises exogenous mitochondria.

For example, in some embodiments, a pharmaceutical composition comprising an exogenous mitochondria from a healthy donor are obtained by a method that involves contacting a cell with an agent that reduces mtDNA copy number, and then incubating the recipient cell for a sufficient period of time for the agent to partially reduce endogenous mtDNA copy number in the recipient cell. In some embodiments, the recipient cell having partially reduced endogenous mtDNA copy number can then be co-incubated with either exogenous mitochondria from a healthy donor, for a sufficient period of time to non-invasively transfer exogenous mitochondria into the recipient cell, thereby generating a mitochondria replaced cell. In other embodiments, the recipient cell having partially reduced endogenous mtDNA copy number can then be co-incubated with either exogenous mtDNA from a healthy donor, for a sufficient period of time to non-invasively transfer exogenous mitochondria into the recipient cell, thereby generating a mitochondria replaced cell. In some embodiments, the mitochondria replaced cell generated by the methods described above comprises greater than 5% of exogenous mtDNA.

In other embodiments, the cells are obtained by a method that involves contacting a cell with an agent that reduces mitochondrial function, and then incubating the recipient cell for a sufficient period of time for the agent to partially reduce endogenous mitochondrial function in the recipient cell. In some embodiments, the recipient cell having partially reduced endogenous mitochondrial function can then be co-incubated with either exogenous mitochondria from a healthy donor, for a sufficient period of time to non-invasively transfer exogenous mitochondria into the recipient cell, thereby generating a mitochondria replaced cell. In other embodiments, the recipient cell having partially reduced endogenous mitochondrial function can then be co-incubated with either exogenous mtDNA from a healthy donor, for a sufficient period of time to non-invasively transfer exogenous mitochondria into the recipient cell, thereby generating a mitochondria replaced cell. In some embodiments, the mitochondria replaced cell generated by the methods described above comprises greater than 5% of exogenous mtDNA. The agent that reduces mitochondrial function can either transiently or permanently reduce mitochondrial function. It is within the skillset of a person skilled in the art to be able to determine whether the agent would transiently (e.g., reversible inhibitor) or permanently (e.g., irreversible inhibitor) reduces mitochondrial function.

In certain embodiments of the pharmaceutical compositions provided herein, the cells are obtained by a method further comprising further comprising contacting the recipient cell with a second active agent prior to co-incubating the recipient cell with exogenous mitochondria and/or exogenous mtDNA. In some embodiments, the second active agent is selected from the group consisting of large molecules, small molecules, or cell therapies, and the second active agent is optionally selected from the group consisting of rapamycin, NR (Nicotinamide Riboside), bezafibrate, idebenone, cysteamine bitartrate (RP103), elamipretide (MTP131), omaveloxolone (RTA408), KH176, Vatiquinone (Epi743), thioctic acid, A0001 (alpha-tocopherolquinone), mitochondrial CoQ10 (MitoQ), SkQ1 (Visomitin), resveratrol, curcumin, ketogenic treatment, hypoxia, and an activator of endocytosis. In specific embodiments, the activator of endocytosis is a modulator of cellular metabolism. In other embodiments, the modulator of cellular metabolism comprises nutrient starvation, a chemical inhibitor, or a small molecule. In further embodiments, the chemical inhibitor or the small molecule is an mTOR inhibitor. In yet further embodiments, said mTOR inhibitor comprises rapamycin or a derivative thereof.

As described above in Section 5.2, various types of cells can be used as recipient cells and donor cells. For example, the present disclosure describes numerous examples where the recipient cells are mammalian cells. However, it is also understood that any cell with a mitochondria can be a recipient cell. Therefore, the recipient cell can also be a plant cell.

In some embodiments, the animal cells are mammalian cells. In specific embodiments, the cells are somatic cells. In further embodiments, the somatic cells are epithelial cells. In yet further embodiments, the epithelial cells are thymic epithelial cells (TECs).

The present disclosure also provides compositions where the somatic cells are immune cells. For example, the compositions can comprise immune cells where the immune cells are T cells, such as exhausted T cells. In some embodiments, the composition includes rejuvenated T cells that contain exogenous mitochondria and/or exogenous mtDNA. For example, senescent T cells or near senescent T cells (e.g., immunosenescent) can serve as a recipient cell and a T cell-derived MirC can be generated using the methods provided herein to produce a T cell with healthy exogenous mitochondria and/or exogenous mtDNA. In specific embodiments, the T cells are CD4+ T cells. In other embodiments, the T cells are CD8+ T cells. In some embodiments, the T cells are chimeric antigen receptor (CAR) T cells. For example, in some embodiments the disclosure provides a MirC that is CAR-T cell, which is efficacious in killing a cancer cell. The MirC derived CART can have prolonged survival to enable increased immunosurveillance, and enhanced cancer cell killing. In other embodiments, the immune cells are phagocytic cells.

As described above, the compositions provided herein can also include a composition for use in delaying senescence and/or extending lifespan in a cell. The composition can include a senescent or near senescent cell having endogenous mitochondria, isolated exogenous mitochondria from a non-senescent cell, and an agent that reduces endogenous mtDNA copy number. The composition can also include a senescent or near senescent cell having endogenous mitochondria, isolated exogenous mitochondria from a non-senescent cell, and an agent that reduces mitochondrial function.

Also provided herein are compositions that include one or more mitochondria replaced cells that are derived from recipient cells that are bone marrow cells. In specific embodiments, the bone marrow cells are a hematopoietic stem cell (HSC), or a mesenchymal stem cell (MSC). For example, an HSC or MSC can be isolated from a subject having or suspected of having a mitochondrial disease, an age-related disease, or otherwise be in need of mitochondrial replacement, and have the endogenous mitochondria replaced with exogenous mitochondria. Subsequently, the HSC or MSC derived MirC can then be transplanted back into the subject in need of mitochondrial replacement. In yet further embodiments, the recipient cells are iPS cells. The compositions can be used in the clinical setting and can be efficacious in treating an age-related disease, treating a mitochondrial disease or disorder, treating a neurodegenerative disease, treating diabetes, or a genetic disease. For example, in some embodiments, the iPSC can be differentiated into a particular cell type prior to administering back into the subject, using methods known in the art.

In other embodiments, provided herein are pharmaceutical compositions that include an isolated population of pluripotent cells having a reduced amount of endogenous mtDNA, wherein the cells are obtained by any of the embodiments described in Section 5.5. In specific embodiments, the isolated population of pluripotent cells are iPS cells.

Administration of cells or compounds described herein is by any of the routes normally used for introducing pharmaceuticals. The pharmaceutical compositions of the invention may comprise a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences,* 17$^{th}$ ed. 1985).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit dose or multi-dose sealed containers, such as ampoules and vials. Solutions and suspensions can be prepared from sterile powders, granules, and tablets of the kind previously described.

The dose administered to a patient, in the context of the present invention should be sufficient to induce a beneficial response in the subject over time, i.e., to prevent, ameliorate, or improve a condition of the subject. The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject. Administration can be accomplished via single or divided doses.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All patents, applications, published applications, and other publications cited herein are incorporated herein by reference in their entirety. In the event that any description of terms set forth conflicts with any document incorporated herein by reference, the description of term set forth herein shall control.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

6. EXAMPLES

The examples in this section are offered by way of illustration, and not by way of limitation. The following examples are presented as exemplary embodiments of the invention. They should not be construed as limiting the broad scope of the invention.

Example I: Optimization of the MirC Protocol Revealed that XbaI Degraded mtDNA in Vitro and the MTS Expression Vector Targeted Mitochondria A scheme of the method used to generate a mitochondria replaced cell (MirC) is provided in FIG. 1A. First, the mammalian expression vector used to express the XbaI restriction enzyme fused to a mitochondrial-targeted sequence (MTS) was engineered by cloning the MTS-XbaI sequence into the pCAGGS vector using standard techniques known in the art (FIG. 1B). Among mitochondrial transfer signals (MTS) being reported we utilized the ND4 signal sequence in this study. The resultant expression vector also contained the puromycin resistance gene to allow for selection (FIG. 1B).

XbaIR is one of the most powerful endonucleases and a standard sequence of mtDNA named under Cambridge reference sequence (CRS) in human mitochondria genome has as many as five recognition sites targeted by the particular endonuclease (FIG. 1D). It was verified by an in vitro endonuclease co-incubation that isolated mtDNA was digested at multiple sites by XbaIR (FIG. 1C). In contrast, NotI digestion of mtDNA showed a single fragment, as predicted by Cambridge Reference Sequence (CRS) of mitochondrial DNA (FIG. 1C).

The gene transfer protocol of plasmid DNA to cells was optimized using Normal Human Dermal Fibroblast (NHDF) cells that expressed enhanced green fluorescent protein (EGFP) by using the Nucleofector electroporation-based transfection method. Following one day of 2 μg/ml puromycin exposure, an efficacy of more than 90% and viability of more than 90% was established (FIG. 1E).

To specifically evaluate the effectiveness of the MTS targeting sequence, a plasmid carrying MTS fused with EGFP was generated by subcloning the EGFP gene in place of the XbaIR gene to generate the pCAGGS-MTS-EGFP-PuroR plasmid (FIG. 1F). Then normal human dermal fibroblasts (NHDF) were transfected with the MTS-EGFP expression vector and the cells were counter stained with TMRM (tetramethylrhodamine, methyl ester), which is a cell-permeant dye that accumulates in active mitochondria with intact membrane potential (FIG. 1G).

Taken together, these results demonstrated that XbaI could be used to digest mitochondrial DNA, the cells could be efficiently transfected without effecting cell viability, and the expression vectors containing a MTS could effectively target mitochondria.

Example II: Endonuclease MTS-XbaIR Treatment Exhibits Improved Degradation of mtDNA Relative to the Conventional Method of EtBr The efficiency and efficacy of the MTS-XbaIR expression vector relative to the conventional method that employs ethidium bromide (EtBr) was evaluated according to the scheme illustrated in FIG. 2A. The placental venous endothelium-derived cell line EPC100 with DsRed labeled mitochondria were cultured in pyruvate-free DMEM (Wako cat #044-29765) with 10% fetal bovine serum (FBS) and 1% penicillin/streptomycin (P/S), and at day 0 the cells were either untreated ("normal"), transfected with the MTS-XbaIR expression vector ("MTS-XbaIR"), or treated with 50 ng/ml of EtBr. At day 1, the cells were cultured in DMEM with 10% FBS, and 1% P/S supplemented with 100 μg/mL pyruvate and 50 μg/mL uridine. Quantitative polymerase chain reaction (qPCR) was performed according to methods known in the art at days 3 and 5 to measure the mtDNA relative to the housekeeping gene, β-actin (Actb). The results demonstrated that XbaIR reduced the mtDNA copy number to 2715.8141, whereas the EtBr treatment only reduced the mtDNA copy number to 5169.1258, which was similar to the DNA copy number of 6189.6867 in untreated cells (FIG. 2B). While the reduction of mtDNA in the endonuclease treated group was superior to that of the group treated with the conventional method, it was not a complete deletion and approximately 30% of the endogenous mtDNA remained (FIG. 2B). Cells with this partial reduction of mtDNA were termed as ρ(−) cells.

The enhanced degradation of endogenous mtDNA in the MTS-XbaIR treated group, relative to the EtBr group was further confirmed by microscopy of the DsRed labeled mitochondria (FIG. 2C). The level of reduction was reflected in the remaining healthy mitochondrial volume estimated by the TMRM staining, which was lower in the XbaIR treated group than that with the conventional method (FIG. 2C). In addition, a FACS analysis of NHDF cells demonstrated a reduction of TMRM after treating with XbaIR (FIG. 2D).

The kinetics of the expression of XbaIR following plasmid gene transfer was examined by qPCR. On day 3, the expression reached the peak and then declined to zero on day 7 (FIG. 2E). Other genes of interest (e.g., GFP) verified the same kinetics as XbaIR (FIG. 2E). Fluorescent images confirmed the enrichment of GFP following in cells transfected with the MTS-EGFP-PuroR plasmid after puromycin selection, as compared to before transfection (FIG. 2F and FIG. 2G). The fraction of GFP positive cells significantly increased to almost 100% by exposing the puromycin for one day (FIG. 2F).

These results demonstrated that the reduction of mtDNA copy number in the XbaI endonuclease treated group was superior to that of the group treated with the conventional method of EtBr, and did not completely delete all of the endogenous mtDNA. Moreover, a brief selection using puromycin enabled significant enrichment of the cells expressing the MTS construct.

Example III: Partial Degradation of Endogenous Mitochondria Using MTS-XbaIR Construct in Recipient Cell Enabled Mitochondria Replacement from Exogenous Donor Cell To evaluate whether exogenous mitochondria from a healthy donor cell could be transferred to a recipient cell with XbaI mediated depletion of mtDNA, NHDF cells were transfected with the MTS-GFP or MTS-XbaIR plasmids and selected using puromycin after 48 hours. After 6 days post-transfection, isolated mitochondria from human cell lines originated from the endothelium of the uterus (named as EPC100) that were labeled with DsRed were transferred to the donor cells. A scheme of the protocol is shown in FIG. 3A.

Following transfection with MTS-GFP or MTS-XbaI and selection with puromycin the mitochondria content was evaluated by TMRM staining. As shown in FIG. 3B, the MTS-GFP transfected cells exhibited a strong staining for TMRM, indicating high levels of mitochondria in the NHDF cells. In contrast, the MTS-XbaI transfected cells (ρ−) exhibited a reduction of the mitochondrial volume, as visualized by TMRM staining (FIG. 3B).

The reduction of mitochondrial DNA was further confirmed by quantifying the number of mitochondrial DNA copies by qPCR of 12S-rRNA after adjusting with β-actin (Actb) in the nucleus (FIG. 3C). On day 6, there was a significant reduction in mitochondrial DNA from MTS-XbaI transfected cells (ρ−), relative to the NHDF control cells transfected with MTS-GFP (FIG. 3C). The significant reduction in mitochondrial DNA in the ρ-cells continued for the length of the assay, which was stopped on day 12. Specifically, the copy numbers dropped to about ⅓ of the original copy numbers on day 6 and further declined to about ¼ on day 12 in the p-cells (FIG. 3C).

Mitochondria were isolated from DsRed-Mt EMCs by differential centrifugation. In brief, the cells were harvested from culture dishes with homogenization buffer [HB: 20 mM HEPES-KOH (pH 7.4), 220 mM mannitol and 70 mM sucrose] containing a protease inhibitor mixture (Sigma-Aldrich, St. Louis, Missouri, USA). The cell pellet was resuspended in HB and incubated on ice for 5 min. The cells were ruptured by 10 strokes of a 27-gauge needle on ice. The homogenate was centrifuged (400 g, 4° C.), 5 min.) two times to remove unbroken cells. The mitochondria were harvested by centrifugation (6000 g, 4° C., 5 min.) and resuspended in HB. The amounts of isolated mitochondria were expressed as protein concentration using a Bio-Rad protein assay kit (Bio-Rad, Richmond, CA, USA). Mitochondrial transfer was conducted by co-incubating isolated mitochondria with cells in 2 ml of standard medium at 37° C. under 5% CO2 for 24 h. Importantly, the co-incubation of isolated mitochondria with ρ(−) cells on day 12 resulted in a significant increase in mtDNA copy number, similar to the levels of control NHDF cells (FIG. 3C).

Consistent with the results shown in FIG. 2C and FIG. 2D, the ρ(−) cells exhibited reduced mitochondria content after MTS-XbaI transfection, as measured by visualization of TMRM. Importantly, the decrease in mitochondria could be rescued by contacting the ρ(−) cells with the isolated exogenous mitochondria, as indicated by the uptake of the DsRed labeled isolated mitochondria (FIG. 3D and FIG. 3E). In contrast, the co-cultivation of DsRed-marked and isolated mitochondria with either NHDF control cells or NHDF cells transfected with the mock transfectant MTS-EGFP expression vector revealed that the exogenous mitochondria gathered around the cells and formed aggregates, but failed to be internalized (FIG. 3D, lower panels). Although a minor portion of the mitochondria were engulfed, most of them stayed outside of the cells with intact endogenous mitochondria, and the intensity of DsRed was maintained during this period. The aggregates of DsRed became smaller, and fewer, and the intensity of DsRed was reduced suggesting that after gathering exogenous mitochondria onto cell membrane, they were engulfed and their membranous portions of mitochondria were rapidly digested.

Comparison between existing methods demonstrated that the endonuclease method of the present invention was more efficacious in generating a mitochondria replaced cell having exogenous mitochondria (FIG. 3F). For example, the endonuclease method of the present invention was compared with (1) the add-on mitochondria transfer method, described in our previous works (see, e.g., Kitani, T., et al, *J Cell Mol Med* (2014) 18, 1694) or (2) a recently reported method (see, e.g., Kim, M. J., et al., Sci Rep 8, 3330, (2018)) that employed spinoculation of isolated mitochondria with metabolically healthy cells (FIG. 3F). Neither of the previously reported methods (i.e., mitochondria add-on; "Mt add-on", or spinoculation at 800×g or 1500×g) demonstrated any significant transfer of exogenous mitochondria, as measured by FACS analysis of DsRed labeled exogenous mitochondria (FIG. 3F). On the other hand, the novel method provided herein that employed MTS-XbaI mediated partial degradation of endogenous mitochondria followed by the non-invasive transfer or exogenous mitochondria (Mt EPC100) demonstrated a significant DsRed positive fraction and increased mean fluorescence intensity after transfer of exogenous mitochondria (FIG. 3F, top right graph, far right line).

Previously established methods used in mitochondria biology utilized cells with a complete deletion of mitochondria ρ(0) cells (see, e.g., U.S. patent application Ser. No. 12/747,771, filed Sep. 23, 2010, and published as US 2011-0008778 A1, which is incorporated by reference herein in its entirety). However, the ρ(0) cells failed to engulf exogenous mitochondria (FIG. 3G-FIG. 3I). Based on these results presented herein, it was hypothesized that the ρ(0) cells failed to engulf exogenous mitochondria due to a shortage of energy necessary to undergo macropinocytosis. To confirm the hypothesis, we designed gene modified cells to generate ρ(0)) cells with an exposure to antimycin that induces mitophagy, and examined the mitochondria transfer level. The results demonstrated that no engulfment of exogenous mitochondria occurred in cells with a complete deletion of mitochondria (FIG. 3G-FIG. 3I). Therefore, these results suggested that a partial deletion of the pre-existing mtDNA, rather than a complete deletion, was a key factor in the macropinocytosis of exogenous and extracellular mitochondria.

In addition, the uptake of DsRed labeled exogenous mitochondria was monitored in ρ(−) cells treated with or without exogenous mitochondria, untransfected cells (add on Mt), or cells treated with the mock MTS-GFP plasmid. The fluorescent intensities of DsRed was quantified every 24 hours using NIH image software. The relative values to the initial intensities were depicted in bar graph (FIG. 3J). The quantification demonstrated that simple add-on mitochondria coincubation and mitochondria coincubation with mock-transfectant increased the intensities at the same rate due to aggregation of the isolated mitochondria, indicating accumulation rather than engulfment of the Ds-red labeled mitochondria. In contrast, the intensity of ρ(−) cells co-incubated with isolated, exogenous mitochondria gradually decreased with time, suggesting that engulfed mitochondria were degraded.

These results demonstrate that the MTS-XbaI expression vector can generate ρ(−) cells that have a partial deletion of endogenous mitochondria, and the mitochondrial content can be rescued by transferring isolated exogenous mitochondria from donor cells. As described herein, the methods of the current invention provide improved efficiency of mitochondrial transfer, relative to previously described methods, such as those performed in combination with centrifugation, or simple "adding on" the mitochondria without partially reducing the endogenous mtDNA. However, mitochondrial transfer was unable to be performed in cells with a complete degradation of endogenous mitochondria (ρ(0) cells), which indicated that the uptake of exogenous mitochondria likely requires energy.

Example IV: Isolated Exogenous Mitochondria Fuse with Endogenous Mitochondria to Transfer Donor mtDNA To further elucidate how mitochondrial transfer of intact mitochondria occurs, the fate of transferred mitochondria into cells was investigated separately on outer and inner membrane and nucleoid. In certain circumstances, transient intermitochondrial fusion events have been observed, where two mitochondria came into close apposition, exchanged soluble inter-membrane space and matrix proteins and reseparated, preserving the original morphology (see, e.g., Liu X et al., *EMBO J.* 2009; 28(20): 3074-3089; Huang X et al. *Proc Natl Acad Sci USA.* 2013; 110(8):2846-2851). Therefore, transient intermitochondrial fusion events were analyzed under the conditions described herein.

Isolated mitochondria from EPC100 donor cells was labeled with DsRed. and recipient cells with EGFP-marked mitochondria were used. A diagram of the protocol employed is illustrated in FIG. 4A. Microscopy images of the temporal contact of the donor and resident mitochondria revealed that no broad mitochondrial fusion was observed (FIG. 4B and FIG. 4C). The majority of the donor mitochondria existed separately from the endogenous mitochondria. In addition, a few transient fusion images were observed, and then the donor mitochondria appeared to run away before it finally disappeared (FIG. 4C).

Mitochondrial transfer was performed according to the protocol illustrated in FIG. 4F. Briefly, the mitochondria of the recipient NHDF cells was marked with DsRed-marked (FIG. 4D), and mitochondria from the donor EPC100 cells was marked with TEAM, which binds to mtDNA and allows tracing of mitochondria (FIG. 4E). The recipient NHDF cells were transfected with the pCAGGS-MTS-XbaIR-P2A-PuroR expression vector, and selected with puromycin on day 2 for 24 hours. On day 6, mitochondrial transfer from TFAM-GFP labeled mitochondria from EPC100 donor cells was performed. Then on day 8, the cells were imaged. Microscopy of the mitochondrial transfer revealed that the donor nucleoid settled in the pre-existing mitochondrial matrices (FIG. 4G). The exogenous mitochondria transiently contacted the mitochondria of recipient, suggesting that mitochondrial nucleoids including TFAMs were transferred to the pre-existing mitochondria via the transient contact.

These results demonstrate that donor mitochondria were transferred into the mitochondrial matrices in the recipient cells and dominate under the reduction of pre-existing mitochondria. Moreover, according to these experiments, almost all isolated mitochondria were engulfed. On the other hand, add-on type of mitochondrial transfer and mock-transfectant did not exhibit the rigorous engulfment, but aggregated major part of these exogenous mitochondria onto the cellular surface.

In summary, the results from Examples III and IV demonstrate that ρ(−) cells degraded the engulfed mitochondria (FIG. 3J), and that the exogenous mitochondria temporally contacted with the pre-existing mitochondria (FIG. 4B-FIG. 4C), while the exogenous mtDNA with TEAM existed in the pre-existing mitochondria (FIG. 4G).

Accordingly, it is hypothesized that the exogenous mitochondria are able to briefly interact with the endogenous mitochondria, and transport mtDNA during the brief contacts. Then, the exogenous mitochondrial membrane complexes can be degraded in the cytosol to provide building blocks for the reconstituted mitochondria. The mitochondria of the recipient cell that receive the exogenous mitochondria are able to gradually reconstitute the mitochondrial membrane complex, and demonstrate the functional recovery.

Example V: SNP Assay Detected Increase in Exogenous Mitochondria after Transfer of Isolated Exogenous Mitochondria To assess the origin of mtDNA following the mtDNA replacement, the different nucleotides identified between NHDF and EPC100 by sequencing the hypervariable region 1 and 2 were used (FIG. 5A and FIG. 5B). While NHDF preserves A at the position of 16362 in CRS, EPC100 harbors a mutation at the same position that resulted in a change from A to G (FIG. 5B). Importantly, evaluation of the mitochondria replaced ρ(−) cells (NHDF ρ(−) MI) demonstrated the presence of both the original nucleotide in a minor wave and the exogenous nucleotide G in a major wave, which indicated that the cells were heteroplasmic (FIG. 5B, bottom panel).

The heteroplasmy in the mitochondria replaced NHDF was further evaluated by the single nucleotide polymorphism assay to detect the difference between the recipient NHDF and the donor EPC100 (FIG. 5C). The HV1 region was amplified using the hmt16318-F primer (5'-agccatt-taccgtacatagcacatt-3' (SEQ ID NO: 6)) and the hmt16414-R primer (5'-cacggaggatggtggtcaag-3' (SEQ) ID NO: 9)), and the SNP was detected using the NHDF specific probe (S'-CTTCTCGTCCCCATG-3' (SEQ ID NO: 5)) and the EPC100 specific probe (5)-CCCTTCTCGCCCCCAT-3' (SEQ ID NO: 7)) (FIG. 5C). The SNP assay results demonstrated that the ratio of EPC100 versus NHDF reached 66.6% on day 12 after the mtDNA replacement (FIG. 5D). This result was an unexpected improvement from previous methods, which resulted in a relatively small portion of extracellular mitochondria being engulfed by human uterine endometrial gland-derived mesenchymal cells and had little effect on the heteroplasmy levels (see, e.g., Kitani, T., et al., *Journal of Cellular and Molecular Medicine,* 18, 1694-1703 (2014)).

These results demonstrate that the methods provided herein for replacement of mtDNA with exogenous mitochondria and/or exogenous mtDNA is completely novel, and an improvement over the existing technology. As described herein, the methods provided demonstrate that the transfer of mitochondria after MTS-XbaI mediated degradation of endogenous mitochondria can result in exogenous mtDNA being the predominant mtDNA.

Example VI: Replaced Mitochondria Generate Energy and MirC Exhibit Phenotypic Recovery Similar to Normal Control Cells Whether the replaced mitochondria work to generate energy was investigated by using Oroboros O2k according to the manufacturer's instructions. Representative oxygen consumption rate curves with native control cells, the ρ(−) cells, and the mitochondria replaced cells were generated and then the respiratory flow and control ratio was calculated (FIG. 6A and FIG. 6B). Basal respiration, the maximum capacity of electron transfer system, and ATP production (Free Routine Activity) all showed similar kinetics and indicated that these indices significantly dropped with the ρ(−) cells (FIG. 6B, upper row). Importantly, these indices recovered to the original values with the mitochondria replaced cells (FIG. 6A and FIG. 6B). Non-mitochondrial ATP production (ROX) was upregulated, and the coupling ratio was downregulated in the ρ(−) cells (FIG. 6B, lower row). The energy providing machinery in the ρ(−) cells inclined to glycolysis from mitochondrial ATP generation and the changes were reversed after the mtDNA replacement with the native cells (FIG. 6B, upper right).

In addition, the phenotypic recovery of the mitochondria replaced cells (MirC) was demonstrated by their proliferative capability (FIG. 6C). Specifically, the ρ(−) cells showed a poor proliferative capability, whereas the MirC recovered to levels near that of the control cells by days 6-12 (FIG. 6C, right).

These results demonstrated that this methodology offers mtDNA replacement with clinically applicable materials, and results in cells with functional mitochondria that enable phenotypic recovery of the mitochondria replaced cells (MirC).

Example VII: Inhibition of mTOR by Rapamycin Enhances Macropinocytosis of Exogenous Mitochondria in ρ(−) Cells To determine a method for increasing the ability of a cell to undergo MirC, the mechanisms that regulate the macropinocytosis of exogenous mitochondria were investigated. Since ρ(−) cells are exhausted of ATP as a result of the reduced mitochondria, it was hypothesized that the intracellular energetic state of ρ(−) cells was similar to a starved state. To this effect, two molecular pathways were investigated: mammalian target of rapamycin complex 1 (mTORC1) and AMP-activated protein kinase (AMPK). mTORC1 is an essential sensor of amino acids, energy, oxygen, and growth factors, and a key regulator of protein, lipid, and nucleotide synthesis. AMPK is a sensor of AMP levels, and the activation results in autophagy, mitochondrial biogenesis, glycolysis, and lipolysis. Both pathways are involved in uptake of extracellular nutrients.

As illustrated in FIG. 6D, to investigate the mechanism of macropinocytosis in ρ(−) cells, starvation was used to stimulate AMPK/mTORC1, while the "drugs" palmitic acid and rapamycin were used to specifically stimulate mTORC1 activation, and suppress mTORC1, respectively. Rapamycin was added into the culture media at the concentration of 50 ng/ml for 24 hours, and cells were exposed to glucose and essential amino acids free media without serum for 1 hour to simulate starvation. Although palmitic acid (PA) was reported to activate mTORC1 at a concentration of 200 μM in vivo, the titration of PA for cultured fibroblasts showed the concentration of 50 μM and the duration of 24 hours was optimal based on the cellular viability. The ratio of phosphorylated AMPK to AMPK and phosphorylated p70 S6 kinase to p70 S6 kinase, which is a downstream target of mTORC1, were examined by using capillary electrophoresis, Wes™ (Protein Simple).

Treatment with PA or rapamycin demonstrated that although AMPK pathway was not significantly activated in ρ(−) cells (FIG. 6G and FIG. 6H), the mTORC1 pathway was drastically suppressed in ρ(−) cells as measured by pS6/S6, at levels similar to starvation and rapamycin (FIG. 6E-FIG. 6F). These results demonstrated that mTORC1 represents an important target for macropinocytosis of mitochondria in ρ(−) cells.

Next, we examined the effects of rapamycin and palmitic acid upon mitochondria engulfment by treating the cells with rapamycin or palmitic acid simultaneously during the mitochondria co-cultivation. A scheme of the protocol is illustrated in FIG. 6I. Briefly, the NHDF recipient cells were transfected with the MTS-XbaI expression vector and cultured with or without rapamycin, or with or without palmitic acid (PA). Puromycin selection for ρ(−) cells expressing the MTS-XbaI was performed after 48 hours. On day 6, transfer of isolated mitochondria marked with DsRed from EPC100 cells was performed. On Day8, FACS analyses were performed to detect the donor mitochondria by measuring DsRed expression in the NHDF recipient cells.

As shown in FIG. 6I-FIG. 6L, rapamycin treatment significantly enhanced the engulfment of the DsRed-labeled isolated, exogenous mitochondria, whereas palmitic acid clearly suppressed it. These experiments were repeated 4 times, and the positive fractions were summarized, which indicated a statistically significant differences in rapamycin and palmitic acid to ρ(−) cells (FIG. 6I and FIG. 6K). Notably, in both mock transfection and add-on type mitochondrial transfer, there were no significant differences. In addition, the results showed that the effect of modulating mTORC1 activity only affected mitochondrial transfer of ρ(−) cells, and had no effect on "add on" or mock transfected cells, which indicated that this mechanism of transferring exogenous mitochondria was unique to the invention provided herein.

These results indicate that activation of mTORC1 by rapamycin during mitochondrial transfer can enhance macropinocytosis of mitochondria. Further, these methods demonstrate that rapamycin, which is a clinically available drug, can be used to increase the efficiency of macropinocytosis for MirC generation.

Example VIII: MtDNA Replacement with Heteroplasmy Reversal in Fibroblasts Derived From Patient with Leigh Syndrome To investigate whether mitochondrial diseased cells could be corrected by using the in-vitro mtDNA replacement technique, primary fibroblasts (7SP) derived from a patient diagnosed with Leigh syndrome having a mtDNA T10158C mutation were used as recipient cells (FIG. 7A). The same protocol described previously in NHDF cells was applied to 7SP fibroblasts. DNA sequencing of mtDNA in the EPC100 donor mitochondria at the 10158th nucleotide was verified to be T (FIG. 7B, top), whereas the 7SP fibroblasts has a mosaic of T in a major wave and C in a minor wave, indicating a heteroplasmy (FIG. 7B, bottom).

The kinetics of the content of mtDNA in 7S fibroblasts was almost the same as in NHDF following the mitochondria replacement (FIG. 7C and FIG. 7J). The time-lapse observation revealed that ρ(−) 7SP fibroblasts exhibited the same behavior with that of ρ(−) NHDF cells. In particular, accumulated aggregates of exogenous mitochondria upon the surface of ρ(−) cells became smaller and less over time and the intensity of DsRed in cytosol rapidly reduced suggesting an efficient engulfment into the cytosol and digestion in the cytosol, which was consistent with the results generated using ρ(−) NHDF cells.

Importantly, the number of m (DNA copies following the mitochondria replacement recovered to the same value with that of the original 7S fibroblasts on day 12 (FIG. 7D). On the other hand, mock transfectant of 7SP fibroblasts (add-on type mitochondria transfer) was unable to even increase the number of mtDNA copies in spite of the same cocultivation with isolated mitochondria under the same conditions, which demonstrated poor transfer of exogenous mitochondria (FIG. 7D, light gray bar).

Whether the mitochondria in 7S fibroblasts contained exogenous and healthy mtDNA was examined by sequencing the mitochondrial genome fragment that included the 10158 nucleotide. As shown in FIG. 7E, the mtDNA sequence of the 7SP cells changed from having a majority of mutant heteroplasmy at the 10158 nucleotide position (large wave of C and a small wave of T) to a majority of wild-type mtDNA (large wave of T and a small wave of C) in the recipient 7SP ρ(−) cells following mitochondria replacement (FIG. 7E, bottom).

To generate quantitative information, a single nucleotide polymorphism (SNP) assay was performed to estimate the heteroplasmy generated using this technology. The ND3 region of mitochondrial DNA was amplified using hmt10085-F primer (5'-CAACACCCTCCTAGCCTTACTACTAA-3' (SEQ ID) NO: 17)) and hmt10184-R primer (5'-GTCGAAGCCGCACTCGTA-3' (SEQ ID NO: 20)), and the EPC100 specific probe (5'-ACATAGAAAAATC-CACCC-3' (SEQ ID NO: 18)) or the 7SP specific probe (5'-CTACATAGAAAAATCCAC-3' (SEQ ID NO: 19)) (FIG. 7F). The results indicated that the original hmt10158 heteroplasmy level in 7SP fibroblasts was about 90% mutant mtDNA (FIG. 7G). The heteroplasmy in the 7SP cells that received the mitochondrial transfer (7SP ρ(−) Mt) exhibited as little as 10% heteroplasmy level on day 12 after the replacement (FIG. 7G), while the mock transfectant (add-on type mitochondria transfer) did not significantly change the heteroplasmy and maintained almost the same ratio or over 90% (FIG. 7H and FIG. 7I). These results indicated that the mitochondrial replacement technology provided herein is superior to the add-on mitochondrial transfer which was reported previously. The ρ(−) cells which went through the endonuclease treatment improved the heteroplasmy to about 75% with about 80% reduction of the number of mtDNA copies.

Taken together these results demonstrate that the methods of generating a mitochondrial replaced cell described herein that use MTS-XbaI to partially reduce endogenous mitochondria can be effectively used in cells from a subject with a mitochondrial disease or disorder to improve the heteroplasmy level and reduce the amount of mutant mtDNA.

Example IX: MtDNA Replacement in Fibroblasts Derived from Patient with Leigh Syndrome Yields Improved Cell Lifespan and Cell Metabolism The functional activity of mitochondrial replaced 7SP fibroblasts was evaluated. As shown in FIG. 8A and FIG. 8B, the proliferation of mitochondrial replaced 7SP fibroblasts (ρ(−) Mt) cells was able to recover to levels equivalent to that of the original 7SP fibroblasts around day 12.

In addition, the mitochondrial replaced 7SP fibroblasts (ρ(−) Mt) cells demonstrated a dramatic extension of lifespan, up to about the 63th population doubling level (PDL) while the doubling time was over 120 hours, which is the threshold of growth arrest (FIG. 8C). The cells received the mtDNA replacement at about the 8th PDL and the reconstituted cells with the healthy mtDNA were able to continue dividing beyond the 55th PDL, which is thought to be the number of times a normal human cell population will divide before cell division stops (i.e., the Hayflick limit). In contrast, the naïve 7S fibroblasts fell into senescence at the 25th PDL (FIG. 8C). Thus, the experiment indicated the mtDNA replacement made a significant impact on the proliferation and lifespan of the mitochondrial diseased cells. Given that senescence increases with aged and cancer cells often involve mitochondrial dysfunction, this methodology might provide a crucial clue in rejuvenation and this might provide a basis for a novel strategy for cancer therapy as well as therapies for other age-related diseases.

The functional effect of mitochondrial transfer in 7S fibroblasts was further evaluated by measuring the cell size (FIG. 8D). The mutation in 7S fibroblasts in the coding sequence of the ND4 gene of Complex I in the respiratory chain resulted in a disturbance of Complex I to transfer electrons coupled with its function to pump protons up from the matrices to intermembrane space. As a result, glycolysis was dominant to the mitochondrial ATP production in 7S fibroblasts and resulted in the compensatory adaptation to be bigger in cellular size to contain more mitochondria despite the damages and poor function (FIG. 8D). Relative to PDL 15 (solid black line), by the PDL 25, the diameter of 7S fibroblasts was about 1.5 times larger than that of NHDF, and the increase in cell size doubled by PDL 35, and eventually the size increased to about 3 to 8 times larger (FIG. 8D, left).

Consistent with the functional recovery of 7SP cells after the mtDNA replacement, the notable increase in cell size observed in the early PDL in 7SP fibroblasts was inhibited following the mitochondria replacement (FIG. 8D), right). Moreover, the size of mitochondria replaced 7SP cells, which received the exogenous mitochondria at PDL 8, was maintained through up to the 50th PDL (FIG. 8D, right). In addition, the concentration of Citrate synthetase (CS) was two times more in 7SP fibroblasts by the 10th PDL than the CS concentration in NHDF cells, which is in agreement with the increase in size-up of 7SP fibroblasts (data not shown).

In order to confirm that the observed improvement in cell function after mitochondria replacement was not due to contamination with other cell types, a short tandem repeat (STR) assay was performed that can definitely discriminate cells with different origins (FIG. 8E). Importantly, the patterns of STR in mitochondria replaced cells at different time point were completely identical to that of the original 7SP fibroblasts (FIG. 8E), which indicated no contamination. Furthermore, a RT-PCR revealed that the transfer of exogenous mitochondria derived from cells that express telomerase and E6, did not transform the primary fibroblasts into cancer cells (FIG. 8F).

Taken together, these results demonstrated that mitochondrial transfer of exogenous isolated mitochondria having wild-type mtDNA into 7SP cells, which are derived from a patient with Leigh Syndrome, increased the lifespan of 7SP cells, and improved the cellular function. Importantly, the transfer did not transform the mitochondrial replaced 7SP cells into cancer cells.

Example X: Transfer of Exogenous Mitochondria to Fibroblasts Derived from a Patient With Leigh Syndrome Yielded Functional Mitochondria The functional effect of mitochondrial replacement in the 7SP fibroblasts was further evaluated by analyzing the cells' respiratory function by using Oroboros O2k (FIG. 9A). Quantification of the results indicated that the basal respiration and ATP production (Free Routine Activity) continued to decrease from the $10^{th}$ PDL to the 20th PDL after the generation of a mitochondrial replaced cell and the maximum capacity of electron transfer system kept the original levels of 7SP fibroblasts (FIG. 9B). By the 30th PDL after transfer of exogenous mitochondria, all three indices of the respiratory function (Routine, ETS, and Free routine activity) were elevated, and even surpassed the levels of the original cells (FIG. 9B). These results indicated that there was a brief delay to reconstitute the electron transfer system with a healthy and non-mutated complex I following the mtDNA replacement. Proton leakage showed the same kinetics with that of the non-mitochondrial ATP production, which steadily improved from the early phase (FIG. 9B).

These results demonstrated that transfer of exogenous mitochondria into fibroblasts derived from a patient with a mitochondrial disease or disorder can yield functional mitochondria.

Example XI: Transfer of Exogenous Mitochondria can Dissipate Chronic and Sustained Reactive Oxygen Species (ROS) Generation In order to characterize the properties of 7SP fibroblast-derived MirC, both a reperfusion and a starvation model under a culture condition were used for 7SP fibroblast-derived MirC, the original 7SP fibroblast, and NHDF as a control. These stress conditions induce apoptosis in cultured cells, the extent of which can be quantified by AnnexinV as an early marker and propidium iodide (PI) as a late marker. Among environmental insults, the reperfusion injuries are mainly attributed to mitochondrial dysfunction. Cells predisposed to mitochondrial dysfunction due to mtDNA mutation are more fragile to the reperfusion injuries than healthy cells.

Cells were seeded on 6 well plate at $1\times10^5$ cells per well. The next day, 600 μM $H_2O_2$ (FUJIFILM Wako Pure Chemical) was added to cells for the reperfusion model or essential amino-acid-free ("-EAA") DMEM (FUJIFILM Wako Pure Chemical) without serum was used as the culture media for the starvation model. After 3 h $H_2O_2$ or 48 h starvation treatment, cells were washed with PBS and collected to centrifugal tube. Annexin V-FITC and PI solution were added in cells and allowed to react for 30 minutes at room temperature protecting from light. Then cells were rapidly subjected to FCM analysis using 488 and 561 nm laser lines. Fluorescence data were collected using SH800 (Sony). The flow cytometry files were analyzed by using FlowJo software (TreeStar).

The results indicated that 7SP cells, which originate from a subject with Leigh syndrome, were highly susceptible to both forms of stress (i.e., $H_2O_2$ and starvation). As shown in FIG. 10A-10D, 7SP cells treated with $H_2O_2$ exhibited a significant increase in both early and late apoptosis. In the reperfusion model ($H_2O_2$), NHDF did not exhibit any significant damages in the process of apoptosis based on AnnexinV and PI staining (FIG. 10B-FIG. 10D). However, this mild reperfusion stress induced apoptosis in 7SP fibroblasts. In contrast, the positive fractions of both Annexin V and PI in 7SP fibroblast-derived MirC were significantly lower than the parental 7SP fibroblast, and near the levels of NHDF cells (FIG. 10B-FIG. 10D). Importantly, there were no significant differences between 7SP fibroblast-derived MirC and NHDF, suggesting that the MirC regained the capability to tolerate this mild reperfusion damages.

The same trends as the reperfusion were recognized using the starvation model (FIG. 10E-FIG. 10H). Higher apoptosis in both an early and late phase was showed in 7SP fibroblasts, whereas 7SP fibroblast-derived MirC exhibited the almost same levels of apoptosis, basal values, as NHDF, which was significantly lower than those in the original 7SP fibroblasts (FIG. 10F-FIG. 10H). These results further confirm the mitochondrial replacement method of the present invention improves the functional recovery of the recipient cell.

These results demonstrated that the transfer of exogenous mitochondria from a healthy cell into a cell with mutant mtDNA can improve the function of the recipient cell.

Example XII: Transfer of Exogenous Mitochondria into Recipient Cells Reverted Early Stage Senescence-Associated Secretory Phenotype (SASP)

This example demonstrates that transfer of exogenous mitochondria into recipient cells reverted early stage senescence-associated secretory phenotype (SASP). A SASP consisting of inflammatory cytokines, growth factors, and proteases is a characteristic feature of senescent cells.

To determine whether transfer of exogenous mitochondria into senescent cells could revert the SASP, the expression levels of the representative SASP cytokines, IL-6 and IL-8, chemokine, CXCL-1, and growth factor, ICAM1 were quantitatively measured at the transcript levels for NHDF, 7SP fibroblast, and 7SP fibroblast-derived MirC cells, whose PDLs were almost the same, about 15 to 20 (FIG. 11). IL-6 was significantly higher in 7SP fibroblasts than those in NHDF and 7SP fibroblast-derived MirC, whereas the other three factors did not show any significant difference among these cells. At this PDL, 7SP fibroblasts did not exhibit a typical SASP, but only higher IL-6 expression, suggesting the early phase of senescence. Importantly, the process of the early-stage senescence in this PDL of 7SP fibroblast-derived MirC could be reverted.

Taken together, these data demonstrate that mitochondria replacement is able to not only treat mitochondrial diseases with mutations of mtDNA, but also rejuvenate senescent cells, such as cells involved in an array of diseases, including neurodegenerative, cardiovascular, metabolic, and autoimmune diseases, and even cancers.

Example XIII: IPS Cells Generated from mtDNA Replaced Fibroblasts

To determine whether inducible pluripotent stem cells (iPSCs) could be generated using cells derived from patients with a long deletion of mtDNA, we attempted to build iPSC from 7SP fibroblasts using the standard methods with Sendai virus carrying Oct3/4, Klf4, Sox2, and c-Myc (OKSM), which worked well for NHDF. A diagram of the protocol design is provided in FIG. 12A.

Alkaline phosphatase staining (AP staining), which detects iPSCs colonies at the early stage, demonstrated that the original 7SP fibroblasts-derived colonies seemed to be with crumbling appearances, whereas the mitochondria replaced 7SP fibroblasts-derived colonies were solid on day 21 (FIG. 12B). In contrast, the ρ(−) 7SP fibroblasts that did not receive mtDNA replacement did not generate any colonies (FIG. 12B). Several lines of iPS cells were able to be generated from the mitochondria replaced 7S fibroblasts, as measured by AP staining (FIG. 12C and FIG. 12D). The iPSC clones were stable in culture and exhibited similar morphology between independent colonies (FIG. 12E). Immunohistochemistry staining confirmed the expression of the human pluripotent stem cell markers SOX2, OCT3/4, NANOG, SSEA4, TRA1-81, and TRA1-60 on the mitochondria replaced 7SP fibroblasts-derived colonies overexpressing OKSM (FIG. 12F).

The iPSC generated by the methods described herein were further compared to the commercially available KYOU-DXR0109B Human Induced Pluripotent Stem (IPS) Cells [201B7]. Importantly, the mitochondria replaced 7SP fibroblasts showed the same level of efficiency with the iPS generation with that of healthy fibroblasts. Additionally, in agreement with previous studies, qPCR of 12S-rRNA, normalized to nuclear β-actin, demonstrated that the iPS cells generated by mitochondrial replaced 7SP fibroblasts exhibited half of the mtDNA contents relative to control, and the mtDNA levels were similar to that of the 201B7 iPSC standard (FIG. 12G).

Moreover, the hmt10158 heteroplasmy level was less than 10% in the generated iPSCs (FIG. 12H). Quantification of the absolute mtDNA copy number confirmed the reduced level of mtDNA and reduction in mutant mtDNA (FIG. 12I).

These results demonstrate that iPSCs can be generated using the mitochondrial replacement technology provided herein, and could be applicable in the clinical field because this whole procedure used only materials adaptable to clinics.

Example XIV: Mitochondria Replacement of Mitochondria from Donor Cell Alters Recipient Cell's Lifespan Cell This example demonstrates that mtDNA replacement can alter the lifespan of the recipient cell. In order to validate the hypothesis that the mitochondria replacement can rejuvenate senescent cells, two models were estimated in respect of cell cycle capabilities, such as doubling time and PDL at the growth arrest.

NHDFs and TIG1 embryonic lung cells with early PDL (around 5 to 10, called. "young") and late PDL (around 40 to 45, called "old") were utilized to design the models. One model involved young cells replaced with mitochondria derived from old cells, designated as "O2Y," and another model involved old cells replaced with mitochondria derived from young cells, designated as "Y2O" (FIG. 13A).

The extent of the exchange of mtDNA was evaluated by TaqMan SNP genotyping assay, based on the difference of the single nucleotide of mtDNA at the 16145 position between NHDF and TIG1, which are A and G, respectively (FIG. 13B). NHDF-derived MirC clearly showed that more than 90% of endogenous mtDNA (hmt16145-A) was replaced with TIG1-derived mtDNA (hmt16145-G) (FIG. 13C). The small percentage of hmt16145-A detected in the parental TIG1 cells was considered to be the background error (FIG. 13C).

In addition, the Y2O model clearly demonstrated a regain of the lifespan in old cells to around 65 PDLs (FIG. 13D). Control old cells and mock transfectant showed the growth arrest at 55 PDLs, which is consistent with the Hayflick limit. On the other hand, O2Y demonstrated the reduced lifespan of young cells at about 45 PDLs (FIG. 13E). The difference, around 10 PDLs, in both models could be attributed to exogenous mtDNA. These results demonstrate that transfer of exogenous mitochondria from a young cell to an old cell can rejuvenate cells.

Example XV: Optimization of Mitochondria Replaced Cell (MirC) from Human Primary T Cells Using mRNA Transfection This example describes the generation of mitochondria replaced Cell (MirC) from human primary T cells by using mRNA transfection.

Prior to the experiments, use of human primary T cells were approved by our institutional ethical committee. Peripheral blood was drawn from a healthy volunteer and centrifuged using percoll with a specific gravity of 1.077 at 400 g for 35 minutes at 20 degree to separate lymphocytes. Isolated lymphocytes of $1\times10^6$ cells per ml were seeded onto a 96-well flat plate coated with anti-CD3 and anti-CD28 antibodies. The plate was prepared by incubating with Sug/ml of anti-CD3 and 1 μg/ml of anti-CD28 of overnight and pre-warmed at 37° C. 2 hours prior to the seeding. On the next day of the seeding, IL-7 and IL-15 were added to the medium at a concentration of 20 μg/ml and 10 ng/ml, respectively. Medium was changed every third day with IL-7 and IL-15 at the same concentration as the initial addition.

Transfection was performed using the MaxCyte electroporator, which meets the standard of GMP/GCP, according to the manufacturer's protocol. mRNA was created according to the manufacturer's protocol in mMESSAGE mMACHINE T7 Ultra Kit (Thermo Fisher), with slight modifications. Briefly, a DNA template for mRNA was prepared from the plasmid carrying the DNA sequence without refining the fragment following endonuclease digestion, in order to reduce the possibility of mixing RNase up as lower as possible (FIG. 14A).

The results indicated that the non-refining DNA template for mRNA creation of EGFP led to nearly a 100% gene transfer efficiency with high expression and high viability at 24 hours after the gene transfection (FIG. 14B and FIG. 14C). No antibiotics selection was required using this method due to the high transfection efficiency. In addition, transfection of MTS-XbaIR resulted in a reduction in mitochondrial membrane potentials, which could be attributed to the reduction of in endogenous mtDNA (FIG. 14D).

In order to determine the optimal protocol with respect to the timing of isolated mitochondria co-incubation, fluorescent images of human primary T cells that received mRNA of GFP by electroporation using MaxCyte ATX were taken over an 8-day period, as indicated (FIG. 14E). The fluorescent images of control electroporated cells (FIG. 14F, upper panels) where cells were transfected with a GFP plasmid showed similar kinetics as that in fibroblasts. Expression peaked at day 2 and disappeared by day 8. In contrast, cells that received MTS-GFP mRNA (FIG. 14F, lower panel) showed higher expression within 4 hours post-electroporation and an earlier disappearance on day 6 than those in cells transferred with the plasmid.

The protein expression of GFP in cells receiving the MTS-GFP mRNA was evaluated by western blotting analysis using a capillary electrophoresis. The peak expression occurred at day 4, and expression was lost by day 6, as illustrated in the western blot (FIG. 14H) and quantified in FIG. 14G. Quantification of kinetics of XbaIR transcript levels were performed by qPCR and revealed that the transcript expressions of the endonuclease were quite highest at 4 hours post-gene transfer (FIG. 14I). The XbaIR transcript levels rapidly decreased by day2, and were negligible by day 6 (FIG. 14I). The mitochondrial contents were estimated by quantifying 12S rRNA (FIG. 14J), and demonstrated that mitochondria decreased to about 30% by day 2, and was maintained at less than 20% throughout the length of the experiment.

Taken together, these results demonstrate that mRNA transfection of an endonuclease, such as XbaI, fused to an MTS can efficiently degrade the host mtDNA, and can be used to generate a mitochondria replaced Cell (MirC) from human primary T cells.

Example XVI: Generation of Mitochondria Replaced Cell (MirC) from Human Primary T Cells Using mRNA Transfection After determining the optimal time point for performing mitochondrial transfer in human primary T cells from Example XV, mitochondria co-incubation was performed on day? to prevent digestion of exogenous mtDNA by any remaining endonuclease. A scheme of the MirC protocol for human primary T cells is shown in FIG. 15A.

In order to determine the heteroplasmy of mtDNA in the recipient human primary T cells following mitochondria replacement, the difference of mtDNAs between the donor mitochondria and the recipient cells was determined by TaqMan SNP genotyping assay. Sequencing of the D-loop of mtDNA in normal human primary T cells and EPC100 (mitochondria donor cells) showed a difference in 2 nucleotide positions (nucleotides 218 and 224 mtDNA), which were C/C and T/T for T cells and EPC100 cells, respectively (FIG. 15B). To delineate the standard curve for TaqMan SNP genotyping assay, the fragment of variable region encompassing the 218 and 224 nucleotides of mtDNA was subcloned into pBluescript SK(−). The polymorphic nucleotides were mapped on the human Cambridge Reference Sequence, and primers and probes were designed to amplify and target the desired region of the D-loop, where the probes had FAM and VIC fluorophore (FIG. 15C). Using TaqMan polymerase with 5' exonuclease activity, qPCR was carried out and threshold cycle (Ct value) was determined, which was fit to a standard curve created using several different copy numbers of the above mentioned plasmids for each sequence. Following the somatic mitochondria replacement, the origin of EPC100 mtDNA dominated in human T cells on both day 7 and day 12, whereas mock transfectants that received electroporation without genetic material and were coincubated with isolated mitochondria at the same protocol as MirC exhibited the exogenous origin of mtDNA less than 10% on day 7, and the background levels on day 12 (FIG. 15D)) This demonstrated that the MTS-XbaIR mRNA facilitated efficient mitochondrial transfer in human primary T cells.

Next, to evaluate the effect that the mitochondrial transfer had on the function of the MirC human T cells, respirometry experiments were performed using Oroboros O2k. The results demonstrated a recovery of ATP production and coupling efficiency in human T cell-derived MirC on day 7, whereas ρ(−) human T cells that were generated by XbaIR mRNA transfer with electroporation maintained the loss of ATP production throughout the experiment (FIG. 15E). Representative raw data using coupling-control protocol (CCP) are depicted in FIG. 15F and FIG. 15G, and show that MirC T cells are able to restore mitochondrial respiration.

These results demonstrated that human primary T cells are capable of mitochondria replacement to generate MirC using GMP graded electroporator, such as the electroporator produced by MaxCyte Inc.

Example XVII: Generation of Mitochondria Replaced Cell (MirC) from Mouse Primary T Cells Using mRNA Transfection Further characterizations of T cell-derived MirC were executed for murine T cells. The isolation of murine T cells from suspension solutions obtained from the spleen was performed using the EasySep Mouse Isolation Kit (STEM CELL Technologies, Inc.), which provides highly purified T cell population by negative selection using magnets. Isolated murine T cells ($1\times10^6$ cells per ml) were seeded onto 96-wells plate with Dynabeads mouse T-Activator CD3/CD28 (Invitrogen, Inc.) at a bead-to-cell ratio of 1:1 and recombinant IL-2 at 30U/ml. The medium to cultivate murine T cells was determined with respect to cell growth and CD3 expression, and RPMI1640 was found to be superior to TexMACS (FIG. 16A). For example, viability and total cell number were higher in cells cultured in RPMI1640, as compared to TexMACS. The medium was changed every third or fourth day.

Next, electroporation of murine T cells was performed using the Nucleofector machine and mRNA. The kinetics of GFP expression following mRNA transfer were similar to human T cells (FIG. 16B). For example, 6 hours after electroporation of MTS-GFP mRNA, almost all of the cells were found to strongly express GFP (FIG. 16B). This demonstrated that the MTS-GFP was transfected with high efficiency. The intensity of GFP rapidly declined with time, and eventually disappeared on day 6 following the electroporation (FIG. 16B).

Transfection of the MTS-XbaI mRNA indicated that murine T cells exhibited a milder decline of XbaIR transcript expression relative to human T cells, and persisted even at a low level on day 6 (FIG. 16C). Quantification of 12S rRNA levels as a surrogate marker for mtDNA, indicated that the murine mtDNA persisted even on day 6 at about 40% of the control (FIG. 16D). Next, coincubation of Ds-Red labeled exogenous mitochondria and ρ(−) murine T cells on day 5 was performed (FIG. 16E). Despite the longer persistence of XbaIR, and lower levels of endogenous mtDNA reduction, relative to human T cells, FACS analysis of engulfed fluorescence-labeled mitochondria 48 hours following the co-incubation with isolated mitochondria revealed a significant positive fraction (9.73%) of T cells expressing exogenous mitochondria (FIG. 16F) The percentage of positive cells expressing exogenous mitochondria was even higher than that in fibroblast experiments, demonstrating that this protocol for murine T cells could be optimal to generate T cell-derived MirC.

Example XVIII: Transfer of Exogenous Mitochondria to T Cells Reverted Senescence This example demonstrates that mitochondria replacement was successful in murine T cells, and rejuvenated senescent T cells.

To evaluate whether exogenous mitochondria could be successfully transferred to generate murine T cell-derived MirC, mtDNA heteroplasmy levels were of BL6 (recipient) cells and NZB (donor) cells. Two-consecutive polymorphisms at 2766 and 2767 mtDNA for ND1 was verified (FIG. 17A). Specifically, the BL6 mitochondria contained AT at positions 2766 and 2767 of mtDNA, whereas the NZB mitochondria contained GC at the same positions. A primer set and two probes were designed to discriminate the polymorphism using a different fluorophore for each of the GC and AT polymorphisms (FIG. 17B). In addition, two separate plasmids were generated to express the GC and AT polymorphisms, respectively, and a standard curve was generated to facilitate the quantitative estimation of heteroplasmy in MirC.

Quantification of the mitochondria replacement (XbaIR Mt) in BL6 cells that were transfected with MTS-XbaI and co-incubated with mitochondria isolated from NZB mice, demonstrated an overwhelming domination of exogenous mtDNA, whereas mock transfectants that were coincubated with isolated mitochondria following electroporation under the absence of mRNA of the endonuclease did not engulf any exogenous mtDNA (FIG. 17C). This result demonstrated that T cells are permissive to mitochondria replacement.

Because the results described herein demonstrated fibroblast-derived MirC could undergo rejuvenation in vitro (FIG. 13), T cell-derived MirC was also examined for rejuvenation potential. Recipient cells from old murine T cells were prepared from the spleen of mice (C57BL/6) that were more than 80 weeks old, and donor murine mitochondria were isolated from the liver of mice (C57BL/6) around 10 weeks old. Telomere length has been reported to shorten with age. Therefore, telomere length was measured by using Absolute mouse Telomere Length Quantification qPCR Assay Kit (ScienCell, Inc). Following the treatment of old murine cells with the MTS-XbaIR mRNA and co-incubation with exogenous mitochondria from the young donor cells to generate the MirC (Young to Old: YtoO), telomere length was observed to have a 1.7-fold increase in length, relative to the original old T cells (FIG. 17D). This demonstrated that the mitochondrial replaced cells exhibit characteristics of rejuvenation.

In addition, SASP was evaluated using the same representative set of makers described previously (FIG. 11). The measurement of CXCL1, ICAM1, IL-6, and IL-8 revealed that Murine T cell-derived MirC decreased IL-6 and CXCI-1, and showed no change in ICAM-1 and IL-8 (FIG. 17E). These results indicated a decrease in SASP for the MirC T cells.

Moreover, senescent T cells have been found to exhibit higher DNA damage response (DDR), compared with young T cells. Therefore, DDR was measured using the histone 2 A (H2A) phosphorylation antibody, for the MirC and the original T cells. The results indicated that the positive fraction for DDR was lower in the MirC (1.53%), compared with the original T cells (4.75%) (FIG. 17F). Thus, the MirC T cells had lower levels of DDR, indicating a reversal of senescent behavior.

These in vitro results support that the somatic mitochondria replacement was verified in the MirC mtDNA, and the replacement resulted in numerous changes that were indicative of a reversal of senescence in the MirC T cells.

Example XIX: Tumor Growth is Mitigated by Adoptive Cell Transplantation (ACT) Using MirC Derived from Old T Cells Containing Exogenous Mitochondria from Young Mice To examine the functional potential of the mitochondria replacement that rejuvenated senescent cells, an adoptive cell transplantation (ACT) experiment was performed. The AE17 mesothelioma cell line derived from the peritoneal cavity of C57BL/6J mice injected with asbestos fibers was used to develop tumor formation in mice Previous experiments using this model have shown that tumor growth is mitigated by ACT of young syngeneic T cells, but not by ACT of old syngeneic T cells (Jackaman et al. Oncolmmunology 2019; 8(4): 1-16).

To determine whether the rejuvenated old T cells, generated by transferring isolated exogenous mitochondria from a young mouse to a T cell from an old mouse, exhibited functional activity, AE17 cells were subcutaneous injected into three groups of old mice (Group 1: old mice with ACT of T cells from young mouse; Group 2: old mice; or Group 3: old mice with ACT of MirC derived from a T cell of an old mouse transferred with exogenous mitochondria from a young mouse (FIG. 18A). The old T cell-derived MirC were evaluated for their capability to suppress the tumor growth. C57BL/6 mice aged 22 to 24 months were utilized in the ACT experiment. The young mice used in the experiment were 2 to 3 months old mice. In addition of body weight measurements, tumor growth was measured using NIH image of photographs taken every 3 days (FIG. 18B). AE17 inoculation was executed on day −14 with $2\times10^6$ cells suspended in 100 μL Matrigel, and the day of T cell transfer was considered to be day 0. On day0, $2\times10^6$ cells of either young T cells or old T cell-derived MirC were intravenously injected into tumor-bearing mice. On the same day, recombinant IL-2 (2 μg) was intraperitoneally injected once, followed by two more injections on day 2 and day 3.

The body weight in each group did not show significant differences (FIG. 18C). However, the tumors were attenuated in both the Group 1 mice (old mice with young T cells) the Group 3 mice (old mice with old T cell-derived MirC), whereas the tumors steady grew in the Group 2 (mock) mice (FIG. 18D). The relative mean masses showed similar trends as the individual mice, demonstrating that the MirC behaved like the young T cells (FIG. 18E).

To verify the presence of infused T cells in the animals, T cells derived from GFP transgenic mice were transplanted into the syngeneic C57BL/6 mice, the peripheral blood and the spleen were examined to track the donor cells (FIG. 18F). A two-dimensional plot with FSC versus FL-1 to detect GFP fluorescence was generated to clarify the rare population. Negative controls using C57BL/6 mice (left upper panel), and positive controls using GFP transgenic mice (left lower panel) were generated for both the peripheral blood and the spleen (FIG. 18G). The definitive population of T cells expressing GFP fluorescence were recognized in both samples, although the fractions were 0.057% and 0.9% in the peripheral blood and the spleen, respectively (FIG. 18G). The transferred T cells in this protocol were detected on day 6 following the transplantation (FIG. 18H), which validated that this protocol could be used to evaluate the capability of the transferred cell. In addition, the percentage of chimerism following infusion of the exogenous T cells was found to increase when a greater amount of cells were infused (FIG. 18I).

These results clearly demonstrate that ex vivo MirC generation using mitochondria from young mice into T cells from an old mouse can effectively function in vivo, and reduce tumor burden at similar levels as T cells from young mice.

Example XX: Hematopoietic Stem Cells are Capable of MirC Generation

To date, gene transfer methods for hematopoietic stem cells have mainly involved the use of viral vectors, because the targets were mainly genetic disorders that require a sustainable gene expression of the deficient gene. Consequently, electroporation is not used in current protocols of gene transfer of hematopoietic stem cells because of the need to generate a permanent gene expression. In contrast, the objective of the mitochondrial replacement technology provided herein is to achieve temporal high expression of the exonuclease.

Based on the experiments for fibroblasts and T cells, the condition of Nucleofector/electroporation with mRNA was adjusted, and several conditions were examined for murine fetal liver-derived Sca-1 positive cells (FIG. 19A), which are considered to be an enriched population for hematopoietic stem cells (HSCs). Among several conditions, three conditions (program X-001, Y-001, and T-030 that are code number in the machine provider) were evaluated by immunofluorescence and cell viability (FIG. 19A). The experimental conditions were termed MTS-GFP1, 2, and 3 according to the program that was used (program X-001, Y-001, and T-030, respectively).

Further examinations were performed by FACS analysis for the mean fluorescent intensities (MFI) on day1 following the electroporation with mRNA of GFP (FIG. 19B). The results indicated that the optimal condition was the X-001 program (MTS-GFP1) because although the right shift of MFI in the condition was little, it was significant compared with the others (FIG. 19B). Murine bone marrow-derived Sca-1 cells were coincubated with mitochondria isolated from the syngeneic murine cells that are a stable gene-modified cell line expressing DsRed fluorescence. 3-D fluorescent imaging of the bone marrow-derived Sca-1 cells 48 hours after the co-incubation showed that the exogenous mitochondria were engulfed (FIG. 19C). The mitochondrial transfer efficiency was estimated by FACS analysis for DsRed fluorescent axis, and revealed that a subpopulation of about 10% of the Sca-1 exhibited a right ward shift of the fluorescent, suggesting that BM-derived Sca-1 positive cells could undergo somatic mitochondria replacement (FIG. 19D). However, the transfer of exogenous mitochondria in the MTS-GFP expression cells without depletion of endogenous mitochondria was too low for clinical application.

Next, we examined whether this mitochondria replacement procedure via generation of ρ(−) cells using MTS-XbaIR mRNA transfer could be applicable to hematopoietic stem cells (FIG. 19E). The Real hematopoietic stem cell population is considered as c-kit$^+$, Sca-1$^+$, Lineage$^-$, CD34$^-$ (called as KSLC) that is around 0.005% in the whole bone marrow cells (Wilkinson, A. C. et al. *Nature,* 571 (7763): 117-121 (2019). Following FACS sorting for KSL cells from murine bone marrow-derived cells (FIG. 19F), the KSL cells were cultivated for 5 days in the presence of stem cell factors and TPO with polyvinyl alcohol (PVA). Macroscopically, the KSL cells maintained the morphology and exhibited a short doubling time of 19 hours (FIG. 19G).

The heteroplasmy changes were evaluated using the TaqMan SNP genotyping assay, as described above. A scheme of the assay is shown in FIG. 19H. Murine KSLC-derived MirC demonstrated that the exogenous mtDNA with polymorphism in NZB was 99.9% on day6 following the endonuclease mRNA transfer with electroporation (FIG. 19I), which indicated that the exogenous mtDNA almost completely replaced the endogenous mtDNA of CL57BL/6. These results demonstrated that hematopoietic stem cells are permissive to this technology to generate MirC.

Example XXI: Droplet Digital PCR (ddPCR) for Measurement of mtDNA and Heteroplasmy This example demonstrates that mitochondrial DNA (mtDNA) can be assayed for the presence of a specific mtDNA sequence, such as a mutation in mtDNA, using digital PCR (dPCR). Droplet Digital PCR (ddPCR) is a method for performing digital PCR that is based on water-oil emulsion droplet technology.

Primary skin fibroblasts derived from patients with mitochondrial disease were analyzed. The patient information is provided below in Table 1.

TABLE 1

Patient information

| Sample | Disease | Mutation | Age | Sex | Inheritance |
|---|---|---|---|---|---|
| BK01 | MELAS | mtDNA A3243G (mt-tRNA) | 30 | Male | Mother |
| BK02 | Leigh Syndrome | mtDNA T10158C (Complex I · MT-ND3) | 6 | Female | De Novo |
| BK04 | Leigh Syndrome | mtDNA T9185C (Complex V · MT-ATP6) | 1 | Female | N.D. |

Cells from the target population were encapsulated into droplets at a concentration of one cell per droplet with the PCR mixture including primers and probes. Cell density was optimized to generate a single cell in a single droplet, and the fibroblasts were finally diluted in $1\times10^6$ cell/mL for ddPCR. After single-cell encapsulation, cell lysis and amplification of the target sequence were performed within the droplets. The number of droplets with a fluorescent signal indicated the number of cells carrying the target or reference gene.

Briefly, a 20× primer/probe mix was prepared as described below in Table 2. The standard ddPCR master mix was a 25 μL mix that includes the aforementioned primer/probe mix, template DNA and 2× ddPCR super mix.

TABLE 2 dPCR Primer and Probe Mix

| 20× Primer/Probe Mix | Volume (μL) per 100 μL |
|---|---|
| 100 μM F1 primer | 10 |
| 100 μM R1 primer | 10 |
| 100 μM labeled probe | 5 |
| PCR grade water | 75 |

TABLE 3 dPCR Reaction Master Mix

| Reagent | Volume (μL) per 25 μL Reaction |
|---|---|
| 2× ddPCR super mix | 12.5 |
| 20× Primer/Probe Mix | 1.25 |
| Template (100 ng/μL) | 1 |
| PCR grade water | 10.25 |

Samples were loaded into an 8-chamber cartridge using 20 μL of the prepared qPCR sample followed by 70 μL of droplet generation oil in the adjacent wells. A rubber gasket was stretched across the top of the chambers to ensure a vacuum seal. Each 8-chamber cartridge was loaded onto the QX100 droplet generator producing 20,000 droplets per sample. Using a 50 μL multichannel pipette, 40 μL of the generated droplets were transferred to a 96-well plate and heat sealed with pierceable foil. The plate was placed in a thermal cycler using standard 2-step q PCR thermal cycling conditions with a 50% (3° C./sec) ramp rate. Prior to running thermal cycling conditions, primer/probe sets were optimized using a temperature gradient to optimize the anneal/extend temperature.

TABLE 4 dPCR Cycling Conditions

| dPCR Cycling Conditions | Temp (° C.) | Time (sec) |
|---|---|---|
| Initial Hot Start/denaturation | 95 | 600 |
| Steps 1-2 are repeated through 40 cycles | | |
| Step 1 | 94 | 30 |
| Step 2 | 60 | 60 |
| Step 3 | 98 | 600 |
| Step 4 | 12 | infinity |

Following thermal cycling, the plate was loaded onto the QX100 droplet reader and end-point reactions were analyzed. Poisson statistical analysis of the numbers of positive and negative droplets yields absolute quantitation of the target sequence.

Before examining diseased cells, the specificity for the probes to be designed for a mutated sequence and the sensitivity for the probes to be designed for a non-mutated sequence were evaluated by using normal human dermal fibroblasts (NHDF cells) that have a non-mutated sequence (the same as Cambridge Reference Sequence) (FIG. 20A-FIG. 20C). The dots in left lower area indicated no cells in the droplet. Evaluation of the three different probe sets clearly detected the non-mutated sequence (lower right in BK01 (FIG. 20A), upper left in BK02 (FIG. 20B), and upper left in BK04 (FIG. 20C)), and did not detect the mutant sequence (upper left in BK01 (FIG. 20A), lower right in BK02 (FIG. 20B) and BK04 (FIG. 20C)).

ddPCR of fibroblasts obtained from BK01 indicated a few percentage of double positive population, and the majority was cells with homoplasmy of mutated mtDNA (FIG. 20D). There was no significant population with homoplasmy of non-mutated mtDNA in a single cell. In addition, BK02 showed a minor portion of double positive cells, which indicated a heteroplasmy in a single cell level, defined as microheteroplasmy (FIG. 20E). The results from BK02 revealed a major population of homoplasmy of mutant mtDNA, and no population with homoplasmy of non-mutated mtDNA was not recognized.

Taken together, these results demonstrated that homoplasmy and heteroplasmy can be accurately, and quantitatively evaluated at a single cell level. In addition, the results demonstrate that the mtDNA of a subject with mitochondrial disease can be accurately measured, which could be useful for evaluating therapeutic compositions prior to transplantation in a subject or monitoring the mtDNA content prior to and/or after therapy.

Example XXII: MtDNA Replacement in Recipient Hematopoietic Stem or Progenitor Cells (HSPCs) from Donor cGMP Manufactured Bone-Marrow Derived Mesenchymal Stromal Cells (BM-MSCs)

This example demonstrates that hematopoietic stem or progenitor cells (HSPCs) can be ex vivo modulated using the mtDNA replacement methods provided herein for therapy.

Modulation of HSPCs can be performed ex vivo in connection with a stem cell transplant. Briefly, peripheral blood stem cells are mobilized and a blood sample is obtained from the patient. Peripheral hematopoietic stem or progenitor cells (HSPCs), e.g., CD34+ cells are isolated and sent to a manufacturing facility. At the manufacturing facility, the mitochondria is partially depleted according to the methods provided herein.

Donor mitochondria are isolated using current Good Manufacturing Practice (cGMP) manufactured bone-marrow derived Mesenchymal Stromal Cells (BM-MSCs) obtained from a cell repository (e.g., Waisman Biomanufacturing). The initial bone marrow aspirates are collected with full informed consent and in compliance with federal regulations (e.g., 21 CFR 1271). The aspirates are processed under cGMPs and banked at an early passage for subsequent expansion.

The donor mitochondria from the BM-MSCs are transferred to cultured HSPCs, changing the heteroplasmy. The modified HSPCs are sent back to the medical center for autologous transplantation (i.e., into the same subject that the HSPCs were isolated). Prior to transplantation the patient receives minimal treatment that can include a non-myeloablative regimen, such as partial irradiation or sub-lethal dose of anti-cancer drugs, such as busulfan. The modified HSPCs, only containing the allogenic donor mitochondria, are transfused back into the patient.

This example demonstrates that HSPCs can be ex vivo modulated using the mtDNA replacement methods provided herein for therapy that does not involve transplantation of allogenic HSPCs.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. An in vitro method of preparing a mitochondria replaced cell, comprising:

(a) contacting a cell comprising dysfunctional mitochondria with a polynucleotide encoding a fusion protein comprising XbaI endonuclease with a mitochondrial targeting sequence (MTS) for a sufficient period of time for the fusion protein to reduce approximately 70% of endogenous mitochondrial DNA (mtDNA) copy number in the cell; and (b) subsequently contacting the cell with exogenous mitochondria comprising exogenous nucleoid or exogenous mtDNA isolated from a healthy donor for a sufficient period of time to non-invasively transfer the exogenous mitochondria, exogenous nucleoid, or exogenous mtDNA into the cell, thereby generating the mitochondria replaced cell with improved mitochondrial function compared to that of the cell prior to mitochondrial replacement, wherein the dysfunctional mitochondria synthesize reduced amounts of ATP by oxidative phosphorylation relative to healthy mitochondria, and wherein the exogenous nucleoid or exogenous mtDNA lasts for 12 days within the cell.

2. The method of claim 1, wherein the cell is
(a) a hematopoietic stem cell;
(b) a mesenchymal stem cell; or
(c) an immune cell.

3. The method of claim 2, wherein the immune cell is a T cell, a phagocyte, or a macrophage.

4. The method of claim 3, wherein the T cell is a CD4+ T cell, a CD8+ T cell, or a chimeric antigen receptor T cell.

5. The method of claim 1, wherein the improved mitochondrial function comprises improved ATP production, improved oxygen consumption, and/or improved respiratory capacity.

6. The method of claim 1, wherein the cell is a primary cell.

7. The method of claim 3, wherein the T cell is exhausted.

* * * * *

SEQUENCE LISTING

```
Sequence total quantity: 47
SEQ ID NO: 1            moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 1
tcatccatgg ggacgagaag ggat                                          24

SEQ ID NO: 2            moltype = DNA  length = 24
FEATURE                 Location/Qualifiers
misc_feature            1..24
                        note = Description of Artificial Sequence: Synthetic
                         oligonucleotide
misc_difference         15
                        note = a, c, t, g, unknown or other
source                  1..24
                        mol_type = other DNA
                        organism = synthetic construct
SEQUENCE: 2
tcatccatgg gggcnagaag ggat                                          24

SEQ ID NO: 3            moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
```

```
                         organism = synthetic construct
SEQUENCE: 3
tcatccatgg ggacgagaag ggat                                            24

SEQ ID NO: 4             moltype = DNA  length = 24
FEATURE                  Location/Qualifiers
misc_feature             1..24
                         note = Description of Artificial Sequence: Synthetic
                          oligonucleotide
source                   1..24
                         mol_type = other DNA
                         organism = synthetic construct
SEQUENCE: 4
tcatccatgg gggcgagaag ggat                                            24

SEQ ID NO: 5             moltype = DNA  length = 15
FEATURE                  Location/Qualifiers
misc_feature             1..15
                         note = Description of Artificial Sequence: Synthetic probe
source                   1..15
                         mol_type = other DNA
                         organism = synthetic construct
SEQUENCE: 5
cttctcgtcc ccatg                                                      15

SEQ ID NO: 6             moltype = DNA  length = 25
FEATURE                  Location/Qualifiers
misc_feature             1..25
                         note = Description of Artificial Sequence: Synthetic primer
source                   1..25
                         mol_type = other DNA
                         organism = synthetic construct
SEQUENCE: 6
agccatttac cgtacatagc acatt                                           25

SEQ ID NO: 7             moltype = DNA  length = 16
FEATURE                  Location/Qualifiers
misc_feature             1..16
                         note = Description of Artificial Sequence: Synthetic probe
source                   1..16
                         mol_type = other DNA
                         organism = synthetic construct
SEQUENCE: 7
cccttctcgc ccccat                                                     16

SEQ ID NO: 8             moltype = DNA  length = 200
FEATURE                  Location/Qualifiers
misc_feature             1..200
                         note = Description of Artificial Sequence: Synthetic
                          polynucleotide
source                   1..200
                         mol_type = other DNA
                         organism = synthetic construct
SEQUENCE: 8
cagtacatag tacataaagc catttaccgt acatagcaca ttacagtcaa atcccttctc  60
gtccccatgg atgacccccc tcagataggg gtcccttgac caccatcctc cgtgaaatca  120
atatcccgca caagagtgct actctcctcg ctccgggccc ataacacttg ggggtagcta  180
aagtgaactg tatccgacat                                                 200

SEQ ID NO: 9             moltype = DNA  length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 9
cacggaggat ggtggtcaag                                                 20

SEQ ID NO: 10            moltype = DNA  length = 53
FEATURE                  Location/Qualifiers
misc_feature             1..53
                         note = Description of Artificial Sequence: Synthetic
                          oligonucleotide
source                   1..53
                         mol_type = other DNA
                         organism = synthetic construct
SEQUENCE: 10
accacaactc aacggctaca tagaaaaatc caccccttac gagtgcggct tcg            53
```

```
SEQ ID NO: 11          moltype = DNA  length = 53
FEATURE                Location/Qualifiers
misc_feature           1..53
                       note = Description of Artificial Sequence: Synthetic
                        oligonucleotide
source                 1..53
                       mol_type = other DNA
                       organism = synthetic construct
SEQUENCE: 11
accacaactc aacggctaca tagaaaaacc caccccttac gagtgcggct tcg        53

SEQ ID NO: 12          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 12
acatagaaaa acccacccct tacg                                        24

SEQ ID NO: 13          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 13
acatagaaaa acccacccct tacg                                        24

SEQ ID NO: 14          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 14
acatagaaaa atccacccct tacg                                        24

SEQ ID NO: 15          moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 15
acatagaaaa atccacccct tacg                                        24

SEQ ID NO: 16          moltype = DNA  length = 200
FEATURE                Location/Qualifiers
misc_feature           1..200
                       note = Description of Artificial Sequence: Synthetic
                        polynucleotide
source                 1..200
                       mol_type = other DNA
                       organism = synthetic construct
SEQUENCE: 16
tataaatagt accgttaact tccaattaac tagttttgac aacattcaaa aaagagtaat  60
aaacttcgcc ttaattttaa taatcaacac cctcctagcc ttactactaa taattattac  120
attttgacta ccacaactca acggctacat agaaaaatcc accccttacg agtgcggctt  180
cgaccctata tcccccgccc                                              200

SEQ ID NO: 17          moltype = DNA  length = 26
FEATURE                Location/Qualifiers
misc_feature           1..26
                       note = Description of Artificial Sequence: Synthetic primer
source                 1..26
                       mol_type = other DNA
                       organism = synthetic construct
SEQUENCE: 17
caacaccctc ctagccttac tactaa                                      26
```

```
SEQ ID NO: 18           moltype = DNA  length = 18
FEATURE                 Location/Qualifiers
misc_feature            1..18
                        note = Description of Artificial Sequence: Synthetic probe
source                  1..18
                        mol_type = other DNA
                        organism = synthetic construct
SEQUENCE: 18
acatagaaaa atccaccc                                             18

SEQ ID NO: 19           moltype = DNA  length = 18
FEATURE                 Location/Qualifiers
misc_feature            1..18
                        note = Description of Artificial Sequence: Synthetic probe
source                  1..18
                        mol_type = other DNA
                        organism = synthetic construct
SEQUENCE: 19
ctacatagaa aaatccac                                             18

SEQ ID NO: 20           moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 20
gtcgaagccg cactcgta                                             18

SEQ ID NO: 21           moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 21
tacttaacca cc                                                   12

SEQ ID NO: 22           moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 22
tacttgacca cc                                                   12

SEQ ID NO: 23           moltype = DNA  length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
SEQUENCE: 23
caagcaagta cagcaaccaa ccctcaacta tcacacatca                     40

SEQ ID NO: 24           moltype = DNA  length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
SEQUENCE: 24
caagcaagta cagcaatcaa ccttcaacta tcacacatca                     40

SEQ ID NO: 25           moltype = DNA  length = 400
FEATURE                 Location/Qualifiers
misc_feature            1..400
                        note = Description of Artificial Sequence: Synthetic
```

```
                         polynucleotide
source                  1..400
                        mol_type = other DNA
                        organism = synthetic construct
SEQUENCE: 25
attctaattt aaactattct ctgttctttc atggggaagc agatttgggt accacccaag  60
tattgactca cccatcaaca accgctatgt atttcgtaca ttactgccag ccaccatgaa  120
tattgtacgg taccataaat acttgaccac ctgtagtaca taaaaaccca atccacatca  180
aaaccccctc cccatgctta caagcaagta cagcaatcaa ccctcaacta tcacacatca  240
actgcaactc caaagccacc cctcacccac taggatacca acaaacctac ccacccttaa  300
cagtacatag tacataaagc catttaccgt acatagcaca ttacagtcaa atcccttctc  360
gtccccatgg atgacccccc tcagataggg gtcccttgac                        400

SEQ ID NO: 26           moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 26
ctctgttctt tcatggggaa gc                                           22

SEQ ID NO: 27           moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 27
atccatgggg acgagaaggg a                                            21

SEQ ID NO: 28           moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 28
ccttgttccc agaggttcaa atc                                          23

SEQ ID NO: 29           moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 29
tctttattaa tatcctaaca ctcc                                         24

SEQ ID NO: 30           moltype = DNA  length = 29
FEATURE                 Location/Qualifiers
misc_feature            1..29
                        note = Description of Artificial Sequence: Synthetic
                         oligonucleotide
source                  1..29
                        mol_type = other DNA
                        organism = synthetic construct
SEQUENCE: 30
aaaggatccc cttgttccca gaggttcaa                                    29

SEQ ID NO: 31           moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 31
tgttctttat taatgcccta acact                                        25
```

```
SEQ ID NO: 32          moltype = DNA  length = 200
FEATURE                Location/Qualifiers
misc_feature           1..200
                       note = Description of Artificial Sequence: Synthetic
                        polynucleotide
source                 1..200
                       mol_type = other DNA
                       organism = synthetic construct
SEQUENCE: 32
gcgtaagact taaaaccttg ttcccagagg ttcaaatcct ctccctaata gtgttcttta  60
ttaatatcct aacactcctc gtccccattc taatcgccat agccttccta acattagtag  120
aacgcaaaat cttagggtac atacaactac gaaaaggccc taacattgtt ggtccatacg  180
gcattttaca accatttgca                                              200

SEQ ID NO: 33          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 33
tgccgtatgg accaacaatg                                              20

SEQ ID NO: 34          moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 34
gaatggggac gaggagtgtt aggatattaa taaagaacac t                      41

SEQ ID NO: 35          moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 35
gaatggggac gaggagtgtt agggcattaa taaagaacac t                      41

SEQ ID NO: 36          moltype = AA  length = 28
FEATURE                Location/Qualifiers
REGION                 1..28
                       note = Description of Unknown: COX10 MTS peptide
source                 1..28
                       mol_type = protein
                       organism = unidentified
SEQUENCE: 36
MAASPHTLSS RLLTGCVGGS VWYLERRT                                     28

SEQ ID NO: 37          moltype = AA  length = 24
FEATURE                Location/Qualifiers
REGION                 1..24
                       note = Description of Unknown: COX8 MTS peptide
source                 1..24
                       mol_type = protein
                       organism = unidentified
SEQUENCE: 37
MSVLTPLLLR SLTGSARRLM VPRA                                         24

SEQ ID NO: 38          moltype = DNA  length = 17
FEATURE                Location/Qualifiers
misc_feature           1..17
                       note = Description of Artificial Sequence: Synthetic probe
source                 1..17
                       mol_type = other DNA
                       organism = synthetic construct
SEQUENCE: 38
agcaatcaac cttcaac                                                 17

SEQ ID NO: 39          moltype = DNA  length = 15
FEATURE                Location/Qualifiers
```

-continued

```
misc_feature          1..15
                      note = Description of Artificial Sequence: Synthetic probe
source                1..15
                      mol_type = other DNA
                      organism = synthetic construct
SEQUENCE: 39
caaccaaccc tcaac                                                  15

SEQ ID NO: 40         moltype = DNA  length = 22
FEATURE               Location/Qualifiers
misc_feature          1..22
                      note = Description of Artificial Sequence: Synthetic primer
source                1..22
                      mol_type = other DNA
                      organism = synthetic construct
SEQUENCE: 40
ccccatgctt acaagcaagt ac                                          22

SEQ ID NO: 41         moltype = DNA  length = 22
FEATURE               Location/Qualifiers
misc_feature          1..22
                      note = Description of Artificial Sequence: Synthetic primer
source                1..22
                      mol_type = other DNA
                      organism = synthetic construct
SEQUENCE: 41
ttggagttgc agttgatgtg tg                                          22

SEQ ID NO: 42         moltype =   length =
SEQUENCE: 42
000

SEQ ID NO: 43         moltype =   length =
SEQUENCE: 43
000

SEQ ID NO: 44         moltype =   length =
SEQUENCE: 44
000

SEQ ID NO: 45         moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 45
MNSTVNFQLT SFDNIQK                                                17

SEQ ID NO: 46         moltype = AA  length = 47
FEATURE               Location/Qualifiers
REGION                1..47
                      note = Description of Artificial Sequence: Synthetic
                       polypeptide
source                1..47
                      mol_type = protein
                      organism = synthetic construct
SEQUENCE: 46
MNFALILMIN TLLALLLMII TFWLPQLNGY MEKSTPYECG FDPMSPA               47

SEQ ID NO: 47         moltype = AA  length = 50
FEATURE               Location/Qualifiers
REGION                1..50
                      note = Description of Artificial Sequence: Synthetic
                       polypeptide
source                1..50
                      mol_type = protein
                      organism = synthetic construct
SEQUENCE: 47
MFFINILTLL VPILIAMAFL TLVERKILGY MQLRKGPNIV GPYGILQPFA            50
```